US010526375B2

(12) United States Patent
Tharakaraman et al.

(10) Patent No.: US 10,526,375 B2
(45) Date of Patent: Jan. 7, 2020

(54) HUMAN ADAPTATION OF H7 HA

(71) Applicant: Massachusetts Institute of Technology, Cambridge, MA (US)

(72) Inventors: Kannan Tharakaraman, Arlington, MA (US); Rahul Raman, Waltham, MA (US); Akila Jayaraman, Waltham, MA (US); Nathan Wilson Stebbins, Cambridge, MA (US); Ram Sasisekharan, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 609 days.

(21) Appl. No.: 14/896,062

(22) PCT Filed: Jun. 5, 2014

(86) PCT No.: PCT/US2014/041149
§ 371 (c)(1),
(2) Date: Dec. 4, 2015

(87) PCT Pub. No.: WO2014/197723
PCT Pub. Date: Dec. 11, 2014

(65) Prior Publication Data
US 2016/0130306 A1 May 12, 2016

Related U.S. Application Data

(60) Provisional application No. 61/831,509, filed on Jun. 5, 2013.

(51) Int. Cl.
| C07K 14/005 | (2006.01) |
| C12N 7/00 | (2006.01) |
| G01N 33/68 | (2006.01) |
| A61K 39/00 | (2006.01) |
| C12Q 1/70 | (2006.01) |
| C07K 16/10 | (2006.01) |
| G01N 33/569 | (2006.01) |

(52) U.S. Cl.
CPC ........ *C07K 14/005* (2013.01); *C07K 16/1018* (2013.01); *C12N 7/00* (2013.01); *C12Q 1/701* (2013.01); *G01N 33/56983* (2013.01); *G01N 33/68* (2013.01); *A61K 39/00* (2013.01); *C07K 2317/33* (2013.01); *C07K 2317/76* (2013.01); *C12N 2760/16122* (2013.01); *C12N 2760/16134* (2013.01); *G01N 2333/11* (2013.01); *G01N 2469/10* (2013.01)

(58) Field of Classification Search
None
See application file for complete search history.

(56) References Cited

U.S. PATENT DOCUMENTS

| 4,166,452 A | 9/1979 | Generales, Jr. |
| 4,270,537 A | 6/1981 | Romaine |
| 4,472,509 A | 9/1984 | Gansow et al. |
| 4,596,556 A | 6/1986 | Morrow et al. |
| 4,692,411 A | 9/1987 | Ghose |
| 4,790,824 A | 12/1988 | Morrow et al. |
| 4,816,567 A | 3/1989 | Cabilly et al. |
| 4,886,499 A | 12/1989 | Cirelli et al. |
| 4,938,948 A | 7/1990 | Ring et al. |
| 4,940,460 A | 7/1990 | Casey et al. |
| 4,941,880 A | 7/1990 | Burns |
| 5,015,235 A | 5/1991 | Crossman |
| 5,021,236 A | 6/1991 | Gries et al. |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,417,662 A | 5/1995 | Hjertman et al. |
| 5,466,220 A | 11/1995 | Brenneman |
| 5,480,381 A | 1/1996 | Weston |
| 5,500,161 A | 3/1996 | Andrianov et al. |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,649,912 A | 7/1997 | Peterson |
| 5,698,390 A | 12/1997 | Houghton et al. |
| 5,704,911 A | 1/1998 | Parsons |
| 5,741,957 A | 4/1998 | Deboer et al. |
| 5,750,172 A | 5/1998 | Meade et al. |
| 5,756,687 A | 5/1998 | Denman et al. |
| 5,827,690 A | 10/1998 | Meade et al. |
| 5,893,397 A | 4/1999 | Peterson et al. |
| 5,993,412 A | 11/1999 | Deily et al. |
| 2005/0106660 A1 | 5/2005 | Vogt et al. |
| 2006/0058510 A1 | 3/2006 | Skerra et al. |
| 2006/0088908 A1 | 4/2006 | Skerra et al. |

(Continued)

FOREIGN PATENT DOCUMENTS

| WO | WO-91/11465 A1 | 8/1991 |
| WO | WO-97/013537 A1 | 4/1997 |

(Continued)

OTHER PUBLICATIONS

Harvey et al., Restrictions to the Adaptation of Influenza A Virus H5 Hemagglutinin to the Human Host, 2004, Journal of Virology, vol. 78, No. 1, pp. 502-507.*

(Continued)

*Primary Examiner* — Benjamin P Blumel
(74) *Attorney, Agent, or Firm* — Choate, Hall & Stewart LLP; Brenda Hershbach Jarrell

(57) ABSTRACT

The present invention provides, among other things, systems (e.g., comprising compositions and/or methods) for diagnosis, prophylaxis, treatment, prevention, and/or characterization of influenza transmission and/or infection. The present invention also provides methods for monitoring influenza variants for their potential to present a pandemic risk to humans.

19 Claims, 17 Drawing Sheets

Specification includes a Sequence Listing.

(56) References Cited

U.S. PATENT DOCUMENTS

| | | | |
|---|---|---|---|
| 2007/0128223 | A1 | 6/2007 | Tang et al. |
| 2010/0285564 | A1 | 11/2010 | Skerra et al. |
| 2010/0317547 | A1 | 12/2010 | Gregory et al. |
| 2011/0257032 | A1 | 10/2011 | Sasisekharan et al. |
| 2012/0219585 | A1 | 8/2012 | Raman et al. |

FOREIGN PATENT DOCUMENTS

| | | | |
|---|---|---|---|
| WO | WO-97/037705 | A1 | 10/1997 |
| WO | WO-99/034850 | A1 | 7/1999 |
| WO | WO-2006/056464 | A2 | 6/2006 |
| WO | WO-2008/073161 | A2 | 6/2008 |
| WO | WO-2009/089119 | A2 | 7/2009 |

OTHER PUBLICATIONS

Chen et al., The Receptor Binding Specificity of the Live Attenuated Influenza H2 and H6 Vaccine Viruses Contributes to Vaccine Immunogenicity and Protection in Ferrets, 2011, Journal of Virology, pp. 2780-2786.*
Chen et al., Human infections with the emerging avian infl uenza A H7N9 virus from wet market poultry: clinical analysis and characterisation of viral genome, 2013, vol. 381, pp. 1916-1925.*
Allison, A.C., The mode of action of immunological adjuvants, Dev. Biol. Stand., 92:3-11 (1998).
Altschul, S. F. and Gish, W., Local Alignment Statistics, Methods in Enzymology, 266:460-480 (1996).
Altschul, S. F. et al., Gapped BLAST and PSI-BLAST: a new generation of protein database search programs, Nucleic Acids Res., 25(17): 3389-3402 (1997).
Altschul, S.F. et al., Basic local alignment search tool, J. Mol. Biol., 215: 403-410 (1990).
Baylor, N.W. et al., Aluminum salts in vaccines—US perspective, Vaccine, 20(Suppl. 3):S18-23 (2002).
Cao, M. et al., Enhancement of the protective effect of inactivated influenza virus vaccine by cytokines, Vaccine, 10(4):238-242 (1992).
Chandrasekaran, A. et al., Glycan topology determines human adaptation of avian H5N1 virus hemagglutinin, Nat. Biotechnol, 26:107-113 (2008).
Connor, R. J. et al., Receptor specificity in human, avian, and equine H2 and H3 influenza virus isolates, Virology, 205(1):17-23 (1994).
Cooper, C. L. et al., Safety and immunogenicity of CPG 7909 injection as an adjuvant to Fluarix influenza vaccine, Vaccine, 22:3136-3143 (2004).
Cunha, B.A., Influenza: historical aspects of epidemics and pandemics, Infectious disease clinics of North America, 18(1): 141-155 (2004).
Eisen, M.B. et al., Binding of the influenza A virus to cell-surface receptors: structures of five hemagglutinin-sialyloligosaccharide complexes determined by X-ray crystallography, Virology, 232(1):19-31 (1997).
Ekiert, D. et al., Antibody recognition of a highly conserved influenza virus epitope, Science, 324(5924): 246-251 (2009).
Fishwild, D.M. et al., High-avidity human IgG kappa monoclonal antibodies from a novel strain of minilocus transgenic mice, Nat. Biotechnol., 14:845-51 (1996).
Fouchier, R.A. et al. Avian influenza A virus (H7N7) associated with human conjunctivitis and a fatal case of acute respiratory distress syndrome, PNAS, 101(5):1356-1361 (2004).
Gamblin, S.J. et al., The structure and receptor binding properties of the 1918 influenza hemagglutinin, Science, 303:1838-42 (2004).
Gao, H.N. et al. Clinical findings in 111 cases of influenza A (H7N9) virus infection, New England Journal of Medicine, 368(24): 2277-85 (2013).
Gao, R. et al., Human infection with a novel avian-origin influenza A (H7N9) virus, New England Journal of Medicine, 368(20):1888-1897 (2013).
Ghochikyan, A. et al., Prototype Alzheimer's disease epitope vaccine induced strong Th2-type anti-Abeta antibody response with Alum to Quil A adjuvant switch, Vaccine, 24(13):2275-82 (2006).
Ha, Y. et al., X-ray structure of the hemagglutinin of a potential H3 avian progenitor of the 1968 Hong Kong pandemic influenza virus, Virology, 309:209-18 (2003).
Ha, Y. et al., X-ray structures of H5 avian and H9 swine influenza virus hemagglutinins bound to avian and human receptor analogs, Proc. Natl. Acad. Sci. USA, 98(20):11181-6 (2001).
Hensley, S.E. et al. Hemagglutinin receptor binding avidity drives influenza A virus antigenic drift, Science, 326(5953):734-736 (2009).
International Search Report for PCT/US2014/41149, 5 pages (dated Dec. 22, 2014).
Jayaraman, A. et al. A single base-pair change in 2009 H1N1 hemagglutinin increases human receptor affinity and leads to efficient airborne viral transmission in ferrets, PLoS One, 6(3):e17616 (2011).
Jayasena, S.D., Aptamers: an emerging class of molecules that rival antibodies in diagnostics, Clin. Chem., 45(9):1628-50 (1999).
Katz, J. M. et al., A nonionic block co-polymer adjuvant (CRL1005) enhances the immunogenicity and protective efficacy of inactivated influenza vaccine in young and aged mice, Vaccine, 18:2177-2187 (2000).
Kohl, A. et al., Designed to be stable: crystal structure of a consensus ankyrin repeat protein, PNAS, 100(4): 1700-1705 (2003).
Kreuter, J. and Liehl, E., Long-term studies of microencapsulated and adsorbed influenza vaccine nanoparticles, J. Pharm. Sci., 70(4):367-71 (1981).
Li, Q. et al., Epidemiology of human infections with avian influenza A(H7N9) virus in china, New England Journal of Medicine, 370(6): 520-32 (2013).
Li, W. et al., Positive selection on hemagglutinin and neuraminidase genes of H1N1 influenza viruses,Virology Journal, 8(183):1-9 (2011).
Lin, Y. P. et al., Evolution of the receptor binding properties of the influenza A(H3N2) hemagglutinin, PNAS, 109(52): 21474-21479 (2012).
Liu, J. et al., Structures of receptor complexes formed by hemagglutinins from the Asian Influenza pandemic of 1957, Proc. Natl. Acad. Sci. U S A, 106(40): 17175 (2009).
Maines, T.R. et al. Transmission and pathogenesis of swine-origin 2009 A(H1N1) influenza viruses in ferrets and mice, Science, 325(5939):484-487 (2009).
Marks, J.D. et al., By-passing immunization: Human antibodies from V-gene libraries displayed on phage, J. Mol. Biol., 222:581-97 (1991).
Marks, J.D. et al., By-passing immunization: building high affinity human antibodies by chain shuffling, Bio/technology, 10:779-83 (1992).
Matrosovich, M.N. et al. Human and avian influenza viruses target different cell types in cultures of human airway epithelium, PNAS, 101(13):4620-4624 (2004).
Mostow, S.R. et al., Application of the single radial diffusion test for assay of antibody to influenza type A viruses, J. Clin. Microbiol., 2(6):531-540 (1975).
NCBI Accession No. A45539, Subtype H7 influenza virus: comparative antigenic and molecular analysis of the HA-, M-, and NS-genes, [database online], retrieved on Sep. 26, 2014, http://www.ncbi.nlm.nih.gov/protein/A45539?report=genpept.
Nicholls, J.M. et al. Sialic acid receptor detection in the human respiratory tract: evidence for widespread distribution of potential binding sites for human and avian influenza viruses, Respir. Res., 8(73) 1-7 (2007).
Pappas, C. et al. Single gene reassortants identify a critical role for PB1, HA, and NA in the high virulence of the 1918 pandemic influenza virus, PNAS, 105(8):3064-3069 (2008).
Phillips, N.C. and Emili, A. et al. Enhanced antibody response to liposome-associated protein antigens: preferential stimulation of IgG2a/b production, Vaccine, 10:151-158 (1992).
Reisfeld, R.A. and Cheresh, D.A, Human tumour-associated antigens: targets for monoclonal antibody-mediated cancer therapy, Cancer Surv. 4(1):271-90 (1985).
Riechmann, L. et al., Reshaping human antibodies for therapy, Nature, 332:323-7 (1988).

(56) References Cited

OTHER PUBLICATIONS

Rogers, G. N. and Paulson, J.C., Receptor determinants of human and animal influenza virus isolates: differences in receptor specificity of the H3 hemagglutinin based on species of origin, Virology, 127:361-73 (1983).
Rogers, G.N. et al., Single amino acid substitutions in influenza haemagglutinin change receptor binding specificity, Nature, 304:76-8 (1983).
Russell, R. J. et al., Avian and human receptor binding by hemagglutinins of influenza A viruses, Glycoconj. J., 23(1-2):85-92 (2006).
Russell, R., et al., H1 and H7 influenza haemagglutinin structures extend a structural classification of haemagglutinin subtypes, Virology, 325:287-296 (2004).
Sauter, N.K. et al., Binding of influenza virus hemagglutinin to analogs of its cell-surface receptor, sialic acid: analysis by proton nuclear magnetic resonance spectroscopy and X-ray crystallography, Biochemistry, 30(40):9609-21 (1992).
Schild, G.C. et al, A single-radial-immunodiffusion technique for the assay of influenza haemagglutinin antigen: Proposals for an assay method for the haemagglutinin content of influenza vaccines, Bull. World Health Organ., 52:223-31 (1975).
Schild, G.C. et al., Single-radial-haemolysis: a new method for the assay of antibody to influenza haemagglutinin, Bull. World Health Organ., 52:43-50 (1975).
Shinya, K. et al., Avian flu: influenza virus receptors in the human airway, Nature, 440:435-436 (2006).
Skehel, J.J. and Wiley, D.C., Receptor binding and membrane fusion in virus entry: the influenza hemagglutinin, Annu. Rev. Biochem., 69:531-569 (2000).
Skerra, A., 'Anticalins': a new class of engineered ligand-binding proteins with antibody-like properties, J. Biotechnol., 74:257-75 (2001).
Skerra, A., Engineered protein scaffolds for molecular recognition, J. Mol. Recogn., 13:167-187 (2000).
Soundararajan, V. et al., Networks link antigenic and receptor-binding sites of influenza hemagglutinin: mechanistic insight into fitter strain propagation, Sci. Rep., 1(200): 1-7 (2011).
Srinivasan et al., Quantitative Description of Glycan-Receptor Binding of Influenza A Virus H7 Hemagglutinin, PLOS ONE, 8(2):e49590-e49597 (2013).
Srinivasan, A. et al. Quantitative biochemical rationale for differences in transmissibility of 1918 pandemic influenza A viruses, PNAS, 105(8):2800-2805 (2008).
Stevens, J. et al., Recent avian H5N1 viruses exhibit increased propensity for acquiring human receptor specificity, J. Mol. Biol., 381(5):1382-1394 (2008).
Stevens, J. et al., Structure and receptor specificity of the hemagglutinin from an H5N1 influenza virus, Science, 312:404-10 (2006).
Stevens, J. et al., Structure of the uncleaved human H1 hemagglutinin from the extinct 1918 influenza virus, Science, 303:1866-70 (2004).
Sui, J. et al., Structural and functional bases for broad-spectrum neutralization of avian and human influenza A viruses, Nat. Struct. Mol. Biol., 16(3): 265-73 (2009).
Tuerk, C. and Gold, L., Systematic evolution of ligands by exponential enrichment: RNA ligands to bacteriophage T4 DNA polymerase, Science, 249:505-510 (1990).
Tumpey, T. M. et al., Characterization of the reconstructed 1918 Spanish influenza pandemic virus, Science, 310:77-80 (2005).
Tumpey, T.M. et al. A two-amino acid change in the hemagglutinin of the 1918 influenza virus abolishes transmission, Science, 315; 655-659 (2007).
Uiprasertkul, M. et al., Influenza A H5N1 replication sites in humans, Emerg. Infect. Dis. 11(7):1036-41 (2005).
Unkeless, J.C. et al. Structure and function of human and murine receptors for IgG, Annu. Rev. Immunol., 6:251-281 (1988).
Van Hoevan, N. et al. Human HA and polymerase subunit PB2 proteins confer transmission of an avian influenza virus through the air, PNAS, 106(9):3366-3371 (2009).
Verhoeyen, M. et al., Reshaping human antibodies: grafting an antilysozyme activity, Science. 239:1534-6 (1988).
Written Opinion for PCT/US2014/41149, 15 pages (dated Dec. 22, 2014).
Xu, R. et al., Structure, receptor binding, and antigenicity of influenza virus hemagglutinins from the 1957 H2N2 pandemic, J. Virol., 84(4): 1715-21 (2010).
Hoogenboom, H.R. et al., Construction and expression of antibody-tumor necrosis factor fusion proteins, Mol. Immunol., 28(9):1027-37 (1991).
Kwon, T.Y. et al. Genetic characterization of H7N2 influenza virus isolated from pigs, Vet. Microbiol., 153:393-397 (2011).
Liu, D. et al., Origin and diversity of novel avian influenza A H7N9 viruses causing human infection: phylogenetic, structural, and coalescent analyses, Lancet, 381: 1926-32 (2013).
Lonberg, N. and Huszar, D., Human antibodies from transgenic mice, Int. Rev. Immunol.,13:65-93 (1995).
Lonberg, N. et al., Antigen-specific human antibodies from mice comprising four distinct genetic modifications, Nature, 368:856-9 (1994).
Losman, M. J. et al., Baboon anti-idiotype antibodies mimic a carcinoembryonic antigen epitope, Int. J. Cancer, 46:310-4 (1990).
Mbawuike, I. N. et al., Enhancement of the protective efficacy of inactivated influenza A virus vaccine in aged mice by IL-2 liposomes, Vaccine, 8(4):347-352 (1990).
Milstein, C. and Cuello, A.C., Hybrid hybridomas and their use in immunohistochemistry, Nature, 305(5934):537-40 (1983).
Murali, R. et al. Antibody like peptidomimetics as large scale immunodetection probes, Cell Mol Biol (Noisy-le-grand), 49(2):209-16 (2003).
Payne, L. G. et al., Poly[di(carboxylatophenoxy)phosphazene] (PCPP) is a potent immunoadjuvant for an influenza vaccine, Vaccine, 16(1):92-98 (1998).
Schade, R. et al., Specificity of Chicken (IgY) versus Rabbit (IgG) Antibodies Raised against Cholecystokinin Octapeptide (CCK-8), ALTEX 13(5):80-85 (1996).

\* cited by examiner

SEQUENCE LISTING

```
<160> NUMBER OF SEQ ID NOS: 65

<210> SEQ ID NO 1
<211> LENGTH: 106
<212> TYPE: PRT
<213> ORGANISM: Artificial Sequence
<220> FEATURE:
<223> OTHER INFORMATION: HA Sequence Element 1
<220> FEATURE:
<221> NAME/KEY: MISC_FEATURE
<222> LOCATION: (2)..(2)
<223> OTHER INFORMATION: X= Tyr or Phe
<220> FEATURE:
<221> NAME/KEY: MISC_FEATURE
<222> LOCATION: (4)..(33)
<223> OTHER INFORMATION: X= any amino acid
<220> FEATURE:
<221> NAME/KEY: MISC_FEATURE
<222> LOCATION: (34)..(34)
<223> OTHER INFORMATION: X = absent or any amino acid
<220> FEATURE:
<221> NAME/KEY: MISC_FEATURE
<222> LOCATION: (35)..(35)
<223> OTHER INFORMATION: X = absent or any amino acid
<220> FEATURE:
<221> NAME/KEY: MISC_FEATURE
<222> LOCATION: (36)..(36)
<223> OTHER INFORMATION: X = absent or any amino acid
<220> FEATURE:
<221> NAME/KEY: MISC_FEATURE
<222> LOCATION: (37)..(37)
<223> OTHER INFORMATION: X = absent or any amino acid
<220> FEATURE:
<221> NAME/KEY: MISC_FEATURE
<222> LOCATION: (38)..(38)
<223> OTHER INFORMATION: X = absent or any amino acid
<220> FEATURE:
<221> NAME/KEY: MISC_FEATURE
<222> LOCATION: (39)..(39)
<223> OTHER INFORMATION: X = absent or any amino acid
<220> FEATURE:
<221> NAME/KEY: MISC_FEATURE
<222> LOCATION: (40)..(40)
<223> OTHER INFORMATION: X = absent or any amino acid
<220> FEATURE:
<221> NAME/KEY: MISC_FEATURE
<222> LOCATION: (41)..(41)
<223> OTHER INFORMATION: X = absent or any amino acid
<220> FEATURE:
<221> NAME/KEY: MISC_FEATURE
<222> LOCATION: (42)..(42)
<223> OTHER INFORMATION: X = absent or any amino acid
<220> FEATURE:
<221> NAME/KEY: MISC_FEATURE
<222> LOCATION: (43)..(43)
<223> OTHER INFORMATION: X = absent or any amino acid
```

```
<220> FEATURE:
<221> NAME/KEY: MISC_FEATURE
<222> LOCATION: (44)..(44)
<223> OTHER INFORMATION: X = absent or any amino acid
<220> FEATURE:
<221> NAME/KEY: MISC_FEATURE
<222> LOCATION: (45)..(45)
<223> OTHER INFORMATION: X = absent or any amino acid
<220> FEATURE:
<221> NAME/KEY: MISC_FEATURE
<222> LOCATION: (46)..(46)
<223> OTHER INFORMATION: X = absent or any amino acid
<220> FEATURE:
<221> NAME/KEY: MISC_FEATURE
<222> LOCATION: (47)..(47)
<223> OTHER INFORMATION: X = absent or any amino acid
<220> FEATURE:
<221> NAME/KEY: MISC_FEATURE
<222> LOCATION: (48)..(48)
<223> OTHER INFORMATION: X = absent or any amino acid
<220> FEATURE:
<221> NAME/KEY: MISC_FEATURE
<222> LOCATION: (50)..(54)
<223> OTHER INFORMATION: X = any amino acid
<220> FEATURE:
<221> NAME/KEY: MISC_FEATURE
<222> LOCATION: (55)..(55)
<223> OTHER INFORMATION: X = absent or any amino acid
<220> FEATURE:
<221> NAME/KEY: MISC_FEATURE
<222> LOCATION: (56)..(56)
<223> OTHER INFORMATION: X = absent or any amino acid
<220> FEATURE:
<221> NAME/KEY: MISC_FEATURE
<222> LOCATION: (57)..(57)
<223> OTHER INFORMATION: X = absent or any amino acid
<220> FEATURE:
<221> NAME/KEY: MISC_FEATURE
<222> LOCATION: (58)..(58)
<223> OTHER INFORMATION: X = absent or any amino acid
<220> FEATURE:
<221> NAME/KEY: MISC_FEATURE
<222> LOCATION: (59)..(59)
<223> OTHER INFORMATION: X = absent or any amino acid
<220> FEATURE:
<221> NAME/KEY: MISC_FEATURE
<222> LOCATION: (60)..(60)
<223> OTHER INFORMATION: X = absent or any amino acid
<220> FEATURE:
<221> NAME/KEY: MISC_FEATURE
<222> LOCATION: (61)..(61)
<223> OTHER INFORMATION: X = absent or any amino acid
<220> FEATURE:
<221> NAME/KEY: MISC_FEATURE
<222> LOCATION: (62)..(62)
<223> OTHER INFORMATION: X = absent or any amino acid
<220> FEATURE:
<221> NAME/KEY: MISC_FEATURE
<222> LOCATION: (63)..(63)
<223> OTHER INFORMATION: X = absent or any amino acid
<220> FEATURE:
<221> NAME/KEY: MISC_FEATURE
<222> LOCATION: (64)..(64)
<223> OTHER INFORMATION: X = absent or any amino acid
<220> FEATURE:
<221> NAME/KEY: MISC_FEATURE
<222> LOCATION: (65)..(65)
<223> OTHER INFORMATION: X = absent or any amino acid
<220> FEATURE:
<221> NAME/KEY: MISC_FEATURE
<222> LOCATION: (66)..(66)
<223> OTHER INFORMATION: X = absent or any amino acid
<220> FEATURE:
<221> NAME/KEY: MISC_FEATURE
<222> LOCATION: (67)..(67)
<223> OTHER INFORMATION: X = absent or any amino acid
```

<220> FEATURE:
<221> NAME/KEY: MISC_FEATURE
<222> LOCATION: (68)..(68)
<223> OTHER INFORMATION: X = absent or any amino acid
<220> FEATURE:
<221> NAME/KEY: MISC_FEATURE
<222> LOCATION: (69)..(69)
<223> OTHER INFORMATION: X = absent or any amino acid
<220> FEATURE:
<221> NAME/KEY: MISC_FEATURE
<222> LOCATION: (71)..(95)
<223> OTHER INFORMATION: X = any amino acid
<220> FEATURE:
<221> NAME/KEY: MISC_FEATURE
<222> LOCATION: (96)..(96)
<223> OTHER INFORMATION: X = absent or any amino acid
<220> FEATURE:
<221> NAME/KEY: MISC_FEATURE
<222> LOCATION: (97)..(97)
<223> OTHER INFORMATION: X = absent or any amino acid
<220> FEATURE:
<221> NAME/KEY: MISC_FEATURE
<222> LOCATION: (98)..(98)
<223> OTHER INFORMATION: X = absent or any amino acid
<220> FEATURE:
<221> NAME/KEY: MISC_FEATURE
<222> LOCATION: (99)..(99)
<223> OTHER INFORMATION: X = absent or any amino acid
<220> FEATURE:
<221> NAME/KEY: MISC_FEATURE
<222> LOCATION: (100)..(100)
<223> OTHER INFORMATION: X = absent or any amino acid
<220> FEATURE:
<221> NAME/KEY: MISC_FEATURE
<222> LOCATION: (102)..(103)
<223> OTHER INFORMATION: X = any amino acid

<400> SEQUENCE: 1

Cys Xaa Pro Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Cys Xaa Xaa Xaa Xaa Xaa Xaa Xaa Xaa Xaa Xaa Xaa Xaa Xaa Xaa
50                  55                  60

Xaa Xaa Xaa Xaa Xaa Trp Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Trp Xaa Xaa His His Pro
            100                 105

<210> SEQ ID NO 2
<211> LENGTH: 106
<212> TYPE: PRT
<213> ORGANISM: Artificial Sequence
<220> FEATURE:
<223> OTHER INFORMATION: HA Sequence Element 1
<220> FEATURE:
<221> NAME/KEY: MISC_FEATURE
<222> LOCATION: (4)..(29)
<223> OTHER INFORMATION: X= any amino acid
<220> FEATURE:
<221> NAME/KEY: MISC_FEATURE
<222> LOCATION: (30)..(30)
<223> OTHER INFORMATION: X = absent or any amino acid
<220> FEATURE:
<221> NAME/KEY: MISC_FEATURE
<222> LOCATION: (31)..(31)
<223> OTHER INFORMATION: X = absent or any amino acid -continued

```
<220> FEATURE:
<221> NAME/KEY: MISC_FEATURE
<222> LOCATION: (32)..(32)
<223> OTHER INFORMATION: X = absent or any amino acid
<220> FEATURE:
<221> NAME/KEY: MISC_FEATURE
<222> LOCATION: (33)..(33)
<223> OTHER INFORMATION: X = absent or any amino acid
<220> FEATURE:
<221> NAME/KEY: MISC_FEATURE
<222> LOCATION: (34)..(34)
<223> OTHER INFORMATION: X = absent or any amino acid
<220> FEATURE:
<221> NAME/KEY: MISC_FEATURE
<222> LOCATION: (35)..(35)
<223> OTHER INFORMATION: X = absent or any amino acid
<220> FEATURE:
<221> NAME/KEY: MISC_FEATURE
<222> LOCATION: (36)..(36)
<223> OTHER INFORMATION: X = absent or any amino acid
<220> FEATURE:
<221> NAME/KEY: MISC_FEATURE
<222> LOCATION: (37)..(37)
<223> OTHER INFORMATION: X = absent or any amino acid
<220> FEATURE:
<221> NAME/KEY: MISC_FEATURE
<222> LOCATION: (38)..(38)
<223> OTHER INFORMATION: X = absent or any amino acid
<220> FEATURE:
<221> NAME/KEY: MISC_FEATURE
<222> LOCATION: (39)..(39)
<223> OTHER INFORMATION: X = absent or any amino acid
<220> FEATURE:
<221> NAME/KEY: MISC_FEATURE
<222> LOCATION: (40)..(40)
<223> OTHER INFORMATION: X = absent or any amino acid
<220> FEATURE:
<221> NAME/KEY: MISC_FEATURE
<222> LOCATION: (41)..(41)
<223> OTHER INFORMATION: X = absent or any amino acid
<220> FEATURE:
<221> NAME/KEY: MISC_FEATURE
<222> LOCATION: (42)..(42)
<223> OTHER INFORMATION: X = absent or any amino acid
<220> FEATURE:
<221> NAME/KEY: MISC_FEATURE
<222> LOCATION: (43)..(43)
<223> OTHER INFORMATION: X = absent or any amino acid
<220> FEATURE:
<221> NAME/KEY: MISC_FEATURE
<222> LOCATION: (44)..(44)
<223> OTHER INFORMATION: X = absent or any amino acid
<220> FEATURE:
<221> NAME/KEY: MISC_FEATURE
<222> LOCATION: (45)..(45)
<223> OTHER INFORMATION: X = absent or any amino acid
<220> FEATURE:
<221> NAME/KEY: MISC_FEATURE
<222> LOCATION: (47)..(47)
<223> OTHER INFORMATION: X = Ala or Thr
<220> FEATURE:
<221> NAME/KEY: MISC_FEATURE
<222> LOCATION: (48)..(48)
<223> OTHER INFORMATION: X = Ala or Ser
<220> FEATURE:
<221> NAME/KEY: MISC_FEATURE
<222> LOCATION: (50)..(54)
<223> OTHER INFORMATION: X = any amino acid
<220> FEATURE:
<221> NAME/KEY: MISC_FEATURE
<222> LOCATION: (55)..(55)
<223> OTHER INFORMATION: X = absent or any amino acid
<220> FEATURE:
<221> NAME/KEY: MISC_FEATURE
<222> LOCATION: (56)..(56)
<223> OTHER INFORMATION: X = absent or any amino acid
<220> FEATURE:
<221> NAME/KEY: MISC_FEATURE
<222> LOCATION: (57)..(57)
```

```
<223> OTHER INFORMATION: X = absent or any amino acid
<220> FEATURE:
<221> NAME/KEY: MISC_FEATURE
<222> LOCATION: (58)..(58)
<223> OTHER INFORMATION: X = absent or any amino acid
<220> FEATURE:
<221> NAME/KEY: MISC_FEATURE
<222> LOCATION: (59)..(59)
<223> OTHER INFORMATION: X = absent or any amino acid
<220> FEATURE:
<221> NAME/KEY: MISC_FEATURE
<222> LOCATION: (60)..(60)
<223> OTHER INFORMATION: X = absent or any amino acid
<220> FEATURE:
<221> NAME/KEY: MISC_FEATURE
<222> LOCATION: (61)..(61)
<223> OTHER INFORMATION: X = absent or any amino acid
<220> FEATURE:
<221> NAME/KEY: MISC_FEATURE
<222> LOCATION: (62)..(62)
<223> OTHER INFORMATION: X = absent or any amino acid
<220> FEATURE:
<221> NAME/KEY: MISC_FEATURE
<222> LOCATION: (63)..(63)
<223> OTHER INFORMATION: X = absent or any amino acid
<220> FEATURE:
<221> NAME/KEY: MISC_FEATURE
<222> LOCATION: (64)..(64)
<223> OTHER INFORMATION: X = absent or any amino acid
<220> FEATURE:
<221> NAME/KEY: MISC_FEATURE
<222> LOCATION: (65)..(65)
<223> OTHER INFORMATION: X = absent or any amino acid
<220> FEATURE:
<221> NAME/KEY: MISC_FEATURE
<222> LOCATION: (66)..(66)
<223> OTHER INFORMATION: X = absent or any amino acid
<220> FEATURE:
<221> NAME/KEY: MISC_FEATURE
<222> LOCATION: (67)..(67)
<223> OTHER INFORMATION: X = absent or any amino acid
<220> FEATURE:
<221> NAME/KEY: MISC_FEATURE
<222> LOCATION: (68)..(68)
<223> OTHER INFORMATION: X = absent or any amino acid
<220> FEATURE:
<221> NAME/KEY: MISC_FEATURE
<222> LOCATION: (69)..(69)
<223> OTHER INFORMATION: X = absent or any amino acid
<220> FEATURE:
<221> NAME/KEY: MISC_FEATURE
<222> LOCATION: (71)..(95)
<223> OTHER INFORMATION: X = any amino acid
<220> FEATURE:
<221> NAME/KEY: MISC_FEATURE
<222> LOCATION: (96)..(96)
<223> OTHER INFORMATION: X = absent or any amino acid
<220> FEATURE:
<221> NAME/KEY: MISC_FEATURE
<222> LOCATION: (97)..(97)
<223> OTHER INFORMATION: X = absent or any amino acid
<220> FEATURE:
<221> NAME/KEY: MISC_FEATURE
<222> LOCATION: (98)..(98)
<223> OTHER INFORMATION: X = absent or any amino acid
<220> FEATURE:
<221> NAME/KEY: MISC_FEATURE
<222> LOCATION: (99)..(99)
<223> OTHER INFORMATION: X = absent or any amino acid
<220> FEATURE:
<221> NAME/KEY: MISC_FEATURE
<222> LOCATION: (100)..(100)
<223> OTHER INFORMATION: X = absent or any amino acid
<220> FEATURE:
<221> NAME/KEY: MISC_FEATURE
<222> LOCATION: (102)..(103)
<223> OTHER INFORMATION: X = any amino acid

<400> SEQUENCE: 2
```

```
Cys Tyr Pro Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Thr Xaa Xaa
            35                  40                  45

Cys Xaa Xaa Xaa Xaa Xaa Xaa Xaa Xaa Xaa Xaa Xaa Xaa
    50                  55                  60

Xaa Xaa Xaa Xaa Xaa Trp Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Trp Xaa Xaa His His Pro
            100                 105
```

<210> SEQ ID NO 3
<211> LENGTH: 106
<212> TYPE: PRT
<213> ORGANISM: Artificial Sequence
<220> FEATURE:
<223> OTHER INFORMATION: HA Sequence Element 1
<220> FEATURE:
<221> NAME/KEY: MISC_FEATURE
<222> LOCATION: (4)..(30)
<223> OTHER INFORMATION: X = any amino ac

```
<222> LOCATION: (42)..(42)
<223> OTHER INFORMATION: X = absent or any amino acid
<220> FEATURE:
<221> NAME/KEY: MISC_FEATURE
<222> LOCATION: (43)..(43)
<223> OTHER INFORMATION: X = absent or any amino acid
<220> FEATURE:
<221> NAME/KEY: MISC_FEATURE
<222> LOCATION: (44)..(44)
<223> OTHER INFORMATION: X = absent or any amino acid
<220> FEATURE:
<221> NAME/KEY: MISC_FEATURE
<222> LOCATION: (45)..(45)
<223> OTHER INFORMATION: X = absent or any amino acid
<220> FEATURE:
<221> NAME/KEY: MISC_FEATURE
<222> LOCATION: (47)..(47)
<223> OTHER INFORMATION: X = Ala or Thr
<220> FEATURE:
<221> NAME/KEY: MISC_FEATURE
<222> LOCATION: (48)..(48)
<223> OTHER INFORMATION: X = Ala or Ser
<220> FEATURE:
<221> NAME/KEY: MISC_FEATURE
<222> LOCATION: (50)..(54)
<223> OTHER INFORMATION: X = any amino acid
<220> FEATURE:
<221> NAME/KEY: MISC_FEATURE
<222> LOCATION: (55)..(55)
<223> OTHER INFORMATION: X = absent or any amino acid
<220> FEATURE:
<221> NAME/KEY: MISC_FEATURE
<222> LOCATION: (56)..(56)
<223> OTHER INFORMATION: X = absent or any amino acid
<220> FEATURE:
<221> NAME/KEY: MISC_FEATURE
<222> LOCATION: (57)..(57)
<223> OTHER INFORMATION: X = absent or any amino acid
<220> FEATURE:
<221> NAME/KEY: MISC_FEATURE
<222> LOCATION: (58)..(58)
<223> OTHER INFORMATION: X = absent or any amino acid
<220> FEATURE:
<221> NAME/KEY: MISC_FEATURE
<222> LOCATION: (59)..(59)
<223> OTHER INFORMATION: X = absent or any amino acid
<220> FEATURE:
<221> NAME/KEY: MISC_FEATURE
<222> LOCATION: (60)..(60)
<223> OTHER INFORMATION: X = absent or any amino acid
<220> FEATURE:
<221> NAME/KEY: MISC_FEATURE
<222> LOCATION: (61)..(61)
<223> OTHER INFORMATION: X = absent or any amino acid
<220> FEATURE:
<221> NAME/KEY: MISC_FEATURE
<222> LOCATION: (62)..(62)
<223> OTHER INFORMATION: X = absent or any amino acid
<220> FEATURE:
<221> NAME/KEY: MISC_FEATURE
<222> LOCATION: (63)..(63)
<223> OTHER INFORMATION: X = absent or any amino acid
<220> FEATURE:
<221> NAME/KEY: MISC_FEATURE
<222> LOCATION: (64)..(64)
<223> OTHER INFORMATION: X = absent or any amino acid
<220> FEATURE:
<221> NAME/KEY: MISC_FEATURE
<222> LOCATION: (65)..(65)
<223> OTHER INFORMATION: X = absent or any amino acid
<220> FEATURE:
<221> NAME/KEY: MISC_FEATURE
<222> LOCATION: (66)..(66)
<223> OTHER INFORMATION: X = absent or any amino acid
<220> FEATURE:
<221> NAME/KEY: MISC_FEATURE
<222> LOCATION: (67)..(67)
<223> OTHER INFORMATION: X = absent or any amino acid
<220> FEATURE:
```

```
<221> NAME/KEY: MISC_FEATURE
<222> LOCATION: (68)..(68)
<223> OTHER INFORMATION: X = absent or any amino acid
<220> FEATURE:
<221> NAME/KEY: MISC_FEATURE
<222> LOCATION: (69)..(69)
<223> OTHER INFORMATION: X = absent or any amino acid
<220> FEATURE:
<221> NAME/KEY: MISC_FEATURE
<222> LOCATION: (71)..(71)
<223> OTHER INFORMATION: X = Ile or Leu
<220> FEATURE:
<221> NAME/KEY: MISC_FEATURE
<222> LOCATION: (72)..(72)
<223> OTHER INFORMATION: X = Thr or Val
<220> FEATURE:
<221> NAME/KEY: MISC_FEATURE
<222> LOCATION: (73)..(95)
<223> OTHER INFORMATION: X = any amino acid
<220> FEATURE:
<221> NAME/KEY: MISC_FEATURE
<222> LOCATION: (96)..(96)
<223> OTHER INFORMATION: X = absent or any amino acid
<220> FEATURE:
<221> NAME/KEY: MISC_FEATURE
<222> LOCATION: (97)..(97)
<223> OTHER INFORMATION: X = absent or any amino acid
<220> FEATURE:
<221> NAME/KEY: MISC_FEATURE
<222> LOCATION: (98)..(98)
<223> OTHER INFORMATION: X = absent or any amino acid
<220> FEATURE:
<221> NAME/KEY: MISC_FEATURE
<222> LOCATION: (99)..(99)
<223> OTHER INFORMATION: X = absent or any amino acid
<220> FEATURE:
<221> NAME/KEY: MISC_FEATURE
<222> LOCATION: (100)..(100)
<223> OTHER INFORMATION: X = absent or any amino acid
<220> FEATURE:
<221> NAME/KEY: MISC_FEATURE
<222> LOCATION: (102)..(103)
<223> OTHER INFORMATION: X = any amino acid

<400> SEQUENCE: 3

Cys Tyr Pro Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Thr Xaa Xaa
        35                  40                  45

Cys Xaa Xaa Xaa Xaa Xaa Xaa Xaa Xaa Xaa Xaa Xaa Xaa Xaa
    50                  55                  60

Xaa Xaa Xaa Xaa Xaa Trp Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Trp Xaa Xaa His His Pro
            100                 105

<210> SEQ ID NO 4
<211> LENGTH: 10
<212> TYPE: PRT
<213> ORGANISM: Artificial Sequence
<220> FEATURE:
<223> OTHER INFORMATION: HA Sequence Element 1

<400> SEQUENCE: 4

Gln Leu Ser Ser Ile Ser Ser Phe Glu Lys
 1               5                  10
```

```
<210> SEQ ID NO 5
<211> LENGTH: 106
<212> TYPE: PRT
<213> ORGANISM: Artificial Sequence
<220> FEATURE:
<223> OTHER INFORMATION: HA Sequence Element 1
<220> FEATURE:
<221> NAME/KEY: MISC_FEATURE
<222> LOCATION: (4)..(26)
<223> OTHER INFORMATION: X = any amino acid
<220> FEATURE:
<221> NAME/KEY: MISC_FEATURE
<222> LOCATION: (27)..(27)
<223> OTHER INFORMATION: X = absent or any amino acid
<220> FEATURE:
<221> NAME/KEY: MISC_FEATURE
<222> LOCATION: (28)..(28)
<223> OTHER INFORMATION: X = absent or any amino acid
<220> FEATURE:
<221> NAME/KEY: MISC_FEATURE
<222> LOCATION: (29)..(29)
<223> OTHER INFORMATION: X = absent or any amino acid
<220> FEATURE:
<221> NAME/KEY: MISC_FEATURE
<222> LOCATION: (30)..(30)
<223> OTHER INFORMATION: X = absent or any amino acid
<220> FEATURE:
<221> NAME/KEY: MISC_FEATURE
<222> LOCATION: (31)..(31)
<223> OTHER INFORMATION: X = absent or any amino acid
<220> FEATURE:
<221> NAME/KEY: MISC_FEATURE
<222> LOCATION: (32)..(32)
<223> OTHER INFORMATION: X = absent or any amino acid
<220> FEATURE:
<221> NAME/KEY: MISC_FEATURE
<222> LOCATION: (33)..(33)
<223> OTHER INFORMATION: X = absent or any amino acid
<220> FEATURE:
<221> NAME/KEY: MISC_FEATURE
<222> LOCATION: (34)..(34)
<223> OTHER INFORMATION: X = absent or any amino acid
<220> FEATURE:
<221> NAME/KEY: MISC_FEATURE
<222> LOCATION: (35)..(35)
<223> OTHER INFORMATION: X = absent or any amino acid
<220> FEATURE:
<221> NAME/KEY: MISC_FEATURE
<222> LOCATION: (36)..(36)
<223> OTHER INFORMATION: X = absent or any amino acid
<220> FEATURE:
<221> NAME/KEY: MISC_FEATURE
<222> LOCATION: (37)..(37)
<223> OTHER INFORMATION: X = absent or any amino acid
<220> FEATURE:
<221> NAME/KEY: MISC_FEATURE
<222> LOCATION: (38)..(38)
<223> OTHER INFORMATION: X = absent or any amino acid
<220> FEATURE:
<221> NAME/KEY: MISC_FEATURE
<222> LOCATION: (39)..(39)
<223> OTHER INFORMATION: X = absent or any amino acid
<220> FEATURE:
<221> NAME/KEY: MISC_FEATURE
<222> LOCATION: (40)..(40)
<223> OTHER INFORMATION: X = absent or any amino acid
<220> FEATURE:
<221> NAME/KEY: MISC_FEATURE
<222> LOCATION: (41)..(41)
<223> OTHER INFORMATION: X = absent or any amino acid
<220> FEATURE:
<221> NAME/KEY: MISC_FEATURE
<222> LOCATION: (42)..(42)
<223> OTHER INFORMATION: X = absent or any amino acid
<220> FEATURE:
<221> NAME/KEY: MISC_FEATURE
<222> LOCATION: (43)..(43)
```

```
<223> OTHER INFORMATION: X = absent or any amino acid
<220> FEATURE:
<221> NAME/KEY: MISC_FEATURE
<222> LOCATION: (44)..(44)
<223> OTHER INFORMATION: X = absent or any amino acid
<220> FEATURE:
<221> NAME/KEY: MISC_FEATURE
<222> LOCATION: (45)..(45)
<223> OTHER INFORMATION: X = absent or any amino acid
<220> FEATURE:
<221> NAME/KEY: MISC_FEATURE
<222> LOCATION: (47)..(47)
<223> OTHER INFORMATION: X = Ser or Asn
<220> FEATURE:
<221> NAME/KEY: MISC_FEATURE
<222> LOCATION: (48)..(48)
<223> OTHER INFORMATION: X = Ala or Ser
<220> FEATURE:
<221> NAME/KEY: MISC_FEATURE
<222> LOCATION: (50)..(54)
<223> OTHER INFORMATION: X = any amino acid
<220> FEATURE:
<221> NAME/KEY: MISC_FEATURE
<222> LOCATION: (55)..(55)
<223> OTHER INFORMATION: X = absent or any amino acid
<220> FEATURE:
<221> NAME/KEY: MISC_FEATURE
<222> LOCATION: (56)..(56)
<223> OTHER INFORMATION: X = absent or any amino acid
<220> FEATURE:
<221> NAME/KEY: MISC_FEATURE
<222> LOCATION: (57)..(57)
<223> OTHER INFORMATION: X = absent or any amino acid
<220> FEATURE:
<221> NAME/KEY: MISC_FEATURE
<222> LOCATION: (58)..(58)
<223> OTHER INFORMATION: X = absent or any amino acid
<220> FEATURE:
<221> NAME/KEY: MISC_FEATURE
<222> LOCATION: (59)..(59)
<223> OTHER INFORMATION: X = absent or any amino acid
<220> FEATURE:
<221> NAME/KEY: MISC_FEATURE
<222> LOCATION: (60)..(60)
<223> OTHER INFORMATION: X = absent or any amino acid
<220> FEATURE:
<221> NAME/KEY: MISC_FEATURE
<222> LOCATION: (61)..(61)
<223> OTHER INFORMATION: X = absent or any amino acid
<220> FEATURE:
<221> NAME/KEY: MISC_FEATURE
<222> LOCATION: (62)..(62)
<223> OTHER INFORMATION: X = absent or any amino acid
<220> FEATURE:
<221> NAME/KEY: MISC_FEATURE
<222> LOCATION: (63)..(63)
<223> OTHER INFORMATION: X = absent or any amino acid
<220> FEATURE:
<221> NAME/KEY: MISC_FEATURE
<222> LOCATION: (64)..(64)
<223> OTHER INFORMATION: X = absent or any amino acid
<220> FEATURE:
<221> NAME/KEY: MISC_FEATURE
<222> LOCATION: (65)..(65)
<223> OTHER INFORMATION: X = absent or any amino acid
<220> FEATURE:
<221> NAME/KEY: MISC_FEATURE
<222> LOCATION: (66)..(66)
<223> OTHER INFORMATION: X = absent or any amino acid
<220> FEATURE:
<221> NAME/KEY: MISC_FEATURE
<222> LOCATION: (67)..(67)
<223> OTHER INFORMATION: X = absent or any amino acid
<220> FEATURE:
<221> NAME/KEY: MISC_FEATURE
<222> LOCATION: (68)..(68)
<223> OTHER INFORMATION: X = absent or any amino acid
<220> FEATURE:
<221> NAME/KEY: MISC_FEATURE
```

-continued

<222> LOCATION: (69)..(69)
<223> OTHER INFORMATION: X = absent or any amino acid
<220> FEATURE:
<221> NAME/KEY: MISC_FEATURE
<222> LOCATION: (71)..(95)
<223> OTHER INFORMATION: X = any amino acid
<220> FEATURE:
<221> NAME/KEY: MISC_FEATURE
<222> LOCATION: (96)..(96)
<223> OTHER INFORMATION: X = absent or any amino acid
<220> FEATURE:
<221> NAME/KEY: MISC_FEATURE
<222> LOCATION: (97)..(97)
<223> OTHER INFORMATION: X = absent or any amino acid
<220> FEATURE:
<221> NAME/KEY: MISC_FEATURE
<222> LOCATION: (98)..(98)
<223> OTHER INFORMATION: X = absent or any amino acid
<220> FEATURE:
<221> NAME/KEY: MISC_FEATURE
<222> LOCATION: (99)..(99)
<223> OTHER INFORMATION: X = absent or any amino acid
<220> FEATURE:
<221> NAME/KEY: MISC_FEATURE
<222> LOCATION: (100)..(100)
<223> OTHER INFORMATION: X = absent or any amino acid
<220> FEATURE:
<221> NAME/KEY: MISC_FEATURE
<222> LOCATION: (102)..(103)
<223> OTHER INFORMATION: X = any amino acid

<400> SEQUENCE: 5

```
Cys Tyr Pro Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Ser Xaa Xaa
        35                  40                  45

Cys Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Trp Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Trp Xaa Xaa His His Pro
            100                 105
```

<210> SEQ ID NO 6
<211> LENGTH: 106
<212> TYPE: PRT
<213> ORGANISM: Artificial Sequence
<220> FEATURE:
<223> OTHER INFORMATION: HA Sequence Element 1
<220> FEATURE:
<221> NAME/KEY: MISC_FEATURE
<222> LOCATION: (4)..(30)
<223> OTHER INFORMATION: X = any amino acid
<220> FEATURE:
<221> NAME/KEY: MISC_FEATURE
<222> LOCATION: (31)..(31)
<223> OTHER INFORMATION: X = absent or any amino acid
<220> FEATURE:
<221> NAME/KEY: MISC_FEATURE
<222> LOCATION: (32)..(32)
<223> OTHER INFORMATION: X = absent or any amino acid
<220> FEATURE:
<221> NAME/KEY: MISC_FEATURE
<222> LOCATION: (33)..(33)
<223> OTHER INFORMATION: X = absent or any amino acid
<220> FEATURE:
<221> NAME/KEY: MISC_FEATURE

```
<222> LOCATION: (34)..(34)
<223> OTHER INFORMATION: X = absent or any amino acid
<220> FEATURE:
<221> NAME/KEY: MISC_FEATURE
<222> LOCATION: (35)..(35)
<223> OTHER INFORMATION: X = absent or any amino acid
<220> FEATURE:
<221> NAME/KEY: MISC_FEATURE
<222> LOCATION: (36)..(36)
<223> OTHER INFORMATION: X = absent or any amino acid
<220> FEATURE:
<221> NAME/KEY: MISC_FEATURE
<222> LOCATION: (37)..(37)
<223> OTHER INFORMATION: X = absent or any amino acid
<220> FEATURE:
<221> NAME/KEY: MISC_FEATURE
<222> LOCATION: (38)..(38)
<223> OTHER INFORMATION: X = absent or any amino acid
<220> FEATURE:
<221> NAME/KEY: MISC_FEATURE
<222> LOCATION: (39)..(39)
<223> OTHER INFORMATION: X = absent or any amino acid
<220> FEATURE:
<221> NAME/KEY: MISC_FEATURE
<222> LOCATION: (40)..(40)
<223> OTHER INFORMATION: X = absent or any amino acid
<220> FEATURE:
<221> NAME/KEY: MISC_FEATURE
<222> LOCATION: (41)..(41)
<223> OTHER INFORMATION: X = absent or any amino acid
<220> FEATURE:
<221> NAME/KEY: MISC_FEATURE
<222> LOCATION: (42)..(42)
<223> OTHER INFORMATION: X = absent or any amino acid
<220> FEATURE:
<221> NAME/KEY: MISC_FEATURE
<222> LOCATION: (43)..(43)
<223> OTHER INFORMATION: X = absent or any amino acid
<220> FEATURE:
<221> NAME/KEY: MISC_FEATURE
<222> LOCATION: (44)..(44)
<223> OTHER INFORMATION: X = absent or any amino acid
<220> FEATURE:
<221> NAME/KEY: MISC_FEATURE
<222> LOCATION: (45)..(45)
<223> OTHER INFORMATION: X = absent or any amino acid
<220> FEATURE:
<221> NAME/KEY: MISC_FEATURE
<222> LOCATION: (47)..(47)
<223> OTHER INFORMATION: X = Ser or Asn
<220> FEATURE:
<221> NAME/KEY: MISC_FEATURE
<222> LOCATION: (48)..(48)
<223> OTHER INFORMATION: X = Ala or Ser
<220> FEATURE:
<221> NAME/KEY: MISC_FEATURE
<222> LOCATION: (50)..(54)
<223> OTHER INFORMATION: X = any amino acid
<220> FEATURE:
<221> NAME/KEY: MISC_FEATURE
<222> LOCATION: (55)..(55)
<223> OTHER INFORMATION: X = absent or any amino acid
<220> FEATURE:
<221> NAME/KEY: MISC_FEATURE
<222> LOCATION: (56)..(56)
<223> OTHER INFORMATION: X = absent or any amino acid
<220> FEATURE:
<221> NAME/KEY: MISC_FEATURE
<222> LOCATION: (57)..(57)
<223> OTHER INFORMATION: X = absent or any amino acid
<220> FEATURE:
<221> NAME/KEY: MISC_FEATURE
<222> LOCATION: (58)..(58)
<223> OTHER INFORMATION: X = absent or any amino acid
<220> FEATURE:
<221> NAME/KEY: MISC_FEATURE
<222> LOCATION: (59)..(59)
<223> OTHER INFORMATION: X = absent or any amino acid
<220> FEATURE:
```

```
<221> NAME/KEY: MISC_FEATURE
<222> LOCATION: (60)..(60)
<223> OTHER INFORMATION: X = absent or any amino acid
<220> FEATURE:
<221> NAME/KEY: MISC_FEATURE
<222> LOCATION: (61)..(61)
<223> OTHER INFORMATION: X = absent or any amino acid
<220> FEATURE:
<221> NAME/KEY: MISC_FEATURE
<222> LOCATION: (62)..(62)
<223> OTHER INFORMATION: X = absent or any amino acid
<220> FEATURE:
<221> NAME/KEY: MISC_FEATURE
<222> LOCATION: (63)..(63)
<223> OTHER INFORMATION: X = absent or any amino acid
<220> FEATURE:
<221> NAME/KEY: MISC_FEATURE
<222> LOCATION: (64)..(64)
<223> OTHER INFORMATION: X = absent or any amino acid
<220> FEATURE:
<221> NAME/KEY: MISC_FEATURE
<222> LOCATION: (65)..(65)
<223> OTHER INFORMATION: X = absent or any amino acid
<220> FEATURE:
<221> NAME/KEY: MISC_FEATURE
<222> LOCATION: (66)..(66)
<223> OTHER INFORMATION: X = absent or any amino acid
<220> FEATURE:
<221> NAME/KEY: MISC_FEATURE
<222> LOCATION: (67)..(67)
<223> OTHER INFORMATION: X = absent or any amino acid
<220> FEATURE:
<221> NAME/KEY: MISC_FEATURE
<222> LOCATION: (68)..(68)
<223> OTHER INFORMATION: X = absent or any amino acid
<220> FEATURE:
<221> NAME/KEY: MISC_FEATURE
<222> LOCATION: (69)..(69)
<223> OTHER INFORMATION: X = absent or any amino acid
<220> FEATURE:
<221> NAME/KEY: MISC_FEATURE
<222> LOCATION: (72)..(72)
<223> OTHER INFORMATION: X = Thr or His
<220> FEATURE:
<221> NAME/KEY: MISC_FEATURE
<222> LOCATION: (73)..(95)
<223> OTHER INFORMATION: X = any amino acid
<220> FEATURE:
<221> NAME/KEY: MISC_FEATURE
<222> LOCATION: (96)..(96)
<223> OTHER INFORMATION: X = absent or any amino acid
<220> FEATURE:
<221> NAME/KEY: MISC_FEATURE
<222> LOCATION: (97)..(97)
<223> OTHER INFORMATION: X = absent or any amino acid
<220> FEATURE:
<221> NAME/KEY: MISC_FEATURE
<222> LOCATION: (98)..(98)
<223> OTHER INFORMATION: X = absent or any amino acid
<220> FEATURE:
<221> NAME/KEY: MISC_FEATURE
<222> LOCATION: (99)..(99)
<223> OTHER INFORMATION: X = absent or any amino acid
<220> FEATURE:
<221> NAME/KEY: MISC_FEATURE
<222> LOCATION: (100)..(100)
<223> OTHER INFORMATION: X = absent or any amino acid
<220> FEATURE:
<221> NAME/KEY: MISC_FEATURE
<222> LOCATION: (102)..(103)
<223> OTHER INFORMATION: X = any amino acid

<400> SEQUENCE: 6

Cys Tyr Pro Xaa Xaa Xaa Xaa Xaa Xaa Xaa Xaa Xa

```
Xaa Xaa Xaa Xaa Xaa Xaa Xaa Xaa Xaa Xaa Xaa Xaa Ser Xaa Xaa
            35                  40                  45

Cys Xaa Xaa Xaa Xaa Xaa Xaa Xaa Xaa Xaa Xaa Xaa Xaa Xaa Xaa
 50                  55                  60

Xaa Xaa Xaa Xaa Xaa Trp Leu Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
                 85                  90                  95

Xaa Xaa Xaa Xaa Trp Xaa Xaa His His Pro
            100                 105

<210> SEQ ID NO 7
<211> LENGTH: 10
<212> TYPE: PRT
<213> ORGANISM: Artificial Sequence
<220> FEATURE:
<223> OTHER INFORMATION: HA Sequence Element 1
<220> FEATURE:
<221> NAME/KEY: MISC_FEATURE
<222> LOCATION: (1)..(1)
<223> OTHER INFORMATION: X= Leu or Ile
<220> FEATURE:

```
<223> OTHER INFORMATION: X = absent or any amino acid
<220> FEATURE:
<221> NAME/KEY: MISC_FEATURE
<222> LOCATION: (35)..(35)
<223> OTHER INFORMATION: X = absent or any amino acid
<220> FEATURE:
<221> NAME/KEY: MISC_FEATURE
<222> LOCATION: (36)..(36)
<223> OTHER INFORMATION: X = absent or any amino acid
<220> FEATURE:
<221> NAME/KEY: MISC_FEATURE
<222> LOCATION: (37)..(37)
<223> OTHER INFORMATION: X = absent or any amino acid
<220> FEATURE:
<221> NAME/KEY: MISC_FEATURE
<222> LOCATION: (38)..(38)
<223> OTHER INFORMATION: X = absent or any amino acid
<220> FEATURE:
<221> NAME/KEY: MISC_FEATURE
<222> LOCATION: (39)..(39)
<223> OTHER INFORMATION: X = absent or any amino acid
<220> FEATURE:
<221> NAME/KEY: MISC_FEATURE
<222> LOCATION: (40)..(40)
<223> OTHER INFORMATION: X = absent or any amino acid
<220> FEATURE:
<221> NAME/KEY: MISC_FEATURE
<222> LOCATION: (41)..(41)
<223> OTHER INFORMATION: X = absent or any amino acid
<220> FEATURE:
<221> NAME/KEY: MISC_FEATURE
<222> LOCATION: (42)..(42)
<223> OTHER INFORMATION: X = absent or any amino acid
<220> FEATURE:
<221> NAME/KEY: MISC_FEATURE
<222> LOCATION: (43)..(43)
<223> OTHER INFORMATION: X = absent or any amino acid
<220> FEATURE:
<221> NAME/KEY: MISC_FEATURE
<222> LOCATION: (44)..(44)
<223> OTHER INFORMATION: X = absent or any amino acid
<220> FEATURE:
<221> NAME/KEY: MISC_FEATURE
<222> LOCATION: (45)..(45)
<223> OTHER INFORMATION: X = absent or any amino acid
<220> FEATURE:
<221> NAME/KEY: MISC_FEATURE
<222> LOCATION: (50)..(54)
<223> OTHER INFORMATION: X = any amino acid
<220> FEATURE:
<221> NAME/KEY: MISC_FEATURE
<222> LOCATION: (55)..(55)
<223> OTHER INFORMATION: X = absent or any amino acid
<220> FEATURE:
<221> NAME/KEY: MISC_FEATURE
<222> LOCATION: (56)..(56)
<223> OTHER INFORMATION: X = absent or any amino acid
<220> FEATURE:
<221> NAME/KEY: MISC_FEATURE
<222> LOCATION: (57)..(57)
<223> OTHER INFORMATION: X = absent or any amino acid
<220> FEATURE:
<221> NAME/KEY: MISC_FEATURE
<222> LOCATION: (58)..(58)
<223> OTHER INFORMATION: X = absent or any amino acid
<220> FEATURE:
<221> NAME/KEY: MISC_FEATURE
<222> LOCATION: (59)..(59)
<223> OTHER INFORMATION: X = absent or any amino acid
<220> FEATURE:
<221> NAME/KEY: MISC_FEATURE
<222> LOCATION: (60)..(60)
<223> OTHER INFORMATION: X = absent or any amino acid
<220> FEATURE:
<221> NAME/KEY: MISC_FEATURE
<222> LOCATION: (61)..(61)
<223> OTHER INFORMATION: X = absent or any amino acid
<220> FEATURE:
<221> NAME/KEY: MISC_FEATURE
```

```
<222> LOCATION: (62)..(62)
<223> OTHER INFORMATION: X = absent or any amino acid
<220> FEATURE:
<221> NAME/KEY: MISC_FEATURE
<222> LOCATION: (63)..(63)
<223> OTHER INFORMATION: X = absent or any amino acid
<220> FEATURE:
<221> NAME/KEY: MISC_FEATURE
<222> LOCATION: (64)..(64)
<223> OTHER INFORMATION: X = absent or any amino acid
<220> FEATURE:
<221> NAME/KEY: MISC_FEATURE
<222> LOCATION: (65)..(65)
<223> OTHER INFORMATION: X = absent or any amino acid
<220> FEATURE:
<221> NAME/KEY: MISC_FEATURE
<222> LOCATION: (66)..(66)
<223> OTHER INFORMATION: X = absent or any amino acid
<220> FEATURE:
<221> NAME/KEY: MISC_FEATURE
<222> LOCATION: (67)..(67)
<223> OTHER INFORMATION: X = absent or any amino acid
<220> FEATURE:
<221> NAME/KEY: MISC_FEATURE
<222> LOCATION: (68)..(68)
<223> OTHER INFORMATION: X = absent or any amino acid
<220> FEATURE:
<221> NAME/KEY: MISC_FEATURE
<222> LOCATION: (69)..(69)
<223> OTHER INFORMATION: X = absent or any amino acid
<220> FEATURE:
<221> NAME/KEY: MISC_FEATURE
<222> LOCATION: (71)..(95)
<223> OTHER INFORMATION: X = any amino acid
<220> FEATURE:
<221> NAME/KEY: MISC_FEATURE
<222> LOCATION: (96)..(96)
<223> OTHER INFORMATION: X = absent or any amino acid
<220> FEATURE:
<221> NAME/KEY: MISC_FEATURE
<222> LOCATION: (97)..(97)
<223> OTHER INFORMATION: X = absent or any amino acid
<220> FEATURE:
<221> NAME/KEY: MISC_FEATURE
<222> LOCATION: (98)..(98)
<223> OTHER INFORMATION: X = absent or any amino acid
<220> FEATURE:
<221> NAME/KEY: MISC_FEATURE
<222> LOCATION: (99)..(99)
<223> OTHER INFORMATION: X = absent or any amino acid
<220> FEATURE:
<221> NAME/KEY: MISC_FEATURE
<222> LOCATION: (100)..(100)
<223> OTHER INFORMATION: X = absent or any amino acid
<220> FEATURE:
<221> NAME/KEY: MISC_FEATURE
<222> LOCATION: (102)..(103)
<223> OTHER INFORMATION: X = any amino acid

<400> SEQUENCE: 8

Cys Tyr Pro Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Ser Ser Ala
            35                  40                  45

Cys Xaa Xaa Xaa Xaa Xaa Xaa Xaa Xaa Xaa Xaa Xaa Xaa Xaa Xaa
    50                  55                  60

Xaa Xaa Xaa Xaa Xaa Trp Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95
```

Xaa Xaa Xaa Xaa Trp Xaa Xaa His His Pro
            100             105

```
<210> SEQ ID NO 9
<211> LENGTH: 106
<212> TYPE: PRT
<213> ORGANISM: Artificial Sequence
<220> FEATURE:
<223> OTHER INFORMATION: HA Sequence Element 1
<220> FEATURE:
<221> NAME/KEY: MISC_FEATURE
<222> LOCATION: (4)..(30)
<223> OTHER INFORMATION: X = any amino acid
<220> FEATURE:
<221> NAME/KEY: MISC_FEATURE
<222> LOCATION: (31)..(31)
<223> OTHER INFORMATION: X = absent or any amino acid
<220> FEATURE:
<221> NAME/KEY: MISC_FEATURE
<222> LOCATION: (32)..(32)
<223> OTHER INFORMATION: X = absent or any amino acid
<220> FEATURE:
<221> NAME/KEY: MISC_FEATURE
<222> LOCATION: (33)..(33)
<223> OTHER INFORMATION: X = absent or any amino acid
<220> FEATURE:
<221> NAME/KEY: MISC_FEATURE
<222> LOCATION: (34)..(34)
<223> OTHER INFORMATION: X = absent or any amino acid
<220> FEATURE:
<221> NAME/KEY: MISC_FEATURE
<222> LOCATION: (35)..(35)
<223> OTHER INFORMATION: X = absent or any amino acid
<220> FEATURE:
<221> NAME/KEY: MISC_FEATURE
<222> LOCATION: (36)..(36)
<223> OTHER INFORMATION: X = absent or any amino acid
<220> FEATURE:
<221> NAME/KEY: MISC_FEATURE
<222> LOCATION: (37)..(37)
<223> OTHER INFORMATION: X = absent or any amino acid
<220> FEATURE:
<221> NAME/KEY: MISC_FEATURE
<222> LOCATION: (38)..(38)
<223> OTHER INFORMATION: X = absent or any amino acid
<220> FEATURE:
<221> NAME/KEY: MISC_FEATURE
<222> LOCATION: (39)..(39)
<223> OTHER INFORMATION: X = absent or any amino acid
<220> FEATURE:
<221> NAME/KEY: MISC_FEATURE
<222> LOCATION: (40)..(40)
<223> OTHER INFORMATION: X = absent or any amino acid
<220> FEATURE:
<221> NAME/KEY: MISC_FEATURE
<222> LOCATION: (41)..(41)
<223> OTHER INFORMATION: X = absent or any amino acid
<220> FEATURE:
<221> NAME/KEY: MISC_FEATURE
<222> LOCATION: (42)..(42)
<223> OTHER INFORMATION: X = absent or any amino acid
<220> FEATURE:
<221> NAME/KEY: MISC_FEATURE
<222> LOCATION: (43)..(43)
<223> OTHER INFORMATION: X = absent or any amino acid
<220> FEATURE:
<221> NAME/KEY: MISC_FEATURE
<222> LOCATION: (44)..(44)
<223> OTHER INFORMATION: X = absent or any amino acid
<220> FEATURE:
<221> NAME/KEY: MISC_FEATURE
<222> LOCATION: (45)..(45)
<223> OTHER INFORMATION: X = absent or any amino acid
<220> FEATURE:
<221> NAME/KEY: MISC_FEATURE
<222> LOCATION: (50)..(54)
<223> OTHER INFORMATION: X = any amino acid
<220> FEATURE:
```

```
<221> NAME/KEY: MISC_FEATURE
<222> LOCATION: (55)..(55)
<223> OTHER INFORMATION: X = absent or any amino acid
<220> FEATURE:
<221> NAME/KEY: MISC_FEATURE
<222> LOCATION: (56)..(56)
<223> OTHER INFORMATION: X = absent or any amino acid
<220> FEATURE:
<221> NAME/KEY: MISC_FEATURE
<222> LOCATION: (57)..(57)
<223> OTHER INFORMATION: X = absent or any amino acid
<220> FEATURE:
<221> NAME/KEY: MISC_FEATURE
<222> LOCATION: (58)..(58)
<223> OTHER INFORMATION: X = absent or any amino acid
<220> FEATURE:
<221> NAME/KEY: MISC_FEATURE
<222> LOCATION: (59)..(59)
<223> OTHER INFORMATION: X = absent or any amino acid
<220> FEATURE:
<221> NAME/KEY: MISC_FEATURE
<222> LOCATION: (60)..(60)
<223> OTHER INFORMATION: X = absent or any amino acid
<220> FEATURE:
<221> NAME/KEY: MISC_FEATURE
<222> LOCATION: (61)..(61)
<223> OTHER INFORMATION: X = absent or any amino acid
<220> FEATURE:
<221> NAME/KEY: MISC_FEATURE
<222> LOCATION: (62)..(62)
<223> OTHER INFORMATION: X = absent or any amino acid
<220> FEATURE:
<221> NAME/KEY: MISC_FEATURE
<222> LOCATION: (63)..(63)
<223> OTHER INFORMATION: X = absent or any amino acid
<220> FEATURE:
<221> NAME/KEY: MISC_FEATURE
<222> LOCATION: (64)..(64)
<223> OTHER INFORMATION: X = absent or any amino acid
<220> FEATURE:
<221> NAME/KEY: MISC_FEATURE
<222> LOCATION: (65)..(65)
<223> OTHER INFORMATION: X = absent or any amino acid
<220> FEATURE:
<221> NAME/KEY: MISC_FEATURE
<222> LOCATION: (66)..(66)
<223> OTHER INFORMATION: X = absent or any amino acid
<220> FEATURE:
<221> NAME/KEY: MISC_FEATURE
<222> LOCATION: (67)..(67)
<223> OTHER INFORMATION: X = absent or any amino acid
<220> FEATURE:
<221> NAME/KEY: MISC_FEATURE
<222> LOCATION: (68)..(68)
<223> OTHER INFORMATION: X = absent or any amino acid
<220> FEATURE:
<221> NAME/KEY: MISC_FEATURE
<222> LOCATION: (69)..(69)
<223> OTHER INFORMATION: X = absent or any amino acid
<220> FEATURE:
<221> NAME/KEY: MISC_FEATURE
<222> LOCATION: (73)..(95)
<223> OTHER INFORMATION: X = any amino acid
<220> FEATURE:
<221> NAME/KEY: MISC_FEATURE
<222> LOCATION: (96)..(96)
<223> OTHER INFORMATION: X = absent or any amino acid
<220> FEATURE:
<221> NAME/KEY: MISC_FEATURE
<222> LOCATION: (97)..(97)
<223> OTHER INFORMATION: X = absent or any amino acid
<220> FEATURE:
<221> NAME/KEY: MISC_FEATURE
<222> LOCATION: (98)..(98)
<223> OTHER INFORMATION: X = absent or any amino acid
<220> FEATURE:
<221> NAME/KEY: MISC_FEATURE
<222> LOCATION: (99)..(99)
<223> OTHER INFORMATION: X = absent or any amino acid
```

```
<220> FEATURE:
<221> NAME/KEY: MISC_FEATURE
<222> LOCATION: (100)..(100)
<223> OTHER INFORMATION: X = absent or any amino acid
<220> FEATURE:
<221> NAME/KEY: MISC_FEATURE
<222> LOCATION: (102)..(103)
<223> OTHER INFORMATION: X = any amino acid

<400> SEQUENCE: 9

Cys Tyr Pro Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Ser Ser Ala
        35                  40                  45

Cys Xaa Xaa Xaa Xaa Xaa Xaa Xaa Xaa Xaa Xaa Xaa Xaa Xaa
        50                  55                  60

Xaa Xaa Xaa Xaa Xaa Trp Leu Ile Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Trp Xaa Xaa His His Pro
            100                 105

<210> SEQ ID NO 10
<211> LENGTH: 8
<212> TYPE: PRT
<213> ORGANISM: Artificial Sequence
<220> FEATURE:
<223> OTHER INFORMATION: HA Sequence Element 1
<220> FEATURE:
<221> NAME/KEY: MISC_FEATURE
<222> LOCATION: (6)..(7)
<223> OTHER INFORMATION: X= any naturally occuring amino acid
<220> FEATURE:
<221> NAME/KEY: MISC_FEATURE
<222> LOCATION: (8)..(8)
<223> OTHER INFORMATION: X= Lys or Arg

<400> SEQUENCE: 10

Asn Asp Ala Ala Glu Xaa Xaa Xaa
1               5

<210> SEQ ID NO 11
<211> LENGTH: 16
<212> TYPE: PRT
<213> ORGANISM: Artificial Sequence
<220> FEATURE:
<223> OTHER INFORMATION: HA Sequence Element 1
<220> FEATURE:
<221> NAME/KEY: MISC_FEATURE
<222> LOCATION: (8)..(8)
<223> OTHER INFORMATION: X= any naturally occuring amino acid
<220> FEATURE:
<221> NAME/KEY: MISC_FEATURE
<222> LOCATION: (10)..(11)
<223> OTHER INFORMATION: X= any naturally occuring amino acid

<400> SEQUENCE: 11

Tyr Glu Glu Leu Lys His Leu Xaa Ser Xaa Xaa Asn His Phe Glu Lys
1               5                   10                  15

<210> SEQ ID NO 12
<211> LENGTH: 8
<212> TYPE: PRT
<213> ORGANISM: Artificial Sequence
```

<220> FEATURE:
<223> OTHER INFORMATION: HA Sequence Element 2

<400> SEQUENCE: 12

Gly Ala Ile Ala Gly Phe Ile Glu
1 5

<210> SEQ ID NO 13
<211> LENGTH: 23
<212> TYPE: PRT
<213> ORGANISM: Artificial Sequence
<220> FEATURE:
<223> OTHER INFORMATION: HA Sequence Element 2
<220> FEATURE:
<221> NAME/KEY: MISC_FEATURE
<222> LOCATION: (2)..(5)
<223> OTHER INFORMATION: X = any amino acid
<220> FEATURE:
<221> NAME/KEY: MISC_FEATURE
<222> LOCATION: (6)..(6)
<223> OTHER INFORMATION: X = absent or any amino acid
<220> FEATURE:
<221> NAME/KEY: MISC_FEATURE
<222> LOCATION: (7)..(7)
<223> OTHER INFORMATION: X = absent or any amino acid
<220> FEATURE:
<221> NAME/KEY: MISC_FEATURE
<222> LOCATION: (8)..(8)
<223> OTHER INFORMATION: X = absent or any amino acid
<220> FEATURE:
<221> NAME/KEY: MISC_FEATURE
<222> LOCATION: (9)..(9)
<223> OTHER INFORMATION: X = absent or any amino acid
<220> FEATURE:
<221> NAME/KEY: MISC_FEATURE
<222> LOCATION: (10)..(10)
<223> OTHER INFORMATION: X = absent or any amino acid
<220> FEATURE:
<221> NAME/KEY: MISC_FEATURE
<222> LOCATION: (11)..(11)
<223> OTHER INFORMATION: X = absent or any amino acid
<220> FEATURE:
<221> NAME/KEY: MISC_FEATURE
<222> LOCATION: (12)..(12)
<223> OTHER INFORMATION: X = absent or any amino acid
<220> FEATURE:
<221> NAME/KEY: MISC_FEATURE
<222> LOCATION: (13)..(13)
<223> OTHER INFORMATION: X = absent or any amino acid
<220> FEATURE:
<221> NAME/KEY: MISC_FEATURE
<222> LOCATION: (14)..(14)
<223> OTHER INFORMATION: X = absent or any amino acid
<220> FEATURE:
<221> NAME/KEY: MISC_FEATURE
<222> LOCATION: (15)..(15)
<223> OTHER INFORMATION: X = absent or any amino acid

<400> SEQUENCE: 13

Pro Xaa Xaa Xaa Xaa Xaa Xaa Xaa Xaa Xaa Xaa Xaa Xaa Xaa Xaa Gly
1 5 10 15

Ala Ile Ala Gly Phe Ile Glu
20

<210> SEQ ID NO 14
<211> LENGTH: 17
<212> TYPE: PRT
<213> ORGANISM: Artificial Sequence
<220> FEATURE:
<223> OTHER INFORMATION: HA Sequence Element 2
<220> FEATURE:
<221> NAME/KEY: MISC_FEATURE
<222> LOCATION: (3)..(3)
<223> OTHER INFORMATION: X= Ile or Val
<220> FEATURE:
<221> NAME/KEY: MISC_FEATURE
<222> LOCATION: (7)..(9)
<223> OTHER INFORMATION: X = any amino acid

<400> SEQUENCE: 14

Pro Ser Xaa Gln Ser Arg Xaa Xaa Xaa Gly Ala Ile Ala Gly Phe Ile
1 5 10 15

Glu

<210> SEQ ID NO 15
<211> LENGTH: 17
<212> TYPE: PRT
<213> ORGANISM: Artificial Sequence
<220> FEATURE:
<223> OTHER INFORMATION: HA Sequence Element 2
<220> FEATURE:
<221> NAME/KEY: MISC_FEATURE
<222> LOCATION: (2)..(2)
<223> OTHER INFORMATION: X= any amino acid
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (7)..(9)
<223> OTHER INFORMATION: X = any amino acid

<400> SEQUENCE: 15

Pro Xaa Lys Xaa Thr Arg Xaa Xaa Xaa Gly Ala Ile Ala Gly Phe Ile
1 5 10 15

Glu

<210> SEQ ID NO 16
<211> LENGTH: 21
<212> TYPE: PRT
<213> ORGANISM: Artificial Sequence
<220> FEATURE:
<223> OTHER INFORMATION: HA Sequence Element 2
<220> FEATURE:
<221> NAME/KEY: MISC_FEATURE
<222> LOCATION: (4)..(6)
<223> OTHER INFORMATION: X = any amino acid
<220> FEATURE:
<221> NAME/KEY: MISC_FEATURE
<222> LOCATION: (8)..(9)
<223> OTHER INFORMATION: X = any amino acid
<220> FEATURE:
<221> NAME/KEY: MISC_FEATURE
<222> LOCATION: (11)..(13)
<223> OTHER INFORMATION: X = any amino acid

<400> SEQUENCE: 16

Pro Gln Arg Xaa Xaa Xaa Arg Xaa Xaa Arg Xaa Xaa Xaa Gly Ala Ile
1 5 10 15

Ala Gly Phe Ile Glu
20

<210> SEQ ID NO 17
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 17

Met Asn Thr Gln Ile Leu Val Phe Ala Leu Ile Ala Ile Ile Pro Thr
1 5 10 15

```
Asn Ala Asp Lys Ile Cys Leu Gly His His Ala Val Ser Asn Gly Thr
             20                  25                  30

Lys Val Asn Thr Leu Thr Glu Arg Gly Val Glu Val Asn Ala Thr
         35                  40                  45

Glu Thr Val Glu Arg Thr Asn Ile Pro Arg Ile Cys Ser Lys Gly Lys
 50                  55                  60

Arg Thr Val Asp Leu Gly Gln Cys Gly Leu Leu Gly Thr Ile Thr Gly
 65                  70                  75                  80

Pro Pro Gln Cys Asp Gln Phe Leu Glu Phe Ser Ala Asp Leu Ile Ile
                 85                  90                  95

Glu Arg Arg Glu Gly Ser Asp Val Cys Tyr Pro Gly Lys Phe Val Asn
                100                 105                 110

Glu Glu Ala Leu Arg Gln Ile Leu Arg Glu Ser Gly Gly Ile Asp Lys
            115                 120                 125

Glu Ala Met Gly Phe Thr Tyr Ser Gly Ile Arg Thr Asn Gly Ala Thr
130                 135                 140

Ser Ser Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asn Pro Ala Leu Ile Val Trp Gly Ile His
                180                 185                 190

His Ser Gly Ser Thr Ala Glu Gln Thr Lys Leu Tyr Gly Ser Gly Asn
            195                 200                 205

Lys Leu Val Thr Val Gly Ser Ser Asn Tyr Gln Gln Ser Phe Val Pro
210                 215                 220

Ser Pro Gly Ala Arg Thr Gln Val Asn Gly Gln Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
                260                 265                 270

Ser Met Gly Ile Gln Ser Gly Val Gln Val Asp Ala Asp Cys Glu Gly
            275                 280                 285

Asp Cys Tyr Tyr Ser Gly Gly Thr Ile Ile Ser Asn Leu Pro Phe Gln
290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
                355                 360                 365

Gln Gly Glu Gly Thr Ala Ala Asp Tyr Lys Ser Thr Gln Ser Ala Ile
            370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Thr Glu Val Glu Lys Gln Ile
                405                 410                 415

Gly Asn Val Ile Asn Trp Thr Arg Asp Ser Ile Thr Glu Val Trp Ser
                420                 425                 430
```

```
Tyr Asn Ala Glu Leu Leu Val Ala Met Glu Asn Gln His Thr Ile Asp
            435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
                500                 505                 510

Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Ala Met Gly Leu
530                 535                 540

Val Phe Ile Cys Val Lys Asn Gly Asn Met Arg Cys Thr Ile Cys Ile
545                 550                 555                 560
```

<210> SEQ ID NO 18
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 18

```
Met Asn Thr Gln Ile Leu Val Phe Ala Le

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Val Met Gly Leu
    530                 535                 540

Val Phe Ile Cys Val Lys Asn Gly Asn Met Arg Cys Thr Ile Cys Ile
545                 550                 555                 560

<210> SEQ ID NO 19
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 19

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

```
Glu Thr Val Glu Arg Thr Asn Ile Pro Arg Ile Cys Ser Lys Gly Lys
 50                  55                  60

Arg Thr Val Asp Leu Gly Gln Cys Gly Leu Leu Gly Thr Ile Thr Gly
 65                  70                  75                  80

Pro Pro Gln Cys Asp Gln Phe Leu Glu Phe Ser Ala Asp Leu Ile Ile
                     85                  90                  95

Glu Arg Arg Glu Gly Ser Asp Val Cys Tyr Pro Gly Lys Phe Val Asn
                 100                 105                 110

Glu Glu Ala Leu Arg Gln Ile Leu Arg Glu Ser Gly Gly Ile Asp Lys
                 115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                 165                 170                 175

Tyr Lys Asn Thr Arg Lys Ser Pro Ala Leu Ile Val Trp Gly Ile His
                 180                 185                 190

His Ser Val Ser Thr Ala Glu Gln Thr Lys Leu Tyr Gly Ser Gly Asn
                 195                 200                 205

Lys Leu Val Thr Val Gly Ser Ser Asn Tyr Gln Gln Ser Phe Val Pro
210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                 245                 250                 255

Asn Gly Ala Phe Ile Ala Pro Asp Arg Ala Ser Phe Leu Arg Gly Lys
                 260                 265                 270

Ser Met Gly Ile Gln Ser Gly Val Gln Val Asp Ala Asn Cys Glu Gly
                 275                 280                 285

Asp Cys Tyr His Ser Gly Gly Thr Ile Ile Ser Asn Leu Pro Phe Gln
                 290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                 325                 330                 335

Lys Gly Arg Gly Leu Phe Gly Ala Ile Ala Gly Phe Ile Glu Asn Gly
                 340                 345                 350

Trp Glu Gly Leu Ile Asp Gly Trp Tyr Gly Phe Arg His Gln Asn Ala
                 355                 360                 365

Gln Gly Glu Gly Thr Ala Ala Asp Tyr Lys Ser Thr Gln Ser Ala Ile
370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                 405                 410                 415

Gly Asn Val Ile Asn Trp Thr Arg Asp Ser Ile Thr Glu Val Trp Ser
                 420                 425                 430

Tyr Asn Ala Glu Leu Leu Val Ala Met Glu Asn Gln His Thr Ile Asp
                 435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
```

```
            465                 470                 475                 480
His Lys Cys Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
                500                 505                 510

Asp Pro Val Lys Leu Ser Ser Gly Tyr Lys Asp Val Ile Leu Trp Phe
                515                 520                 525

Ser Phe Gly Ala Ser Cys Phe Ile Leu Leu Ala Ile Val Met Gly Leu
    530                 535                 540

Val Phe Ile Cys Val Lys Asn Gly Asn Met Arg Cys Thr Ile Cys Ile
545                 550                 555                 560

<210> SEQ ID NO 20
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 20

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
                100                 105                 110

Glu Glu Ala Leu Arg Gln Ile Leu Arg Glu Ser Gly Gly Ile Asp Lys
            115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
                180                 185                 190

His Ser Val Ser Thr Ala Glu Gln Thr Lys Leu Tyr Gly Ser Gly Asn
            195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Ile Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
                260                 265                 270

Ser Met Gly Ile Gln Ser Gly Val Gln Val Asp Ala Asn Cys Glu Gly
```

```
            275                 280                 285
Asp Cys Tyr His Ser Gly Gly Thr Ile Ile Ser Asn Leu Pro Phe Gln
    290                 295                 300
Asn Ile Asp Ser Arg Ala Val Gly Lys Cys Pro Arg Tyr Val Lys Gln
305                 310                 315                 320
Arg Ser Leu Leu Leu Ala Thr Gly Met Lys Asn Val Pro Glu Ile Pro
                325                 330                 335
Lys Gly Arg Gly Leu Phe Gly Ala Ile Ala Gly Phe Ile Glu Asn Gly
            340                 345                 350
Trp Glu Gly Leu Ile Asp Gly Trp Tyr Gly Phe Arg His Gln Asn Ala
            355                 360                 365
Gln Gly Glu Gly Thr Ala Ala Asp Tyr Lys Ser Thr Gln Ser Ala Ile
        370                 375                 380
Asp Gln Ile Thr Gly Lys Leu Asn Arg Leu Ile Glu Lys Thr Asn Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
            420                 425                 430
Tyr Asn Ala Glu Leu Leu Val Ala Met Glu Asn Gln His Thr Ile Asp
            435                 440                 445
Leu Ala Asp Ser Glu Met Asp Lys Leu Tyr Glu Arg Val Lys Arg Gln
        450                 455                 460
Leu Arg Glu Asn Ala Glu Glu Asp Gly Thr Gly Cys Phe Glu Ile Phe
465                 470                 475                 480
His Lys Cys Asp Asp Asp Cys Met Ala Ser Ile Arg Asn Asn Thr Tyr
                485                 490                 495
Asp His Ser Lys Tyr Arg Glu Glu Ala Met Gln Asn Arg Ile Gln Ile
            500                 505                 510
Asp Pro Val Lys Leu Ser Ser Gly Tyr Lys Asp Val Ile Leu Trp Phe
        515                 520                 525
Ser Phe Gly Ala Ser Cys Phe Ile Leu Leu Ala Ile Val Met Gly Leu
    530                 535                 540
Val Phe Ile Cys Val Lys Asn Gly Asn Met Arg Cys Thr Ile Cys Ile
545                 550                 555                 560

<210> SEQ ID NO 21
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 21

Met Asn Thr Gln Ile Leu Val Phe Ala Leu Ile

```
                85                  90                  95
Glu Arg Arg Glu Gly Ser Asp Val Cys Tyr Pro Gly Lys Phe Val Asn
            100                 105                 110
Glu Glu Ala Leu Arg Gln Ile Leu Arg Glu Ser Gly Gly Ile Asp Lys
            115                 120                 125
Glu Ala Met Gly Phe Thr Tyr Ser Gly Ile Arg Thr Asn Gly Ala Thr
            130                 135                 140
Ser Ala Cys Arg Arg Ser Gly Ser Ser Phe Tyr Ala Glu Met Lys Trp
145                 150                 155                 160
Leu Leu Ser Asn Thr Asp Asn Ala Ala Phe Pro Gln Met Thr Lys Ser
                165                 170                 175
Tyr Lys Asn Thr Arg Lys Ser Pro Ala Leu Ile Val Trp Gly Ile His
                180                 185                 190
His Ser Val Ser Thr Ala Glu Gln Thr Lys Leu Tyr Gly Ser Gly Asn
                195                 200                 205
Lys Leu Val Thr Val Gly Ser Ser Asn Tyr Gln Gln Ser Phe Val Pro
            210                 215                 220
Ser Pro Gly Ala Arg Pro Gln Val Asn Gly Leu Ser Gly Arg Ile Asp
225                 230                 235                 240
Phe His Trp Leu Met Leu Asn Pro Asn Asp Thr Val Thr Phe Ser Phe
                245                 250                 255
Asn Gly Ala Phe Ile Ala Pro Asp Arg Ala Ser Phe Leu Arg Gly Lys
            260                 265                 270
Ser Met Gly Ile Gln Ser Gly Val Gln Val Asp Ala Asn Cys Glu Gly
            275                 280                 285
Asp Cys Tyr His Ser Gly Gly Thr Ile Ile Ser Asn Leu Pro Phe Gln
            290                 295                 300
Asn Ile Asp Ser Arg Ala Val Gly Lys Cys Pro Arg Tyr Val Lys Gln
305                 310                 315                 320
Arg Ser Leu Leu Leu Ala Thr Gly Met Lys Asn Val Pro Glu Ile Pro
                325                 330                 335
Lys Gly Arg Gly Leu Phe Gly Ala Ile Ala Gly Phe Ile Glu Asn Gly
            340                 345                 350
Trp Glu Gly Leu Ile Asp Gly Trp Tyr Gly Phe Arg His Gln Asn Ala
            355                 360                 365
Gln Gly Glu Gly Thr Ala Ala Asp Tyr Lys Ser Thr Gln Ser Ala Ile
            370                 375                 380
Asp Gln Ile Thr Gly Lys Leu Asn Arg Leu Ile Glu Lys Thr Asn Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
            420                 425                 430
Tyr Asn Ala Glu Leu Leu Val Ala Met Glu Asn Gln His Thr Ile Asp
            435                 440                 445
Leu Ala Asp Ser Glu Met Asp Lys Leu Tyr Glu Arg Val Lys Arg Gln
450                 455                 460
Leu Arg Glu Asn Ala Glu Glu Asp Gly Thr Gly Cys Phe Glu Ile Phe
465                 470                 475                 480
His Lys Cys Asp Asp Asp Cys Met Ala Ser Ile Arg Asn Asn Thr Tyr
                485                 490                 495
Asp His Ser Lys Tyr Arg Glu Glu Ala Met Gln Asn Arg Ile Gln Ile
            500                 505                 510
```

```
Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Val Met Gly Leu
        530                 535                 540

Val Phe Ile Cys Val Lys Asn Gly Asn Met Arg Cys Thr Ile Cys Ile
545                 550                 555                 560

<210> SEQ ID NO 22
<211> LENGTH: 560
<212> TYPE: PRT
<213> ORGANISM: Artificial Sequence
<220> FEATURE:
<223> OTHER INFORMATION: H7N9 Influenza virus sequence

<400> SEQUENCE: 22

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320
```

```
Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Val Met Gly Leu
    530                 535                 540

Val Phe Ile Cys Val Lys Asn Gly Asn Met Arg Cys Thr Ile Cys Ile
545                 550                 555                 560

<210> SEQ ID NO 23
<211> LENGTH: 559
<212> TYPE: PRT
<213> ORGANISM: Artificial Sequence
<220> FEATURE:
<223> OTHER INFORMATION: H7N9 influenza virus sequence

<400> SEQUENCE: 23

Met Asn Thr Gln Ile Leu Val Phe Ala Leu Ile Ala Ile Ile Pro Thr
1               5                   10                  15

Asn Ala Asp L

```
Glu Ala Met Gly Phe Thr Tyr Ser Gly Ile Arg Thr Asn Gly Ala Thr
    130                 135                 140
Ser Ala Cys Arg Arg Ser Gly Ser Ser Phe Tyr Ala Glu Met Lys Trp
145                 150                 155                 160
Leu Leu Ser Asn Thr Asp Asn Ala Ala Phe Pro Gln Met Thr Lys Ser
                165                 170                 175
Tyr Lys Asn Thr Arg Lys Ser Pro Ala Leu Ile Val Trp Gly Ile His
            180                 185                 190
His Ser Val Ser Thr Ala Glu Gln Thr Lys Leu Tyr Gly Ser Gly Asn
        195                 200                 205
Lys Leu Val Thr Val Gly Ser Ser Asn Tyr Gln Gln Ser Phe Val Pro
    210                 215                 220
Ser Pro Gly Ala Arg Pro Gln Val Asn Gly Leu Ser Gly Arg Ile Asp
225                 230                 235                 240
Phe His Trp Leu Met Leu Asn Pro Asn Asp Thr Ile Thr Phe Ser Phe
                245                 250                 255
Asn Gly Ala Phe Ile Ala Pro Asp Arg Ala Ser Phe Leu Arg Gly Lys
            260                 265                 270
Ser Met Gly Ile Gln Ser Gly Val Gln Val Asp Ala Asn Cys Glu Gly
        275                 280                 285
Asp Cys Tyr His Ser Gly Gly Thr Ile Ile Ser Asn Leu Pro Phe Gln
    290                 295                 300
Asn Ile Asp Ser Arg Ala Val Gly Lys Cys Pro Arg Tyr Val Lys Gln
305                 310                 315                 320
Arg Ser Leu Leu Leu Ala Thr Gly Met Lys Asn Val Pro Glu Ile Pro
                325                 330                 335
Lys Gly Arg Gly Leu Phe Gly Ala Ile Ala Gly Phe Ile Glu Asn Gly
            340                 345                 350
Trp Glu Gly Leu Ile Asp Gly Trp Tyr Gly Phe Arg His Gln Asn Ala
        355                 360                 365
Gln Gly Glu Gly Thr Ala Ala Asp Tyr Lys Ser Thr Gln Ser Ala Ile
    370                 375                 380
Asp Gln Ile Thr Gly Lys Leu Asn Arg Leu Ile Glu Lys Thr Asn Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
            420                 425                 430
Tyr Asn Ala Glu Leu Leu Val Ala Met Glu Asn Gln His Thr Ile Asp
        435                 440                 445
Leu Ala Asp Ser Glu Met Asp Lys Leu Tyr Glu Arg Val Lys Arg Gln
    450                 455                 460
Leu Arg Glu Asn Ala Glu Glu Asp Gly Thr Gly Phe Glu Ile Phe His
465                 470                 475                 480
Lys Cys Asp Asp Asp Cys Met Ala Ser Ile Arg Asn Asn Thr Tyr Asp
                485                 490                 495
His Ser Lys Tyr Arg Glu Glu Ala Met Gln Asn Arg Ile Gln Ile Asp
            500                 505                 510
Pro Val Lys Leu Ser Ser Gly Tyr Lys Asp Val Ile Leu Trp Phe Ser
    515                 520                 525
Phe Gly Ala Ser Cys Phe Ile Leu Leu Ala Ile Val Met Gly Leu Val
530                 535                 540
```

```
Phe Ile Cys Val Lys Asn Gly Asn Met Arg Cys Thr Ile Cys Ile
545                 550                 555
```

<210> SEQ ID NO 24
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 24

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350
```

```
Trp Glu Gly Leu Ile Asp Gly Trp Tyr Gly Phe Arg His Gln Asn Ala
            355                 360                 365
Gln Gly Glu Gly Thr Ala Ala Asp Tyr Lys Ser Thr Gln Ser Ala Ile
    370                 375                 380
Asp Gln Ile Thr Gly Lys Leu Asn Arg Leu Ile Glu Lys Thr Asn Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
            420                 425                 430
Tyr Asn Ala Glu Leu Leu Val Ala Met Glu Asn Gln His Thr Ile Asp
        435                 440                 445
Leu Ala Asp Ser Glu Met Asp Lys Leu Tyr Glu Arg Val Lys Arg Gln
450                 455                 460
Leu Arg Glu Asn Ala Glu Glu Asp Gly Thr Gly Cys Phe Glu Ile Phe
465                 470                 475                 480
His Lys Cys Asp Asp Cys Met Ala Ser Ile Arg Asn Asn Thr Tyr
                485                 490                 495
Asp His Ser Lys Tyr Arg Glu Glu Ala Met Gln Asn Arg Ile Gln Ile
            500                 505                 510
Asp Pro Val Lys Leu Ser Ser Gly Tyr Lys Asp Val Ile Leu Trp Phe
        515                 520                 525
Ser Phe Gly Ala Ser Cys Phe Ile Leu Leu Ala Ile Val Met Gly Leu
    530                 535                 540
Val Phe Ile Cys Val Lys Asn Gly Asn Met Arg Cys Thr Ile Cys Ile
545                 550                 555                 560

<210> SEQ ID NO 25
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 25

Met Asn Thr Gln Ile Leu Val Phe Ala Leu Ile Ala Ile Ile Pro Thr
1               5                   10                  15
Asn Ala Asp Lys Ile Cys Leu Gly His His Ala Val Ser Asn Gly Thr
            20                  25                  30
Lys Val Asn Thr Leu Thr Glu Arg Gly Val Glu Val Val Asn Ala Thr
        35                  40                  45
Glu Thr Val Glu Arg Thr Asn Ile Pro Arg Ile Cys Ser Lys Gly Lys
50                  55                  60
Met Thr Val Asp Leu Gly Gln Cys Gly Leu Leu Gly Thr Ile Thr Gly
65                  70                  75                  80
Pro Pro Gln Cys Asp Gln Phe Leu Glu Phe Ser Ala Asp Leu Ile Ile
                85                  90                  95
Glu Arg Arg Glu Gly Ser Asp Val Cys Tyr Pro Gly Lys Phe Val Asn
            100                 105                 110
Glu Glu Ala Leu Arg Gln Ile Leu Arg Glu Ser Gly Gly Ile Asp Lys
        115                 120                 125
Glu Ala Met Gly Phe Thr Tyr Ser Gly Ile Arg Thr Asn Gly Ala Thr
    130                 135                 140
Ser Ala Cys Arg Arg Ser Gly Ser Ser Phe Tyr Ala Glu Met Lys Trp
145                 150                 155                 160
```

```
Leu Leu Ser Asn Thr Asp Asn Ala Ala Phe Pro Gln Met Thr Lys Ser
            165                 170                 175

Tyr Lys Asn Thr Arg Lys Ser Pro Ala Leu Ile Val Trp Gly Ile His
        180                 185                 190

His Ser Val Ser Thr Ala Glu Gln Thr Lys Leu Tyr Gly Ser Gly Asn
    195                 200                 205

Lys Leu Val Thr Val Gly Ser Ser Asn Tyr Gln Gln Ser Phe Val Pro
210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
    450                 455                 460

Leu Arg Glu Asn Ala Glu Glu Asp Gly Thr Gly Cys Phe Glu Ile Phe
465                 470                 475                 480

His Lys Cys Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Val Met Gly Leu
    530                 535                 540

Val Phe Ile Cys Val Lys Asn Gly Asn Met Arg Cys Thr Ile Cys Ile
545                 550                 555                 560

<210> SEQ ID NO 26
<211> LENGTH: 560
<212> TYPE: PRT
```

<213> ORGANISM: Artificial Sequence
<220> FEATURE:
<223> OTHER INFORMATION: H7N9 influenza virus sequence

<400> SEQUENCE: 26

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
```

```
                385                 390                 395                 400
Gln Phe Glu Leu Ile Asp Asn Glu Phe Asn Glu Val Glu Lys Gln Ile
                    405                 410                 415
Gly Asn Val Ile Asn Trp Thr Arg Asp Ser Ile Thr Glu Val Trp Ser
                420                 425                 430
Tyr Asn Ala Glu Leu Leu Val Ala Met Glu Asn Gln His Thr Ile Asp
                435                 440                 445
Leu Ala Asp Ser Glu Met Asp Lys Leu Tyr Glu Arg Val Lys Arg Gln
            450                 455                 460
Leu Arg Glu Asn Ala Glu Glu Asp Gly Thr Gly Cys Phe Glu Ile Phe
465                 470                 475                 480
His Lys Cys Asp Asp Asp Cys Met Ala Ser Ile Arg Asn Asn Thr Tyr
                    485                 490                 495
Asp His Ser Lys Tyr Arg Glu Glu Ala Met Gln Asn Arg Ile Gln Ile
                500                 505                 510
Asp Pro Val Lys Leu Ser Ser Gly Tyr Lys Asp Val Ile Leu Trp Phe
                515                 520                 525
Ser Phe Gly Ala Ser Cys Phe Ile Leu Leu Ala Ile Val Met Gly Leu
            530                 535                 540
Val Phe Ile Cys Val Lys Asn Gly Asn Met Arg Cys Thr Ile Cys Ile
545                 550                 555                 560

<210> SEQ ID NO 27
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 27

Met Asn Thr Gln Ile Leu Val Phe Ala Leu Ile Ala Ile Ile Pro Thr
1               5                   10                  15
Asn Ala Asp Lys Ile Cys Leu Gly His His Ala Val Ser Asn Gly Thr
                20                  25                  30
Lys Val Asn Thr Leu Thr Glu Arg Gly Val Glu Val Val Asn Ala Thr
            35                  40                  45
Glu Thr Val Glu Arg Thr Asn Ile Pro Arg Ile Cys Ser Lys Gly Lys
        50                  55                  60
Met Thr Val Asp Leu Gly Gln Cys Gly Leu Leu Gly Thr Ile Thr Gly
65                  70                  75                  80
Pro Pro Gln Cys Asp Gln Phe Leu Glu Phe Ser Ala Asp Leu Ile Ile
                85                  90                  95
Glu Arg Arg Glu Gly Ser Asp Val Cys Tyr Pro Gly Lys Phe Val Asn
                100                 105                 110
Glu Glu Ala Leu Arg Gln Ile Leu Arg Glu Ser Gly Gly Ile Asp Lys
            115                 120                 125
Glu Ala Met Gly Phe Thr Tyr Ser Gly Ile Arg Thr Asn Gly Ala Thr
        130                 135                 140
Ser Ala Cys Arg Arg Ser Gly Ser Ser Phe Tyr Ala Glu Met Lys Trp
145                 150                 155                 160
Leu Leu Ser Asn Thr Asp Asn Ala Ala Phe Pro Gln Met Thr Lys Ser
                165                 170                 175
Tyr Lys Asn Thr Arg Lys Ser Pro Ala Leu Ile Val Trp Gly Ile His
                180                 185                 190
His Ser Val Ser Thr Ala Glu Gln Thr Lys Leu Tyr Gly Ser Gly Asn
```

```
            195                 200                 205
Lys Leu Val Thr Val Gly Ser Ser Asn Tyr Gln Gln Ser Phe Val Pro
    210                 215                 220
Ser Pro Gly Ala Arg Pro Gln Val Asn Gly Leu Ser Gly Arg Ile Asp
225                 230                 235                 240
Phe His Trp Leu Met Leu Asn Pro Asn Asp Thr Val Thr Phe Ser Phe
                245                 250                 255
Asn Gly Ala Phe Ile Ala Pro Asp Arg Ala Ser Phe Leu Arg Gly Lys
                260                 265                 270
Ser Met Gly Ile Gln Ser Gly Val Gln Val Asp Ala Asn Cys Glu Gly
            275                 280                 285
Asp Cys Tyr His Ser Gly Gly Thr Ile Ile Ser Asn Leu Pro Phe Gln
            290                 295                 300
Asn Ile Asp Ser Arg Ala Val Gly Lys Cys Pro Arg Tyr Val Lys Gln
305                 310                 315                 320
Arg Ser Leu Leu Leu Ala Thr Gly Met Lys Asn Val Pro Glu Ile Pro
                325                 330                 335
Lys Gly Arg Gly Leu Phe Gly Ala Ile Ala Gly Phe Ile Glu Asn Gly
                340                 345                 350
Trp Glu Gly Leu Ile Asp Gly Trp Tyr Gly Phe Arg His Gln Asn Ala
            355                 360                 365
Gln Gly Glu Gly Thr Ala Ala Asp Tyr Lys Ser Thr Gln Ser Ala Ile
            370                 375                 380
Asp Gln Ile Thr Gly Lys Leu Asn Arg Leu Ile Glu Lys Thr Asn Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
                420                 425                 430
Tyr Asn Ala Glu Leu Leu Val Ala Met Glu Asn Gln His Thr Ile Asp
            435                 440                 445
Leu Ala Asp Ser Glu Met Asp Lys Leu Tyr Glu Arg Val Lys Arg Gln
            450                 455                 460
Leu Arg Glu Asn Ala Glu Glu Asp Gly Thr Gly Cys Phe Glu Ile Phe
465                 470                 475                 480
His Lys Cys Asp Asp Cys Met Ala Ser Ile Arg Asn Asn Thr Tyr
                485                 490                 495
Asp His Ser Lys Tyr Arg Glu Glu Ala Met Gln Asn Arg Ile Gln Ile
                500                 505                 510
Asp Pro Val Lys Leu Ser Ser Gly Tyr Lys Asp Val Ile Leu Trp Phe
            515                 520                 525
Ser Phe Gly Ala Ser Cys Phe Ile Leu Leu Ala Ile Val Met Gly Leu
            530                 535                 540
Val Phe Ile Cys Val Lys Asn Gly Asn Met Arg Cys Thr Ile Cys Ile
545                 550                 555                 560

<210> SEQ ID NO 28
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 28

Met Asn Thr Gln Ile Leu Val Phe Ala Leu Ile Ala

-continued

```
1               5                   10                  15
Asn Ala Asp Lys Ile Cys Leu Gly His His Ala Val Ser Asn Gly Thr
                20                  25                  30
Lys Val Asn Thr Leu Thr Glu Arg Gly Val Glu Val Asn Ala Thr
                35                  40                  45
Glu Thr Val Glu Arg Thr Asn Ile Pro Arg Ile Cys Ser Lys Gly Lys
            50                  55                  60
Arg Thr Val Asp Leu Gly Gln Cys Gly Leu Leu Gly Thr Ile Thr Gly
65                  70                  75                  80
Pro Pro Gln Cys Asp Gln Phe Leu Glu Phe Ser Ala Asp Leu Ile Ile
                85                  90                  95
Glu Arg Arg Glu Gly Ser Asp Val Cys Tyr Pro Gly Lys Phe Val Asn
                100                 105                 110
Glu Glu Ala Leu Arg Gln Ile Leu Arg Glu Ser Gly Ile Asp Lys
                115                 120                 125
Glu Ala Met Gly Phe Thr Tyr Ser Gly Ile Arg Thr Asn Gly Ala Thr
            130                 135                 140
Ser Ala Cys Arg Arg Ser Gly Ser Ser Phe Tyr Ala Glu Met Lys Trp
145                 150                 155                 160
Leu Leu Ser Asn Thr Asp Asn Ala Ala Phe Pro Gln Ile Thr Lys Ser
                165                 170                 175
Tyr Lys Asn Thr Arg Lys Ser Pro Ala Leu Ile Val Trp Gly Ile His
                180                 185                 190
His Ser Val Ser Thr Ala Glu Gln Thr Lys Leu Tyr Gly Ser Gly Asn
                195                 200                 205
Lys Leu Val Thr Val Gly Ser Ser Asn Tyr Gln Gln Ser Phe Val Pro
                210                 215                 220
Ser Pro Gly Ala Arg Pro Gln Val Asn Gly Leu Ser Gly Arg Ile Asp
225                 230                 235                 240
Phe His Trp Leu Met Leu Asn Pro Asn Asp Thr Val Thr Phe Ser Phe
                245                 250                 255
Asn Gly Ala Phe Ile Ala Pro Asp Arg Ala Ser Phe Leu Arg Gly Lys
                260                 265                 270
Ser Met Gly Ile Gln Ser Gly Val Gln Val Asp Ala Asn Cys Glu Gly
                275                 280                 285
Asp Cys Tyr His Ser Gly Gly Thr Ile Ile Ser Asn Leu Pro Phe Gln
                290                 295                 300
Asn Ile Asp Ser Arg Ala Val Gly Lys Cys Pro Arg Tyr Val Lys Gln
305                 310                 315                 320
Arg Ser Leu Leu Leu Ala Thr Gly Met Lys Asn Val Pro Glu Ile Pro
                325                 330                 335
Lys Gly Arg Gly Leu Phe Gly Ala Ile Ala Gly Phe Ile Glu Asn Gly
                340                 345                 350
Trp Glu Gly Leu Ile Asp Gly Trp Tyr Gly Phe Arg His Gln Asn Ala
                355                 360                 365
Gln Gly Glu Gly Thr Ala Ala Asp Tyr Lys Ser Thr Gln Ser Ala Ile
                370                 375                 380
Asp Gln Ile Thr Gly Lys Leu Asn Arg Leu Ile Glu Lys Thr Asn Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
                420                 425                 430
```

```
Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
                500                 505                 510

Asp Pro Val Lys Leu Ser Ser Gly Tyr Lys Asp Val Ile Leu Trp Phe
                515                 520                 525

Ser Phe Gly Ala Ser Cys Phe Ile Leu Leu Ala Ile Val Met Gly Leu
530                 535                 540

Val Phe Ile Cys Val Lys Asn Gly Asn Met Arg Cys Thr Ile Cys Ile
545                 550                 555                 560

<210> SEQ ID NO 29
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 29

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Arg Thr Asn Ile Pro Arg Ile Cys Ser Lys Gly Lys
    50                  55                  60

Met Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
                100                 105                 110

Glu Glu Ala Leu Arg Gln Ile Leu Arg Glu Ser Gly Gly Ile Asp Lys
            115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
                180                 185                 190

His Ser Val Ser Thr Ala Glu Gln Thr Lys Leu Tyr Gly Ser Gly Asn
            195                 200                 205

Lys Leu Val Thr Val Gly Ser Ser Asn Tyr Gln Gln Ser Phe Val Pro
210                 215                 220

Ser Pro Gly Ala Arg Pro Gln Val Asn Gly Leu Ser Gly Arg Ile Asp
225                 230                 235                 240
```

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Val Met Gly Leu
    530                 535                 540

Val Phe Ile Cys Val Lys Asn Gly Asn Met Arg Cys Thr Ile Cys Ile
545                 550                 555                 560

<210> SEQ ID NO 30
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 30

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

-continued

Glu Thr Val Glu Arg Thr Asn Ile Pro Arg Ile Cys Ser Lys Gly Lys
     50                  55                  60

Lys Thr Val Asp Leu Gly Gln Cys Gly Leu Gly Thr Ile Thr Gly
 65              70                  75                  80

Pro Pro Gln Cys Asp Gln Phe Leu Glu Phe Ser Ala Asp Leu Ile Ile
             85                  90                  95

Glu Arg Arg Glu Gly Ser Asp Val Cys Tyr Pro Gly Lys Phe Val Asn
         100                 105                 110

Glu Glu Ala Leu Arg Gln Ile Leu Arg Glu Ser Gly Ile Asp Lys
         115                 120             125

Glu Ala Met Gly Phe Thr Tyr Ser Gly Ile Arg Thr Asn Gly Ala Thr
     130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                 165                 170                 175

Tyr Lys Asn Thr Arg Lys Ser Pro Ala Leu Ile Val Trp Gly Ile His
             180                 185                 190

His Ser Val Ser Thr Ala Glu Gln Thr Lys Leu Tyr Gly Ser Gly Asn
         195                 200                 205

Lys Leu Val Thr Val Gly Ser Ser Asn Tyr Gln Gln Ser Phe Val Pro
210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                 245                 250                 255

Asn Gly Ala Phe Ile Ala Pro Asp Arg Ala Ser Phe Leu Arg Gly Lys
             260                 265                 270

Ser Met Gly Ile Gln Ser Gly Val Gln Val Asp Ala Asn Cys Glu Gly
         275                 280                 285

Asp Cys Tyr His Ser Gly Gly Thr Ile Ile Ser Asn Leu Pro Phe Gln
         290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                 325                 330                 335

Lys Gly Arg Gly Leu Phe Gly Ala Ile Ala Gly Phe Ile Glu Asn Gly
             340                 345                 350

Trp Glu Gly Leu Ile Asp Gly Trp Tyr Gly Phe Arg His Gln Asn Ala
         355                 360                 365

Gln Gly Glu Gly Thr Ala Ala Asp Tyr Lys Ser Thr Gln Ser Ala Ile
     370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                 405                 410                 415

Gly Asn Val Ile Asn Trp Thr Arg Asp Ser Ile Thr Glu Val Trp Ser
             420                 425                 430

Tyr Asn Ala Glu Leu Leu Val Ala Met Glu Asn Gln His Thr Ile Asp
         435                 440                 445

Leu Ala Asp Ser Glu Met Asp Lys Leu Tyr Glu Arg Val Lys Arg Gln
     450                 455                 460

```
Leu Arg Glu Asn Ala Glu Asp Gly Thr Gly Cys Phe Glu Ile Phe
465                 470                 475                 480

His Lys Cys Asp Asp Cys Met Ala Ser Ile Arg Asn Asn Thr Tyr
            485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Val Met Gly Leu
530                 535                 540

Val Phe Ile Cys Val Lys Asn Gly Asn Met Arg Cys Thr Ile Cys Ile
545                 550                 555                 560
```

<210> SEQ ID NO 31
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 31

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Gly Glu Val Val Asn Ala Thr
        35                  40                  45

Glu Thr Val Glu Arg Thr Asn Ile Pro Arg Ile Cys Ser Lys Gly Lys
50                  55                  60

Lys Thr Val Asp Leu Gly Gln Gly Gly Pro Arg Gly Thr Ile Thr Gly
65                  70                  75                  80

Pro Pro Gln Cys Asp Gln Phe Leu Glu Phe Ser Ala Asp Leu Ile Met
            85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
            165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
210                 215                 220

Ser Pro Gly Ala Arg Pro Gln Val Asn Gly Gln Ser Gly Arg Ile Asp
225                 230                 235                 240

Phe His Trp Leu Met Leu Asn Pro Asn Asp Thr Val Thr Phe Ser Phe
            245                 250                 255

Asn Gly Ala Phe Ile Ala Pro Asp Arg Ala Ser Phe Leu Arg Gly Lys
            260                 265                 270
```

Ser Met Gly Ile Gln Ser Gly Val Gln Val Asp Ala Asn Cys Glu Gly
                275                 280                 285

Asp Cys Tyr His Ser Gly Gly Thr Ile Ile Ser Asn Leu Pro Phe Gln
            290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
                355                 360                 365

Gln Gly Glu Gly Thr Ala Ala Asp Tyr Lys Ser Thr Gln Ser Ala Ile
            370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
                420                 425                 430

Tyr Asn Ala Glu Leu Leu Val Ala Met Glu Asn Gln His Thr Ile Asp
            435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Val Met Gly Leu
530                 535                 540

Val Phe Ile Cys Val Lys Asn Gly Asn Met Arg Cys Thr Ile Cys Ile
545                 550                 555                 560

<210> SEQ ID NO 32
<211> LENGTH: 560
<212> TYPE: PRT
<213> ORGANISM: Artificial Sequence
<220> FEATURE:
<223> OTHER INFORMATION: H7N9 influenza cirus sequence

<400> SEQUENCE: 32

Met Asn Thr Gln Ile Leu Val Phe Ala Leu Ile Ala

```
Pro Pro Gln Cys Asp Gln Phe Leu Glu Phe Ser Ala Asp Leu Ile Ile
             85                  90                  95

Glu Arg Arg Glu Gly Ser Asp Val Cys Tyr Pro Gly Lys Phe Val Asn
        100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
            195                 200                 205

Lys Leu Val Thr Val Gly Ser Ser Asn Tyr Gln Gln Ser Phe Val Pro
        210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
                260                 265                 270

Ser Met Gly Ile Gln Ser Gly Val Gln Val Asp Ala Asn Cys Glu Gly
            275                 280                 285

Asp Cys His His Ser Gly Gly Thr Ile Ile Ser Asn Leu Pro Phe Gln
            290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
        370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
            435                 440                 445

Leu Ala Asp Ser Glu Met Asp Lys Leu Tyr Glu Arg Val Lys Arg Gln
        450                 455                 460

Leu Arg Glu Asn Ala Glu Glu Asp Gly Thr Gly Cys Phe Glu Ile Phe
465                 470                 475                 480

His Lys Cys Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
```

```
            500                 505                 510
Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Val Met Gly Leu
            530                 535                 540

Val Phe Ile Cys Val Lys Asn Gly Asn Met Arg Cys Thr Ile Cys Ile
545                 550                 555                 560

<210> SEQ ID NO 33
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 33

Met Asn Thr Gln Ile Leu Val

```
                    305                 310                 315                 320
Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
        370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
                420                 425                 430

Tyr Asn Ala Glu Leu Leu Val Ala Met Glu Asn Gln His Thr Ile Asp
            435                 440                 445

Leu Ala Asp Ser Glu Met Asp Lys Leu Tyr Glu Arg Val Lys Arg Gln
    450                 455                 460

Leu Arg Glu Asn Ala Glu Asp Gly Thr Gly Cys Phe Glu Ile Phe
465                 470                 475                 480

His Lys Cys Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Val Met Gly Leu
    530                 535                 540

Val Phe Ile Cys Val Lys Asn Gly Asn Met Arg Cys Thr Ile Cys Ile
545                 550                 555                 560

<210> SEQ ID NO 34
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 34

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
```

-continued

```
            115                 120                 125
Glu Ala Met Gly Phe Thr Tyr Ser Gly Ile Arg Thr Asn Gly Ala Thr
130                 135                 140
Ser Ala Cys Arg Arg Ser Gly Ser Ser Phe Tyr Ala Glu Met Lys Trp
145                 150                 155                 160
Leu Leu Ser Asn Thr Asp Asn Ala Ala Phe Pro Gln Met Thr Lys Ser
                165                 170                 175
Tyr Lys Asn Thr Arg Lys Ser Pro Ala Leu Ile Val Trp Gly Ile His
                180                 185                 190
His Ser Val Ser Thr Ala Glu Gln Thr Lys Leu Tyr Gly Ser Gly Asn
            195                 200                 205
Lys Leu Val Thr Val Gly Ser Ser Asn Tyr Gln Gln Ser Phe Val Pro
210                 215                 220
Ser Pro Gly Ala Arg Pro Gln Val Asn Gly Ile Ser Gly Arg Ile Asp
225                 230                 235                 240
Phe His Trp Leu Met Leu Asn Pro Asn Asp Thr Val Thr Phe Ser Phe
                245                 250                 255
Asn Gly Ala Phe Ile Ala Pro Asp Arg Ala Ser Phe Leu Arg Gly Lys
                260                 265                 270
Ser Met Gly Ile Gln Ser Gly Val Gln Val Asp Ala Asn Cys Glu Gly
            275                 280                 285
Asp Cys Tyr His Ser Gly Gly Thr Ile Ile Ser Asn Leu Pro Phe Gln
            290                 295                 300
Asn Ile Asp Ser Arg Ala Val Gly Lys Cys Pro Arg Tyr Val Lys Gln
305                 310                 315                 320
Arg Ser Leu Leu Leu Ala Thr Gly Met Lys Asn Val Pro Glu Ile Pro
                325                 330                 335
Lys Gly Arg Gly Leu Phe Gly Ala Ile Ala Gly Phe Ile Glu Asn Gly
                340                 345                 350
Trp Glu Gly Leu Ile Asp Gly Trp Tyr Gly Phe Arg His Gln Asn Ala
            355                 360                 365
Gln Gly Glu Gly Thr Ala Ala Asp Tyr Lys Ser Thr Gln Ser Ala Ile
370                 375                 380
Asp Gln Ile Thr Gly Lys Leu Asn Arg Leu Ile Glu Lys Thr Asn Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
                420                 425                 430
Tyr Asn Ala Glu Leu Leu Val Ala Met Glu Asn Gln His Thr Ile Asp
            435                 440                 445
Leu Ala Asp Ser Glu Met Asp Lys Leu Tyr Glu Arg Val Lys Arg Gln
            450                 455                 460
Leu Arg Glu Asn Ala Glu Glu Asp Gly Thr Gly Cys Phe Glu Ile Phe
465                 470                 475                 480
His Lys Cys Asp Asp Asp Cys Met Ala Ser Ile Arg Asn Asn Thr Tyr
                485                 490                 495
Asp His Ser Lys Tyr Arg Glu Glu Ala Met Gln Asn Arg Ile Gln Ile
            500                 505                 510
Asp Pro Val Lys Leu Ser Ser Gly Tyr Lys Asp Val Ile Leu Trp Phe
            515                 520                 525
Ser Phe Gly Ala Ser Cys Phe Ile Leu Leu Ala Ile Val Met Gly Leu
530                 535                 540
```

```
Val Phe Ile Cys Val Lys Asn Gly Asn Met Arg Cys Thr Ile Cys Ile
545                 550                 555                 560

<210> SEQ ID NO 35
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 35

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Ile Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350
```

```
Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
        370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
450                 455                 460

Leu Arg Glu Asn Ala Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Val Met Gly Leu
530                 535                 540

Val Phe Ile Cys Val Lys Asn Gly Asn Met Arg Cys Thr Ile Cys Ile
545                 550                 555                 560

<210> SEQ ID NO 36
<211> LENGTH: 560
<212> TYPE: PRT
<213> ORGANISM: Artificial Sequence
<220> FEATURE:
<223> OTHER INFORMATION: H7N9 influenza virus sequence

<400> S

-continued

```
Leu Leu Ser Asn Thr Asp Asn Ala Ala Phe Pro Gln Met Thr Lys Ser
                165                 170                 175
Tyr Lys Asn Thr Arg Lys Ser Pro Ala Leu Ile Val Trp Gly Ile His
            180                 185                 190
His Ser Val Ser Thr Ala Glu Gln Thr Lys Leu Tyr Gly Ser Gly Asn
        195                 200                 205
Lys Leu Val Thr Val Gly Ser Ser Asn Tyr Gln Gln Ser Phe Val Pro
    210                 215                 220
Ser Pro Gly Ala Arg Pro Gln Val Asn Gly Leu Ser Gly Arg Ile Asp
225                 230                 235                 240
Phe His Trp Leu Met Leu Asn Pro Asn Asp Thr Val Thr Phe Ser Phe
                245                 250                 255
Asn Gly Ala Phe Ile Ala Pro Asp Arg Ala Ser Phe Leu Arg Gly Lys
            260                 265                 270
Ser Met Gly Ile Gln Ser Gly Val Gln Val Asp Ala Asn Cys Glu Gly
        275                 280                 285
Asp Cys Tyr His Ser Gly Gly Thr Ile Ile Ser Asn Leu Pro Phe Gln
    290                 295                 300
Asn Ile Asp Ser Arg Ala Val Gly Lys Cys Pro Arg Tyr Val Lys Gln
305                 310                 315                 320
Arg Ser Leu Leu Leu Ala Thr Gly Met Lys Asn Val Pro Glu Ile Pro
                325                 330                 335
Lys Gly Arg Gly Leu Phe Gly Ala Ile Ala Gly Phe Ile Glu Asn Gly
            340                 345                 350
Trp Glu Gly Leu Ile Asp Gly Trp Tyr Gly Phe Arg His Gln Asn Ala
        355                 360                 365
Gln Gly Glu Gly Thr Ala Ala Asp Tyr Lys Ser Thr Gln Ser Ala Ile
    370                 375                 380
Asp Gln Ile Thr Gly Lys Leu Asn Arg Leu Ile Glu Lys Thr Asn Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
            420                 425                 430
Tyr Asn Ala Glu Leu Leu Val Ala Met Glu Asn Gln His Thr Ile Asp
        435                 440                 445
Leu Ala Asp Ser Glu Met Asp Lys Leu Tyr Glu Arg Val Lys Arg Gln
    450                 455                 460
Leu Arg Glu Asn Ala Glu Glu Asp Gly Thr Gly Cys Phe Glu Ile Phe
465                 470                 475                 480
His Lys Cys Asp Asp Cys Met Ala Ser Ile Arg Asn Asn Thr Tyr
                485                 490                 495
Asp His Ser Lys Tyr Arg Glu Glu Ala Met Gln Asn Arg Ile Gln Ile
        500                 505                 510
Asp Pro Val Lys Leu Ser Ser Gly Tyr Lys Asp Val Ile Leu Trp Phe
    515                 520                 525
Ser Phe Gly Ala Ser Cys Phe Ile Leu Leu Ala Ile Val Met Gly Leu
530                 535                 540
Val Phe Ile Cys Val Lys Asn Gly Asn Met Arg Cys Thr Ile Cys Ile
545                 550                 555                 560

<210> SEQ ID NO 37
<211> LENGTH: 560
```

<212> TYPE: PRT
<213> ORGANISM: Artificial Sequence
<220> FEATURE:
<223> OTHER INFORMATION: H7N9 influenza virus sequence

<400> SEQUENCE: 37

```
Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380
```

```
Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
            405                 410                 415

Gly Asn Val Ile Asn Trp Thr Arg Asp Ser Ile Thr Glu Val Trp Ser
        420                 425                 430

Tyr Asn Ala Glu Leu Leu Val Ala Met Glu Asn Gln His Thr Ile Asp
    435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Val Met Gly Leu
530                 535                 540

Val Phe Ile Cys Val Lys Asn Gly Asn Met Arg Cys Thr Ile Cys Ile
545                 550                 555                 560

<210> SEQ ID NO 38
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 38

Met Asn Thr Gln Ile Leu Val Phe Ala Leu Ile Ala Ile Ile Pro Ala
1                   5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Arg Thr Asn Ile Pro Arg Ile Cys Ser Lys Gly Lys
        50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190
```

His Ser Val Ser Thr Ala Glu Gln Thr Lys Leu Tyr Gly Ser Gly Asn
            195                 200                 205

Lys Leu Val Thr Val Gly Ser Ser Asn Tyr Gln Gln Ser Phe Val Pro
        210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                    245                 250                 255

Asn Gly Ala Phe Ile Ala Pro Asp Arg Ala Ser Phe Leu Arg Gly Lys
                260                 265                 270

Ser Met Gly Ile Gln Ser Gly Val Gln Val Asp Ala Asn Cys Glu Gly
            275                 280                 285

Asp Cys His His Ser Gly Gly Thr Ile Ile Ser Asn Leu Pro Phe Gln
        290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                    325                 330                 335

Lys Gly Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
        370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                    405                 410                 415

Gly Asn Val Ile Asn Trp Thr Arg Asp Ser Ile Thr Glu Val Trp Ser
                420                 425                 430

Tyr Asn Ala Glu Leu Leu Val Ala Met Glu Asn Gln His Thr Ile Asp
            435                 440                 445

Leu Ala Asp Ser Glu Met Asp Lys Leu Tyr Glu Arg Val Lys Arg Gln
        450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                    485                 490                 495

Asp His Ser Lys Tyr Arg Glu Glu Ala Met Gln Asn Arg Ile Gln Ile
                500                 505                 510

Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Val Met Gly Leu
        530                 535                 540

Val Phe Ile Cys Val Lys Asn Gly Asn Met Arg Cys Thr Ile Cys Ile
545                 550                 555                 560

<210> SEQ ID NO 39
<211> LENGTH: 206
<212> TYPE: PRT
<213> ORGANISM: Artificial Sequence
<220> FEATURE:
<223> OTHER INFORMATION: H7N9 influenza virus sequence

<400> SEQUENCE: 39

```
Gly Met Ile Asp Gly Trp Tyr Gly Phe Arg His Gln Asn Ala Gln Gly
  1               5                  10                  15

Glu Gly Thr Ala Ala Asp Tyr Lys Ser Thr Gln Ser Ala Ile Asp Gln
             20                  25                  30

Ile Thr Gly Lys Leu Asn Arg Leu Ile Glu Lys Thr Asn Gln Gln Phe
         35                  40                  45

Glu Leu Ile Asp Asn Glu Phe Thr Glu Val Glu Lys Gln Ile Gly Asn
 50                  55                  60

Val Ile Asn Trp Thr Arg Asp Ser Ile Thr Glu Val Trp Ser Tyr Asn
 65                  70                  75                  80

Ala Glu Leu Leu Val Ala Met Glu Asn Gln His Thr Ile Asp Leu Ala
                 85                  90                  95

Asp Ser Glu Met Asp Lys Leu Tyr Glu Arg Val Lys Arg Gln Leu Arg
                100                 105                 110

Glu Asn Ala Glu Glu Asp Gly Thr Gly Cys Phe Glu Ile Phe His Lys
            115                 120                 125

Cys Asp Asp Asp Cys Met Ala Ser Ile Arg Asn Asn Thr Tyr Asp His
        130                 135                 140

Ser Lys Tyr Arg Glu Glu Ala Met Gln Asn Arg Ile Gln Ile Asp Pro
145                 150                 155                 160

Val Lys Leu Ser Ser Gly Tyr Lys Asp Val Ile Leu Trp Phe Ser Phe
                165                 170                 175

Gly Ala Ser Cys Phe Ile Leu Leu Ala Ile Ala Met Gly Leu Val Phe
                180                 185                 190

Ile Cys Val Lys Asn Gly Asn Met Arg Cys Thr Ile Cys Ile
                195                 200                 205
```

<210> SEQ ID NO 40
<211> LENGTH: 206
<212> TYPE: PRT
<213> ORGANISM: Artificial Sequence
<220> FEATURE:
<223> OTHER INFORMATION: H7N9 influenza virus sequence
<400> SEQUENCE: 40

```
Gly Met Ile Asp Gly Trp Tyr Gly Phe Arg His Gln Asn Ala Gln Gly
  1               5                  10                  15

Glu Gly Thr Ala Ala Asp Tyr Lys Ser Thr Gln Ser Ala Ile Asp Gln
             20                  25                  30

Ile Thr Gly Lys Leu Asn Arg Leu Ile Glu Lys Thr Asn Gln Gln Phe
         35                  40                  45

Glu Leu Ile Asp Asn Glu Phe Asn Glu Val Glu Lys Gln Ile Gly Asn
 50                  55                  60

Val Ile Asn Trp Thr Arg Asp Ser Ile Thr Glu Val Trp Ser Tyr Asn
 65                  70                  75                  80

Ala Glu Leu Leu Val Ala Met Glu Asn Gln His Thr Ile Asp Leu Ala
                 85                  90                  95

Asp Ser Glu Met Asp Lys Leu Tyr Glu Arg Val Lys Arg Gln Leu Arg
                100                 105                 110

Glu Asn Ala Glu Glu Asp Gly Thr Gly Cys Phe Glu Ile Phe His Lys
            115                 120                 125

Cys Asp Asp Asp Cys Met Ala Ser Ile Arg Asn Asn Thr Tyr Asp His
        130                 135                 140

Ser Lys Tyr Arg Glu Glu Ala Met Gln Asn Arg Ile Gln Ile Asp Pro
145                 150                 155                 160
```

Val Lys Leu Ser Ser Gly Tyr Lys Asp Val Ile Leu Trp Phe Ser Phe
            165                 170                 175

Gly Ala Ser Cys Phe Ile Leu Leu Ala Ile Val Met Gly Leu Val Phe
            180                 185                 190

Ile Cys Val Lys Asn Gly Asn Met Arg Cys Thr Ile Cys Ile
        195                 200                 205

<210> SEQ ID NO 41
<211> LENGTH: 206
<212> TYPE: PRT
<213> ORGANISM: Artificial Sequence
<220> FEATURE:
<223> OTHER INFORMATION: H7N9 influenza virus sequence

<400> SEQUENCE: 41

Gly Met Ile Asp Gly Trp Tyr Gly Phe Arg His Gln Asn Ala Gln Gly
1               5                   10                  15

Glu Gly Thr Ala Ala Asp Tyr Lys Ser Thr Gln Ser Ala Ile Asp Gln
            20                  25                  30

Ile Thr Gly Lys Leu Asn Arg Leu Ile Glu Lys Thr Asn Gln Gln Phe
        35                  40                  45

Glu Leu Ile Asp Asn Glu Phe Thr Glu Val Lys Gln Ile Gly Asn
    50                  55                  60

Val Ile Asn Trp Thr Arg Asp Ser Ile Thr Glu Val Trp Ser Tyr Asn
65                  70                  75                  80

Ala Glu Leu Leu Val Ala Met Glu Asn Gln His Thr Ile Asp Leu Ala
                85                  90                  95

Asp Ser Glu Met Asp Lys Leu Tyr Glu Arg Val Lys Arg Gln Leu Arg
            100                 105                 110

Glu Asn Ala Glu Glu Asp Gly Thr Gly Cys Phe Glu Ile Phe His Lys
        115                 120                 125

Cys Asp Asp Asp Cys Met Ala Ser Ile Arg Asn Asn Thr Tyr Asp His
130                 135                 140

Ser Lys Tyr Arg Glu Glu Ala Met Gln Asn Arg Ile Gln Ile Asp Pro
145                 150                 155                 160

Val Lys Leu Ser Ser Gly Tyr Lys Asp Val Ile Leu Trp Phe Ser Phe
            165                 170                 175

Gly Ala Ser Cys Phe Ile Leu Leu Ala Ile Ala Met Gly Leu Val Phe
            180                 185                 190

Ile Cys Val Lys Asn Gly Asn Met Arg Cys Thr Ile Cys Ile
        195                 200                 205

<210> SEQ ID NO 42
<211> LENGTH: 560
<212> TYPE: PRT
<213> ORGANISM: Artificial Sequence
<220> FEATURE:
<223> OTHER INFORMATION: H7N9 influenza virus sequence
<220> FEATURE:
<221> NAME/KEY: misc_feature
<222> LOCATION: (204)..(273)
<223> OTHER INFORMATION: Xaa can be any naturally occurring amino acid

<400> SEQUENCE: 42

Met Asn Ala Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr

```
                35                  40                  45
Glu Thr Val Glu Arg Thr Asn Ile Pro Arg Ile Cys Ser Lys Gly Lys
 50                  55                  60

Arg Thr Val Asp Leu Gly Gln Cys Gly Leu Leu Gly Thr Ile Thr Gly
 65                  70                  75                  80

Pro Pro Gln Cys Asp Gln Phe Leu Glu Phe Ser Ala Asp Leu Ile Ile
                 85                  90                  95

Glu Arg Arg Glu Gly Ser Asp Val Cys Tyr Pro Gly Lys Phe Val Asn
                100                 105                 110

Glu Glu Ala Leu Arg Gln Ile Leu Arg Glu Ser Gly Gly Ile Asp Lys
                115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
                180                 185                 190

His Ser Val Ser Thr Ala Glu Gln Thr Lys Leu Xaa Xaa Xaa Xaa Xaa
                195                 200                 205

Xaa Xaa Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
                260                 265                 270

Xaa Met Gly Ile Gln Ser Gly Val Gln Val Asp Ala Asn Cys Glu Gly
                275                 280                 285

Asp Cys Tyr His Ser Gly Gly Thr Ile Ile Ser Asn Leu Pro Phe Gln
290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
                340                 345                 350

Trp Glu Gly Leu Thr Asp Gly Trp Tyr Gly Phe Arg His Gln Asn Ala
                355                 360                 365

Gln Gly Glu Gly Thr Ala Ala Asp Tyr Lys Ser Thr Gln Ser Ala Ile
                370                 375                 380

Asp Gln Ile Thr Gly Lys Phe Asn Arg Leu Ile Gly Lys Thr His Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
                420                 425                 430

Tyr Asn Ala Glu Leu Leu Val Ala Met Glu Asn Gln His Thr Ile Asp
                435                 440                 445

Leu Ala Asp Ser Glu Met Asp Lys Leu Tyr Glu Arg Val Lys Arg Gln
                450                 455                 460
```

Leu Arg Glu Asn Ala Glu Asp Gly Thr Gly Cys Phe Glu Ile Phe
465                 470                 475                 480

His Lys Cys Asp Asp Cys Met Ala Ser Ile Arg Asn Asn Thr Tyr
            485                 490                 495

Asp Arg Ser Lys Ser Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Val Met Gly Leu
530                 535                 540

Val Phe Ile Cys Val Lys Asn Gly Asn Met Arg Cys Thr Ile Cys Ile
545                 550                 555                 560

<210> SEQ ID NO 43
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 43

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Ile Pro Arg Ile Cys Ser Lys Gly Lys
50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ser Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Thr Phe Ile Ala Pro Asp Arg Ala Ser Phe Leu Arg Gly Lys
            260                 265                 270

```
Ser Met Gly Ile Gln Ser Gly Val Gln Val Asp Ala Asn Cys Glu Gly
            275                 280                 285
Asp Cys Tyr His Ser Gly Gly Thr Ile Met Ser Asn Leu Pro Phe Gln
        290                 295                 300
Asn Ile Asp Ser Arg Ala Val Gly Lys Cys Pro Arg Tyr Val Lys Gln
305                 310                 315                 320
Gly Ser Leu Leu Leu Ala Thr Gly Met Lys Asn Val Pro Glu Ile Pro
                325                 330                 335
Lys Gly Arg Gly Leu Phe Gly Ala Ile Ala Gly Phe Ile Glu Asn Gly
            340                 345                 350
Trp Glu Gly Leu Ile Asp Gly Trp Tyr Gly Phe Arg His Gln Asn Ala
        355                 360                 365
Gln Gly Glu Gly Thr Ala Ala Asp Tyr Lys Ser Thr Gln Ser Ala Ile
    370                 375                 380
Asp Gln Ile Thr Gly Lys Phe Asn Arg Leu Ile Glu Lys Thr His Gln
385                 390                 395                 400
Gln Phe Glu Leu Ile Asp Asn Glu Phe Asn Glu Val Glu Lys Gln Ile
                405                 410                 415
Gly Asn Val Ile Asn Trp Thr Arg Asp Ser Ile Thr Glu Val Trp Ser
            420                 425                 430
Tyr Asn Ala Glu Leu Leu Val Ala Met Glu Asn Gln His Thr Ile Asp
        435                 440                 445
Leu Ala Asp Ser Glu Met Asp Lys Leu Tyr Glu Arg Val Lys Arg Gln
    450                 455                 460
Leu Arg Glu Asn Ala Glu Asp Gly Thr Gly Cys Phe Glu Ile Phe
465                 470                 475                 480
His Lys Cys Asp Asp Cys Met Ala Ser Ile Arg Asn Asn Thr Tyr
                485                 490                 495
Asp His Ser Lys Ser Arg Glu Glu Ala Met Gln Asn Arg Ile Gln Ile
            500                 505                 510
Asp Pro Val Lys Leu Ser Ser Gly Tyr Lys Asp Val Ile Leu Trp Phe
        515                 520                 525
Ser Phe Gly Ala Ser Cys Phe Ile Leu Leu Ala Ile Val Met Gly Leu
    530                 535                 540
Val Phe Ile Cys Val Lys Asn Gly Asn Met Arg Cys Thr Ile Cys Ile
545                 550                 555                 560

<210> SEQ ID NO 44
<211> LENGTH: 560
<212> TYPE: PRT
<213> ORGANISM: Artificial Sequence
<220> FEATURE:
<223> OTHER INFORMATION: H7N9 influenza virus sequence
<220> FEATURE:
<221> NAME/KEY: MISC_FEATURE
<222> LOCATION: (68)..(230)
<223> OTHER INFORMATION: X= any na

```
Asn Ala Asp Lys Ile Cys Leu Gly His His Ala Val Ser Asn Gly Thr
             20                  25                  30

Lys Val Asn Thr Leu Thr Glu Arg Gly Val Glu Val Asn Ala Thr
         35                  40                  45

Glu Thr Val Glu Arg Thr Asn Ile Pro Arg Ile Cys Ser Lys Gly Lys
 50                  55                  60

Arg Thr Val Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa
             100                 105                 110

Xaa Xaa Xaa Xaa Xaa Xaa Xaa Xaa Xaa Xaa Xaa Xaa Xaa Xaa Xaa
             115                 120                 125

Xaa Xaa Xaa Xaa Xaa Xaa Xaa Xaa Xaa Xaa Xaa Xaa Xaa Xaa Xaa
             130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
             165                 170                 175

Xaa Xaa Xaa Xaa Xaa Xaa Xaa Xaa Xaa Xaa Xaa Xaa Xaa Xaa Xaa
             180                 185                 190

Xaa Xaa Xaa Xaa Xaa Xaa Xaa Xaa Xaa Xaa Xaa Xaa Xaa Xaa Xaa
             195                 200                 205

Xaa Xaa Xaa Xaa Xaa Xaa Xaa Xaa Xaa Xaa Xaa Xaa Xaa Xaa Xaa
             210                 215                 220

Xaa Xaa Xaa Xaa Xaa Xaa Gln Val Asn Gly Leu Ser Gly Arg Ile Asp
225                 230                 235                 240

Phe His Trp Leu Met Leu Asn Pro Asn Asp Thr Val Xaa Xaa Xaa Xaa
                 245                 250                 255

Xaa Xaa Xaa Xaa Xaa Xaa Xaa Xaa Xaa Xaa Xaa Xaa Xaa Xaa Xaa
             260                 265                 270

Xaa Xaa Xaa Xaa Xaa Xaa Xaa Xaa Xaa Xaa Xaa Xaa Xaa Xaa Xaa
             275                 280                 285

Xaa Xaa Xaa Xaa Xaa Xaa Xaa Xaa Xaa Xaa Xaa Xaa Xaa Xaa Xaa
             290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
             325                 330                 335

Xaa Xaa Xaa Xaa Xaa Xaa Xaa Xaa Xaa Xaa Xaa Xaa Xaa Xaa Xaa
             340                 345                 350

Xaa Xaa Xaa Xaa Xaa Xaa Xaa Xaa Xaa Xaa Xaa Xaa Xaa Xaa Xaa
             355                 360                 365

Xaa Xaa Xaa Xaa Xaa Xaa Ala Asp Tyr Lys Ser Thr Gln Ser Ala Ile
             370                 375                 380

Asp Gln Ile Thr Gly Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
             405                 410                 415

Xaa Xaa Xaa Xaa Xaa Xaa Xaa Xaa Xaa Xaa Xaa Xaa Xaa Xaa Xaa
             420                 425                 430
```

Xaa Xaa Xaa Glu Leu Leu Val Ala Met Glu Asn Gln His Thr Ile Asp
            435                 440                 445

Leu Ala Asp Ser Glu Met Asp Lys Leu Tyr Glu Arg Val Lys Arg Gln
450                 455                 460

Leu Arg Glu Asn Ala Glu Asp Gly Thr Gly Cys Phe Glu Ile Phe
465                 470                 475                 480

His Lys Cys Asp Asp Asp Cys Met Ala Ser Ile Arg Asn Asn Thr Tyr
            485                 490                 495

Asp His Ser Lys Ser Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Val Met Gly Leu
530                 535                 540

Val Phe Ile Cys Val Lys Asn Gly Asn Met Arg Cys Thr Ile Cys Ile
545                 550                 555                 560

<210> SEQ ID NO 45
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 45

Met Asn Thr Gln Ile Leu Val Phe Ala Leu Ile Ala Ile

```
Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
        275                 280                 285

Asp Cys Tyr His Ser Gly Gly Thr Ile Ile Ser Asn Leu Pro Phe Gln
    290                 295                 300

Asn Ile Asp Ser Arg Ala Val Gly Lys Cys Pro Arg Tyr Val Lys Gln
305                 310                 315                 320

Arg Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Asn Glu Val Glu Lys Gln Ile
                405                 410                 415

Gly Asn Val Ile Asn Trp Thr Arg Asp Ser Ile Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asp Lys Leu Tyr Glu Arg Val Lys Arg Gln
450                 455                 460

Leu Arg Glu Asn Ala Glu Glu Asp Gly Thr Gly Cys Phe Glu Ile Phe
465                 470                 475                 480

His Lys Cys Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
        515                 520                 525

Ser Phe Gly Ala Ser Cys Phe Ile Leu Leu Ala Ile Val Met Gly Leu
    530                 535                 540

Val Phe Ile Cys Val Lys Asn Gly Asn Met Arg Cys Thr Ile Cys Ile
545                 550                 555                 560

<210> SEQ ID NO 46
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 46

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45
```

-continued

```
Glu Thr Val Glu Arg Thr Asn Ile Pro Arg Ile Cys Ser Lys Gly Lys
    50              55              60

Met Thr Val Asp Leu Gly Gln Cys Gly Leu Leu Gly Thr Ile Thr Gly
65              70              75              80

Pro Pro Gln Cys Asp Gln Phe Leu Glu Phe Ser Ala Asp Leu Ile Ile
                85              90              95

Glu Arg Arg Glu Gly Ser Asp Val Cys Tyr Pro Gly Lys Phe Val Asn
            100             105             110

Glu Glu Ala Leu Arg Gln Ile Leu Arg Glu Ser Gly Gly Ile Asp Lys
            115             120             125

Glu Ala Met Gly Phe Thr Tyr Ser Gly Ile Arg Thr Asn Gly Ala Thr
    130             135             140

Ser Ala Cys Arg Arg Ser Gly Ser Ser Phe Tyr Ala Glu Met Lys Trp
145             150             155             160

Leu Leu Ser Asn Thr Asp Asn Ala Ala Phe Pro Gln Met Thr Lys Ser
                165             170             175

Tyr Lys Asn Thr Arg Lys Ser Pro Ala Leu Ile Val Trp Gly Ile His
            180             185             190

His Ser Val Ser Thr Ala Glu Gln Thr Lys Leu Tyr Gly Ser Gly Asn
            195             200             205

Lys Leu Val Thr Val Gly Ser Ser Asn Tyr Gln Gln Ser Phe Val Pro
    210             215             220

Ser Pro Gly Ala Arg Pro Gln Val Asn Gly Leu Ser Gly Arg Ile Asp
225             230             235             240

Phe His Trp Leu Met Leu Asn Pro Asn Asp Thr Val Thr Phe Ser Phe
                245             250             255

Asn Gly Ala Phe Ile Ala Pro Asp Arg Ala Ser Phe Leu Arg Gly Lys
            260             265             270

Ser Met Gly Ile Gln Ser Gly Val Gln Val Asp Ala Asn Cys Glu Gly
    275             280             285

Asp Cys Tyr His Ser Gly Gly Thr Ile Ile Ser Asn Leu Pro Phe Gln
    290             295             300

Asn Ile Asp Ser Arg Ala Val Gly Lys Cys Pro Arg Tyr Val Lys Gln
305             310             315             320

Arg Ser Leu Leu Leu Ala Thr Gly Met Lys Asn Val Pro Glu Ile Pro
            325             330             335

Lys Gly Arg Gly Leu Phe Gly Ala Ile Ala Gly Phe Ile Glu Asn Gly
            340             345             350

Trp Glu Gly Leu Ile Asp Gly Trp Tyr Gly Phe Arg His Gln Asn Ala
    355             360             365

Gln Gly Glu Gly Thr Ala Ala Asp Tyr Lys Ser Thr Gln Ser Ala Ile
    370             375             380

Asp Gln Ile Thr Gly Lys Leu Asn Arg Leu Ile Glu Lys Thr Asn Gln
385             390             395             400

Gln Phe Glu Leu Ile Asp Asn Glu Phe Asn Glu Val Glu Lys Gln Ile
                405             410             415

Gly Asn Val Ile Asn Trp Thr Arg Asp Ser Ile Thr Glu Val Trp Ser
            420             425             430

Tyr Asn Ala Glu Leu Leu Val Ala Met Glu Asn Gln His Thr Ile Asp
            435             440             445

Leu Ala Asp Ser Glu Met Asp Lys Leu Tyr Glu Arg Val Lys Arg Gln
    450             455             460

Leu Arg Glu Asn Ala Glu Glu Asp Gly Thr Gly Cys Phe Glu Ile Phe
```

```
                465              470              475              480
His Lys Cys Asp Asp Cys Met Ala Ser Ile Arg Asn Asn Thr Tyr
                    485              490              495

Asp His Ser Lys Tyr Arg Glu Glu Ala Met Gln Asn Arg Ile Gln Ile
                500              505              510

Asp Pro Val Lys Leu Ser Ser Gly Tyr Lys Asp Val Ile Leu Trp Phe
                515              520              525

Ser Phe Gly Ala Ser Cys Phe Ile Leu Leu Ala Ile Val Met Gly Leu
            530              535              540

Val Phe Ile Cys Val Lys Asn Gly Asn Met Arg Cys Thr Ile Cys Ile
545              550              555              560

<210> SEQ ID NO 47
<211> LENGTH: 560
<212> TYPE: PRT
<213> ORGANISM: Artificial Sequence
<220> FEATURE:
<223> OTHER INFORMATION: H7N9 influenza virus sequence

<400> SEQUENCE: 47

Met Asn Thr Gln Ile Leu Val Phe Ala Leu Ile Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Arg Thr Asn Ile Pro Arg Ile Cys Ser Lys Gly Lys
    50                  55                  60

Met Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Ala Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Ser Pro Ala Leu Ile Val Trp Gly Ile His
            180                 185                 190

His Ser Val Ser Thr Ala Glu Gln Thr Lys Leu Tyr Gly Ser Gly Asn
        195                 200                 205

Lys Leu Val Thr Val Gly Ser Ser Asn Tyr Gln Gln Ser Phe Val Pro
    210                 215                 220

Ser Pro Gly Ala Arg Pro Gln Val Asn Gly Leu Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Gly Val Gln Val Asp Ala Asn Cys Glu Gly
```

275 280 285

Asp Cys Tyr His Ser Gly Gly Thr Ile Ile Ser Asn Leu Pro Phe Gln
290 295 300

Asn Ile Asp Ser Arg Ala Val Gly Lys Cys Pro Arg Tyr Val Lys Gln
305 310 315 320

Arg Ser Leu Leu Leu Ala Thr Gly Met Lys Asn Val Pro Glu Ile Pro
325 330 335

Lys Gly Arg Gly Leu Phe Gly Ala Ile Ala Gly Phe Ile Glu Asn Gly
340 345 350

Trp Glu Gly Leu Ile Asp Gly Trp Tyr Gly Phe Arg His Gln Asn Ala
355 360 365

Gln Gly Glu Gly Thr Ala Ala Asp Tyr Lys Ser Thr Gln Ser Ala Ile
370 375 380

Asp Gln Ile Thr Gly Lys Leu Asn Arg Leu Ile Glu Lys Thr Asn Gln
385 390 395 400

Gln Phe Glu Leu Ile Asp Asn Glu Phe Asn Glu Val Glu Lys Gln Ile
405 410 415

Gly Asn Val Ile Asn Trp Thr Arg Asp Ser Ile Thr Glu Val Trp Ser
420 425 430

Tyr Asn Ala Glu Leu Leu Val Ala Met Glu Asn Gln His Thr Ile Asp
435 440 445

Leu Ala Asp Ser Glu Met Asp Lys Leu Tyr Glu Arg Val Lys Arg Gln
450 455 460

Leu Arg Glu Asn Ala Glu Glu Asp Gly Thr Gly Cys Phe Glu Ile Phe
465 470 475 480

His Lys Cys Asp Asp Asp Cys Met Ala Ser Ile Arg Asn Asn Thr Tyr
485 490 495

Asp His Ser Lys Tyr Arg Glu Glu Ala Met Gln Asn Arg Ile Gln Ile
500 505 510

Asp Pro Val Lys Leu Ser Ser Gly Tyr Lys Asp Val Ile Leu Trp Phe
515 520 525

Ser Phe Gly Ala Ser Cys Phe Ile Leu Leu Ala Ile Val Met Gly Leu
530 535 540

Val Phe Ile Cys Val Lys Asn Gly Asn Met Arg Cys Thr Ile Cys Ile
545 550 555 560

<210> SEQ ID NO 48
<211> LENGTH: 566
<212> TYPE: PRT
<213> ORGANISM: Artificial Sequence
<220> FEATURE:
<223> OTHER INFORMATION: H3N2 influenza virus sequence

<400> SEQUENCE: 48

Met Lys Thr Ile Ile Ala Leu Ser Tyr Ile Phe Cys Leu Ala Leu Gly
1 5 10 15

Gln Asp Leu Pro Gly Asn Asp Asn Ser Thr Ala Thr Leu Cys Leu Gly
20 25 30

His His Ala Val Pro Asn Gly Thr Leu Val Lys Thr Ile Thr Asp Asp
35 40 45

Gln Ile Glu Val Thr Asn Ala Thr Glu Leu Val Gln Ser Ser Ser Thr
50 55 60

Gly Lys Ile Cys Asn Asn Pro His Arg Ile Leu Asp Gly Ile Asp Cys
65 70 75 80

Thr Leu Ile Asp Ala Leu Leu Gly Asp Pro His Cys Asp Val Phe Gln

```
                    85                  90                  95
Asn Glu Thr Trp Asp Leu Phe Val Glu Arg Ser Lys Ala Phe Ser Asn
               100                 105                 110
Cys Tyr Pro Tyr Asp Val Pro Asp Tyr Ala Ser Leu Arg Ser Leu Val
               115                 120                 125
Ala Ser Ser Gly Thr Leu Glu Phe Ile Thr Glu Gly Phe Thr Trp Thr
               130                 135                 140
Gly Val Thr Gln Asn Gly Gly Ser Asn Ala Cys Lys Arg Gly Pro Gly
145                 150                 155                 160
Ser Gly Phe Phe Ser Arg Leu Asn Trp Leu Thr Lys Ser Gly Ser Thr
               165                 170                 175
Tyr Pro Val Leu Asn Val Thr Met Pro Asn Asn Asp Asn Phe Asp Lys
               180                 185                 190
Leu Tyr Ile Trp Gly Ile His His Pro Ser Thr Asn Gln Glu Gln Thr
               195                 200                 205
Ser Leu Tyr Val Gln Ala Ser Gly Arg Val Thr Val Ser Thr Arg Arg
               210                 215                 220
Ser Gln Gln Thr Ile Ile Pro Asn Ile Gly Ser Arg Pro Trp Val Arg
225                 230                 235                 240
Gly Leu Ser Ser Arg Ile Ser Ile Tyr Trp Thr Ile Val Lys Pro Gly
                   245                 250                 255
Asp Val Leu Val Ile Asn Ser Asn Gly Asn Leu Ile Ala Pro Arg Gly
                   260                 265                 270
Tyr Phe Lys Met Arg Thr Gly Lys Ser Ser Ile Met Arg Ser Asp Ala
                   275                 280                 285
Pro Ile Asp Thr Cys Ile Ser Glu Cys Ile Thr Pro Asn Gly Ser Ile
290                 295                 300
Pro Asn Asp Lys Pro Phe Gln Asn Val Asn Lys Ile Thr Tyr Gly Ala
305                 310                 315                 320
Cys Pro Lys Tyr Val Lys Gln Asn Thr Leu Lys Leu Ala Thr Gly Met
                   325                 330                 335
Arg Asn Val Pro Glu Lys Gln Thr Arg Gly Leu Phe Gly Ala Ile Ala
                   340                 345                 350
Gly Phe Ile Glu Asn Gly Trp Glu Gly Met Ile Asp Gly Trp Tyr Gly
                   355                 360                 365
Phe Arg His Gln Asn Ser Glu Gly Thr Gly Gln Ala Ala Asp Leu Lys
                   370                 375                 380
Ser Thr Gln Ala Ala Ile Asp Gln Ile Asn Gly Lys Leu Asn Arg Val
385                 390                 395                 400
Ile Glu Lys Thr Asn Glu Lys Phe His Gln Ile Glu Lys Glu Phe Ser
                   405                 410                 415
Glu Val Glu Gly Arg Ile Gln Asp Leu Glu Lys Tyr Val Glu Asp Thr
                   420                 425                 430
Lys Ile Asp Leu Trp Ser Tyr Asn Ala Glu Leu Leu Val Ala Leu Glu
                   435                 440                 445
Asn Gln His Thr Ile Asp Leu Thr Asp Ser Glu Met Asn Lys Leu Phe
                   450                 455                 460
Glu Lys Thr Arg Arg Gln Leu Arg Glu Asn Ala Glu Glu Met Gly Asn
465                 470                 475                 480
Gly Cys Phe Lys Ile Tyr His Lys Cys Asp Asn Ala Cys Ile Glu Ser
                   485                 490                 495
Ile Arg Asn Gly Thr Tyr Asp His Asp Val Tyr Arg Asp Glu Ala Leu
                   500                 505                 510
```

```
Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Val Leu Leu Gly Phe Ile Met Trp Ala Cys Gln Arg Gly Asn Ile
545                 550                 555                 560

Arg Cys Asn Ile Cys Ile
                565

<210> SEQ ID NO 49
<211> LENGTH: 566
<212> TYPE: PRT
<213> ORGANISM: Artificial Sequence
<220> FEATURE:
<223> OTHER INFORMATION: H1N1 influenza virus sequence

<400> SEQUENCE: 49

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Lys Phe Glu Ile Phe Pro Lys Thr Ser Ser Trp Pro Asn His Glu
    130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
            180                 185                 190

Leu Trp Gly Val His His Pro Pro Thr Gly Thr Asp Gln Gln Ser Leu
        195                 200                 205

Tyr Gln Asn Ala Asp Ala Tyr Val Ser Val Gly Ser Ser Lys Tyr Asn
    210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
                245                 250                 255

Ile Thr Phe Glu Ala Thr Gly Asn Leu Ile Ala Pro Trp Tyr Ala Phe
            260                 265                 270

Ala Leu Asn Arg Gly Ser Gly Ser Gly Ile Ile Thr Ser Asp Ala Pro
        275                 280                 285

Val His Asp Cys Asn Thr Lys Cys Gln Thr Pro His Gly Ala Ile Asn
    290                 295                 300
```

```
Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Arg Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Phe His Asp Ser Asn Val Arg Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 50
<211> LENGTH: 562
<212> TYPE: PRT
<213> ORGANISM: Artificial Sequence
<220> FEATURE:
<223> OTHER INFORMATION: H2N2 influenza virus sequence

<400> SEQUENCE: 50

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95
```

```
Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
            115                 120                 125

Val Lys Ile Leu Pro Lys Asp Arg Trp Thr Gln His Thr Thr Thr Gly
130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
            195                 200                 205

Gly Thr Tyr Val Ser Val Gly Thr Ser Thr Leu Asn Lys Arg Ser Thr
            210                 215                 220

Pro Asp Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Gly Asn Cys
            275                 280                 285

Glu Thr Lys Cys Gln Thr Pro Leu Gly Ala Ile Asn Thr Thr Leu Pro
            290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
            355                 360                 365

Asp Gln Gly Ser Gly Tyr Ala Ala Asp Lys Glu Ser Thr Gln Lys Ala
370                 375                 380

Phe Asp Gly Ile Thr Asn Arg Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
            435                 440                 445

Asp Phe His Asp Ser Asn Val Lys Asn Leu Tyr Asp Lys Val Lys Met
            450                 455                 460

Gln Leu Arg Asp Asn Val Lys Glu Leu Gly Asn Gly Cys Phe Glu Phe
465                 470                 475                 480

Tyr Pro Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510
```

```
Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
        530                 535                 540

Gly Ile Ser Phe Trp Met Cys Ser Asn Gly Ser Leu Gln Cys Arg Ile
545                 550                 555                 560

Cys Ile

<210> SEQ ID NO 51
<211> LENGTH: 570
<212> TYPE: PRT
<213> ORGANISM: Artificial Sequence
<220> FEATURE:
<223> OTHER INFORMATION: Lectin sequence

<400> SEQUENCE: 51

Met Arg Leu Val Ala Lys Leu Leu Tyr Leu Ala Val Leu Ala Ile Cys
1               5                   10                  15

Gly Leu Gly Ile His Gly Ala Leu Thr His Pro Arg Val Thr Pro Pro
            20                  25                  30

Val Tyr Pro Ser Val Ser Phe Asn Leu Thr Gly Ala Asp Thr Tyr Glu
        35                  40                  45

Pro Phe Leu Arg Ala Leu Gln Glu Lys Val Ile Leu Gly Asn His Thr
    50                  55                  60

Ala Phe Asp Leu Pro Val Leu Asn Pro Glu Ser Gln Val Ser Asp Ser
65                  70                  75                  80

Asn Arg Phe Val Leu Val Pro Leu Thr Asn Pro Ser Gly Asp Thr Val
                85                  90                  95

Thr Leu Ala Ile Asp Val Val Asn Leu Tyr Val Val Ala Phe Ser Ser
            100                 105                 110

Asn Gly Lys Ser Tyr Phe Phe Ser Gly Ser Thr Ala Val Gln Arg Asp
        115                 120                 125

Asn Leu Phe Val Asp Thr Thr Gln Glu Glu Leu Asn Phe Thr Gly Asn
    130                 135                 140

Tyr Thr Ser Leu Glu Arg Gln Val Gly Phe Gly Arg Val Tyr Ile Pro
145                 150                 155                 160

Leu Gly Pro Lys Ser Leu Asp Gln Ala Ile Ser Ser Leu Arg Thr Tyr
                165                 170                 175

Thr Leu Thr Ala Gly Asp Thr Lys Pro Leu Ala Arg Gly Leu Leu Val
            180                 185                 190

Val Ile Gln Met Val Ser Glu Ala Ala Arg Phe Arg Tyr Ile Glu Leu
        195                 200                 205

Arg Ile Arg Thr Ser Ile Thr Asp Ala Ser Glu Phe Thr Pro Asp Leu
    210                 215                 220

Leu Met Leu Ser Met Glu Asn Asn Trp Ser Ser Met Ser Ser Glu Ile
225                 230                 235                 240

Gln Gln Ala Gln Pro Gly Gly Ile Phe Ala Gly Val Val Gln Leu Arg
                245                 250                 255

Asp Glu Arg Asn Asn Ser Ile Glu Val Thr Asn Phe Arg Arg Leu Phe
            260                 265                 270

Glu Leu Thr Tyr Ile Ala Val Leu Leu Tyr Gly Cys Ala Pro Val Thr
        275                 280                 285

Ser Ser Ser Tyr Ser Asn Asn Ala Ile Asp Ala Gln Ile Ile Lys Met
    290                 295                 300

Pro Val Phe Arg Gly Gly Glu Tyr Glu Lys Val Cys Ser Val Val Glu
```

-continued 305 310 315 320

Val Thr Arg Arg Ile Ser Gly Trp Asp Gly Leu Cys Val Asp Val Arg
325 330 335

Tyr Gly His Tyr Ile Asp Gly Asn Pro Val Gln Leu Arg Pro Cys Gly
340 345 350

Asn Glu Cys Asn Gln Leu Trp Thr Phe Arg Thr Asp Gly Thr Ile Arg
355 360 365

Trp Leu Gly Lys Cys Leu Thr Ala Ser Ser Ser Val Met Ile Tyr Asp
370 375 380

Cys Asn Thr Val Pro Pro Glu Ala Thr Lys Trp Val Val Ser Ile Asp
385 390 395 400

Gly Thr Ile Thr Asn Pro His Ser Gly Leu Val Leu Thr Ala Pro Gln
405 410 415

Ala Ala Glu Gly Thr Ala Leu Ser Leu Glu Asn Asn Ile His Ala Ala
420 425 430

Arg Gln Gly Trp Thr Val Gly Asp Val Glu Pro Leu Val Thr Phe Ile
435 440 445

Val Gly Tyr Lys Gln Met Cys Leu Arg Glu Asn Gly Glu Asn Asn Phe
450 455 460

Val Trp Leu Glu Asp Cys Val Leu Asn Arg Val Gln Gln Glu Trp Ala
465 470 475 480

Leu Tyr Gly Asp Gly Thr Ile Arg Val Asn Ser Asn Arg Ser Leu Cys
485 490 495

Val Thr Ser Glu Asp His Glu Pro Ser Asp Leu Ile Val Ile Leu Lys
500 505 510

Cys Glu Gly Ser Gly Asn Gln Arg Trp Val Phe Asn Thr Asn Gly Thr
515 520 525

Ile Ser Asn Pro Asn Ala Lys Leu Leu Met Asp Val Ala Gln Arg Asp
530 535 540

Val Ser Leu Arg Lys Ile Ile Leu Tyr Arg Pro Thr Gly Asn Pro Asn
545 550 555 560

Gln Gln Trp Ile Thr Thr Thr His Pro Ala
565 570

<210> SEQ ID NO 52
<211> LENGTH: 569
<212> TYPE: PRT
<213> ORGANISM: Artificial Sequence
<220> FEATURE:
<223> OTHER INFORMATION: Lectin sequence

<400> SEQUENCE: 52

Met Lys Val Val Ala Thr Ile Leu Tyr Leu Val Val Leu Ala Ile Cys
1 5 10 15

Gly Leu Gly Ile His Gly Ala His Pro Thr His Ser Ala Pro Pro Thr
20 25 30

Val Tyr Pro Ser Val Ser Phe Asn Leu Thr Glu Ala Asn Ser Asn Glu
35 40 45

Tyr Arg His Phe Leu Gln Glu Leu Arg Gly Lys Val Ile Leu Gly Ser
50 55 60

His Arg Ala Phe Asp Leu Pro Val Leu Asn Pro Glu Ser Lys Val Ser
65 70 75 80

Asp Ser Asp Arg Phe Val Leu Val Arg Leu Thr Asn Pro Ser Arg Lys
85 90 95

Lys Val Thr Leu Ala Ile Asp Val Val Thr Phe Tyr Val Val Ala Phe

```
            100                 105                 110
Ala Gln Asn Asp Arg Ser Tyr Phe Phe Ser Gly Ser Ser Glu Val Gln
        115                 120                 125

Arg Glu Asn Leu Phe Val Asp Thr Thr Gln Glu Asp Leu Asn Phe Lys
130                 135                 140

Gly Asp Tyr Thr Ser Leu Glu His Gln Val Gly Phe Gly Arg Val Tyr
145                 150                 155                 160

Ile Pro Leu Gly Pro Lys Ser Leu Ala Gln Ser Ile Ser Ser Leu Ser
                165                 170                 175

Thr Tyr Lys Ser Ser Ala Gly Asp Asn Lys Arg Leu Ala Arg Ser Leu
            180                 185                 190

Leu Val Val Ile Gln Met Val Ser Glu Ala Ala Arg Phe Arg Tyr Ile
        195                 200                 205

Gln Leu Arg Ile Gln Ala Ser Ile Thr Asp Ala Lys Glu Phe Thr Pro
    210                 215                 220

Asp Leu Leu Met Leu Ser Met Glu Asn Lys Trp Ser Ser Met Ser Ser
225                 230                 235                 240

Glu Ile Gln Gln Ala Gln Pro Gly Gly Ala Phe Ala Gln Val Val Lys
                245                 250                 255

Leu Leu Asp Gln Arg Asn His Pro Ile Asp Val Thr Asn Phe Arg Arg
            260                 265                 270

Leu Phe Gln Leu Thr Ser Val Ala Val Leu His Gly Cys Pro Thr
        275                 280                 285

Val Thr Lys Met Pro Ala Tyr Ile Ile Lys Met Pro Val Phe Asn Gly
    290                 295                 300

Gly Glu Asp Glu Glu Arg Cys Ser Val Glu Glu Val Thr Arg Arg
305                 310                 315                 320

Ile Gly Gly Arg Asp Gly Phe Cys Ala Glu Val Lys Asn Gly Asp Glu
                325                 330                 335

Lys Asp Gly Thr Pro Val Gln Leu Ser Ser Cys Gly Glu Gln Ser Asn
            340                 345                 350

Gln Gln Trp Thr Phe Ser Thr Asp Gly Thr Ile Gln Ser Leu Gly Lys
        355                 360                 365

Cys Leu Thr Thr Ser Ser Val Met Ile Tyr Asn Cys Lys Val Val
    370                 375                 380

Pro Pro Glu Ser Thr Lys Trp Val Val Ser Ile Asp Gly Thr Ile Thr
385                 390                 395                 400

Asn Pro Arg Ser Gly Leu Val Leu Thr Ala Pro Lys Ala Ala Glu Gly
                405                 410                 415

Thr Leu Val Ser Leu Glu Lys Asn Val His Ala Ala Arg Gln Gly Trp
            420                 425                 430

Ile Val Gly Asn Val Glu Pro Leu Val Thr Phe Ile Val Gly Tyr Glu
        435                 440                 445

Gln Met Cys Leu Glu Thr Asn Pro Gly Asn Asn Asp Val Ser Leu Gly
    450                 455                 460

Asp Cys Ser Val Lys Ser Ala Ser Lys Val Asp Gln Lys Trp Ala Leu
465                 470                 475                 480

Tyr Gly Asp Gly Thr Ile Arg Val Asn Asn Asp Arg Ser Leu Cys Val
                485                 490                 495

Thr Ser Glu Gly Lys Ser Ser Asn Glu Pro Ile Ile Ile Leu Lys Cys
            500                 505                 510

Leu Gly Trp Ala Asn Gln Arg Trp Val Phe Asn Thr Asp Gly Thr Ile
        515                 520                 525
```

```
Ser Asn Pro Asp Ser Lys Leu Val Met His Val Asp Gln Asn Asp Val
            530                 535                 540

Pro Leu Arg Lys Ile Ile Leu Ser His Pro Ser Gly Thr Ser Asn Gln
545                 550                 555                 560

Gln Trp Ile Ala Ser Thr His Pro Ala
                565

<210> SEQ ID NO 53
<211> LENGTH: 286
<212> TYPE: PRT
<213> ORGANISM: Artificial Sequence
<220> FEATURE:
<223> OTHER INFORMATION: Lectin sequence

<400> SEQUENCE: 53

Met Ser Phe Gln Gly His Gly Ile Tyr Tyr Ile Ala Ser Ala Tyr Val
1               5                   10                  15

Ala Asn Thr Arg Leu Ala Leu Ser Glu Asp Ser Ser Ala Asn Lys Ser
            20                  25                  30

Pro Asp Val Ile Ile Ser Ser Asp Ala Val Asp Pro Leu Asn Asn Leu
        35                  40                  45

Trp Leu Ile Glu Pro Val Gly Glu Ala Asp Thr Tyr Thr Val Arg Asn
    50                  55                  60

Ala Phe Ala Gly Ser Tyr Met Asp Leu Ala Gly His Ala Ala Thr Asp
65                  70                  75                  80

Gly Thr Ala Ile Ile Gly Tyr Arg Pro Thr Gly Gly Asp Asn Gln Lys
                85                  90                  95

Trp Ile Ile Ser Gln Ile Asn Asp Val Trp Lys Ile Lys Ser Lys Glu
            100                 105                 110

Thr Gly Thr Phe Val Thr Leu Leu Asn Gly Asp Gly Gly Thr Gly
        115                 120                 125

Thr Val Val Gly Trp Gln Asn Ile Thr Asn Asn Thr Ser Gln Asn Trp
    130                 135                 140

Thr Phe Gln Lys Leu Ser Gln Thr Gly Ala Asn Val His Ala Thr Leu
145                 150                 155                 160

Leu Ala Cys Pro Ala Leu Arg Gln Asp Phe Lys Ser Tyr Leu Ser Asp
                165                 170                 175

Gly Leu Tyr Leu Val Leu Thr Arg Asp Gln Ile Ser Ser Ile Trp Gln
            180                 185                 190

Ala Ser Gly Leu Gly Ser Thr Pro Trp Arg Ser Glu Ile Phe Asp Cys
        195                 200                 205

Asp Asp Phe Ala Thr Val Phe Lys Gly Ala Val Ala Lys Trp Gly Asn
    210                 215                 220

Glu Asn Phe Lys Ala Asn Gly Phe Ala Leu Leu Cys Gly Leu Met Phe
225                 230                 235                 240

Gly Ser Lys Ser Ser Gly Ala His Ala Tyr Asn Trp Phe Val Glu Arg
                245                 250                 255

Gly Asn Phe Ser Thr Val Thr Phe Phe Glu Pro Gln Asn Gly Thr Tyr
            260                 265                 270

Ser Ala Asn Ala Trp Asp Tyr Lys Ala Tyr Phe Gly Leu Phe
        275                 280                 285

<210> SEQ ID NO 54
<211> LENGTH: 292
<212> TYPE: PRT
<213> ORGANISM: Artificial Sequence
```

<220> FEATURE:
<223> OTHER INFORMATION: Lectin sequence

<400> SEQUENCE: 54

Met Ser Phe Glu Gly His Gly Ile Tyr His Ile Pro His Ala His Val
1               5                   10                  15

Ala Asn Ile Arg Met Ala Leu Ala Asn Arg Gly Ser Gly Gln Asn Gly
            20                  25                  30

Thr Pro Val Ile Ala Trp Asp Ser Asn Asp Ala Phe Asp His Met
        35                  40                  45

Trp Leu Val Glu Pro Thr Gly Glu Ala Asp Thr Tyr Thr Ile His Asn
    50                  55                  60

Val Ser Thr Gly Thr Tyr Met Asp Val Thr Ala Ser Val Ala Asp
65              70                  75                  80

Asn Thr Pro Ile Ile Gly Tyr Gln Arg Thr Gly Asn Asp Asn Gln Lys
                85                  90                  95

Trp Ile Ile Arg Gln Val Gln Thr Asp Gly Asp Arg Pro Trp Lys
            100                 105                 110

Ile Gln Cys Lys Ala Thr Gly Thr Phe Ala Thr Leu Tyr Ser Gly Gly
        115                 120                 125

Gly Ser Gly Thr Ala Ile Val Gly Trp Arg Leu Val Asn Ser Asn Gly
    130                 135                 140

Asn Gln Asp Trp Val Phe Gln Lys Leu Ser Gln Thr Ser Val Asn Val
145                 150                 155                 160

His Ala Thr Leu Leu Ala Cys Gly Ala Thr Val Gly Gln Asp Phe Lys
                165                 170                 175

Asn Tyr Leu Tyr Asp Gly Leu Tyr Leu Val Leu Pro Arg Asp Arg Ile
            180                 185                 190

Ser Ala Ile Trp Lys Ala Ser Gly Leu Gly Glu Thr Ala Arg Arg Asp
        195                 200                 205

Gly Ile Tyr Asp Ser Asp Glu Phe Ala Met Thr Phe Lys Ser Ala Ala
    210                 215                 220

Ala Thr Trp Gly Lys Glu Asn Phe Lys Ala Asp Gly Phe Ala Ile Leu
225                 230                 235                 240

Cys Gly Met Met Phe Gly Thr Lys Ala Ser Thr Asn Arg His Ala Tyr
                245                 250                 255

Asn Trp Val Val Glu Arg Gly Ser Phe Ser Thr Val Thr Phe Phe Glu
            260                 265                 270

Pro Gln Asn Gly Thr Tyr Ser Asp Asp Ala Trp Gly Tyr Lys Ala Tyr
        275                 280                 285

Phe Gly Leu Phe
    290

<210> SEQ ID NO 55
<211> LENGTH: 91
<212> TYPE: PRT
<213> ORGANISM: Artificial Sequence
<220> FEATURE:
<223> OTHER INFORMATION: HA Sequence Element 1
<220> FEATURE:
<221> NAME/KEY: MISC_FEATURE
<222> LOCATION: (5)..(34)
<223> OTHER INFORMATION: X = any amino acid
<220> FEATURE:
<221> NAME/KEY: MISC_FEATURE
<222> LOCATION: (36)..(64)
<223> OTHER INFORMATION: X = any amino acid
<220> FEATURE:
<221> NAME/KEY: MISC_FEATURE

```
<222> LOCATION: (66)..(69)
<223> OTHER INFORMATION: X = any amino acid
<220> FEATURE:
<221> NAME/KEY: MISC_FEATURE
<222> LOCATION: (71)..(76)
<223> OTHER INFORMATION: X = any amino acid
<220> FEATURE:
<221> NAME/KEY: MISC_FEATURE
<222> LOCATION: (78)..(88)
<223> OTHER INFORMATION: X = any amino acid

<400> SEQUENCE: 55

Cys Tyr Pro Gly Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Arg Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Ala Xaa Xaa Xaa Xaa Met Xaa Xaa Xaa Xaa Xaa Pro Xaa Xaa Xaa Xaa
65                  70                  75                  80

Xaa Xaa Xaa Xaa Xaa Xaa Xaa Xaa His His Ser
            85                  90

<210> SEQ ID NO 56
<211> LENGTH: 560
<212> TYPE: PRT
<213> ORGANISM: Artificial Sequence
<220> FEATURE:
<223> OTHER INFORMATION: H7N8 influenza virus sequence

<400> SEQUENCE: 56

Met Asn Thr Gln Ile Leu Ala Leu Ile Ala Cys Met Leu Ile Gly Ala
1               5                   10                  15

Lys Gly Asp Lys Ile Cys Leu Gly His His Ala Val Ala Asn Gly Thr
            20                  25                  30

Lys Val Asn Thr Leu Thr Glu Arg Gly Ile Glu Val Val Asn Ala Thr
        35                  40                  45

Glu Thr Val Glu Thr Ala Asn Ile Lys Lys Ile Cys Thr Gln Gly Lys
    50                  55                  60

Arg Pro Thr Asp Leu Gly Gln Cys Gly Leu Leu Gly Thr Leu Ile Gly
65                  70                  75                  80

Pro Pro Gln Cys Asp Gln Phe Leu Glu Phe Asp Ala Asp Leu Ile Ile
                85                  90                  95

Glu Arg Arg Glu Gly Thr Asp Val Cys Tyr Pro Gly Lys Phe Thr Asn
            100                 105                 110

Glu Glu Ser Leu Arg Gln Ile Leu Arg Gly Ser Gly Ile Asp Lys
        115                 120                 125

Glu Ser Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Ser Asp Asn Ala Ala Phe Pro Gln Met Thr Lys Ser
                165                 170                 175

Tyr Arg Asn Pro Arg Asn Lys Pro Ala Leu Ile Ile Trp Gly Val His
            180                 185                 190

His Ser Gly Ser Ala Thr Glu Gln Thr Lys Leu Tyr Gly Ser Gly Asn
        195                 200                 205
```

Lys Leu Ile Thr Val Gly Ser Ser Lys Tyr Gln Gln Ser Phe Thr Pro
210                 215                 220

Ser Pro Gly Ala Arg Pro Gln Val Asn Gly Gln Ser Gly Arg Ile Asp
225                 230                 235                 240

Phe His Trp Leu Leu Leu Asp Pro Asn Asp Thr Val Thr Phe Thr Phe
                245                 250                 255

Asn Gly Ala Phe Ile Ala Pro Asp Arg Ala Ser Phe Phe Arg Gly Glu
                260                 265                 270

Ser Leu Gly Val Gln Ser Asp Val Pro Leu Asp Ser Gly Cys Glu Gly
                275                 280                 285

Asp Cys Phe His Asn Gly Gly Thr Ile Val Ser Ser Leu Pro Phe Gln
290                 295                 300

Asn Ile Asn Pro Arg Thr Val Gly Lys Cys Pro Arg Tyr Val Lys Gln
305                 310                 315                 320

Thr Ser Leu Leu Leu Ala Thr Gly Met Arg Asn Val Pro Glu Asn Pro
                325                 330                 335

Lys Thr Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
                355                 360                 365

Gln Gly Glu Gly Thr Ala Ala Asp Tyr Lys Thr Thr Gln Ser Ala Ile
                370                 375                 380

Asp Gln Ile Thr Gly Lys Leu Asn Arg Leu Ile Asp Lys Thr Asn Gln
385                 390                 395                 400

Gln Phe Glu Leu Ile Asp Asn Glu Phe Ser Glu Ile Glu Gln Gln Ile
                405                 410                 415

Gly Asn Val Ile Asn Trp Thr Arg Asp Ser Met Thr Glu Val Trp Ser
                420                 425                 430

Tyr Asn Ala Glu Leu Leu Val Ala Met Glu Asn Gln His Thr Ile Asp
                435                 440                 445

Leu Ala Asp Ser Glu Met Asn Lys Leu Tyr Glu Arg Val Arg Lys Gln
450                 455                 460

Leu Arg Glu Asn Ala Glu Glu Asp Gly Thr Gly Cys Phe Glu Ile Phe
465                 470                 475                 480

His Lys Cys Asp Asp Gln Cys Met Glu Ser Ile Arg Asn Asn Thr Tyr
                485                 490                 495

Asp His Thr Gln Tyr Arg Ala Glu Ser Leu Gln Asn Arg Ile Gln Ile
                500                 505                 510

Asp Pro Val Lys Leu Ser Ser Gly Tyr Lys Asp Ile Ile Leu Trp Phe
                515                 520                 525

Ser Phe Gly Ala Ser Cys Phe Leu Leu Leu Ala Ile Ala Met Gly Leu
530                 535                 540

Val Phe Ile Cys Ile Lys Asn Gly Asn Met Arg Cys Thr Ile Cys Ile
545                 550                 555                 560

<210> SEQ ID NO 57
<211> LENGTH: 560
<212> TYPE: PRT
<213> ORGANISM: Artificial Sequence
<220> FEATURE:
<223> OTHER INFORMATION: H7N7 Influenza virus sequence

<400> SEQUENCE: 57

Met Asn Thr Gln Ile Leu Ala Leu Ile Ala Cys Met Leu Ile Gly Ala
1               5

```
Lys Gly Asp Lys Ile Cys Leu Gly His His Ala Val Ala Asn Gly Thr
            20                  25                  30
Lys Val Asn Thr Leu Thr Glu Arg Gly Ile Glu Val Val Asn Ala Thr
        35                  40                  45
Glu Thr Val Glu Thr Ala Asn Ile Lys Lys Ile Cys Thr Gln Gly Lys
50                  55                  60
Arg Pro Thr Asp Leu Gly Gln Cys Gly Leu Leu Gly Thr Leu Ile Gly
65                  70                  75                  80
Pro Pro Gln Cys Asp Gln Phe Leu Glu Phe Asp Ala Asp Leu Ile Ile
                85                  90                  95
Glu Arg Arg Glu Gly Thr Asp Val Cys Tyr Pro Gly Lys Phe Thr Asn
                100                 105                 110
Glu Glu Ser Leu Arg Gln Ile Leu Arg Gly Ser Gly Gly Ile Asp Lys
            115                 120                 125
Glu Ser Met Gly Phe Thr Tyr Ser Gly Ile Arg Thr Asn Gly Val Thr
130                 135                 140
Ser Ala Cys Arg Arg Ser Gly Ser Ser Phe Tyr Ala Glu Met Lys Trp
145                 150                 155                 160
Leu Leu Ser Asn Ser Asp Asn Ala Ala Phe Pro Gln Met Thr Lys Ser
                165                 170                 175
Tyr Arg Asn Pro Arg Asn Lys Pro Ala Leu Ile Ile Trp Gly Val His
                180                 185                 190
His Ser Gly Ser Ala Thr Glu Gln Thr Lys Leu Tyr Gly Ser Gly Asn
            195                 200                 205
Lys Leu Ile Thr Val Gly Ser Ser Lys Tyr Gln Gln Ser Phe Thr Pro
210                 215                 220
Ser Pro Gly Ala Arg Pro Gln Val Asn Gly Gln Ser Gly Arg Ile Asp
225                 230                 235                 240
Phe His Trp Leu Leu Leu Asp Pro Asn Asp Thr Val Thr Phe Thr Phe
                245                 250                 255
Asn Gly Ala Phe Ile Ala Pro Asp Arg Ala Ser Phe Phe Arg Gly Glu
                260                 265                 270
Ser Leu Gly Val Gln Ser Asp Val Pro Leu Asp Ser Gly Cys Glu Gly
            275                 280                 285
Asp Cys Phe His Asn Gly Gly Thr Ile Val Ser Ser Leu Pro Phe Gln
290                 295                 300
Asn Ile Asn Pro Arg Thr Val Gly Lys Cys Pro Arg Tyr Val Lys Gln
305                 310                 315                 320
Thr Ser Leu Leu Leu Ala Thr Gly Met Arg Asn Val Pro Glu Asn Pro
                325                 330                 335
Lys Thr Arg Gly Leu Phe Gly Ala Ile Ala Gly Phe Ile Glu Asn Gly
                340                 345                 350
Trp Glu Gly Leu Ile Asp Gly Trp Tyr Gly Phe Arg His Gln Asn Ala
            355                 360                 365
Gln Gly Glu Gly Thr Ala Ala Asp Tyr Lys Ser Thr Gln Ser Ala Ile
370                 375                 380
Asp Gln Ile Thr Gly Lys Leu Asn Arg Leu Ile Asp Lys Thr Asn Gln
385                 390                 395                 400
Gln Phe Glu Leu Ile Asp Asn Glu Phe Ser Glu Ile Glu Gln Gln Ile
                405                 410                 415
Gly Asn Val Ile Asn Trp Thr Arg Asp Ser Met Thr Glu Val Trp Ser
                420                 425                 430
```

-continued

Tyr Asn Ala Glu Leu Leu Val Ala Met Glu Asn Gln His Thr Ile Asp
                435                 440                 445

Leu Ala Asp Ser Glu Met Asn Lys Leu Tyr Glu Arg Val Arg Lys Gln
450                 455                 460

Leu Arg Glu Asn Ala Glu Glu Asp Gly Thr Gly Cys Phe Glu Ile Phe
465                 470                 475                 480

His Lys Cys Asp Asp Gln Cys Met Glu Ser Ile Arg Asn Asn Thr Tyr
                485                 490                 495

Asp His Thr Gln Tyr Arg Thr Glu Ser Leu Gln Asn Arg Ile Gln Ile
                500                 505                 510

Asp Pro Val Lys Leu Ser Ser Gly Tyr Lys Asp Ile Ile Leu Trp Phe
                515                 520                 525

Ser Phe Gly Ala Ser Cys Phe Leu Leu Leu Ala Ile Ala Met Gly Leu
                530                 535                 540

Val Phe Ile Cys Ile Lys Asn Gly Asn Met Arg Cys Thr Ile Cys Ile
545                 550                 555                 560

<210> SEQ ID NO 58
<211> LENGTH: 552
<212> TYPE: PRT
<213> ORGANISM: Artificial Sequence
<220> FEATURE:
<223> OTHER INFORMATION: H7N2 influenza virus sequence

<400> SEQUENCE: 58

Met Asn Ile Gln Ile Leu Ala Phe Ile Ala

```
Asn Asp Thr Val Thr Phe Thr Phe Asn Gly Ala Phe Ile Ala Pro Asp
                245                 250                 255

Arg Ala Ser Phe Phe Arg Gly Glu Ser Leu Gly Val Gln Ser Asp Ala
            260                 265                 270

Pro Leu Asp Ser Ser Cys Arg Gly Asp Cys Phe His Ser Gly Gly Thr
            275                 280                 285

Ile Val Ser Ser Leu Pro Phe Gln Asn Ile Asn Ser Arg Thr Val Gly
            290                 295                 300

Arg Cys Pro Arg Tyr Val Lys Gln Lys Ser Leu Leu Leu Ala Thr Gly
305                 310                 315                 320

Met Arg Asn Val Pro Glu Lys Pro Lys Pro Arg Gly Leu Phe Gly Ala
                325                 330                 335

Ile Ala Gly Phe Ile Glu Asn Gly Trp Glu Gly Leu Ile Asn Gly Trp
            340                 345                 350

Tyr Gly Phe Arg His Gln Asn Ala Gln Gly Glu Gly Thr Ala Ala Asp
            355                 360                 365

Tyr Lys Ser Thr Gln Ser Ala Ile Asp Gln Ile Thr Gly Lys Leu Asn
            370                 375                 380

Arg Leu Ile Gly Lys Thr Asn Gln Gln Phe Glu Leu Ile Asp Asn Glu
385                 390                 395                 400

Phe Asn Glu Ile Glu Gln Gln Ile Gly Asn Val Ile Asn Trp Thr Arg
                405                 410                 415

Asp Ala Met Thr Glu Ile Trp Ser Tyr Asn Ala Glu Leu Leu Val Ala
            420                 425                 430

Met Glu Asn Gln His Thr Ile Asp Leu Ala Asp Ser Glu Met Ser Lys
            435                 440                 445

Leu Tyr Glu Arg Val Lys Lys Gln Leu Arg Glu Asn Ala Glu Glu Asp
450                 455                 460

Gly Thr Gly Cys Phe Glu Ile Phe His Lys Cys Asp Asp Gln Cys Met
465                 470                 475                 480

Glu Ser Ile Arg Asn Asn Thr Tyr Asp His Thr Gln Tyr Arg Thr Glu
                485                 490                 495

Ser Leu Gln Asn Arg Ile Gln Ile Asp Pro Val Lys Leu Ser Ser Gly
            500                 505                 510

Tyr Lys Asp Ile Ile Leu Trp Phe Ser Phe Gly Ala Ser Cys Phe Ile
            515                 520                 525

Leu Leu Ala Ile Ala Met Gly Leu Val Phe Ile Cys Ile Lys Asn Gly
            530                 535                 540

Asn Met Gln Cys Thr Ile Cys Ile
545                 550

<210> SEQ ID NO 59
<211> LENGTH: 569
<212> TYPE: PRT
<213> ORGANISM: Artificial Sequence
<220> FEATURE:
<223> OTHER INFORMATION: H7N7 influenza virus sequence

<400> SEQUENCE: 59

Ser Lys Ser Arg Gly Tyr Lys Met Asn Thr Gln Ile Leu Val Phe Ala
1               5                   10                  15

Leu Val Ala Ser Ile Pro Thr Asn Ala Asp Lys Ile Cys Leu Gly His
            20                  25                  30

His Ala Val Ser Asn Gly Thr Lys Val Asn Thr Leu Thr Glu Arg Gly
            35                  40                  45
```

```
Val Glu Val Val Asn Ala Thr Glu Thr Val Glu Arg Thr Asn Val Pro
    50                  55                  60

Arg Ile Cys Ser Lys Gly Lys Arg Thr Val Asp Leu Gly Gln Cys Gly
65                  70                  75                  80

Leu Leu Gly Thr Ile Thr Gly Pro Pro Gln Cys Asp Gln Phe Leu Glu
                    85                  90                  95

Phe Ser Ala Asp Leu Ile Ile Glu Arg Arg Glu Gly Ser Asp Val Cys
                100                 105                 110

Tyr Pro Gly Lys Phe Val Asn Glu Glu Ala Leu Arg Gln Ile Leu Arg
                115                 120                 125

Glu Ser Gly Gly Ile Asp Lys Glu Thr Met Gly Phe Thr Tyr Ser Gly
130                 135                 140

Ile Arg Thr Asn Gly Thr Thr Ser Ala Cys Arg Arg Ser Gly Ser Ser
145                 150                 155                 160

Phe Tyr Ala Glu Met Lys Trp Leu Leu Ser Asn Thr Asp Asn Ala Ala
                    165                 170                 175

Phe Pro Gln Met Thr Lys Ser Tyr Lys Asn Thr Arg Lys Asp Pro Ala
                180                 185                 190

Leu Ile Ile Trp Gly Ile His His Ser Gly Ser Thr Thr Glu Gln Thr
                    195                 200                 205

Lys Leu Tyr Gly Ser Gly Asn Lys Leu Ile Thr Val Gly Ser Ser Asn
210                 215                 220

Tyr Gln Gln Ser Phe Val Pro Ser Pro Gly Ala Arg Pro Gln Val Asn
225                 230                 235                 240

Gly Gln Ser Gly Arg Ile Asp Phe His Trp Leu Ile Leu Asn Pro Asn
                    245                 250                 255

Asp Thr Val Thr Phe Ser Phe Asn Gly Ala Phe Ile Ala Pro Asp Arg
                260                 265                 270

Ala Ser Phe Leu Arg Gly Lys Ser Met Gly Ile Gln Ser Glu Val Gln
                275                 280                 285

Val Asp Ala Asn Cys Glu Gly Asp Cys Tyr His Ser Gly Gly Thr Ile
                290                 295                 300

Ile Ser Asn Leu Pro Phe Gln Asn Ile Asn Ser Arg Ala Val Gly Lys
305                 310                 315                 320

Cys Pro Arg Tyr Val Lys Gln Glu Ser Leu Leu Leu Ala Thr Gly Met
                    325                 330                 335

Lys Asn Val Pro Glu Ile Pro Lys Arg Arg Arg Arg Gly Leu Phe Gly
                340                 345                 350

Ala Ile Ala Gly Phe Ile Glu Asn Gly Trp Glu Gly Leu Ile Asp Gly
                355                 360                 365

Trp Tyr Gly Phe Arg His Gln Asn Ala Gln Gly Glu Gly Thr Ala Ala
    370                 375                 380

Asp Tyr Lys Ser Thr Gln Ser Ala Ile Asp Gln Ile Thr Gly Lys Leu
385                 390                 395                 400

Asn Arg Leu Ile Glu Lys Thr Asn Gln Gln Phe Glu Leu Ile Asp Asn
                    405                 410                 415

Glu Phe Thr Glu Val Glu Arg Gln Ile Gly Asn Val Ile Asn Trp Thr
                420                 425                 430

Arg Asp Ser Met Thr Glu Val Trp Ser Tyr Asn Ala Glu Leu Leu Val
                435                 440                 445

Ala Met Glu Asn Gln His Thr Ile Asp Leu Ala Asp Ser Glu Met Asn
450                 455                 460

Lys Leu Tyr Glu Arg Val Lys Arg Gln Leu Arg Glu Asn Ala Glu Glu
```

```
            465                 470                 475                 480
Asp Gly Thr Gly Cys Phe Glu Ile Phe His Lys Cys Asp Asp Cys
                    485                 490                 495

Met Ala Ser Ile Arg Asn Asn Thr Tyr Asp His Ser Lys Tyr Arg Glu
                500                 505                 510

Glu Ala Ile Gln Asn Arg Ile Gln Ile Asp Pro Val Lys Leu Ser Ser
            515                 520                 525

Gly Tyr Lys Asp Val Ile Leu Trp Phe Ser Phe Gly Ala Ser Cys Phe
        530                 535                 540

Ile Leu Leu Ala Ile Ala Met Gly Leu Val Phe Ile Cys Val Lys Asn
545                 550                 555                 560

Gly Asn Met Arg Cys Thr Ile Cys Ile
                565

<210> SEQ ID NO 60
<211> LENGTH: 560
<212> TYPE: PRT
<213> ORGANISM: Artificial Sequence
<220> FEATURE:
<223> OTHER INFORMATION: H7N6 influenza virus sequence

<400> SEQUENCE: 60

Met Asn Thr Gln Ile Leu Val Phe Ala Leu Val Ala Ile Ile Pro Thr
1               5                   10                  15

```
                260                 265                 270
Ser Ile Gly Ile Gln Ser Gly Val Gln Val Asp Ala Gly Cys Glu Gly
                275                 280                 285

Asn Cys Tyr His Asn Gly Gly Thr Ile Ile Ser Asn Leu Pro Phe Gln
            290                 295                 300

Asn Ile Asn Ser Arg Ala Val Gly Lys Cys Pro Arg Tyr Val Lys Gln
305                 310                 315                 320

Glu Ser Leu Leu Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
            370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Thr Glu Val Glu Lys Gln Ile
                405                 410                 415

Gly Asn Val Ile Asn Trp Thr Arg Asp Ser Met Thr Glu Val Trp Ser
                420                 425                 430

Tyr Asn Ala Glu Leu Leu Val Ala Met Glu Asn Gln His Thr Ile Asp
            435                 440                 445

Leu Ala Asp Ser Glu Met Asn Lys Leu Tyr Glu Arg Val Arg Arg Gln
450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Lys Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Ala Met Gly Leu
            530                 535                 540

Val Phe Ile Cys Val Lys Asn Gly Asn Met Arg Cys Thr Ile Cys Ile
545                 550                 555                 560

<210> SEQ ID NO 61
<211> LENGTH: 560
<212> TYPE: PRT
<213> ORGANISM: Artificial Sequence
<220> FEATURE:
<223> OTHER INFORMATION: H7N5 influenza virus sequence

<400> SEQUENCE: 61

Met Asn Thr Gln Ile Leu Ala Leu Ile Ala Cys Met Leu Ile Gly Ala
1               5                   10                  15

Glu Gly Asp Lys Ile Cys Leu Gly His His Ala Val Ala Asn Gly Thr
            20                  25                  30

Lys Val Asn Thr Leu Thr Glu Arg Gly Ile Glu Val Val Asn Ala Thr
        35                  40                  45

Glu Thr Val Glu Thr Ala Asp Ile Lys Lys Ile Cys Thr Gln Gly Lys
    50                  55                  60

Arg Pro Thr Asp Leu Gly Gln Cys Gly Leu Leu Gly Thr Leu Ile Gly
```

```
                65                  70                  75                  80
Pro Pro Gln Cys Asp Gln Phe Leu Glu Phe Asp Ala Asp Leu Ile Ile
                    85                  90                  95
Glu Arg Arg Glu Gly Thr Asp Val Cys Tyr Pro Gly Lys Phe Thr Asn
                    100                 105                 110
Glu Glu Ser Leu Arg Gln Ile Leu Arg Gly Ser Gly Ile Asp Lys
                    115                 120                 125
Glu Ser Met Gly Phe Thr Tyr Ser Gly Ile Arg Thr Asn Gly Ala Thr
        130                 135                 140
Ser Ala Cys Arg Arg Ser Gly Ser Ser Phe Tyr Ala Glu Met Lys Trp
145                 150                 155                 160
Leu Leu Ser Asn Ser Asp Asn Ala Ala Phe Pro Gln Met Thr Lys Ser
                    165                 170                 175
Tyr Arg Asn Pro Arg Asn Lys Pro Ala Leu Ile Ile Trp Gly Val His
                    180                 185                 190
His Ser Gly Ser Ala Thr Glu Gln Thr Lys Leu Tyr Gly Ser Gly Asn
        195                 200                 205
Lys Leu Ile Thr Val Gly Ser Ser Lys Tyr Gln Gln Ser Phe Thr Pro
210                 215                 220
Ser Pro Gly Ala Arg Pro Gln Val Asn Gly Gln Ser Gly Arg Ile Asp
225                 230                 235                 240
Phe His Trp Leu Leu Leu Asp Pro Asn Asp Thr Val Thr Phe Thr Phe
                    245                 250                 255
Asn Gly Ala Phe Ile Ala Pro Asp Arg Ala Ser Phe Phe Arg Gly Glu
                    260                 265                 270
Ser Leu Gly Val Gln Ser Asp Val Pro Leu Asp Ser Gly Cys Glu Gly
        275                 280                 285
Asn Cys Phe His Ser Gly Gly Thr Ile Val Ser Ser Leu Pro Phe Gln
        290                 295                 300
Asn Ile Asn Pro Arg Thr Val Gly Lys Cys Pro Arg Tyr Val Lys Gln
305                 310                 315                 320
Thr Ser Leu Leu Leu Ala Thr Gly Met Arg Asn Val Pro Glu Asn Pro
                    325                 330                 335
Lys Thr Arg Gly Leu Phe Gly Ala Ile Ala Gly Phe Ile Glu Asn Gly
                    340                 345                 350
Trp Glu Gly Leu Ile Asp Gly Trp Tyr Gly Phe Arg His Gln Asn Ala
        355                 360                 365
Gln Gly Glu Gly Thr Ala Ala Asp Tyr Lys Ser Thr Gln Ser Ala Ile
        370                 375                 380
Asp Gln Ile Thr Gly Lys Leu Asn Arg Leu Ile Asp Lys Thr Asn Gln
385                 390                 395                 400
Gln Phe Glu Leu Ile Asp Asn Glu Phe Ser Glu Ile Glu Gln Gln Ile
                    405                 410                 415
Gly Asn Val Ile Asn Trp Thr Arg Asp Ser Met Thr Glu Met Trp Ser
                    420                 425                 430
Tyr Asn Ala Glu Leu Leu Val Ala Met Glu Asn Gln His Thr Ile Asp
        435                 440                 445
Leu Ala Asp Ser Glu Met Asn Lys Leu Tyr Glu Arg Val Arg Lys Gln
450                 455                 460
Leu Arg Glu Asn Ala Glu Glu Asp Gly Thr Gly Cys Phe Glu Ile Phe
465                 470                 475                 480
His Lys Cys Asp Asp Gln Cys Met Glu Ser Ile Arg Asn Asn Thr Tyr
                    485                 490                 495
```

```
Asp His Thr Gln Tyr Arg Thr Glu Ser Leu Gln Asn Arg Ile Gln Ile
                500                 505                 510

Asp Pro Val Lys Leu Ser Ser Gly Tyr Lys Asp Ile Ile Leu Trp Phe
            515                 520                 525

Ser Phe Gly Ala Ser Cys Phe Leu Leu Ala Ile Ala Met Gly Leu
530                 535                 540

Val Phe Ile Cys Ile Lys Asn Gly Asn Met Arg Cys Thr Ile Cys Ile
545                 550                 555                 560

<210> SEQ ID NO 62
<211> LENGTH: 560
<212> TYPE: PRT
<213> ORGANISM: Artificial Sequence
<220> FEATURE:
<223> OTHER INFORMATION: H7N3 influenza virus sequence

<400> SEQUENCE: 62

Met Asn Thr Gln Ile Leu Ala Leu Ile Ala Cys Met Leu Ile Gly Ala
1               5                   10                  15

Lys Gly Asp Lys Ile Cys Leu Gly His His Ala Val Ala Asn Gly Thr
            20                  25                  30

Lys Val Asn Thr Leu Thr Glu Arg Gly Ile Glu Val Val Asn Ala Thr
        35                  40                  45

Glu Thr Val Glu Thr Ala Asn Ile Lys Lys Ile Cys Thr Gln Gly Lys
50                  55                  60

Arg Pro Thr Asp Leu Gly Gln Cys Gly Leu Leu Gly Thr Leu Ile Gly
65                  70                  75                  80

Pro Pro Gln Cys Asp Gln Phe Leu Glu Phe Asp Ala Asp Leu Ile Ile
                85                  90                  95

Glu Arg Arg Glu Gly Thr Asp Val Cys Tyr Pro Gly Lys Phe Thr Asn
            100                 105                 110

Glu Glu Ser Leu Arg Gln Ile Leu Arg Gly Ser Gly Gly Ile Asp Lys
        115                 120                 125

Glu Ser Met Gly Phe Thr Tyr Ser Gly Ile Arg Thr Asn Gly Ala Thr
130                 135                 140

Ser Ala Cys Arg Arg Ser Gly Ser Ser Phe Tyr Ala Glu Met Lys Trp
145                 150                 155                 160

Leu Leu Ser Asn Ser Asp Asn Ala Ala Phe Pro Gln Met Thr Lys Ser
                165                 170                 175

Tyr Arg Asn Pro Arg Asn Lys Pro Ala Leu Ile Ile Trp Gly Val His
            180                 185                 190

His Ser Gly Ser Ala Thr Glu Gln Thr Lys Leu Tyr Gly Ser Gly Asn
        195                 200                 205

Lys Leu Ile Thr Val Gly Ser Ser Lys Tyr Gln Gln Ser Phe Thr Pro
210                 215                 220

Ser Pro Gly Ala Arg Pro Gln Val Asn Gly Gln Ser Gly Arg Ile Asp
225                 230                 235                 240

Phe His Trp Leu Leu Leu Asp Pro Asn Asp Thr Val Thr Phe Thr Phe
                245                 250                 255

Asn Gly Ala Phe Ile Ala Pro Asp Arg Ala Ser Phe Phe Arg Gly Glu
            260                 265                 270

Ser Leu Gly Val Gln Ser Asp Val Pro Leu Asp Ser Gly Cys Glu Gly
        275                 280                 285

Asn Cys Phe His Ser Gly Gly Thr Ile Val Ser Ser Leu Pro Phe Gln
290                 295                 300
```

Asn Ile Asn Pro Arg Thr Val Gly Lys Cys Pro Arg Tyr Val Lys Gln
305                 310                 315                 320

Thr Ser Leu Leu Leu Ala Thr Gly Met Arg Asn Val Pro Glu Asn Pro
            325                 330                 335

Lys Thr Arg Gly Leu Phe Gly Ala Ile Ala Gly Phe Ile Glu Asn Gly
        340                 345                 350

Trp Glu Gly Leu Ile Asp Gly Trp Tyr Gly Phe Arg His Gln Asn Ala
    355                 360                 365

Gln Gly Glu Gly Thr Ala Ala Asp Tyr Lys Ser Thr Gln Ser Ala Ile
370                 375                 380

Asp Gln Ile Thr Gly Lys Leu Asn Arg Leu Ile Asp Lys Thr Asn Gln
385                 390                 395                 400

Gln Phe Glu Leu Ile Asp Asn Glu Phe Ser Glu Ile Glu Gln Gln Ile
            405                 410                 415

Gly Asn Val Ile Asn Trp Thr Arg Asp Ser Met Thr Glu Val Trp Ser
        420                 425                 430

Tyr Asn Ala Glu Leu Leu Ile Ala Met Glu Asn Gln His Thr Ile Asp
    435                 440                 445

Leu Ala Asp Ser Glu Met Asn Lys Leu Tyr Glu Arg Val Arg Lys Gln
450                 455                 460

Leu Arg Glu Asn Ala Glu Glu Asp Gly Thr Gly Cys Phe Glu Ile Phe
465                 470                 475                 480

His Lys Cys Asp Asp Gln Cys Met Glu Ser Ile Arg Asn Asn Thr Tyr
            485                 490                 495

Asp His Thr Gln Tyr Arg Thr Glu Ser Leu Gln Asn Arg Ile Gln Ile
        500                 505                 510

Asp Pro Val Lys Leu Ser Ser Gly Tyr Lys Asp Ile Ile Leu Trp Phe
    515                 520                 525

Ser Phe Gly Ala Ser Cys Phe Leu Leu Leu Ala Ile Ala Met Gly Leu
530                 535                 540

Val Phe Ile Cys Ile Lys Asn Gly Asn Met Arg Cys Thr Ile Cys Ile
545                 550                 555                 560

<210> SEQ ID NO 63
<211> LENGTH: 560
<212> TYPE: PRT
<213> ORGANISM: Artificial Sequence
<220> FEATURE:
<223> OTHER INFORMATION: H7N4 influenza virus sequence

<400> SEQUENCE: 63

Met Asn Thr Gln Ile Leu Ala Leu Ile Ala Cys Met Leu Ile Gly Ala
1 5 10 15

Lys Gly Asp Lys Ile Cys Leu Gly His His Ala Val Ala Asn Gly Thr
20 25 30

Lys Val Asn Thr Leu Thr Glu Arg Gly Ile Glu Val Val Asn Ala Thr
35 40 45

Glu Thr Val Glu Thr Ala Asn Ile Lys Lys Ile Cys Thr Gln Gly Lys
50 55 60

Arg Pro Thr Asp Leu Gly Gln Cys Gly Leu Leu Gly Thr Leu Ile Gly
65 70 75 80

Pro Pro Gln Cys Asp Gln Phe Leu Glu Phe Asp Ala Asp Leu Ile Ile
85 90 95

Glu Arg Arg Glu Gly Thr Asp Val Cys Tyr Pro Gly Lys Phe Thr Asn
100 105 110

```
Glu Glu Ser Leu Arg Gln Ile Leu Arg Gly Ser Gly Ile Asp Lys
        115                 120                 125

Glu Ser Met Gly Phe Thr Tyr Ser Gly Ile Arg Thr Asn Gly Ala Thr
    130                 135                 140

Ser Ala Cys Arg Arg Ser Gly Ser Ser Phe Tyr Ala Glu Met Lys Trp
145                 150                 155                 160

Leu Leu Ser Asn Ser Asp Asn Ala Ala Phe Pro Gln Met Thr Lys Ser
                165                 170                 175

Tyr Arg Asn Pro Arg Asn Lys Pro Ala Leu Ile Ile Trp Gly Val His
                180                 185                 190

His Ser Gly Ser Ala Thr Glu Gln Thr Lys Leu Tyr Gly Ser Gly Asn
            195                 200                 205

Lys Leu Ile Thr Val Gly Ser Ser Lys Tyr Gln Gln Ser Phe Thr Pro
        210                 215                 220

Ser Pro Gly Ala Arg Pro Gln Val Asn Gly Gln Ser Gly Arg Ile Asp
225                 230                 235                 240

Phe His Trp Leu Leu Leu Asp Pro Asn Asp Thr Val Thr Phe Thr Phe
                245                 250                 255

Asn Gly Ala Phe Ile Ala Pro Asp Arg Ala Ser Phe Phe Arg Gly Glu
            260                 265                 270

Ser Leu Gly Val Gln Ser Asp Val Pro Leu Asp Ser Gly Cys Glu Gly
        275                 280                 285

Asp Cys Phe His Ser Gly Gly Thr Ile Val Ser Ser Leu Pro Phe Gln
    290                 295                 300

Asn Ile Asn Pro Arg Thr Val Gly Lys Cys Pro Arg Tyr Val Lys Gln
305                 310                 315                 320

Thr Ser Leu Leu Leu Ala Thr Gly Met Arg Asn Val Pro Glu Asn Pro
                325                 330                 335

Lys Thr Arg Gly Leu Phe Gly Ala Ile Ala Gly Phe Ile Glu Asn Gly
                340                 345                 350

Trp Glu Gly Leu Ile Asp Gly Trp Tyr Gly Phe Arg His Gln Asn Ala
            355                 360                 365

Gln Gly Glu Gly Thr Ala Ala Asp Tyr Lys Ser Thr Gln Ser Ala Ile
        370                 375                 380

Asp Gln Ile Thr Gly Lys Leu Asn Arg Leu Ile Asp Lys Thr Asn Gln
385                 390                 395                 400

Gln Phe Glu Leu Ile Asp Asn Glu Phe Ser Glu Ile Glu Gln Gln Ile
                405                 410                 415

Gly Asn Val Ile Asn Trp Thr Arg Asp Ser Met Thr Glu Val Trp Ser
                420                 425                 430

Tyr Asn Ala Glu Leu Leu Val Ala Met Glu Asn Gln His Thr Ile Asp
            435                 440                 445

Leu Ala Asp Ser Glu Met Asn Lys Leu Tyr Glu Arg Val Arg Lys Gln
        450                 455                 460

Leu Arg Glu Asn Ala Glu Glu Asp Gly Thr Gly Cys Phe Glu Ile Phe
465                 470                 475                 480

His Lys Cys Asp Asp Gln Cys Met Glu Ser Ile Arg Asn Asn Thr Tyr
                485                 490                 495

Asn His Thr Gln Tyr Arg Thr Glu Ser Leu Gln Asn Arg Ile Gln Ile
                500                 505                 510

Asp Pro Val Lys Leu Ser Ser Gly Tyr Lys Asp Ile Ile Leu Trp Phe
            515                 520                 525
```

```
Ser Phe Gly Ala Ser Cys Phe Leu Leu Ala Ile Ala Met Gly Leu
    530                 535                 540
Val Phe Ile Cys Ile Lys Asn Gly Asn Met Arg Cys Thr Ile Cys Ile
545                 550                 555                 560
```

<210> SEQ ID NO 64
<211> LENGTH: 560
<212> TYPE: PRT
<213> ORGANISM: Artificial Sequence
<220> FEATURE:
<223> OTHER INFORMATION: H7N1 influenza virus sequence

<400> SEQUENCE: 64

```
Met Asn Thr Gln Ile Leu Val Phe Ala Leu Val Ala Ile Ile Pro Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
                35                  40                  45

Glu Thr Val Glu Arg Thr Asn Val Pro Arg Ile Cys Ser Lys Gly Lys
50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
                100                 105                 110

Glu Glu Ala Leu Arg Gln Ile Leu Arg Glu Ser Gly Gly Ile Asp Lys
                115                 120                 125

Glu Thr Met Gly Phe Thr Tyr Ser Gly Ile Arg Thr Asn Gly Ala Thr
                130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
                180                 185                 190

His Ser Gly Ser Thr Thr Glu Gln Thr Lys Leu Tyr Gly Ser Gly Asn
                195                 200                 205

Lys Leu Ile Thr Val Gly Ser Ser Asn Tyr Gln Gln Ser Phe Val Pro
                210                 215                 220

Ser Pro Gly Ala Arg Pro Gln Val Asn Gly Gln Ser Gly Arg Ile Asp
225                 230                 235                 240

Phe His Trp Leu Met Leu Asn Pro Asn Asp Thr Ile Thr Phe Ser Phe
                245                 250                 255

Asn Gly Ala Phe Ile Ala Pro Asp Arg Ala Ser Phe Leu Arg Gly Lys
                260                 265                 270

Ser Met Gly Ile Gln Ser Gly Val Gln Val Asp Ala Asn Cys Glu Gly
                275                 280                 285

Asn Cys Tyr His Ser Gly Gly Thr Ile Ile Ser Asn Leu Pro Phe Gln
                290                 295                 300

Asn Ile Asn Ser Arg Ala Val Gly Lys Cys Pro Arg Tyr Val Lys Gln
305                 310                 315                 320

Glu Ser Leu Met Leu Ala Thr Gly Met Lys Asn Val Pro Glu Ile Pro
                325                 330                 335
```

Lys Gly Arg Gly Leu Phe Gly Ala Ile Ala Gly Phe Ile Glu Asn Gly
              340                 345                 350

Trp Glu Gly Leu Ile Asp Gly Trp Tyr Gly Phe Arg His Gln Asn Ala
          355                 360                 365

Gln Gly Glu Gly Thr Ala Ala Asp Tyr Lys Ser Thr Gln Ser Ala Ile
      370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Thr Glu Val Glu Lys Gln Ile
              405                 410                 415

Gly Asn Val Ile Asn Trp Thr Arg Asp Ser Ile Thr Glu Val Trp Ser
          420                 425                 430

Tyr Asn Ala Glu Leu Leu Val Ala Met Glu Asn Gln His Thr Ile Asp
      435                 440                 445

Leu Ala Asp Ser Glu Met Asn Lys Leu Tyr Glu Arg Val Arg Arg Gln
450                 455                 460

Leu Arg Glu Asn Ala Glu Glu Asp Gly Thr Gly Cys Phe Glu Ile Phe
465                 470                 475                 480

His Lys Cys Asp Asp Cys Met Ala Ser Ile Arg Asn Asn Thr Tyr
              485                 490                 495

Asp His Ser Lys Tyr Arg Glu Glu Ala Met Gln Asn Arg Ile Gln Ile
          500                 505                 510

Asp Pro Val Lys Leu Ser Ser Gly Tyr Lys Asp Val Ile Leu Trp Phe
          515                 520                 525

Ser Phe Gly Ala Ser Cys Phe Ile Leu Leu Ala Ile Ala Met Gly Leu
      530                 535                 540

Val Phe Ile Cys Val Lys Asn Gly Asn Met Arg Cys Thr Ile Cys Ile
545                 550                 555                 560

<210> SEQ ID NO 65
<211> LENGTH: 560
<212> TYPE: PRT
<213> ORGANISM: Artificial Sequence
<220> FEATURE:
<223> OTHER INFORMATION: H7N3 Influenza virus sequence

<400> SEQUENCE: 65

Met Asn Thr G

```
Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
            180                 185                 190

His Ser Gly Ser Thr Thr Glu Gln Thr Lys Leu Tyr Gly Ser Gly Asn
        195                 200                 205

Lys Leu Ile Thr Val Gly Ser Ser Asn Tyr Gln Gln Ser Phe Val Pro
            210                 215                 220

Ser Pro Gly Ala Arg Pro Gln Val Asn Gly Gln Ser Gly Arg Ile Asp
225                 230                 235                 240

Phe His Trp Leu Met Leu Asn Pro Asn Asp Thr Val Thr Phe Ser Phe
                245                 250                 255

Asn Gly Ala Phe Ile Ala Pro Asp Arg Ala Ser Phe Leu Arg Gly Lys
            260                 265                 270

Ser Met Gly Ile Gln Ser Ser Val Gln Val Asp Ala Asn Cys Glu Gly
        275                 280                 285

Asp Cys Tyr His Ser Gly Gly Thr Ile Ile Ser Asn Leu Pro Phe Gln
            290                 295                 300

Asn Ile Asn Ser Arg Ala Val Gly Lys Cys Pro Arg Tyr Val Lys Gln
305                 310                 315                 320

Glu Ser Leu Met Leu Ala Thr Gly Met Lys Asn Val Pro Glu Ile Pro
                325                 330                 335

Lys Gly Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
        370                 375                 380

Asp Gln Ile Thr Gly Lys Leu Asn Arg Leu Ile Glu Lys Thr Asn Gln
385                 390                 395                 400

Gln Phe Glu Leu Ile Asp Asn Glu Phe Thr Glu Val Glu Lys Gln Ile
                405                 410                 415

Gly Asn Val Ile Asn Trp Thr Arg Asp Ser Met Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asn Lys Leu Tyr Glu Arg Val Lys Arg Gln
450                 455                 460

Leu Arg Glu Asn Ala Glu Glu Asp Gly Thr Gly Cys Phe Glu Ile Phe
465                 470                 475                 480

His Lys Cys Asp Asp Asp Cys Met Ala Ser Ile Arg Asn Asn Thr Tyr
                485                 490                 495

Asp His Ser Arg Tyr Arg Glu Glu Ala Met Gln Asn Arg Ile Gln Ile
            500                 505                 510

Asp Pro Val Lys Leu Ser Ser Gly Tyr Lys Asp Val Ile Leu Trp Phe
            515                 520                 525

Ser Phe Gly Ala Ser Cys Phe Ile Leu Leu Ala Ile Ala Met Gly Leu
        530                 535                 540

Val Phe Ile Cys Val Lys Asn Gly Asn Met Arg Cys Thr Ile Cys Ile
545                 550                 555                 560
```

HUMAN ADAPTATION OF H7 HA FIGURES

B
Mut PI

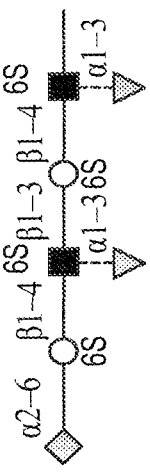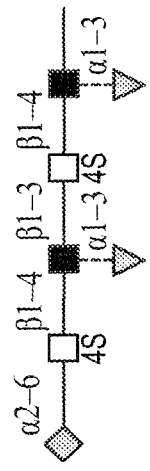
Key: ■ GlcNAc □ GalNAc ○ Gal ● Glc ◇ Neu5Ac ▽ Fucose □ Terminal HexNAc
Long α2-6 umbrella-like topology glycan decoys
N-linked glycans:
α2-6 Type 2 extension branch attached to trimannosyl core
α2-6 LacDiNAc extension branch attached to trimannosyl core
FIG. 9A-1
| FIG. 9A-1 | FIG. 9A-2 |
| | FIG. 9A-4 | FIG. 9A-5 |
| | FIG. 9A-3 | |
| FIG. 9A-6 | FIG. 9A-7 |
FIG. 9A Long α2–6 *umbrella*-like topology glycans that are not decoys N-linked glycans:

*α2–6 linkage on GlcNAc of Type 1/Type 2 extension*

**Long α2–6 *umbrella*-like topology glycan decoys**
O-linked glycans:
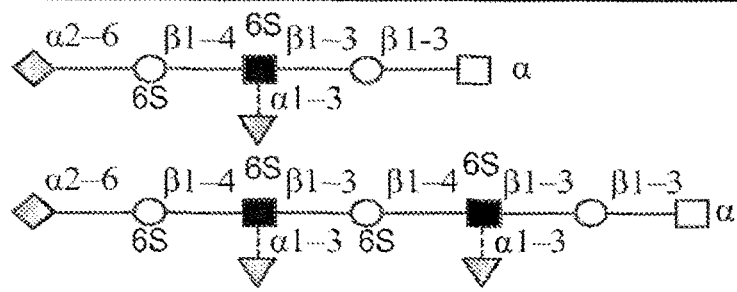
*α2–6 Type 2 extension branch in a Core 1 type structure*
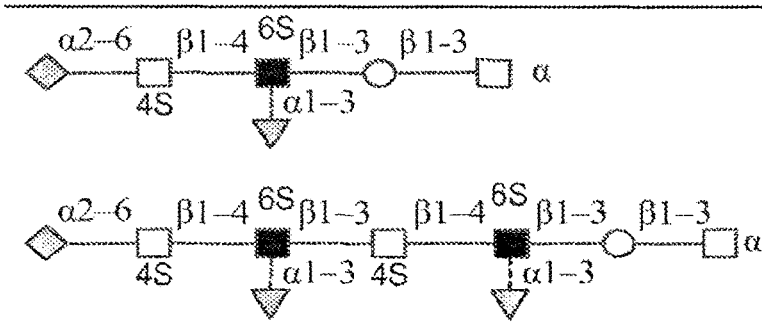
*α2–6 LacDiNAc extension branch in a Core 1 type structure*
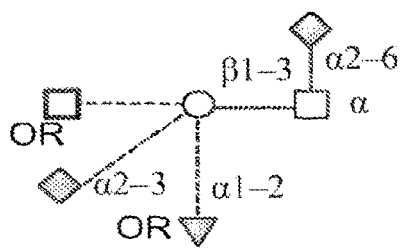
*α2–6 attached to core GalNAc in Core 1 type structure*
FIG. 9A-3

**Long α2–6 *umbrella*-like topology glycan decoys**
O-linked glycans:
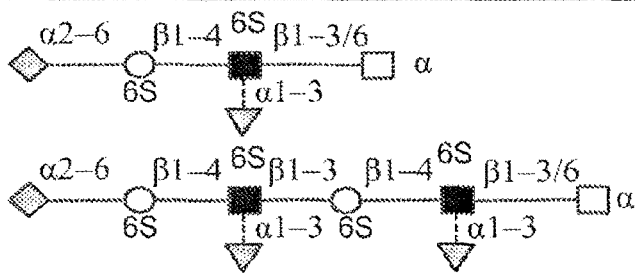
*α2–6 Type 2 extension branch in a Core 2 or 3 or 4 type structure*
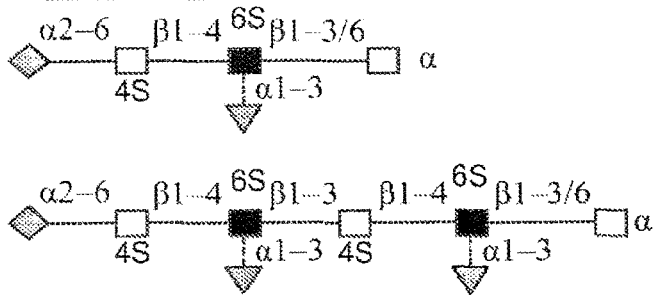
*α2–6 LacDiNAc extension branch in a Core 2 or 3 or 4 type structure*
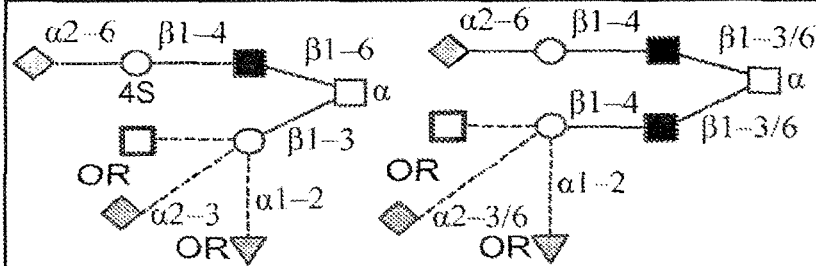
*α2–6 attached to branched Core 2 and Core 4 structures*
FIG. 9A-4

Long α2-6 *umbrella*-like topology glycans that are not decoys

Glycolipids:

*Glucosylceramide Core Ganglio type*

*Glucosylceramide Core Globo type*

Figure 10

α2–3 and α2–6 motif in Cone topology

- Typical of short oligosaccharide or oligosaccharide branch attached to a Core Structure

- Short branch of N-linked Core

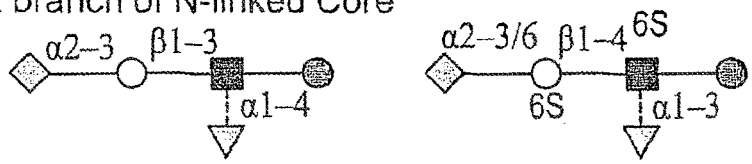

- Short branch of O-linked Core

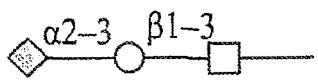

- The Cone topology can also be adopted by longer α2–3 and α2–6 oligosaccharide branch attached to Core Structure ◇ Neu5Ac   ▽ Fuc ○ Gal   ● Glc   ● Man □ GalNAc   ■ GlcNAc Dotted Gray lines, 4S and 6S indicate potential sites for fucosylation and sulfation modifications

HUMAN ADAPTATION OF H7 HA

RELATED APPLICATIONS

This patent application claims priority to U.S. Application No. 61/831,509, entitled "Human Adaptation of H7 HA," filed Jun. 5, 2013, which is hereby incorporated by reference in its entirety.

GOVERNMENT SUPPORT

This invention was made with government support under grant number GM057073 awarded by the National Institutes of Health. The government has certain rights in the invention.

SEQUENCE LISTING

The present specification makes reference to a Sequence Listing (submitted electronically on Jun. 5, 2014 as a .txt file named "SequenceListing.txt"). The .txt file was generated on Jun. 5, 2014 and is 254 kb in size. The entire contents of the Sequence Listing are herein incorporated by reference.

BACKGROUND

Influenza A viruses pose a major public health problem, causing seasonal epidemics and occasional, but devastating global pandemics (Cunha B A (2004) Influenza: historical aspects of epidemics and pandemics, Infectious disease clinics of North America 18(1):141-155), which negatively impacts the global economy.

Birds are natural reservoirs for influenza A viruses, and avian-adapted viruses regularly cross over to humans, either directly (through direct contact) or through an intermediate swine species. Influenza A virus strains rapidly evolve (through antigenic drift) in humans as a consequence of both the complex response of human immune system and rapid geographical movement of human population.

Given the constant evolution of influenza viruses, there is a concern that current avian influenza strains might accumulate mutations that alter their host specificity and allow them to infect humans. The costs of an avian flu pandemic are likely to be significant. In 2005, the threat of such a pandemic resulted in billions of dollars being spent by national governments trying to develop strategies to manage and combat a potential pandemic. Accordingly, improved surveillance techniques and methods of predicting high risk strains of influenza may have value in preventing or minimizing the risk of a human pandemic. There is a well-recognized need for the development of therapeutic agents, specifically including vaccines, for the treatment and/or prevention of influenza infection, particularly of humans. There is also a need for improved surveillance technologies for identifying and/or characterizing emerging strains and there infectivity characteristics.

SUMMARY

The present invention provides compositions and methods for use in the detection, treatment, and/or prevention of influenza transmission and/or infection. In some embodiments, the present invention provides compositions, including therapeutic/pharmaceutical (e.g., vaccine) compositions and components thereof, detection (e.g., diagnostic and/or surveillance) compositions and kits, and methods of identifying, making, and/or using such compositions. The present invention particularly provides compositions and methods relevant to influenza strains with an H7 hemagglutinin (HA).

Among other things, the present invention provides new insights into interaction between HA polypeptides and their receptors, and particularly between H7 HA polypeptides and their receptors. The present invention particularly defines amino acid residues whose presence in an H7 HA can impact receptor tropism. Furthermore, without wishing to be bound by any particular theory, the present invention provides a novel framework for analyzing H7 polypeptides and their evolution. Provided technologies permit prediction of sequence changes that could result in human-infecting strains. Alternatively or additionally, provided technologies can impact selection of components for effective therapeutic and/or prophylactic agents and vaccines.

The present invention provides HA polypeptides and variants having particular amino acid sequence elements (e.g., particular defined residues), nucleic acids that encode them, binding agents that specifically interact with them (and, in some embodiments, discriminate between them and other similar HA polypeptides that, for example, differ in a particular structural feature), as well as various compositions and methods relating to such polypeptides, nucleic acids, and binding agents.

In certain embodiments, the present invention provides a polypeptide whose amino acid sequence includes a sequence element that: is at least five amino acids in length; is substantially identical to corresponding portion of a reference H7 HA polypeptide selected from the group consisting of SEQ ID NO: 17-47, 56-64, and 65, which portion includes amino acid position 228; and has a serine residue at its position corresponding to the reference H7 polypeptide position 228.

In some embodiments, the present invention provides a method of monitoring influenza in a sample comprising: obtaining a sample from a source suspected to contain influenza; contacting the sample with one or more agents that specifically bind to a polypeptide of claim 1; and detecting binding of the agent with the sample, so that presence and/or level of the polypeptide in the sample is determined.

In certain embodiments, the present invention provides a vaccine composition comprising at least one antigen comprising a polypeptide whose amino acid sequence includes a sequence element that: is at least five amino acids in length, is substantially identical to corresponding portion of a reference H7 HA polypeptide selected from the group consisting of SEQ ID NO: 17-47, 56-64, and 65, which portion includes amino acid position 228, and has a serine residue at its position corresponding to the reference H7 HA polypeptide position 228; and a pharmaceutically acceptable carrier.

In some embodiments, the present invention provides a method of providing a vaccine comprising at least one antigen comprising a polypeptide whose amino acid sequence includes a sequence element that: is at least five amino acids in length, is substantially identical to corresponding portion of a reference H7 HA polypeptide selected from the group consisting of SEQ ID NO: 17-47, 56-64, and 65, which portion includes amino acid position 228, and has a serine residue at its position corresponding to the reference H7 HA polypeptide position 228; and formulating the provided at least one antigen into a vaccine composition.

In certain embodiments, the present invention provides a diagnostic kit for determining pandemic risk in a strain of influenza, the kit comprising: at least one antibody agent that binds to a polypeptide whose amino acid sequence includes a sequence element that: is at least five amino acids in length, is substantially identical to corresponding portion of a reference H7 HA polypeptide selected from the group consisting of SEQ ID NO: 17-47, 56-64, and 65, which portion includes amino acid position 228, and has a serine residue at its position corresponding to the reference H7 HA polypeptide position 228.

In some embodiments, the present invention provides a method of identifying a binding agent that competes interaction between HA receptors and HA polypeptides by: providing a collection of test binding agents; contacting the test agents with at least one HA receptor and at least one HA polypeptide that binds to the glycans on HA receptor; and determining that observed binding between the at least one HA receptor and at least one HA polypeptide is reduced when the binding agent is present as compared with when it is absent.

In certain embodiments, the present invention provides a method of identifying human-adapted H7 HA polypeptide variants by: providing at least one test H7 HA polypeptide whose amino acid sequence includes a sequence element that: is at least five amino acids in length, is substantially identical to corresponding portion of a reference H7N9 HA polypeptide selected from the group consisting of SEQ ID NO: 17-47, 56-64, and 65, which portion includes one or more of amino acid positions 122, 131, 135, 137, 145, 156, 158, 159, 174, 186, 189, 190, 192, 193, 196, 202, 222, 224, 225, 227, 228, differs from that of the portion in at least one residue so that the sequence element is not more than 90% identical to the portion; determining whether the test polypeptide shows human binding characteristic by determining one or more of: increased human binding under comparable conditions by the test polypeptide as compared with that of the reference polypeptide in a binding assay, or at least comparable human binding under comparable conditions by the test polypeptide as compared with that observed for a known human-adapted reference HA polypeptide selected from the group consisting of SEQ ID NO.: 48, 49, and 50 in a binding assay.

In some embodiments, the present invention provides a method for identifying human-adapted H7 HA polypeptide variants by: providing at least one test H7 HA polypeptide; and determining whether the test polypeptide shows human binding characteristic by determining one or more of: at least comparable human binding under comparable conditions by the test polypeptide as compared with that observed for the H7 HA polypeptide of claim 1 in a binding assay, or increased human binding under comparable conditions by the test polypeptide as compared with that of a reference non-human-adapted HA polypeptide selected from the group consisting of SEQ ID NO: 17-47, 56-64, and 65 in a binding assay, or at least comparable human binding under comparable conditions by the test polypeptide as compared with that observed for a known human-adapted reference HA polypeptide selected from the group consisting of SEQ ID NO.: 48, 49, and 50 in a binding assay.

In certain embodiments, the present invention provides a binding agent that distinguishes between a reference polypeptide that includes sequence of a reference H7 HA polypeptide selected from the group consisting of SEQ ID NO: 17-47, 56-64, and 65, and a polypeptide of otherwise identical sequence with serine at amino acid position 228.

In some embodiments, the present invention provides a method of raising antibodies by administering to an organism a polypeptide whose amino acid sequence includes a sequence element that: is at least five amino acids in length; is substantially identical to corresponding portion of a reference H7 HA polypeptide selected from the group consisting of SEQ ID NO: 17-47, 56-64, and 65, which portion includes amino acid position 228; and has a serine residue at its position corresponding to the reference H7 HA polypeptide position 228.

In certain embodiments, the present invention provides a method of evaluating vaccine induced cross-reactive antibody responses by: providing a test HA strain for which vaccine has to be developed; determining the antigenic intactness (AI) of the test strain and a reference HA strain, which reference strain has been approved or recommended for vaccine development; and if the AI value of the test strain is at least 80% with the reference strain, suggesting that the two strains are antigenically related to each other.

In some embodiments, the present invention provides a method of evaluating vaccine composition, comprising: providing a test vaccine composition that includes an H7 HA polypeptide whose amino acid sequence includes a sequence element that: is at least five amino acids in length, is substantially identical to corresponding portion of a reference H7 HA polypeptide selected from the group consisting of SEQ ID NO: 17-47, 56-64, and 65, which portion includes amino acid position 228, and has a serine residue at its position corresponding to the reference H7 HA polypeptide position 228; and determining that the test vaccine composition has at least one activity selected from the group consisting of: mediates a protective response, induces a strong antibody response, prevents transmissibility of the virus in ferrets, and combinations thereof.

BRIEF DESCRIPTION OF THE DRAWING

The Figures of the Drawing are for illustration purposes only, not for limitation.

FIG. 1: FIG. 1 presents a phylogenetic tree that illustrates evolutionary distance between and among various different HAs. The branches represent group 1 (labeled on the left) and 2 (labeled on the right) HAs. Closely related subtypes are located on branches close to one another.

FIGS. 2A-D illustrate structures of HA-glycan receptor complexes. (A) Structural model of Anh13 H7 HA Receptor Binding Site (RBS) in complex with avian receptor. The avian receptor is shown as a stick at 40% transparency. The loop and helix regions used to define molecular features of the HA RBS are shown. The side chains of certain amino acids in these regions that make contact with the glycan receptor are also shown. The side chain of Q at 226 position observed in all other H7 HAs (prior to H7N9 outbreak) is shown as stick with 40% transparency to contrast contacts made by L226 and Q226 with the avian receptor. The networks of inter-residue interaction contacts are shown as two-dimensional maps near the corresponding residue positions. The map comprises of circular nodes representing the amino acid positions (which are labeled above the nodes) and shaded according to the degree of inter-residue contact (lightest shade indicating lowest contact and darkest shade indicating highest contact). (B) Structural model of Anh13 H7 HA RBS in complex with human receptor. The human receptor is shown as a stick with 40% transparency. (C) X-ray co-crystal structure of Aichi68 H3 HA RBS in complex with human receptor (PDB ID: 2YPG). The inter-residue interaction network of certain RBS residues is shown similar to what was shown in A, and shows the similarities in the network of residues in 130-, 140- and 220-loop between the H3 and H7 HA. On the other hand, also shown are the differences in the network involving residues in the 190 helix. This difference is brought about by the amino acid differences and also the Gly in H7 HA versus Ser in H3 HA in the 228 position. (D) Structural model of the G228→S mutant of Anh13 H7 HA RBS in complex with human receptor. As shown in the figure, the network involving residues in 190 helix in the mutant is more similar to that observed in H3 HA than the wild-type or reference. The inter-residue contacts networks that are different between the mutant and wild-type or reference HA are shown in dotted circles.

FIG. 3 demonstrates binding of A/Albany/6/58 (Alb58) pandemic H2N2 HA to human tracheal tissue. Alb58 shows extensive binding to apical surface of tracheal tissue section (that predominantly expresses human receptors) even at HA concentration of 10 µg/ml.

FIGS. 4A-B show staining of human alveolus with wild-type or reference and G228S A/Anhui/1/13 hemagglutinin (HA). Human paraffinized tissue sections were stained with recombinant HAs expressed and purified from 292 F cells. The staining by recombinant HA is shown with arrows. The recombinant HAs were precomplexed with primary anti-His and Alexa fluor 488 tagged (light gray) secondary antibodies (for multivalent presentation) before adding to the tissue sections. (A) Staining of the alveolus for the wild-type or reference protein (less intense). (B) Staining of the alveolus for the G228S mutant HA (more intense). This staining pattern is characteristic of avian influenza A viruses. The tissue was also counterstained with propidium iodide (PI) shown in dark gray.

FIGS. 5A-D demonstrate staining of human trachea with wild-type or reference and G228S A/Anhui/1/13 hemagglutinin. Human paraffinized tissue sections were stained with recombinant HAs expressed and purified from 292 F cells. Staining by recombinant HA is shown with arrows. The recombinant HAs were precomplexed with primary anti-His and Alexa fluor 488 tagged (light gray) secondary antibodies (for multivalent presentation) before adding to the tissue sections. (A) Staining of the trachea for the wild-type or reference protein (less intense). (B) Staining of the apical surface of the trachea for the G228S mutant HA (more intense; marked by arrow). One important feature of the G228S protein is the staining of the submucosal gland (C) and the goblet cells (D) in the human trachea. The staining to goblet cells is similar to staining by other human-adapted influenza A virus HA. The tissue was counterstained with propidium iodide (PI) shown in dark gray. Images A, B and C were captured at 25× magnification and Image D was captured at 63× magnification.

FIG. 6 illustrates staining of human trachea with *Sambucus nigra* agglutinin I (SNA I), a lectin known to specifically bind to human receptors. Human paraffinized tissue sections were stained with FITC labeled SNA. SNA I binds to sialic acid linked α2-6 to the penultimate galactose, which are the glycan receptors for human influenza A viruses. SNA I showed staining of the apical surface of the human trachea. SNA-I also stained the mucin secreting goblet cells (marked with *) similar to the Anhui 13 G228S mutant HA. The staining by SNA I (light gray) is shown. Image was captured at 40× magnification. All tissue sections were counterstained with propidium iodide (PI) shown in light gray.

FIG. 7 demonstrates a phylogenic tree of H7 HA amino acid sequences. The tree was constructed using 231 full-length, non-redundant amino acid sequences using the Neighbor-Joining method found in the MEGA 5.1 software. The two major H7 lineages are labeled on the right hand side by double sided arrows. Branches are coded (by lines) according to the number of coevolving residues found in the H7 sequence. A rectangular box marks occurrence of the novel H7N9 virus on the tree.

FIG. 8 illustrates cone-topology (left panel) vs. umbrella-topology (right panel) of α2-3 and α2-6 siaylated glycans. The topology of α2-3 and α2-6 is governed by the glycosidic torsion angles of the trisaccharide motifs—Neu5Acα2-3Galβ1-3/4GlcNAc and Neu5Acα2-6Galβ1-4GlcNAc, respectively. A parameter (θ)—angle between C2 atom of Neu5Ac and C1 atoms of the subsequent Gal and GlcNAc sugars in these trisaccharide motifs has been defined to characterize the topology. Superimposition of the θ contour and the conformational maps of the α2-3 and α2-6 motifs shows that the α2-3 motifs adopt 100% cone-like topology and the α2-6 motifs sampled both cone-like and umbrella-like topologies. In the cone-like topology sampled by α2-3 and α2-6, GlcNAc and subsequent sugars are positioned along a region spanning a cone. Interactions of HA with cone-like topology glycans primarily involves contacts of amino acids at the numbered positions (based on H3 HA numbering) with Neu5Ac and Gal sugars. On the other hand, in umbrella-like topology, which is unique to α2-6, \ GlcNAc and subsequent sugars bend towards the HA binding site (as observed in HA-α2-6 co-crystal structures). Longer α2-6 oligosaccharides (e.g., at least a tetrasaccharide structures) would favor this conformation since it is stabilized by intra-sugar van der Waals contact between acetyl groups of GlcNAc and Neu5Ac. HA interactions with umbrella-like topology glycans involves contacts of amino acids at the numbered positions (based on H3 HA numbering) with GlcNAc and subsequent sugars in addition to contacts with Neu5Ac and Gal sugars.

FIG. 10: FIG. 10 shows exemplary cone-topologies. This Figure illustrates certain exemplary (but not exhaustive) glycan structures that adopt cone-topologies.

DESCRIPTION OF HA SEQUENCE ELEMENTS

HA Sequence Element 1

Figure 2:
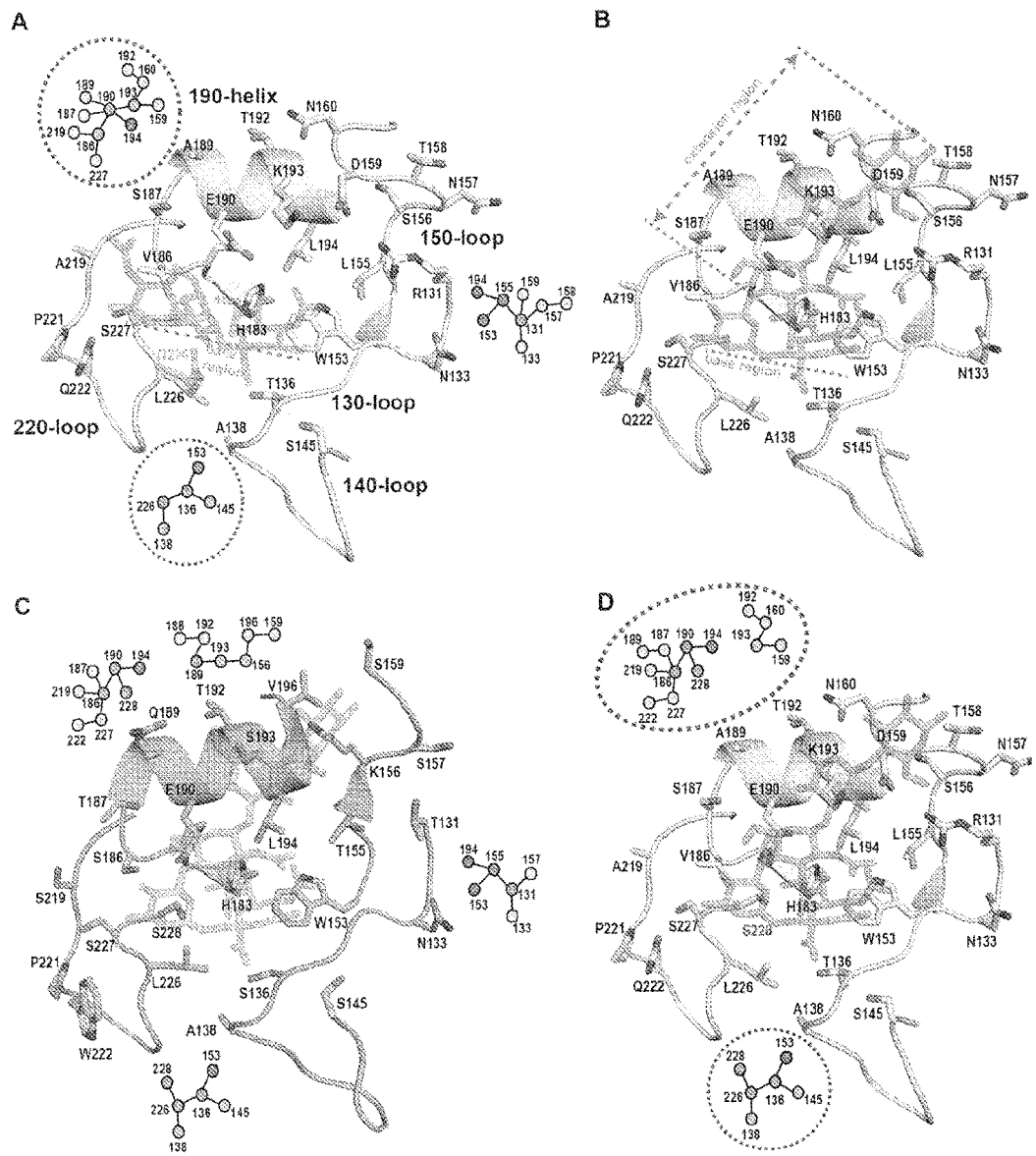
FIG. 2.

HA Sequence Element 1 is a sequence element corresponding approximately to residues 97-185 (where residue positions are assigned using H3 HA as reference) of many HA proteins found in natural influenza isolates. This sequence element has the basic structure:

$$\text{C (Y/F) P } X_1 \text{ C } X_2 \text{ W } X_3 \text{ W } X_4 \text{ H H P,} \quad \text{(SEQ ID NO.: 1)}$$

wherein:

$X_1$ is approximately 30-45 amino acids long;
$X_2$ is approximately 5-20 amino acids long;
$X_3$ is approximately 25-30 amino acids long; and
$X_4$ is approximately 2 amino acids long.

In some embodiments, $X_1$ is about 35-45, or about 35-43, or about 35, 36, 37, 38, 39, 40, 41, 42, or 43 amino acids long. In some embodiments, $X_2$ is about 9-15, or about 9-14, or about 9, 10, 11, 12, 13, or 14 amino acids long. In some embodiments, $X_3$ is about 26-28, or about 26, 27, or 28 amino acids long. In some embodiments, $X_4$ has the sequence (G/A) (I/V). In some embodiments, $X_4$ has the sequence GI; in some embodiments, $X_4$ has the sequence GV; in some embodiments, $X_4$ has the sequence AI; in some embodiments, $X_4$ has the sequence AV. In some embodiments, HA Sequence Element 1 comprises a disulfide bond. In some embodiments, this disulfide bond bridges residues corresponding to positions 97 and 139 (based on the canonical H3 numbering system utilized herein).

In some embodiments, and particularly in H1 polypeptides, $X_1$ is about 43 amino acids long, and/or $X_2$ is about 13 amino acids long, and/or $X_3$ is about 26 amino acids long. In some embodiments, and particularly in H1 polypeptides, HA Sequence Element 1 has the structure:

(SEQ ID NO.: 2)
C Y P $X_{1A}$ T (A/T) (A/S) C $X_2$ W $X_3$ W $X_4$ H H P, wherein:

$X_{1A}$ is approximately 27-42, or approximately 32-42, or approximately 32-40, or approximately 26-41, or approximately 31-41, or approximately 31-39, or approximately 31, 32, 33, 34, 35, 36, 37, 38, 39, or 40 amino acids long, and $X_2$-$X_4$ are as above.

In some embodiments, and particularly in H1 polypeptides, HA Sequence Element 1 has the structure:

(SEQ ID NO.: 3)
C Y P $X_{1A}$ T (A/T) (A/S) C $X_2$ W (I/L) (T/V) $X_{3A}$ W $X_4$ H H P, wherein:

$X_{1A}$ is approximately 27-42, or approximately 32-42, or approximately 32-40, or approximately 32, 33, 34, 35, 36, 37, 38, 39, or 40 amino acids long, $X_{3A}$ is approximately 23-28, or approximately 24-26, or approximately 24, 25, or 26 amino acids long, and $X_2$ and $X_4$ are as above.

In some embodiments, and particularly in H1 polypeptides, HA Sequence Element 1 includes the sequence:

(SEQ ID NO.: 4)
Q L S S I S S F E K, typically within $X_1$, (including within $X_{1A}$) and especially beginning about residue 12 of $X_1$.

In some embodiments, and particularly in H3 polypeptides, $X_1$ is about 39 amino acids long, and/or $X_2$ is about 13 amino acids long, and/or $X_3$ is about 26 amino acids long.

In some embodiments, and particularly in H3 polypeptides, HA Sequence Element 1 has the structure:

(SEQ ID NO.: 5)
C Y P $X_{1A}$ S (S/N) (A/S) C $X_2$ W $X_3$ W $X_4$ H H P, wherein:

$X_{1A}$ is approximately 27-42, or approximately 32-42, or approximately 32-40, or approximately 23-38, or approximately 28-38, or approximately 28-36, or approximately 28, 29, 30, 31, 32, 33, 34, 35, 36, 37, 38, 39, or 40 amino acids long, and $X_2$-$X_4$ are as above.

In some embodiments, and particularly in H3 polypeptides, HA Sequence Element 1 has the structure:

(SEQ ID NO.: 6)
C Y P $X_{1A}$ S (S/N) (A/S) C $X_2$ W L (T/H) $X_{3A}$ W $X_4$ H H P, wherein:

$X_{1A}$ is approximately 27-42, or approximately 32-42, or approximately 32-40, or approximately 32, 33, 34, 35, 36, 37, 38, 39, or 40 amino acids long, $X_{3A}$ is approximately 23-28, or approximately 24-26, or approximately 24, 25, or 26 amino acids long, and $X_2$ and $X_4$ are as above.

In some embodiments, and particularly in H3 polypeptides, HA Sequence Element 1 includes the sequence:

(SEQ ID NO.: 7)
(L/I) (V/I) A S S G T L E F, typically within $X_1$ (including within $X_{1A}$), and especially beginning about residue 12 of $X_1$.

In some embodiments, and particularly in H5 polypeptides, $X_1$ is about 42 amino acids long, and/or $X_2$ is about 13 amino acids long, and/or $X_3$ is about 26 amino acids long.

In some embodiments, and particularly in H5 polypeptides, HA Sequence Element 1 has the structure:

(SEQ ID NO.: 8)
C Y P $X_{1A}$ S S A C $X_2$ W $X_3$ W $X_4$ H H P, wherein:

$X_{1A}$ is approximately 27-42, or approximately 32-42, or approximately 32-40, or approximately 23-38, or approximately 28-38, or approximately 28-36, or approximately 28, 29, 30, 31, 32, 33, 34, 35, 36, 37, 38, 39, or 40 amino acids long, and $X_2$-$X_4$ are as above.

In some embodiments, and particularly in H5 polypeptides, HA Sequence Element 1 has the structure:

(SEQ ID NO.: 9)
C Y P $X_{1A}$ S S A C $X_2$ W L I $X_{3A}$ W $X_4$ H H P, wherein:

$X_{1A}$ is approximately 27-42, or approximately 32-42, or approximately 32-40, or approximately 32, 33, 34, 35, 36, 37, 38, 39, or 40 amino acids long, $X_{3A}$ is approximately 23-28, or approximately 24-26, or approximately 24, 25, or 26 amino acids long, and $X_2$ and $X_4$ are as above.

In some embodiments, and particularly in H5 polypeptides, HA Sequence Element 1 is extended (i.e., at a position corresponding to residues 186-193) by the sequence:

(SEQ ID NO.: 10)
N D A A E X X (K/R)

In some embodiments, and particularly in H5 polypeptides, HA Sequence Element 1 includes the sequence:

(SEQ ID NO.: 11)
Y E E L K H L X S X X N H F E K, typically within $X_1$, and especially beginning about residue 6 of $X_1$.

In some embodiments, and particularly in H7 polypeptides, HA Sequence Element 1 includes the sequence:

(SEQ ID NO.: 55)
C Y P G $X_{30}$ R $X_{29}$ A $X_4$ M $X_6$ P $X_{11}$ H H S, wherein:

$X_N$ means a string of amino acids of length N.

HA Sequence Element 2

HA Sequence Element 2 is a sequence element corresponding approximately to residues 324-340 (again using a numbering system based on H3 HA) of many HA proteins found in natural influenza isolates. This sequence element has the basic structure:

G A I A G F I E (SEQ ID NO.: 12)

In some embodiments, HA Sequence Element 2 has the sequence:

P X₁ G A I A G F I E, (SEQ ID NO.: 13)

wherein:
X₁ is approximately 4-14 amino acids long, or about 8-12 amino acids long, or about 12, 11, 10, 9 or 8 amino acids long. In some embodiments, this sequence element provides the HA0 cleavage site, allowing production of HA1 and HA2.

In some embodiments, and particularly in H1 polypeptides, HA Sequence Element 2 has the structure:

P S (I/V) Q S R X₁₄ G A I A G F I E, (SEQ ID NO.: 14)

wherein:
X₁₄ is approximately 3 amino acids long; in some embodiments, X₁₄ is G (L/I) F.

In some embodiments, and particularly in H3 polypeptides, HA Sequence Element 2 has the structure:

P X K X T R X₁₄ G A I A G F I E, (SEQ ID NO.: 15)

wherein:
X₁₄ is approximately 3 amino acids long; in some embodiments, X₁₄ is G (L/I) F.

In some embodiments, and particularly in H5 polypeptides, HA Sequence Element 2 has the structure:

P Q R X X X R X X R X₁₄ G A I A G F I E, (SEQ ID NO.: 16)

wherein:
X₁₄ is approximately 3 amino acids long; in some embodiments, X₁₄ is G (L/I) F.

Definitions

In order for the present invention to be more readily understood, certain terms are first defined below; those of ordinary skill in the art will appreciate and understand the use and scope of these terms as defined below and/or otherwise used herein.

Adult: As used herein, the term "adult" refers to a human eighteen years of age or older. Body weights among adults can vary widely with a typical range being 90 pounds to 250 pounds.

Affinity: As is known in the art, "affinity" is a measure of the tightness with a particular ligand (e.g., an HA polypeptide) binds to its partner (e.g., an HA receptor). Affinities can be measured in different ways. In some embodiments, affinity is measured by a quantitative assay (e.g., glycan binding assays). In some embodiments, binding partner concentration (e.g., HA receptor, glycan, etc.) may be fixed to be in excess of ligand (e.g., an HA polypeptide) concentration so as to mimic physiological conditions (e.g., viral HA binding to cell surface glycans). Alternatively or additionally, in some embodiments, binding partner (e.g., HA receptor, glycan, etc.) concentration and/or ligand (e.g., an HA polypeptide) concentration may be varied. In some such embodiments, affinity (e.g., binding affinity) may be compared to a reference (e.g., a wild-type HA that mediates infection of a humans) under comparable conditions (e.g., concentrations).

Amino acid: As used herein, term "amino acid," in its broadest sense, refers to any compound and/or substance that can be incorporated into a polypeptide chain. In some embodiments, an amino acid has the general structure $H_2N-C(H)(R)-COOH$. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Amino acid residues network: The term "amino acid residues network" is used to refer to a set of amino acid residues in a polypeptide chain that, although they may be separated from one another along the chain, cluster near one another in space when the chain adopts a folded configuration. Amino acid residues networks on a protein surface are referred to herein as "surface residues networks": those interior to the protein are referred to herein as "core residues networks".

Animal: As used herein, the term "animal" refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by influenza. In some embodiments, an animal may be a transgenic animal, genetically engineered animal, and/or a clone.

Antibody agent: As used herein, the term "antibody agent" refers to an agent that specifically binds to a particular antigen. In some embodiments, the term encompasses any polypeptide with immunoglobulin structural elements sufficient to confer specific binding. Suitable antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In come embodiments, the term encompasses monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain Antibody: As is known in the art, an "antibody" is an immunoglobulin that binds specifically to a particular antigen. The term encompasses immunoglobulins that are naturally produced in that they are generated by an organism reacting to the antigen, and also those that are synthetically produced or engineered. An antibody may be monoclonal or polyclonal. An antibody may be a member of any immunoglobulin class, including any of the human classes: IgG, IgM, IgA, and IgD. A typical immunoglobulin (antibody) structural unit as understood in the art, is known to comprise a tetramer. Each tetramer is composed of two identical pairs of polypeptide chains, each pair having one "light" (approximately 25 kD) and one "heavy" chain (approximately 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. Each variable region is further subdivided into hypervariable (HV) and framework (FR) regions. The hypervariable regions comprise three areas of hypervariability sequence called complementarity determining regions (CDR 1, CDR 2 and CDR 3), separated by four framework regions (FR1, FR2, FR2, and FR4) which form a beta-sheet structure and serve as a scaffold to hold the HV regions in position. The C-terminus of each heavy and light chain defines a constant region consisting of one domain for the light chain (CL) and three for the heavy chain (CH1, CH2 and CH3). In some embodiments, the term "full length" is used in reference to an antibody to mean that it contains two heavy chains and two light chains, optionally associated by disulfide bonds as occurs with naturally-produced antibodies. In some embodiments, an antibody is produced by a cell. In some embodiments, an antibody is produced by chemical synthesis. In some embodiments, an antibody is derived from a mammal. In some embodiments, an antibody is derived from an animal such as, but not limited to, mouse, rat, horse, pig, or goat. In some embodiments, an antibody is produced using a recombinant cell culture system. In some embodiments, an antibody may be a purified antibody (for example, by immune-affinity chromatography). In some embodiments, an antibody may be a human antibody. In some embodiments, an antibody may be a humanized antibody (antibody from non-human species whose protein sequences have been modified to increase their similarity to antibody variants produced naturally in humans). In some embodiments, an antibody may be a chimeric antibody (antibody made by combining genetic material from a non-human source, e.g., mouse, rat, horse, or pig, with genetic material from humans).

Antibody fragment: As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region. In many embodiments, an antibody fragment contains sufficient sequence of the parent antibody of which it is a fragment that it binds to the same antigen as does the parent antibody; in some embodiments, a fragment binds to the antigen with a comparable affinity to that of the parent antibody and/or competes with the parent antibody for binding to the antigen. Examples of antigen binding fragments of an antibody include, but are not limited to, Fab fragment, Fab' fragment, F(ab')2 fragment, scFv fragment, Fv fragment, dsFv diabody, dAb fragment, Fd' fragment, Fd fragment, and an isolated complementarity determining region (CDR) region. An antigen binding fragment of an antibody may be produced by any means. For example, an antigen binding fragment of an antibody may be enzymatically or chemically produced by fragmentation of an intact antibody and/or it may be recombinantly produced from a gene encoding the partial antibody sequence. Alternatively or additionally, antigen binding fragment of an antibody may be wholly or partially synthetically produced. An antigen binding fragment of an antibody may optionally comprise a single chain antibody fragment. Alternatively or additionally, an antigen binding fragment of an antibody may comprise multiple chains which are linked together, for example, by disulfide linkages. An antigen binding fragment of an antibody may optionally comprise a multimolecular complex. A functional antibody fragment typically comprises at least about 50 amino acids and more typically comprises at least about 200 amino acids.

Antigen: An "antigen" is a molecule or entity to which an antibody binds. In some embodiments, an antigen is or comprises a polypeptide or portion thereof. In some embodiments, an antigen is a portion of an infectious agent that is recognized by antibodies. In some embodiments, an antigen is an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In general, an antigen may be or include any chemical entity such as, for example, a small molecule, a nucleic acid, a polypeptide, a carbohydrate, a lipid, a polymer [in some embodiments other than a biologic polymer (e.g., other than a nucleic acid or amino acid polymer)] etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is or comprises a recombinant antigen.

Antigenic Identity: as used herein, the term "antigenic identity" (AI) refers to the percentage fraction of amino acids in a polypeptide of interest, or portion thereof [e.g., in an HA polypeptide, or in an epitope (e.g., an immunodominant epitope) thereof], that are shared with a relevant reference polypeptide (e.g., a parent HA polypeptide that may, for example, be a pandemic HA), or portion thereof. The AI value resulting from comparison of any two polypeptides or sequences can be a number between 0 and 100, with a value of 100 indicating the two polypeptides, or portions thereof, are identical in sequence.

Antiviral agent: As used herein, the term "antiviral agent" refers to a class of medication used specifically for treating viral infections by inhibiting, deactivating, or destroying virus particles. In general, an antiviral agent may be or comprises a compound of any chemical class (e.g., a small molecule, metal, nucleic acid, polypeptide, lipid and/or carbohydrate). In some embodiments, an antiviral agent is or comprises an antibody or antibody mimic. In some embodiments, an antiviral agent is or comprises a nucleic acid agent (e.g., an antisense oligonucleotide, a siRNA, a shRNA, etc) or mimic thereof. In some embodiments, an antiviral agent is or comprises a small molecule. In some embodiments, an antiviral agent is or comprises a naturally-occurring compound (e.g., small molecule). In some embodiments, an antiviral agent has a chemical structure that is generated and/or modified by the hand of man.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Aptamer: As used herein, the term "aptamer" means a macromolecule composed of nucleic acid (e.g., RNA, DNA) that binds tightly to a specific molecular target (e.g., an umbrella topology glycan). A particular aptamer may be described by a linear nucleotide sequence and is typically about 15-60 nucleotides in length. Without wishing to be bound by any theory, it is contemplated that the chain of nucleotides in an aptamer form intramolecular interactions that fold the molecule into a complex three-dimensional shape, and this three-dimensional shape allows the aptamer to bind tightly to the surface of its target molecule. Given the extraordinary diversity of molecular shapes that exist within the universe of all possible nucleotide sequences, aptamers may be obtained for a wide array of molecular targets, including proteins and small molecules. In addition to high specificity, aptamers have very high affinities for their targets (e.g., affinities in the picomolar to low nanomolar range for proteins). Aptamers are chemically stable and can be boiled or frozen without loss of activity. Because they are synthetic molecules, they are amenable to a variety of modifications, which can optimize their function for particular applications. For example, aptamers can be modified to dramatically reduce their sensitivity to degradation by enzymes in the blood for use in in vivo applications. In addition, aptamers can be modified to alter their biodistribution or plasma residence time.

Associated with: Two events or entities are "associated" with one another, as that term is used herein, if the presence, level and/or form of one is correlated with that of the other. For example, a particular entity (e.g., polypeptide) is considered to be associated with a particular disease, disorder, or condition, if its presence, level and/or form correlates with incidence of and/or susceptibility of the disease, disorder, or condition (e.g., across a relevant population). In some embodiments, two or more entities are physically "associated" with one another if they interact, directly or indirectly, so that they are and remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Baby: As used herein, the term "baby" refers to a human under two years of age. Typical body weights for a baby ranges from 3 pounds up to 20 pounds.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can be assessed in any of a variety of contexts—including where interacting entities or moieties are studied in isolation or in the context of more complex systems (e.g., while covalently or otherwise associated with a carrier entity and/or in a biological system or cell).

Binding agent: In general, the term "binding agent" is used herein to refer to any entity that binds to a target of interest (e.g., to an HA polypeptide and/or to a glycan, such as an umbrella-topology glycan) as described herein. In some embodiments, binding agents are competing agents. In some embodiments, binding agents are detection or detecting agents. Binding agents may be of any chemical type. In some embodiments, binding agents are polypeptides (including, e.g., antibodies or antibody fragments); in some such embodiments, binding agents are HA polypeptides and/or variants thereof and/or characteristic portions thereof; in some embodiments, binding agents are polypeptides whose amino acid sequence does not include an HA characteristic sequence (i.e., "Non-HA polypeptides"). In some embodiments, binding agents are small molecules. In some embodiments, binding agents are nucleic acids. In some embodiments, binding agents are aptamers. In some embodiments, binding agents are polymers; in some embodiments, binding agents are non-polymeric. In some embodiments, binding agents are carbohydrates. In some embodiments, binding agents are lectins. In some embodiments, binding agents are peptidomimetics. In some embodiments, binding agents are scaffold proteins. In some embodiments, binding agents are mimotopes. In some embodiments, binding agents are stapled peptides. In certain embodiments, binding agents are nucleic acids, such as DNA or RNA.

Biologically active: As used herein, the phrase "biologically active" refers to a characteristic of any substance that has activity in a biological system (e.g., cell culture, organism, etc.). For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Characteristic portion: As used herein, the term "characteristic portion" is used, in the broadest sense, to refer to a portion of a substance whose presence (or absence) correlates with presence (or absence) of a particular feature, attribute, or activity of the substance. In some embodiments, a characteristic portion of a substance is a portion that is found in the substance and in related substances that share the particular feature, attribute or activity, but not in those that do not share the particular feature, attribute or activity. In certain embodiments, a characteristic portion shares at least one functional characteristic with the intact substance. For example, in some embodiments, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

Characteristic pandemic feature: As used herein the term "characteristic pandemic feature" is one that is found in at least one reference pandemic strain and not in at least one non-pandemic influenza strain. In some embodiments, a characteristic pandemic feature is one that is commonly found in pandemic strains and rarely found in non-pandemic strains. In some embodiments, a characteristic pandemic feature shows prevalence among representative pandemic strains that is at least 130% of that observed among representative non-pandemic strains. In some embodiments, a characteristic pandemic feature shows prevalence among representative pandemic strains that is at least 150%, 200%, 300%, 500% or 1,000% of that observed among representative non-pandemic strains.

Characteristic sequence: A "characteristic sequence" is a sequence that is found in all members of a family of polypeptides or nucleic acids, and therefore can be used by those of ordinary skill in the art to define members of the family.

Characteristic sequence element: As used herein, the phrase "characteristic sequence element" refers to a sequence element found in a polymer (e.g., in a polypeptide or nucleic acid) that represents a characteristic portion of that polymer. In some embodiments, presence of a characteristic sequence element correlates with presence or level of a particular activity or property of the polymer. In some embodiments, presence (or absence) of a characteristic sequence element defines a particular polymer as a member (or not a member) of a particular family or group of such polymers. A characteristic sequence element typically comprises at least two monomers (e.g., amino acids or nucleotides). In some embodiments, a characteristic sequence element includes at least 2, 3, 4, 5, 6, 7, 8, 9, 10, 11, 12, 13, 14, 15, 20, 25, 30, 35, 40, 45, 50, or more monomers (e.g., contiguously linked monomers). In some embodiments, a characteristic sequence element includes at least first and second stretches of contiguous monomers spaced apart by one or more spacer regions whose length may or may not vary across polymers that share the sequence element.

Child: As used herein, the term "child" refers to a human between two and 18 years of age. Body weight can vary widely across ages and specific children, with a typical range being 30 pounds to 150 pounds.

Combination therapy: The term "combination therapy", as used herein, refers to those situations in which two or more different pharmaceutical agents are administered in overlapping regimens so that the subject is simultaneously exposed to both agents.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Figure 8:
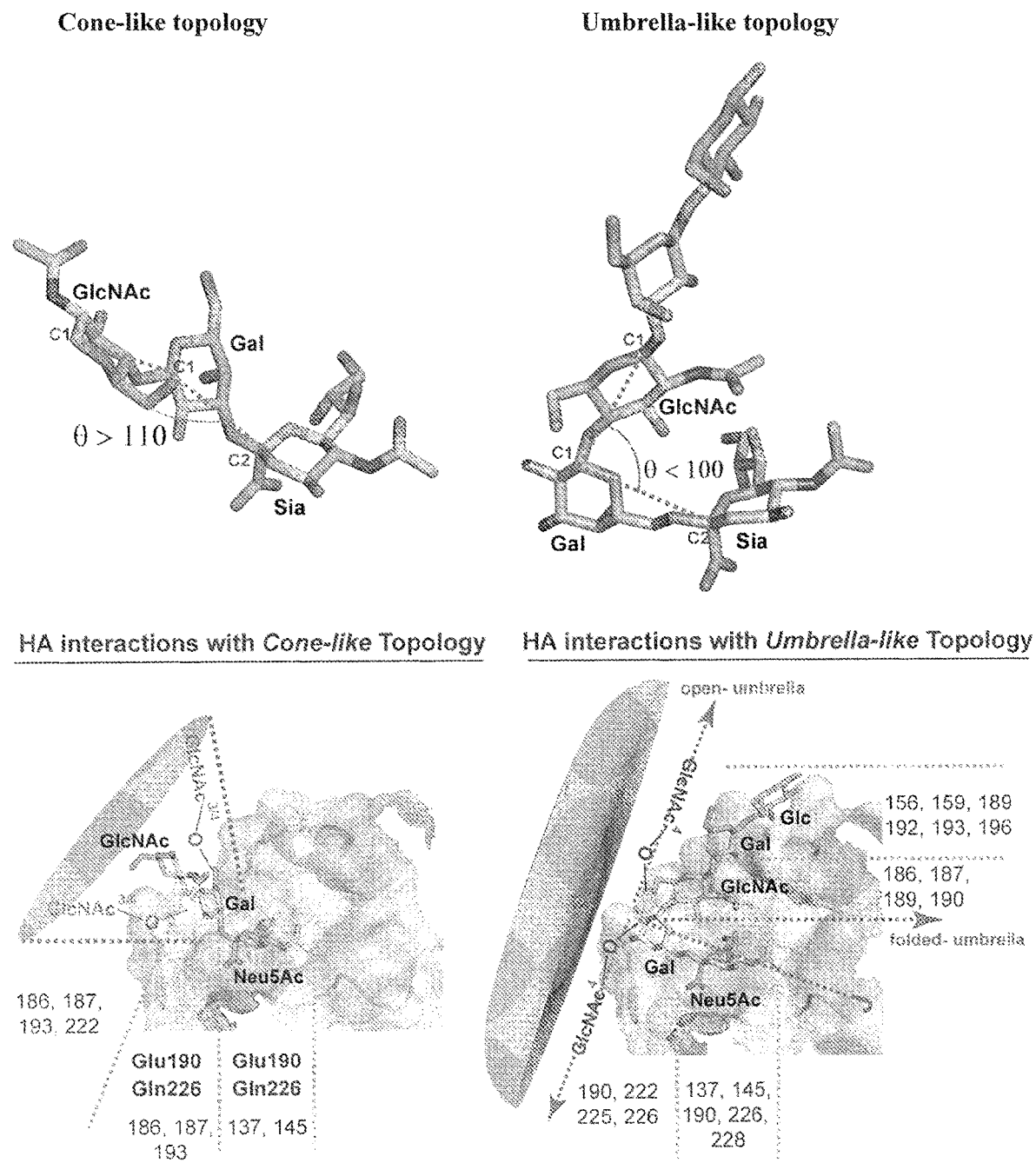
FIG. 8.
Figures 2, 9A:
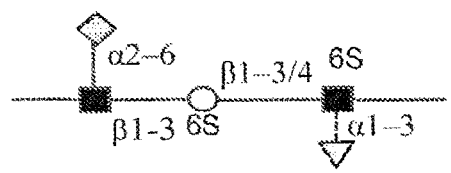
FIGS. 9A(1-7) and 9B show exemplary umbrella-topologies. (A) Certain exemplary (but not exhaustive) N- and O-linked glycan structures that can adopt umbrella-topologies. (B) Certain exemplary (but not exhaustive) O-linked glycan structures that can adopt umbrella-topologies.
Figures 5, 9A:
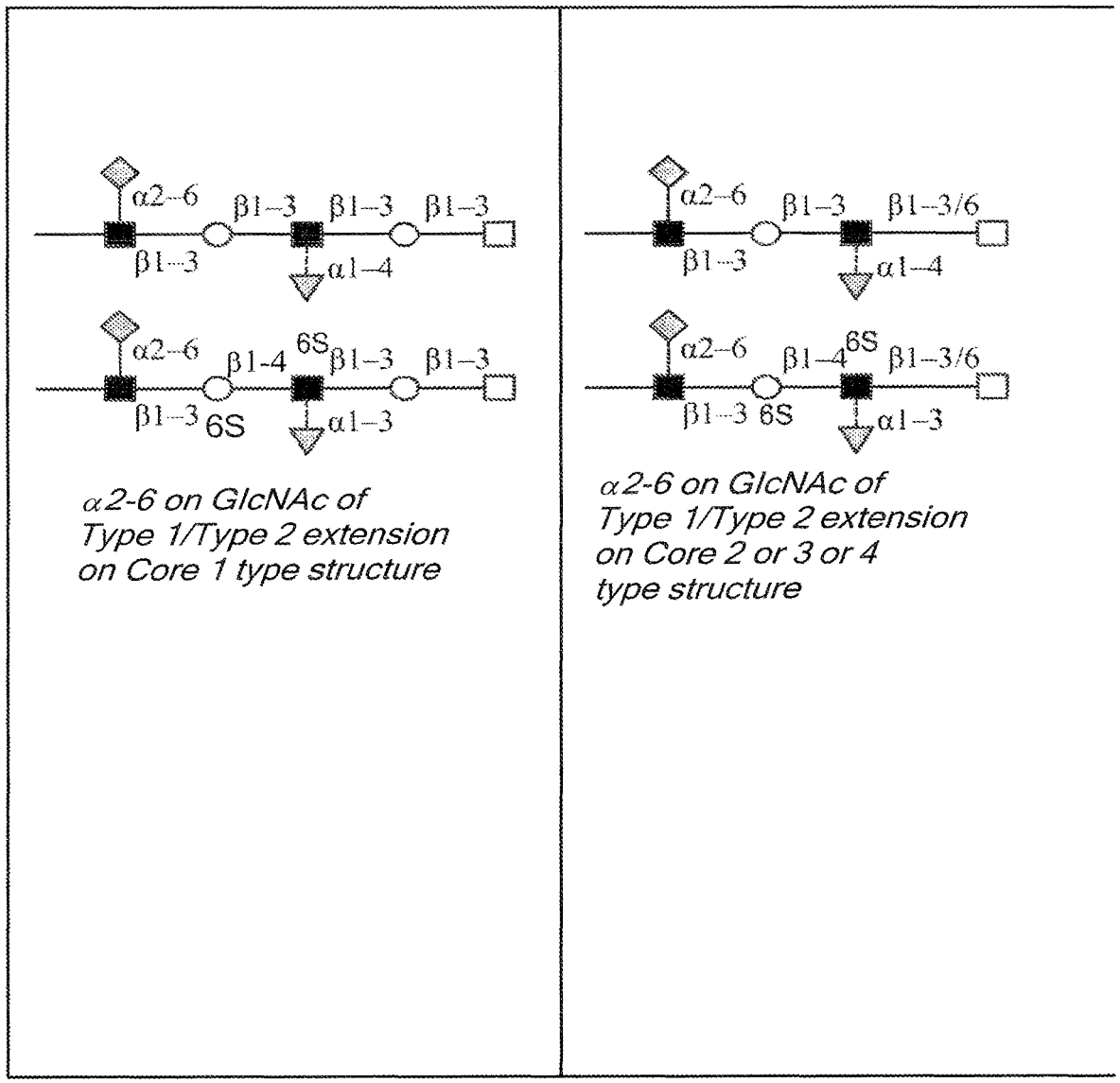
Figures 6, 9A:
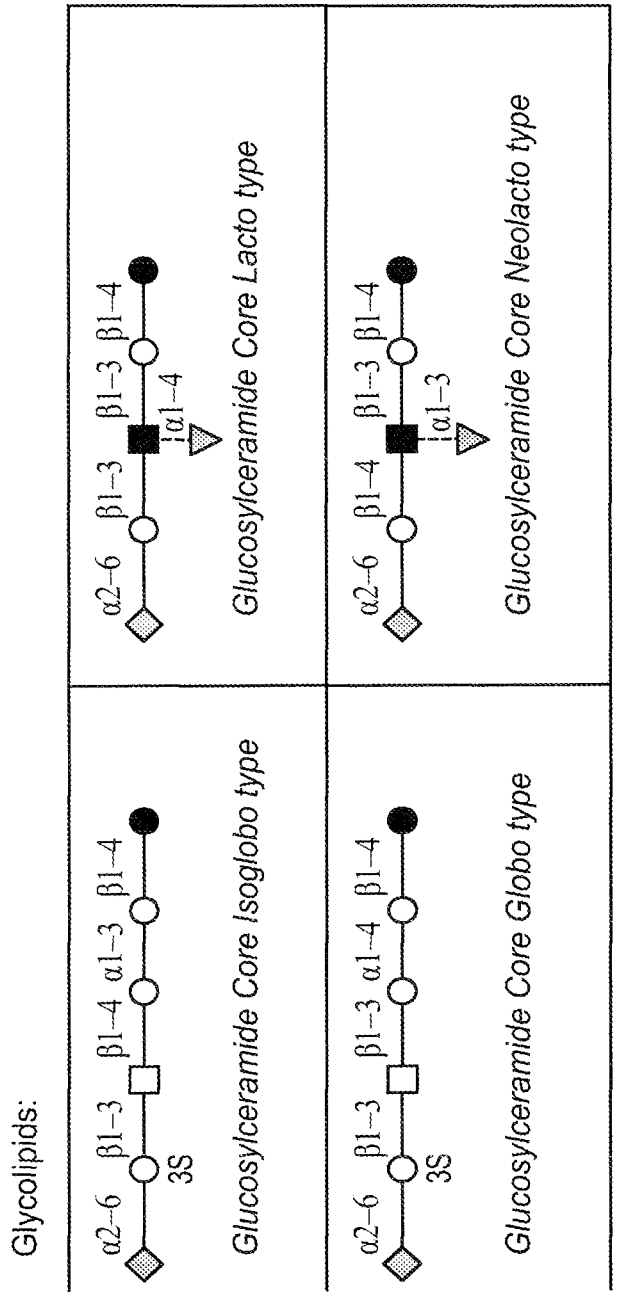
Figure 9A:
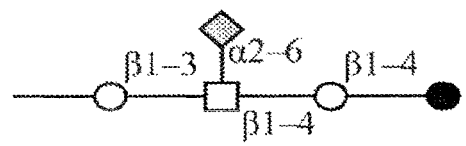
Figure 7:
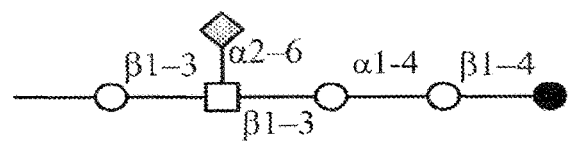
Figure 9B:
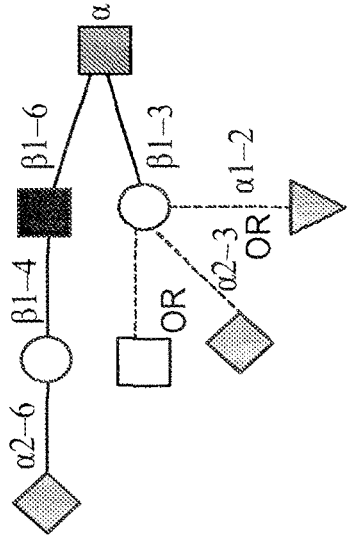
FIG. 9.
Figure 9B:
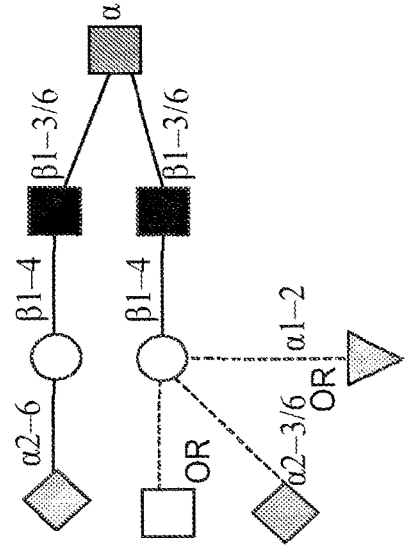
Figure 9B:
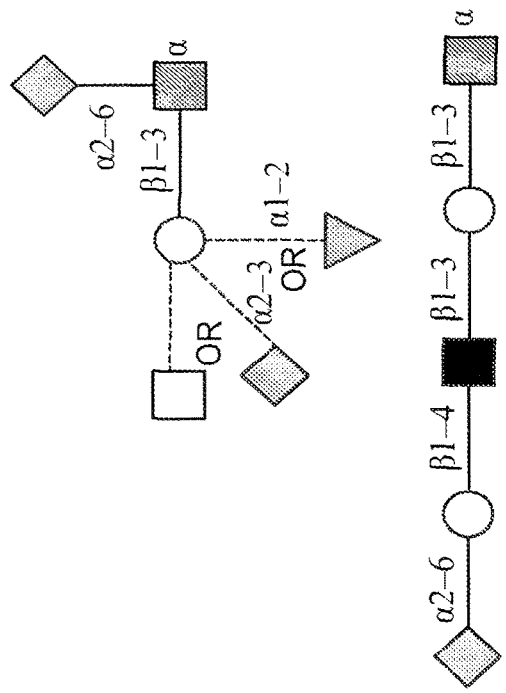
Figure 9B:

Cone-topology: The phrase "cone-topology" is used herein to refer to a 3-dimensional arrangement adopted by certain glycans and in particular by glycans on HA receptors. As illustrated in FIG. 8 (left panel), cone-topology can be adopted by α2-3 sialylated glycans or by α2-6 sialylated glycans, and is typical of short oligonucleotide chains, though some long oligonucleotides can also adopt this conformation. The cone-topology is characterized by the glycosidic torsion angles of Neu5Acα2-3Gal linkage which samples three regions of minimum energy conformations given by $\phi$ (C1-C2-O—C3/C6) value of about −60, about 60, or about 180 and $\psi$ (C2-O—C3/C6-H3/C5) samples −60 to 60. Certain representative (though not exhaustive) samples of glycans that adopt cone-topology are presented in FIG. 10. By way of example only, in some embodiments, cone-topology glycans are oligosaccharides of the following form: Neu5Acα2-3Galβ1-3GlcNAcMan, Neu5Acα2-3/6Galβ1-4GlcNAcMan, Neu5Acα2-3Galβ1-3GalNAc-, and combinations thereof.

Corresponding to: As used herein, the term "corresponding to" is often used to designate the position/identity of an amino acid residue in a polypeptide of interest. Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the $190^{th}$ amino acid in a particular amino acid chain but rather corresponds to the residue found at 190 in the reference polypeptide; those of ordinary skill in the art readily appreciate how to identify "corresponding" amino acids. Typically, residues in HA polypeptides are designated with reference to a canonical wild-type H3 HA, and reference in a polypeptide of interest that correspond to resides in the canonical wild-type H3 HA are described using the numbering of the residues to which they correspond.

Degree of separation removed: As used herein, amino acids that are a "degree of separation removed" are HA amino acids that have indirect effects on glycan binding. For example, one-degree-of-separation-removed amino acids may either: (1) interact with the direct-binding amino acids; and/or (2) otherwise affect the ability of direct-binding amino acids to interact with glycan that is associated with host cell HA receptors; such one-degree-of-separation-removed amino acids may or may not directly bind to glycan themselves. Two-degree-of-separation-removed amino acids either (1) interact with one-degree-of-separation-removed amino acids; and/or (2) otherwise affect the ability of the one-degree-of-separation-removed amino acids to interact with direct-binding amino acids, etc.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Direct-binding amino acids: As used herein, the phrase "direct-binding amino acids" refers to HA polypeptide amino acids which interact directly with one or more glycans that is associated with host cell HA receptors.

Dosage form: As used herein, the terms "dosage form" and "unit dosage form" refer to a physically discrete unit of a therapeutic protein (e.g., antibody) for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

Engineered: The term "engineered", as used herein, describes a polypeptide whose amino acid sequence has been selected by man and/or whose production required action of the hand of man. For example, an engineered HA polypeptide has an amino acid sequence that differs from the amino acid sequences of HA polypeptides found in natural influenza isolates. In some embodiments, an engineered HA polypeptide has an amino acid sequence that differs from the amino acid sequence of HA polypeptides included in the NCBI database.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Functional: As used herein, a "functional" biological molecule is a biological molecule in a form in which it exhibits a property and/or activity by which it is characterized.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs, RNAi-inducing agents, etc. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein—coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Glycan Array: As used herein, the term "glycan array" is used to refer to a set of glycans, optionally immobilized on a solid support. In some embodiments, a glycan array is or comprises a collection of glycans present as an organized arrangement or pattern at two or more locations that are physically separated in space. Typically, a glycan array will have at least 4, 8, 16, 24, 48, 96 or several hundred or thousand discrete locations. In general, provided glycan arrays may have any of a variety of formats. In some embodiments, a glycan array comprises a collection of glycans arranged on a single solid support; in some embodiments, a glycan array comprises a collection of glycans arranged on a plurality of discrete solid supports such as, for example, particulate supports (see, for example, U.S. patent application Ser. No. 13/087,332). In some embodiments, a glycan array is a microarray in that sample locations are separated from one another by a distance of 50-200 microns or less and/or immobilized glycans are present in the nano to micromolar range or nano to picogram range. Array formats known in the art include, for example, those in which each discrete sample location has a scale of, for example, ten microns. Any of a variety of supports may be utilized in glycan arrays. For example, support materials which may be of use in the invention include hydrophobic membranes, for example, nitrocellulose, PVDF or nylon membranes. Such membranes are well known in the art and can be obtained from, for example, Bio-Rad, Hemel Hempstead, UK. Alternatively or additionally, the support on which glycans are arrayed may comprise a metal oxide. Suitable metal oxides include, but are not limited to, titanium oxide, tantalum oxide, and aluminum oxide. Examples of such materials may be obtained from Sigma-Aldrich Company Ltd, Fancy Road, Poole, Dorset. BH12 4QH UK. Still further, in some embodiments, a support is or comprises a metal oxide gel. A metal oxide gel is considered to provide a large surface area within a given macroscopic area to aid immobilization of the carbohydrate-containing molecules. Additional or alternative support materials which may be used in accordance with the present invention include gels, for example silica gels or aluminum oxide gels. Examples of such materials may be obtained from, for example, Merck KGaA, Darmstadt, Germany. In some embodiments, glycan arrays are immobilized on a support that can resist change in size or shape during normal use. For example a support may be a glass slide coated with a component material suitable to be used to array glycans. Also, some composite materials can desirably provide solidity to a support. In some embodiments, glycans are directly attached to the support. In some embodiments, glycans are indirectly attached to the support, for example by being attached to a linker or carrier (e.g., a polypeptide) that is attached to the support. In some embodiments, glycans are covalently attached to the support; in some embodiments, glycans are non-covalently attached to the support. In some embodiments, glycans are reversibly attached to the support (e.g., by way of a cleavable linker and/or a reversible non-covalent interaction). In some embodiments, identity and/or arrangement of glycans in a glycan array is selected so that binding characteristics of polypeptides (e.g., HA polypeptides) of interest can readily be assessed. For example, in some embodiments, glycan arrays for use in accordance with the present invention include one or more cone-topology glycans and/or one or more umbrella-topology glycans. In some embodiments, cone topology glycans and umbrella topology glycans are spatially separated from one another. In some embodiments, a plurality of cone topology glycans, or a plurality of umbrella topology glycans, may be spatially localized together (but optionally apart from glycans of the other type). In some embodiments, glycan arrays for use in accordance with the present invention include one or more α2-3-linked glycans and/or one or more α 2-6-linked glycans. In some embodiments, α2-3-linked glycans and α2-6-linked glycans are spatially separated from one another. In some embodiments, a plurality of α2-3-linked glycans, or a plurality of α2-6-linked glycans, may be spatially localized together (but optionally apart from glycans of the other type). In some embodiments, such arrays include glycans representative of about 10%, 15%, 20%, 25%, 30% 35%, 40%, 45%, 50%, 55%, 60%, 65%, 70%, 75%, 80%, 85%, 90% 95%, or more of the glycans (e.g., the umbrella glycans, which will often be α2-6 sialylated glycans, particularly long α2-6 sialylated glycans) found on human HA receptors, and particularly on human upper respiratory tract HA receptors. In some embodiments, utilized glycan arrays include some or all of the umbrella and/or cone-topology glycan structures explicitly set forth herein. In some embodiments, arrays include at least about 10%, 15%, 20%, 25%, 30% 35%, 40%, 45%, 50%, 55%, 60%, 65%, 70%, 75%, 80%, 85%, 90% 95%, or more of these glycans.

Hemagglutinin (HA) polypeptide: As used herein, the term "hemagglutinin polypeptide" (or "HA polypeptide') refers to a polypeptide whose amino acid sequence i) shows significant identity with that of a reference HA; ii) includes a portion that shows significant identity with a corresponding portion of a reference HA; and/or iii) includes at least one characteristic sequence HA. In many embodiments, identity is considered "significant" for the purposes of defining an HA polypeptide if it is above 80%, 81%, 82%, 83%, 84%, 85%, 86%, 87%, 89%, 90%, 91%, 92%, 93%, 94%, 95%, 96%, 97%, 98%, 99%, or higher. In some embodiments, the portion showing significant identity has a length of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 300, 350, 450, 500, 550, 600 amino acids or more. A wide variety of HA sequences from influenza isolates are known in the art; indeed, the National Center for Biotechnology Information (NCBI) maintains a database (ncbi.nlm.nih.gov/genomes/FLU/) that includes at least 9796 HA sequences. In some embodiments, an HA polypeptide is defined based on its degree of sequence identity with a reference HA found in this database, or a portion thereof. Also, those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, or H16 polypeptides; or of HAs that mediate infection of particular hosts, e.g., avian, camel, canine, cat, civet, environment, equine, human, leopard, mink, mouse, seal, stone martin, swine, tiger, whale, etc. For example, in some embodiments, an HA polypeptide includes one or more characteristic sequence elements found between about residues 97 and about 185, about 324 and about 340, about 96 and about 100, and/or about 130 and about 230 of an HA protein found in a natural isolate of an influenza virus. In some embodiments, an HA polypeptide has an amino acid sequence comprising at least one of HA Sequence Elements 1 and 2, as defined herein. In some embodiments, an HA polypeptide has an amino acid sequence comprising HA Sequence Elements 1 and 2, in some embodiments separated from one another by about 100 to about 200, or by about 125 to about 175, or about 125 to about 160, or about 125 to about 150, or about 129 to about 139, or about 129, about 130, about 131, about 132, about 133, about 134, about 135, about 136, about 137, about 138, or about 139 amino acids. In some embodiments, an HA polypeptide has an amino acid sequence that includes residues at positions within the regions 96-100 and/or 130-230 that participate in glycan binding. In some embodiments, a reference HA polypeptide shows significant binding to human HA receptors and/or shows significant levels of human infectivity. In some embodiments, a reference HA polypeptide does not show significant binding to human HA receptors and/or does not show significant levels of human infectivity.

H7 HA polypeptide: An "H7 HA polypeptide", as that term is used herein, is an HA polypeptide whose amino acid sequence includes at least one sequence element that is characteristic of H7 and distinguishes H7 from other HA subtypes. Representative such sequence elements can be determined by alignments as will be understood by those skilled in the art.

HX polypeptide: An "HX polypeptide", as that term is used herein, is an HA polypeptide whose amino acid sequence includes at least one sequence element that is characteristic of HX and distinguishes HX from other HA subtypes, wherein "X" refers to the numbering of the HA subtype (e.g., wherein when "X"=1, 2, 3, 4, 5, 6, 7, 8, 9, 10, 11, 12, 13, 14, 15, or 16, "HX"=H1, H2, H3, H4, H5, H6, H7, H8, H9, H10, H11, H12, H13, H14, H15, or H16, respectively).

High affinity binding: The term "high affinity binding", as used herein refers to a high degree of tightness with which a particular ligand (e.g., an HA polypeptide) binds to its partner (e.g., an HA receptor). Affinities can be measured by any available method, including those known in the art. In some embodiments, binding is considered to be high affinity if the $K_d$ is about 500 pM or less (e.g., below about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 5 pM, about 4 pM, about 3 pM, about 2 pM, etc.) in binding assays. In some embodiments, binding is considered to be high affinity if the affinity is stronger (e.g., the $K_d$ is lower) for a polypeptide of interest than for a selected reference polypeptide. In some embodiments, binding is considered to be high affinity if the ratio of the $K_d$ for a polypeptide of interest to the $K_d$ for a selected reference polypeptide is 1:1 or less (e.g., 0.9:1, 0.8:1, 0.7:1, 0.6:1, 0.5:1. 0.4:1, 0.3:1, 0.2:1, 0.1:1, 0.05:1, 0.01:1, or less). In some embodiments, binding is considered to be high affinity if the $K_d$ for a polypeptide of interest is about 100% or less (e.g., about 99%, about 98%, about 97%, about 96%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, about 1% or less) of the $K_d$ for a selected reference polypeptide.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Host: The term "host" is used herein to refer to a system (e.g., a cell, organism, etc) in which a polypeptide of interest is present. In some embodiments, a host is a system that is susceptible to infection with a particular infectious agent. In some embodiments, a host is a system that expresses a particular polypeptide of interest.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM 120 weight residue table, a gap length penalty of 12 and a gap penalty of 4. The percent identity between two nucleotide sequences can, alternatively, be determined using the GAP program in the GCG software package using an NWSgapdna.CMP matrix.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Long oligosaccharide: For purposes of the present disclosure, an oligosaccharide is typically considered to be "long" if it includes at least one linear chain that has at least four saccharide residues.

Low affinity binding: The term "low affinity binding", as used herein refers to a low degree of tightness with which a particular ligand (e.g., an HA polypeptide) binds to its partner (e.g., an HA receptor). As described herein, affinities can be measured by any available method, including methods known in the art. In some embodiments, binding is considered to be low affinity if the $K_d$ is about 100 pM or more (e.g., above about 200 pM, 300 pM, 400 pM, 500 pM, 600 pM, 700 pM, 800 pM, 900 pM, 1 nM, 1.1. nM, 1.2 nM, 1.3 nM, 1.4 nM, 1.5 nM, etc.) In some embodiments, binding is considered to be low affinity if the affinity is the same or lower (e.g., the $K_d$ is about the same or higher) for a polypeptide of interest than for a selected reference polypeptide. In some embodiments, binding is considered to be low affinity if the ratio of the $K_d$ for a polypeptide of interest to the $K_d$ for a selected reference polypeptide is 1:1 or more (e.g., 1.1:1, 1.2:1, 1.3:1, 1.4:1, 1.5:1, 1.6:1, 1.7:1, 1.8:1, 1.9:1, 2:1, 3:1, 4:1, 5:1, 10:1 or more). In some embodiments, binding is considered to be low affinity if the $K_d$ for a polypeptide of interest is 100% or more (e.g., 100%, 105%, 110%, 115%, 120%, 125%, 130%, 135%, 140%, 145%, 150%, 155%, 160%, 165%, 170%, 175%, 180%, 185%, 190%, 195%, 200%, 300%, 400%, 500%, 1000%, or more) of the $K_d$ for a selected reference polypeptide.

Mimotope: As used herein, the term "mimotope" refers to a macromolecule which mimics the structure of an epitope. In some embodiments, a mimotope elicits an antibody response identical or similar to that elicited by its corresponding epitope. In some embodiments, an antibody that recognizes an epitope also recognizes a mimotope which mimics that epitope. In some embodiments, a mimotope is a peptide. In some embodiments, a mimotope is a small molecule, carbohydrate, lipid, or nucleic acid. In some embodiments, mimotopes are peptide or non-peptide mimotopes of conserved influenza epitopes. In some embodiments, by mimicking the structure of a defined viral epitope, a mimotope interferes with the ability of influenza virus particles to bind to its natural binding partners, e.g., by binding to the natural binding partner itself.

Mutant: As used herein, the term "mutant" refers to an entity that shows significant structural identity with a reference entity but differs structurally from the reference entity in the presence or level of one or more chemical moieties as compared with the reference entity. In many embodiments, a mutant also differs functionally from its reference entity. In general, whether a particular entity is properly considered to be a "mutant" of a reference entity is based on its degree of structural identity with the reference entity. As will be appreciated by those skilled in the art, any biological or chemical reference entity has certain characteristic structural elements. A mutant, by definition, is a distinct chemical entity that shares one or more such characteristic structural elements. To give but a few examples, a small molecule may have a characteristic core structural element (e.g., a macrocycle core) and/or one or more characteristic pendent moieties so that a mutant of the small molecule is one that shares the core structural element and the characteristic pendent moieties but differs in other pendent moieties and/or in types of bonds present (single vs double, E vs Z, etc) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a mutant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a mutant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a mutant polypeptide does not share at least one characteristic sequence element with a reference polypeptide. In some embodiments, the reference polypeptide has one or more biological activities. In some embodiments, a mutant polypeptide shares one or more of the biological activities of the reference polypeptide. In some embodiments, a mutant polypeptide lacks one or more of the biological activities of the reference polypeptide. In some embodiments, a mutant polypeptide shows a reduced level of one or more biological activities as compared with the reference polypeptide.

Non-natural amino acid: The phrase "non-natural amino acid" refers to an entity having the chemical structure of an amino acid (i.e.:

$$H_2N-\underset{R}{CH}-\overset{O}{\underset{\|}{C}}-OH \quad )$$

and therefore being capable of participating in at least two peptide bonds, but having an R group that differs from those found in nature. In some embodiments, non-natural amino acids may also have a second R group rather than a hydrogen, and/or may have one or more other substitutions on the amino or carboxylic acid moieties.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Pandemic strain: A "pandemic" influenza strain is one that has or has capacity to cause pandemic infection of human populations. In some embodiments, a pandemic strain has caused pandemic infection. In some embodiments, such pandemic infection involves epidemic infection across multiple territories, and particularly across territories that are separated from one another (e.g., by mountains, bodies of water, as part of distinct continents, etc) such that infections ordinarily do not pass between them.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Predominantly present: The term "predominantly present", as used herein, refers to the presence of an entity (e.g., an amino acid residue) at a particular location across a population. For example, an amino acid may be predominantly present if, across a population of polypeptides, a particular amino acid is statistically present at a particular position in at least about 50%, about 55%, about 60%, about 65%, about 70%, about 75%, about 80%, about 85%, about 90%, about 95%, about 96%, about 97%, about 98%, about 99% or more of the polypeptides within a relevant population.

Prevention: The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain l-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Receptor-Binding Site (RBS): As used herein, the term "receptor-binding site" or "RBS" comprises residues spanning positions 56 to 73, 87-96, 127-160 and 183-230 (numbered according to H5 HA crystal structure PDB ID: 2IBX) which include direct-binding amino acids.

Receptor-Binding Site Network (RBSN): The term "receptor-binding site network (RBSN)" refers to a set of amino acid residues that are a part of the RBS that are arranged in three-dimensional space to permit interaction with one another in the context of a folded polypeptide chain. The amino acid residues include direct-binding amino acids that make contacts with glycan receptor in the cone-like and umbrella-like topology Receptor-Binding Site Network (RBSN) Diagram: As used herein, the term "receptor-binding site network (RBSN) diagram" refers to a two-dimensional open connectivity network diagram that captures interactional relationship between amino acids in the RBS.

Receptor-Binding Site Network (RBSN) Score: As used herein, the term "receptor-binding site network (RBSN) score" refers to a score assigned to an amino acid residue in a polypeptide based on the extent of its network of interactions with other amino acids in its close spatial environment (such as the ability of that residue's side chain to interact with side chains of other residues in the polypeptide), and/or on the nature of such interactions, as described herein. For example, as described herein, the RBSN score varies from 0 (absence of any network) to 1 (most networked). The higher the network of an amino acid within the RBS, the more it is structurally constrained to be mutated.

Refractory: The term "refractory" as used herein, refers to any subject that does not respond with an expected clinical efficacy following the administration of provided compositions as normally observed by practicing medical personnel.

Seeding potential: As used herein, the term "seeding potential" refers to a likelihood of an agent (e.g., an infectious agent such as a virus, a bacterium, etc.) to propagate infection. In some embodiments, seeding potential is correlated with the ability of an agent (e.g., an infectious agent such as a virus, a bacterium, etc.) to give rise to variant progeny. For example, a seed strain may have 10%, 15%, 20%, 25%, 30%, 35%, 40%, 45%, 50%, 55%, 60%, 65%, 70%, 75%, 80%, 85%, 90%, 95%, or 100% variant progeny.

Short oligosaccharide: For purposes of the present disclosure, an oligosaccharide is typically considered to be "short" if it has fewer than 4, or certainly fewer than 3, residues in any linear chain.

Small Molecule: In general, a "small molecule" is a molecule that is less than about 5 kilodaltons (kD) in size. In some embodiments, the small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. In some embodiments, in accordance with the present invention, small molecules are not proteins, polypeptides, oligopeptides, peptides, polynucleotides, oligonucleotides, polysaccharides, glycoproteins, proteoglycans, etc.

Specificity: As is known in the art, "specificity" is a measure of the ability of a particular ligand (e.g., an HA polypeptide) to distinguish its binding partner (e.g., a human HA receptor, and particularly a human upper respiratory tract HA receptor) from other potential binding partners (e.g., an avian HA receptor).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial numerical similarity: As used herein, the term "substantial numerical similarity" refers to two values, for example, two RBSN scores, having a numerical value that does not differ by more than 30%.

Substantial sequence homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution. Typical amino acid categorizations are summarized below:

| | | | | | |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul, et al., "Gapped BLAST and PSI-BLAST: a new generation of protein database search programs", Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215(3): 403-410, 1990; Altschul, et al., Methods in Enzymology; Altschul et al., Nucleic Acids Res. 25:3389-3402, 1997; Baxevanis et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial structural similarity: As used herein, the term "substantial structural similarity" refers to presence of shared structural features such as presence and/or identity of particular amino acids at particular positions (see definitions of "shared sequence homology" and "shared sequence identity"). In some embodiments the term "substantial structural similarity" refers to presence and/or identity of structural elements (for example: loops, sheets, helices, H-bond donors, H-bond acceptors, glycosylation patterns, salt bridges, and disulfide bonds). In some other embodiments, the term "substantial structural similarity" refers to three dimensional arrangement and/or orientation of atoms or moieties relative to one another (for example: distance and/or angles between or among them between an agent of interest and a reference agent).

Suffering from: An individual who is "suffering from" a disease, disorder, or condition (e.g., influenza) has been diagnosed with and/or exhibits one or more symptoms of the disease, disorder, or condition.

Susceptible to: An individual who is "susceptible to" a disease, disorder, or condition (e.g., influenza) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition (e.g., the individual has been exposed to Influenza virus). In some embodiments, a risk of developing a disease, disorder, and/or condition is a population-based risk.

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. To give but a few examples, exemplary symptoms of influenza include, but are not limited to, inflammation, fever, nausea, weight loss, loss of appetite, rapid breathing, increase heart rate, high blood pressure, body aches, muscle pain, eye pain, fatigue, malaise, dry cough, runny nose, and/or sore throat. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutic agent: As used herein, the phrase "therapeutic agent" refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" refers to an amount of a therapeutic protein which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance (e.g., provided compositions) that partially or completely alleviates, ameliorates, relives, inhibits, delays onset of, reduces severity of, and/or reduces incidence of one or more symptoms, features, and/or causes of a particular disease, disorder, and/or condition (e.g., influenza). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Umbrella-topology: The phrase "umbrella-topology" is used herein to refer to a 3-dimensional arrangement adopted by certain glycans and in particular by glycans on HA receptors. This is in contrast to glycans having a "cone-topology" as discussed above. As described in PCT Patent Application Nos. PCT/US09/30056 and PCT/US07/18160; incorporated herein by reference, binding to umbrella-topology glycans is characteristic of HA proteins that mediate infection of human hosts. The umbrella-topology is typically adopted only by α2-6 sialylated glycans, and is typical of long (e.g., greater than tetrasaccharide) oligosaccharides. In some embodiments, umbrella-topology glycans are glycans exhibiting a three-dimensional structure substantially similar to the structure presented in FIG. 8 (right panel). In some embodiments, umbrella-topology glycans are glycans which contact HA polypeptides via the amino acid residues shown in FIG. 8 (right panel). In some embodiments, umbrella-topology glycans are glycans which are able to contact and/or specifically bind to the amino acid binding pocket shown in FIG. 8 (right panel). In some embodiments, glycan structural topology is classified based on parameter θ defined as angle between $C_2$ of Sia, $C_1$ of Gal, and $C_1$ of GlcNAc. Values of θ>110° represent cone-like topology adopted by α2-3 and short α2-6 glycans. Values of θ<100° represent umbrella-like topology, such as topology adopted by long α2-6 glycans. An example of umbrella-opology is given by φ angle of Neu5Acα2-6Gal linkage of around −60. In some embodiments, umbrella-topology glycans (e.g., at a site) comprise a greater proportion of long (e.g. multiple lactosamine units) α2-6 oligosaccharide branches than short α2-6 (e.g. single lactosamine) branches. Exemplary N- and O-linked glycan structures capable of adopting an umbrella-topology are found in FIG. 9. In some embodiments, umbrella-topology glycans (e.g., at a site) comprise about 2-fold, about 3-fold, about 4-fold, about 5-fold, about 10-fold, about 20-fold, about 50-fold, or greater than about 50-fold more long α2-6 oligosaccharide branches than short α2-6 (e.g. single lactosamine) branches. In some embodiments, the unique characteristic of HA interactions with umbrella-topology glycans and/or glycan decoys is the HA contact with a glycan comprising sialic acid (SA) and/or SA analogs at the non-reducing end. In some embodiments, chain length of the oligosaccharide is at least a trisaccharide (excluding the SA or SA analog). In some embodiments, umbrella-opology glycans are oligosaccharides of the following form:

Neu5Acα2-6Sug1-Sug2-Sug3 where:

(a) Neu5Ac α2-6 is typically (but not essentially) at the non-reducing end;

(b) Sug1:

(i) is a hexose (frequently Gal or Glc) or hexosamine (GlcNAc or GalNAc) in α or β configuration (frequently β- for N- and O-linked extension and α- in the case of GalNAcα- that is O-linked to glycoprotein);

(ii) no sugars other than Neu5Acα2-6 are attached to any of the non-reducing positions of Sug1 (except when Sug1 is GalNAcα- that is O-linked to the glycoprotein); and/or (iii) non-sugar moieties such as sulfate, phosphate, guanidium, amine, N-acetyl, etc. can be attached to non-reducing positions (typically 6 position) of Sug1 (e.g., to improve contacts with HA);

(c) Sug2 and/or Sug3 is/are:

(i) hexose (frequently Gal or Glc) or hexosamine (GlcNAc or GalNAc) in α or β configuration (frequently β); and/or (ii) sugars (such as Fuc) or non-sugar moieties such as sulfate, phosphate, guanidium, amine, N-acetyl, etc. can be attached to non-reducing positions of Sug2, Sug3, and/or Sug4;

(d) Linkage between any two sugars in the oligosaccharide apart from Neu5Acα2-6 linkage can be 1-2, 1-3, 1-4, and/or 1-6 (typically 1-3 or 1-4); and/or (e) Structure where Neu5Acα2-6 is linked GalNAcα that is O-linked to the glycoprotein and additional sugars are linked to the non-reducing end of GalNAcα for example (i) Neu5Acα2-6(Neu5Acα2-3Galβ1-3)GalNAcα-

(ii) Neu5Acα2-6(Galβ1-3)GalNAcα-.

By way of example only, in some embodiments, umbrella-opology glycans are oligosaccharides of the following form: Neu5Acα2-6Galβ1-4GlcNAcβ1-3Galβ1-4GlcNAc-, Neu5Acα2-6GalNAcβ1-4GlcNAcβ1-3GalNAcβ1-4GlcNAc-, Neu5Acα2-6GlcNAcβ1-3Galβ1-3/4GlcNAc-, Neu5Acα2-6Galβ1-4GlcNAcβ1-3Galβ1-3GalNAcα, Neu5Acα2-6Galβ1-4GlcNAcβ1-3Galβ1-4GlcNAcβ1-3Galβ1-3GalNAcα, Neu5Acα2-6GalNAcβ1-4GlcNAcβ1-3Galβ1-3GalNAcα, Neu5Acα2-6GalNAcβ1-4GlcNAcβ1-3GalNAcβ1-4GlcNAcβ1-3Galβ1-3GalNAcα, Neu5Acα2-6 GalNAcα-β1-3Galα2-3Neu5Ac, Neu5Acα2-6Galβ1-4GlcNAcβ1-3/6GalNAcα, Neu5Acα2-6Galβ1-4GlcNAcβ1-3Galβ1-4GlcNAcβ1-3/6GalNAcα, Neu5Acα2-6GalNAcβ1-4GlcNAcβ1-3/6GalNAcα, Neu5Acα2-6GalNAcβ1-4GlcNAcβ1-3GalNAcβ1-4GlcNAcβ1-3/6GalNAcα, Neu5Acα2-6Galβ1-4GlcNAcβ1-6GalNAcα-β1-3Galα2-3Neu5Ac, Neu5Acα2-6Galβ1-4GlcNAcβ1-3/6GalNAcα-β1-3/6GlcNAcβ1-4Galα2-3/6Neu5Ac, Neu5Acα2-6GlcNAcβ1-3Galβ1-4GlcNAcβ1-3Galβ1-3GalNAc, Neu5Acα2-6GlcNAcβ1-3Galβ1-3GlcNAcβ1-3/6GalNAc, Neu5Acα2-6GlcNAcβ1-3Galβ1-4GlcNAcβ1-3/6GalNAc, Neu5Acα2-6Galβ1-3GalNAcβ1-4Galα1-3Galβ1-4Glc, Neu5Acα2-6Galβ1-4GlcNAcβ1-3Galβ1-4Glc, Neu5Acα2-6Galβ1-3GalNAcβ1-3Galα1-4Galβ1-4Glc, Neu5Acα2-6Galβ1-3GlcNAcβ1-3Galβ1-4Glc, Neu5α2-6Galβ1-4GlcNAcβ1-3GalNAcα, Neu5Acα2-6Galβ1-4GlcNAcβ1-3Galβ1-3GalNAcα, Neu5Acα2-6GalNAc(β1-3Gal-)β1-4Galβ1-4Glc, Neu5Acα2-6GalNAc(β1-3Gal-)β1-3Galα1-4Galβ1-4Glc, and combinations thereof.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Variant: As used herein, the term "variant" refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs double, E vs Z, etc) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

Vector: As used herein, "vector" refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

Wild-type: As used herein, the term "wild-type" has its art-understood meaning that refers to an entity having a structure and/or activity as found in nature in a "normal" (as contrasted with mutant, diseased, altered, etc) state or context. Those of ordinary skill in the art will appreciate that wild-type genes and polypeptides often exist in multiple different forms (e.g., alleles).

DETAILED DESCRIPTION OF CERTAIN EMBODIMENTS

The present invention provides, among other things, methods and compositions relating to detection, treatment, and/or prevention of influenza transmission and/or infection. In some embodiments, the present invention provides vaccine compositions, diagnostic kits, and methods of making vaccine compositions.

Influenza Infection and Hemagglutinin (HA) Polypeptides

Influenza has a long history of pandemics, epidemics, resurgences and outbreaks. Avian influenza is a highly contagious and potentially fatal pathogen, but it currently has only a limited ability to infect humans.

Influenza viruses are RNA viruses which are characterized by a lipid membrane envelope containing two glycoproteins, hemagglutinin (HA) and neuraminidase (NA), embedded in the membrane of the virus particle. The viral genome is made up of several negative sense single stranded RNA molecules. Several proteins are encoded by the viral genome. NA is a viral surface glycoprotein that cleaves terminal sialic acid residues from carbohydrate moieties on the surfaces of infected cells, promoting the release of progeny viruses. HA is one of the major viral surface glycoproteins and involved in the binding of the virus to sialic acids on the surface of susceptible cells (Uiprasertkul et al. Emerg. Infect. Dis. 11:1036, 2005).

Influenza HA is a trimer on virus particles. Influenza HA is synthesized as HA0 by virus post-infection in cells that is cleaved by cellular proteases at the basic cleavage site into mature forms, which is required for proper function of this surface protein and for viral life cycle. The M2 protein is an ion channel protein. The HA, NA, and M2 protein are present in the viral envelope which is derived from the host cell plasma membrane. A ribonucleoprotein complex comprises an RNA segment associated with nucleoprotein (NP) and three polymerases, PA, PB1, and PB2. The M1 protein is associated with both ribonucleoprotien and the envelope.

Mature HA polypeptides are comprised of two domains, (1) a core HA-1 domain known as the sialic acid-binding domain, and (2) the transmembrane stalk of HA, known as HA-2 domain. HA-1 contains the binding site for glycans and it is thought that HA-1 is responsible for mediating binding of HA to the HA-receptor. HA-2 is responsible for presenting the HA-1 domain. Typically, polar and non-polar interactions between the three long HA alpha-helices of the stem of HA monomers provide the main forces for stabilizing the HA trimer. It will be appreciated that HA polypeptides in accordance with the present invention may contain amino acid residues and/or sequences from any HA domain (e.g., core HA-1, transmembrane HA-2, and/or combinations thereof).

In some embodiments, an HA polypeptide in accordance with the present invention contains sequences that are conserved across more than one influenza subtype. For example, analysis of HA sequences from all influenza subtypes showed a set of amino acids in the interface of the HA-1 (head) and HA-2 (stalk) domains that are well conserved and accessible to prospective therapeutic molecules. Studies have also observed the excellent broad spectrum conservation of the HA-1/HA-2 interface membrane proximal epitope region (MPER) that includes the canonical α-helix and residues in its vicinity (Ekiert et al., Science, 324(5924): 246, 2009; Sui et al., Nat Struct Mol Biol. 16(3):265, 2009).

Annual epidemics of influenza occur when the antigenic properties of the viral HA and NA proteins are altered. The mechanism of altered antigenicity is twofold: antigenic shift, caused by genetic rearrangement between human and animal viruses after double infection of host cells, which can cause a pandemic; and antigenic drift, caused by small changes in the HA and NA proteins on the virus surface, which can cause influenza epidemics.

There are 16 known HA subtypes (H1-H16) and 9 NA subtypes (N1-N9), and different influenza strains are named based on the number of the strain's HA and NA subtypes, and different influenza strains are named based on the number of the strain's HA polypeptide and NA polypeptide subtypes, wherein there are different combinations of one HA polypeptide subtype combined with one NA polypeptide subtype (e.g., H1N1, H1N2, H7N9, etc.).

Based on comparisons of amino acid sequence identity and of crystal structures, the HA subtypes have been divided into two main groups and four smaller clades. The different HA subtypes do not necessarily share strong amino acid sequence identity, but the overall 3D structures of the different HA subtypes are similar to one another, with several subtle differences that can be used for classification purposes. For example, the particular orientation of the membrane-distal subdomains in relation to a central α-helix is one structural characteristic commonly used to determine HA subtype (Russell et al., 2004 Virology, 325:287, 2004). Those skilled in the art are well familiar with sequence and other structural similarities and differences that can be used to define and/or to distinguish different subtypes and/or clades of influenza viruses.

Only three (H1, H2, and H3) of the sixteen HA subtypes have thus far become adapted for human infection. One reported characteristic of HAs that have adapted to infect humans (e.g., of HAs from the pandemic H1N1 (1918) and H3N2 (1967-68) influenza subtypes) is their ability to preferentially bind to α2-6 sialylated glycans in comparison with their avian progenitors that preferentially bind to α2-3 sialylated glycans (Skehel & Wiley, 2000 Annu Rev Biochem, 69:531; Rogers, & Paulson, 1983 Virology, 127:361; Rogers et al., 1983 Nature, 304:76; Sauter et al., 1992 Biochemistry, 31:9609; Connor et al., 1994 Virology, 205: 17; Tumpey et al., 2005 Science, 310:77).

Several crystal structures of HAs from H1 (human and swine), H2 (human and avian), H3 (avian) and H5 (avian) subtypes bound to sialylated oligosaccharides (of both α2-3 and α2-6 linkages) are available and provide molecular insights into the specific amino acids that are involved in distinct interactions of the HAs with these glycans (Eisen et al., 1997 Virology, 232:19; Ha et al., 2001 Proc Natl Acad Sci USA, 98:11181; Ha et al., 2003 Virology, 309:209; Gamblin et al., 2004 Science, 303:1838; Stevens et al., 2004 Science, 303:1866; Russell et al., 2006 Glycoconj J 23:85; Stevens et al., 2006 Science, 312:404; Xu R et al., 2010 J Virol 84(4):1715; Liu J, et al., 2009 Proc Natl Acad Sci USA 106(40):17175).

Symptoms and Effects of Influenza Infection

Influenza infection or "flu" is a viral infection predominantly of the nose, throat and bronchial tubes of the human body. As described above, given the presence of several different influenza strains and subtypes, severity of the symptoms associate with influenza infection can vary depending on the type of infection. Symptoms can also become life threatening in those individuals with chronic underlying illnesses (such as cancer, emphysema or diabetes) or those who are immunocompromised. While the severity of the symptoms may vary, there are several hallmark symptoms of an influenza infection such as, but not limited to, inflammation, fever, nausea, weight loss, loss of appetite, rapid breathing, increase heart rate, high blood pressure, body aches, muscle pain, eye pain, fatigue, malaise, dry cough, runny nose, and/or sore throat. As a result, in some embodiments, the manifestation of symptoms within a patient can be used as a prognostic or diagnostic to determine the presence of an influenza infection. In some embodiments, the severity and/or change of symptoms may be used to determined the dosing regiment for an influenza treatment, such as administration of a binding agent. In some embodiments, the onset, severity and/or change of symptoms displayed by the patient, may be used to indicate the need for prophylactic treatment of a patient with a binding agent. In some embodiments, the severity, change and/or ameliortion of symptoms may be used to evaluate a patient's response to a specific type or method of influenza treatment.

HA Receptor

Influenza infection is mediated by interaction of HA with the surface of cells through binding to a glycoprotein receptor. Binding of HA to HA receptors is predominantly mediated by N-linked glycans on the HA receptors. Specifically, HA on the surface of flu virus particles recognizes sialylated glycans that are associated with HA receptors on the surface of the cellular host. After recognition and binding, the host cell engulfs the viral cell and the virus is able to replicate and produce many more virus particles to be distributed to neighboring cells. Some crystal structures of exemplary HA-glycan interactions have been identified and are presented in Table 1:

TABLE 1

Crystal Structures of HA-Glycan Complexes

| Abbreviation (PDB ID) | Virus Strain | Glycan (with assigned coordinates) |
|---|---|---|
| ADkALB76_H1_26 (2WRH) | A/duck/Alberta/76 (H1N1) | Neu5Ac |
| ASI30_H1_23 (1RV0) | A/Swine/Iowa/30 (H1N1) | Neu5Ac |
| ASI30_H1_26 (1RVT) | A/Swine/Iowa/30 (H1N1) | Neu5Acα6Galβ4GlcNAcβ3Galβ4Glc |
| ASC18_H1_26 (2WRG) | A/South Carolina/1/18 (H1N1) | Neu5Acα6Galβ4GlcNAcβ3Gal |

TABLE 1-continued

| Crystal Structures of HA-Glycan Complexes | | |
|---|---|---|
| Abbreviation (PDB ID) | Virus Strain | Glycan (with assigned coordinates) |
| APR34_H1_23 (1RVX) | A/Puerto Rico/8/34 (H1N1) | Neu5Acα3Galβ4GlcNAc |
| APR34_H1_26 (1RVZ) | A/Puerto Rico/8/34 (H1N1) | Neu5Acα6Galβ4GlcNAc |
| ACkNY91_H2_23 (2WR2) | A/chicken/NY/29878/91 (H2N2) | Neu5Acα3Galβ3GlcNAc |
| AckNY91_H2_26 (2WR1) | A/chicken/NY/29878/91 (H2N2) | Neu5Acα6Galβ4GlcNAc |
| AdkON77_H2_23 (2WR3) | A/duck/Ontario/77 (H2N2) | Neu5Acα3Galβ4GlcNAc |
| AdkON77_H2_26 (2WR4) | A/duck/Ontario/77 (H2N2) | Neu5Acα6Galβ4GlcNAc |
| AckPD84_H2_26 (2WRF) | A/chicken/Potsdam/475/84 (H2N2) | Neu5Acα6Gal |
| ASING57_H2_23 (2WRB) | A/Singapore/1/57 (H2N2) | Neu5Ac |
| ASING57_H2_26 (2WR7) | A/Singapore/1/57 (H2N2) | Neu5Acα6Galβ4GlcNAcβ3Gal |
| AJAP57_H2_26(2WRE) | A/Japan/305/57 (H2N2) | Neu5Acα6Gal |
| ADU63_H3_23 (1MQM) | A/Duck/Ukraine/1/63 (H3N8) | Neu5Acα3Gal |
| ADU63_H3_26 (1MQN) | A/Duck/Ukraine/1/63 (H3N8) | Neu5Acα6Gal |
| AAI68_H3_23 (1HGG) | A/Aichi/2/68 (H3N2) | Neu5Acα3Galβ4Glc |
| ADS97_H5_23 (1JSN) | A/Duck/Singapore/3/97 (H5N3) | Neu5Acα3Galβ3GlcNAc |
| ADS97_H5_26(1JSO) | A/Duck/Singapore/3/97 (H5N3) | Neu5Ac |
| Viet1203_04_H5 (2FK0) | A/Vietnam/1203/2004 (H5N1) | |
| Viet1194_04_H5 (2IBX) | A/Vietnam/1194/2004 (H5N1) | |
| ASI30_H1_23 (1RV0) | A/Swine/Iowa/30 (H1N1) | Neu5Ac |
| ASI30_H1_26 (1RVT) | A/Swine/Iowa/30 (H1N1) | Neu5Acα6Galβ4GlcNAcβ3Galβ4Glc |
| APR34_H1_23 (1RVX) | A/Puerto Rico/8/34 (H1N1) | Neu5Acα3Galβ4GlcNAc |
| APR34_H1_26 (1RVZ) | A/Puerto Rico/8/34 (H1N1) | Neu5Acα6Galβ4GlcNAc |
| ADU63_H3_23 (1MQM) | A/Duck/Ukraine/1/63 (H3N8) | Neu5Acα3Gal |
| ADU63_H3_26 (1MQN) | A/Duck/Ukraine/1/63 (H3N8) | Neu5Acα6Gal |
| AAI68_H3_23 (1HGG) | A/Aichi/2/68 (H3N2) | Neu5Acα3Galβ4Glc |
| AAI68_H3_26 (2YPG) | A/Aichi/2/68 (H3N2) | Neu5Acα6Galβ4GlcNAcβ3Galβ4Glc |
| ANOR04_H3_26S (2YP3) | A/Norway/807/2004 (H3N2) | Neu5Acα6Galβ4GlcNAc |
| ANOR04_H3_26L (2YP4) | A/Norway/807/2004 (H3N2) | Neu5Acα6Galβ4GlcNAcβ3Galβ4Glc |
| ANOR04_H3_23 (2YP5) | A/Norway/807/2004 (H3N2) | Neu5Ac |
| AMAL05_H3_23 (2YP9) | A/Malaysia/33386/2005 (H3N2) | Neu5Ac |
| AMAL05_H3_26 (2YP8) | A/Malaysia/33386/2005 (H3N2) | Neu5Ac |
| ADS97_H5_23 (1JSN) | A/Duck/Singapore/3/97 (H5N3) | Neu5Acα3Galβ3GlcNAc |
| ADS97_H5_26(1JSO) | A/Duck/Singapore/3/97 (H5N3) | Neu5Ac |
| Viet04_H5 (2FK0) | A/Vietnam/1203/2004 (H5N1) | |
| AtkIT02_H7 (1TI8) | A/turkey/Italy/214845/05 (H7N3) | |
| ANETH03_H7_23 (4DJ7) | A/Netherlands/219/03 (H7N7) | Neu5Acα3Galβ4Glc |
| ANETH03_H7_26 (4DJ8) | A/Netherlands/219/03 (H7N7) | Neu5Ac |
| ANY05_H7_23 (3M5H) | A/New York/30732-1/05 (H7N2) | Neu5Acα3Gal |
| ANY05_H7_26 (3M5I) | A/New York/30732-1/05 (H7N2) | Neu5Acα6Gal |
| ANY05_H7_26b (3M5J) | A/New York/30732-1/05 (H7N2) | Galβ3(Neu5Acα6)GlcNAc β3Gal |

HA receptors are modified by either α2-3 or α2-6 sialylated glycans near the receptor's HA-binding site, and the type of linkage of the receptor-bound glycan can affect the conformation of the receptor's HA-binding site, thus affecting the receptor's specificity for different HAs.

For example, the glycan binding pocket of avian HA is narrow. According to the present invention, this pocket binds to the trans conformation of α2-3 sialylated glycans, and/or to cone-topology glycans, whether α2-3 or α2-6 linked.

HA receptors in avian tissues, and also in human deep lung and gastrointestinal (GI) tract tissues are characterized by α2-3 sialylated glycan linkages, and furthermore in some embodiments of the present invention, are characterized by glycans, including α2-3 sialylated and/or α2-6 sialylated glycans, which predominantly adopt cone topologies. HA receptors having such cone-topology glycans may be referred to herein as CTHArs.

By contrast, human HA receptors in the bronchus and trachea of the upper respiratory tract are modified by glycans which predominantly adopt umbrella topologies, for example including many α2-6 sialylated glycans. Unlike the α2-3 motif, the α2-6 motif has an additional degree of conformational freedom due to the C6-05 bond (Russell et al., Glycoconj J 23:85, 2006). HAs that bind to such α2-6 sialylated glycans have a more open binding pocket to accommodate the diversity of structures arising from this conformational freedom. Moreover, as described in PCT Patent Application Nos. PCT/US09/30056 and PCT/US07/18160, HAs may need to bind to glycans (e.g., α2-6 sialylated glycans) in an umbrella topology, and particularly may need to bind to such umbrella topology glycans with strong affinity and/or specificity, in order to effectively mediate infection of human upper respiratory tract tissues. HA receptors having umbrella-topology glycans may be referred to herein as UTHArs.

As a result of these spatially restricted glycosylation profiles, humans are not usually infected by viruses containing many wild-type avian HAs (e.g., avian H5). Specifically, because the portions of the human respiratory tract that are most likely to encounter virus (i.e., the trachea and bronchi) lack receptors with cone glycans (e.g., α2-3 sialylated glycans, and/or short glycans) and wild-type avian HAs typically bind primarily or exclusively to receptors associated with cone glycans (e.g., α2-3 sialylated glycans, and/or short glycans), humans rarely become infected with avian viruses. Only when in sufficiently close contact with virus that it can access the deep lung and/or gastrointestinal tract receptors having umbrella glycans (e.g., long α2-6 sialylated glycans) do humans become infected.

H7 HA Polypeptides

H7 influenza A viruses normally circulate among birds. H7 HA infections haven been uncommon in humans, but there have been world-wide reports of infection in people who have direct contact with infected birds. The avian influenza A H7N9 virus is a subgroup among this larger group of H7 viruses. Although some H7 viruses like H7N2, H7N3, and H7N7 have occasionally been found to infect humans, H7N9 has only been isolated previously in birds. No human infection with H7N9 viruses had ever been reported, until in late March 2013, when a novel H7N9 HA was identified that was found to infect humans.

No evidence of ongoing human-to-human transmission for the current H7N9 outbreak has yet been found, this suggests that while the H7N9 virus has acquired novel gene sequence variations that allow it to infect humans, it has not yet acquired the sequence variations that would allow it to sustain efficient transmission between humans. Also, no vaccines currently exist for H7N9 HA.

The novel H7N9 infecting humans results in severe lower respiratory tract infection and mortality (Gao et al. New England Journal of Medicine, (2013)). Detailed sequencing and analysis of the human isolates of H7N9 have offered insights into their potential origin and factors that govern the virus's virulence and pathogenicity (Li et al. New England Journal of Medicine (2013)). The transmission and pathogenicity associated with this virus is unanticipated for several reasons. First, transmission of H7 viruses from birds to mammals has been only reported rarely Kwon et al. Vet. Microbiol 153:393-397 (2011)). Additionally, until the advent of H7N9, human infections with N9 subtype viruses have not been previously reported. Finally, human infections with other H7 viruses (primarily H7N2, H7N3, and H7N7), even with high pathogenicity viruses containing a polybasic cleavage site in HA, have primarily resulted in conjunctivitis or uncomplicated illness, with few exceptions (Fouchier et al. PNAS, 101:1356-1361 (2004)).

Analysis of newly arising H7N9 strains, including A/Shanghai/1/2013, A/Shanghai/2/2013, and A/Anhui/1/2013 indicates that H7N9 is a novel reassorted virus incorporating envelope genes from at least two H7 strains (hemagglutinin, HA, from an H7N3 strain and neuraminidase, NA from an avian-adapted H7N9 strain) with the internal genes from at least two H9N2 avian-adapted influenza strains. Further analysis of the H7N9 gene segments have shown the occurrence of signature amino acids associated with adaptation to human host and virulence. H7N9 strains exhibit hallmark mutations that are thought to correlate with increased virulence and potentially transmission in animal models such as mice and ferrets, including the E627K mutation in PB2 (which is known to play an important role in human-to-human respiratory droplet transmission (Van Hoevan et al. PNAS, 106:3366-3371 (2009)). Furthermore, genetic analysis indicates the presence of mutations, in at least some strains, within the M2 ion channel and NA that confer drug resistance to the adamantanes and oseltamivir, respectively.

In contrast to the above analysis, several of the hallmark features found in highly pathogenic influenza strains (eg., H5N1) including the N66S mutation in PB1-F2, the aforementioned polybasic sequence in the linker between HA1 and HA2, and the PDZ binding motif in C-terminal of NS1 are absent in the H7N9 human isolates analyzed to date. Within this context and given the somewhat confounding genetic and epidemiological evidence of the relative human-adaptation of H7N9, one of the most important outstanding questions is the "status" of the HA protein for these isolates. Characterization of the HA protein is important given its role in virulence (Pappas et al. PNAS, 105:3064-3069 (2008)) and virus neutralization to preexisting antibodies through antigenic memory Hensley et al. Science, 326:734-736 (2009)). Finally, the receptor binding properties of HA, governing a given virus's tissue and organismic tropism is one of the factors that critically govern aerosol transmissibility, including human-to-human transmission.

Previous studies have demonstrated that one important property impacting human adaptation of influenza A virus is a "switch" in the glycan receptor binding specificities of viral HA Skehel and Wiley Annu Rev Biochem, 69:531-569 (2000)). Therefore, together with hallmark mutations in other genes, such as PB2, describing mutations in HA that lead to such a "switch" become important to for surveillance purposes. From the standpoint of human tissue tropism, the HA from human-adapted viruses including pandemic strains show extensive binding to the apical surface of human upper respiratory tissues (such as trachea) and also show characteristic binding characteristic binding to mucin secreting non-ciliated goblet cells on the apical surface and to submucosal glands in ferret respiratory tract Matrosovich et al. PNAS, 101:4620-4624 (2004); Nicholls et al. Respir Res, 8:73 (2007); Srinivasan et al. PNAS, 105:2800-2805 (2008)). Through lectin staining it has been demonstrated previously that these regions in human tracheal sections predominantly display diverse glycan receptors terminated by α2→6 sialic acid linkage (human receptors). It has been demonstrated with H1, H2 and H3 subtypes that this binding property of human-adapted viruses is one of the factors that correlate with their ability to efficiently transmit via respiratory droplets in ferrets—a well-established animal model to measure the potential for airborne human-to-human transmission (Jayaraman et al. PLoS One, 6:e17616 (2011); Maines et al. Science, 325:484-487 (2009)).

In the case of H7N9, studies have speculated that presence of a leucine residue in the 226 position (H3 numbering) of this HA would result in strong binding to human receptors. But further work is required for characterizing the interaction between HA and glycans on HA receptors, particularly for the H7 HA, and specifically for the novel H7N9 subtype.

Engineered and/or Variant HA Polypeptides

The present invention provides (e.g., defines and describes) certain HA polypeptides, specifically including engineered and/or variant HA polypeptides that show overall sequence identity with a reference HA, but for one or more alterations of particular amino acid residues. The present invention also provides fragments of such HA polypeptides, including characteristic fragments (e.g., fragments whose amino acid sequence includes at least one characteristic sequence element).

In some embodiments, the present invention provides (e.g., defines and describes) certain H7 HA polypeptides, specifically including engineered and/or variant H7 HA polypeptides that show overall sequence identity with a reference H7 HA, but for one or more alterations of particular amino acid residues. The present invention also provides fragments of such H7 HA polypeptides, including characteristic fragments (e.g., fragments whose amino acid sequence includes at least one characteristic sequence element).

In some embodiments, provided (e.g., engineered and/or variant) HA polypeptides have different glycan binding characteristics than their corresponding parent or reference HA polypeptides. In some embodiments, provided HA variant polypeptides have greater affinity and/or specificity for umbrella-topology glycans (e.g., as compared with for cone-topology glycans) than do their cognate parent or reference HA polypeptides. In some embodiments, provided HA polypeptides mediate significant human receptor binding and/or human infection and/or transmission (e.g., as assessed in an established or described assay system) than do their cognate parent or reference HA polypeptides.

In some embodiments, provided HA polypeptides bind to umbrella topology glycans (e.g., long α2-6 silaylated glycans such as, for example, Neu5Acα2-6Galβ1-4GlcNAcβ1-3Galβ1-4GlcNAc-) with high affinity. For example, in some embodiments, provided HA polypeptides bind to umbrella topology glycans with an affinity comparable to that observed for a wild-type reference HA that are known to mediate infection in humans (e.g., H1N1 HA or H3N2 HA). In some embodiments, provided HA polypeptides bind to umbrella glycans with an affinity that is at least 25%, 30%, 35%, 40%, 45%, 50%, 55%, 60%, 65%, 70%, 75%, 80%, 85%, 90%, 95%, 96%, 97%, 98%, 99%, or 100% of that observed under comparable conditions for a wild-type reference HA that mediates infection of humans.

In certain embodiments, binding affinity of provided HA polypeptides is assessed over a range of concentrations. Such a strategy provides significantly more information, particularly in multivalent binding assays, than do single-concentration analyses. In some embodiments, for example, binding affinities of provided HA polypeptides are assessed over concentrations ranging over at least 2, 3, 4, 5, 6, 7, 8, 9, 10 or more fold.

In certain embodiments, provided HA polypeptides show high affinity if they show a saturating signal in a multivalent glycan array binding assay such as those described herein. In some embodiments, provided HA polypeptides show high affinity if they show a signal above about 400000 or more (e.g., above about 500000, 600000, 700000, 800000, etc) in such studies. In some embodiments, binding agents as described herein show saturating binding to umbrella glycans over a concentration range of at least 2 fold, 3 fold, 4 fold, 5 fold or more, and in some embodiments over a concentration range as large as 10 fold or more.

Furthermore, in some embodiments, provided HA polypeptides bind to umbrella-topology glycans (and/or to umbrella-topology glycan mimics) more strongly than they bind to cone-topology glycans. In some embodiments, provided HA polypeptides show a relative affinity for umbrella glycans vs cone glycans that is about 10, 9, 8, 7, 6, 5, 4, 3, or 2.

In some embodiments, provided HA polypeptides bind to α2-6 sialylated glycans; in some embodiments, provided HA polypeptides bind preferentially to α2-6 sialylated glycans. In certain embodiments, provided HA polypeptides bind to a plurality of different α2-6 sialylated glycans. In some embodiments, provided HA polypeptides are not able to bind to α2-3 sialylated glycans, and in other embodiments provided HA polypeptides are able to bind to α2-3 sialylated glycans.

In some embodiments, provided HA polypeptides bind to receptors found on human upper respiratory epithelial cells. In certain embodiments, provided HA polypeptides bind to HA receptors in the bronchus and/or trachea. In some embodiments, provided HA polypeptides are not able to bind receptors in the deep lung, and in other embodiments, provided HA polypeptides are able to bind receptors in the deep lung.

In some embodiments, provided HA polypeptides bind to at least about 10%, 15%, 20%, 25%, 30% 35%, 40%, 45%, 50%, 55%, 60%, 65%, 70%, 75%, 80%, 85%, 90% 95% or more of the glycans found on HA receptors in human upper respiratory tract tissues (e.g., epithelial cells).

In some embodiments, provided HA polypeptides are characterized in that they bind to a receptor binding site utilized by a pandemic strain of influenza, and in some embodiments compete with such pandemic strain (or a receptor-binding portion thereof), for binding to such site. In some embodiments, provided HA polypeptides are characterized by substantial numerical similarity between their RBSN score and that of an HA polypeptide found in a pandemic influenza strain.

In some embodiments, provided HA polypeptides display an activity of interest (e.g., binding to umbrella-topology glycans, mediating human infectivity and/or transmissibility, etc) for example binding to umbrella-topology glycans as measured using the glycan array analysis described here where $K_d$ is in the range of sub-picomolar to 10 nanomolar and at a level relative to binding to cone-topology glycans of greater than 2 orders of magnitude; in some embodiments, such relative level is relative to a different activity of the same HA polypeptide (e.g., binning to cone-topology glycans, mediating non-human infectivity and/or transmissibility, etc). In some embodiments, such relative level is relative to the same activity of a different HA polypeptide (e.g., by a reference HA).

In some embodiments, the reference HA with which a provided HA polypeptide shows the specified degree of sequence identity is one that does not mediate significant human receptor binding and/or human infection and/or transmission; in some such embodiments, the provided HA differs from the reference non-human-infecting HA both in the presence vs absence of one or more amino acid residue substitutions as described herein and in ability to mediate significant human receptor binding and/or significant human infection and/or transmission. In some embodiments, the reference HA with which a provided HA polypeptide shows the specified degree of sequence identity does mediate significant human receptor binding and/or significant human infection and/or transmission; in some such embodiments, the provided HA polypeptide shares both one or more amino acid substitutions as describe herein and one or more biological activities (e.g., ability to mediate significant human receptor binding and/or significant human infection and/or transmission) with the human-infecting reference HA.

In some embodiments, representative HAs that do not mediate significant human receptor binding and/or human infection and/or transmission (i.e., non-human-infecting HAs) include H5 HAs, for example, A/duck/Hunan/795/2002 (clade 2.1), A/Viet Nam/1194/2004 (clade 1), A/Indonesia/5/2005 (clade 2.1.3.2), A/bar-headed goose/Qinghai/1A/2005 (clade 2.2), A/Anhui/1/2005 (clade 2.3.4), A/goose/Guiyang/337/2006 (clade 4), A/Cambodia/R0405050/2007 (clade 1.1), A/common magpie/Hong Kong/5052/2007 (clade 2.3.2.1), A/chicken/Viet Nam/NCVD-016/2008 (clade 7.1), A/Egypt/N03072/2010 (clade 2.2.1), and A/Hubei/1/2010 (clade 2.3.2.1). In some embodiments, representative HAs that do not mediate significant human receptor binding and/or human infection and/or transmission (i.e., non-human-infecting HAs) include H7 HAs, for example A/mallard/Netherlands/22/2007(H7N1), A/Guinea fowl/New York/19501-4/2006(H7N2), A/mallard/Interior Alaska/10BM05347R0/2010(H7N3), A/turkey/Italy/214845/05 (H7N3), A/mallard/Missouri/10MO053/2010(H7N4), Netherlands/219/03 (H7N7), A/New York/30732-1/05 (H7N2), A/mallard/California/1390/2010 (H7N5), A/duck/Thailand/CU-LM7302T/2010(H7N6), A/American green-winged teal/Illinois/10OS3329/2010 (H7N7), A/American black duck/Wisconsin/10OS3949/2010(H7N8), and A/guinea fowl/Nebraska/17096-1/2011 (H7N9).

In some embodiments, representative HAs that do mediate significant human receptor binding and/or human infection and/or transmission (i.e., human-infecting HAs) including, for example H3N2 strains including, but not limited to, A/Port Chalmers/1/1973 (H3N2), A/Scotland/840/74 (H3N2), A/Victoria/3/75(H3N2), A/Texas/1/77(H3N2), A/Bangkok/01/1979(H3N2), A/Philippines/2/82(H3N2), A/Christchurch/4/1985(H3N2), A/Mississippi/1/85(H3N2), A/Leningrad/360/1986(H3N2), A/Shanghai/11/87(H3N2), A/Sichuan/02/87(H3N2), A/Beijing/353/89(H3N2), A/Guizhou/54/89(H3N2), A/Beijing/32/92(H3N2), A/Shangdong/9/93(H3N2), A/Johannesburg/33/94(H3N2), A/Wuhan/359/95(H3N2), A/Sydney/5/97(H3N2), A/Moscow/10/99(H3N2), A/Fujian/411/2002(H3N2), A/California/7/2004(H3N2), A/Wellington/1/2004(H3N2), A/Brisbane/10/2007(H3N2), A/Perth/16/2009(H3N2), and A/Victoria/361/2011(H3N2), H1N1 stains including, but not limited to, A/Chile/1/83(H1N1), A/Singapore/6/1986 (H1N1), A/Bayern/7/95(H1N1), A/Beijing/262/95(H1N1), A/New Caledonia/20/1999(H1N1), A/Solomon Islands/3/2006(H1N1), A/Brisbane/59/2007(H1N1), and A/California/07/2009(H1N1), H2N2 strains including, but not limited to, A/Panama/1/66(H2N2), and A/Korea/426/1968(H2N2), and, in certain cases, H9N2 strains including, but not limited to A/guinea fowl/Hong Kong/WF10/99(H9N2), A/wild duck/Nanchang/2-0480/2000(H9N2), A/turkey/Israel/689/2008(H9N2), A/chicken/Zhejiang/HE1/2009(H9N2), and A/chicken/Egypt/115617V/2011(H9N2).

In some embodiments, the present invention provides a novel framework to define amino acid mutations in the HA of circulating avian influenza strains, that could result in a switch in binding preference to human glycan receptors. In some embodiments, the present invention provides a novel framework to analyze molecular features of glycan receptor-binding site (RBS) of a candidate influenza HA in relation to its nearest human-adapted phylogenetic relative pandemic influenza HA. In some embodiments, the present invention demonstrates that currently circulating candidate influenza HAs have evolved such that their RBS molecular features resemble those of pandemic influenza HAs and require fewer amino acid changes to switch receptor specificity. In some embodiments, application of such provided frameworks defines HA polypeptide variants having sequence features and activities as described herein.

In some embodiments, provided HA polypeptide with altered glycan binding characteristics have sequence alternations in residues within or affecting the glycan binding site. In some embodiments, such substitutions are of amino acids that interact directly with bound glycan; in other embodiments, such substitutions are of amino acids that are one degree of separation removed from those that interact with bound glycan, in that the one degree of separation removed-amino acids either (1) interact with the direct-binding amino acids; (2) otherwise affect the ability of the direct-binding amino acids to interact with glycan, but do not interact directly with glycan themselves; or (3) otherwise affect the ability of the direct-binding amino acids to interact with glycan, and also interact directly with glycan themselves. In certain embodiments, provided HA polypeptides contain substitutions of one or more direct-binding amino acids, one or more first degree of separation-amino acids, one or more second degree of separation-amino acids, or any combination of these. In some embodiments, provided HA polypeptides may contain substitutions of one or more amino acids with even higher degrees of separation.

In some embodiments, provided HA polypeptides with altered glycan binding characteristics have sequence alterations in residues that make contact with sugars beyond Neu5Ac and Gal.

In some embodiments, provided HA polypeptides have length of at least 50, 100, 150, 200, 300, 400, 500, or 600 amino acids. In some embodiments, provided HA polypeptides have amino acid residues corresponding to positions 50-220 in the HA region of a reference HA polypeptide. In some embodiments, provided HA polypeptides have amino acid residues corresponding to positions 50-230 in the HA region of a reference HA polypeptide (e.g., H7 HA polypeptide).

In some embodiments, a provided HA polypeptide, and particularly a provided H7 HA polypeptide has a sequence element that is at least 5, 6, 7, 8, 9, 10, 12, 15, or 20 amino acids in length. In some embodiments, a provided HA polypeptide, and particularly a provided H7 HA polypeptide has a sequence element that includes amino acid residues corresponding to positions selected from the group consisting of 131-138, 140-145, 156-160, 190-196, and 219-228. In some embodiments, a provided HA polypeptide, and particularly a provided H7 HA polypeptide has a sequence element that is substantially identical to corresponding portion of a reference HA polypeptide (e.g., H7 HA polypeptide). In some embodiments, a provided HA polypeptide, and particularly a provided H7 HA polypeptide has a sequence element that shows at least 80%, 81%, 82%, 83%, 84%, 85%, 86%, 87%, 88%, 89%, 90%, 91%, 92%, 93%, 94%, 95%, 96%, 97%, 98%, or 99% overall sequence identity to corresponding portion of a reference HA polypeptide (e.g., H7 HA polypeptide). In some embodiments, such portion of the reference HA polypeptide includes amino acid at position 228. In some embodiments, such portion of the reference HA polypeptide includes at least one amino acid position selected from the group consisting of 122, 131, 137, 145, 156, 158, 159, 160, 174, 186, 187, 189, 190, 192, 193, 196, 202, 222, 225, 226, 228, and combinations thereof.

In some embodiments, provided HA polypeptides have at least one amino acid substitution, as compared with a wild-type parent or reference HA. In some embodiments, provided HA polypeptides have at least two, three, four, five or more amino acid substitutions as compared with a cognate wild-type parent or reference HA; in some embodiments provided HA polypeptides have two, three, or four amino acid substitutions. In some embodiments, all such amino acid substitutions are located within the glycan binding site.

In some embodiments, a provided HA polypeptide, and particularly a provided H7 HA polypeptide has one or more amino acid substitutions relative to a wild-type parent or reference HA at residues selected from amino acids that are one degree of separation removed from those that interact with bound glycan, in that the one degree of separation removed-amino acids either (1) interact with the direct-binding amino acids; (2) otherwise affect the ability of the direct-binding amino acids to interact with glycan, but do not interact directly with glycan themselves; or (3) otherwise affect the ability of the direct-binding amino acids to interact with glycan, and also interact directly with glycan themselves, including but not limited to residues 122, 131, 137, 145, 156, 158, 159, 160, 174, 186, 187, 189, 190, 192, 193, 196, 202, 222, 225, 226, and 228.

In some embodiments, provided HA polypeptides, and particularly provided H7 HA polypeptides, have sequence substitutions that reduce or abolish glycosylation at a site corresponding to amino acid 158. In some embodiments, provided HA polypeptides, and particularly provided H7 HA polypeptides, have sequence substitutions that affect and/or alter the identity and/or structure of the glycan linked to a site corresponding to amino acid position 158.

In some embodiments, provided HA polypeptides, and particularly provided H7 HA polypeptides, have sequence substitutions at positions corresponding to one or more of residues 174, 226, and 228. In some embodiments, provided HA polypeptides, and particularly provided H7 HA polypeptides, have sequence substitutions at positions corresponding to one or more of residues 122, 174, 186, 202, 226, and 228. Alternatively or additionally, in some embodiments, provided HA polypeptides have sequence substitutions at positions corresponding to one or more of residues 122, 131, 135, 137, 145, 156, 158, 159, 186, 189, 190, 192, 193, 196, 202, 222, 224, 225, and 227.

In some embodiments, provided HA polypeptides, and particularly provided H7 HA polypeptides, have sequence substitutions at positions corresponding to 226 and 228. In some embodiments, provided HA polypeptides, and particularly provided H7 HA polypeptides, have sequence substitutions at positions corresponding to 174 and 228. In some embodiments, provided HA polypeptides, and particularly provided H7 HA polypeptides, have sequence substitutions at positions corresponding to 174 and 226. In some embodiments, provided HA polypeptides, and particularly provided H7 HA polypeptides, have sequence substitutions at positions corresponding to 174, 226, and 228. In some embodiments, provided HA polypeptides, and particularly provided H7 HA polypeptides, have sequence substitutions at positions corresponding to 122, 226, and 228. In some embodiments, provided HA polypeptides, and particularly provided H7 HA polypeptides, have sequence substitutions at positions corresponding to 186, 226, and 228. In some embodiments, provided HA polypeptides, and particularly provided H7 HA polypeptides, have sequence substitutions at positions corresponding to 202, 226, and 228.

In some embodiments, provided HA polypeptides, and particularly provided H7 HA polypeptides, have sequence substitutions at positions corresponding to 122, 174, 226, and 228. In some embodiments, provided HA polypeptides, and particularly provided H7 HA polypeptides, have sequence substitutions at positions corresponding to 122, 174, 226, and 228. In some embodiments, provided HA polypeptides, and particularly provided H7 HA polypeptides, have sequence substitutions at positions corresponding to 174, 186, 226, and 228. In some embodiments, provided HA polypeptides, and particularly provided H7 HA polypeptides, have sequence substitutions at positions corresponding to 174, 202, 226, and 228. In some embodiments, provided HA polypeptides, and particularly provided H7 HA polypeptides, have sequence substitutions at positions corresponding to 122, 174, 186, 202, 226, and 228. In some embodiments, provided HA polypeptides, and particularly provided H7 HA polypeptides, have sequence substitutions at positions corresponding to 122, 131, 135, 137, 145, 156, 158, 159, 174, 186, 189, 190, 192, 193, 196, 202, 222, 224, 225, 226, 227, and 228.

In some embodiments, provided HA polypeptides, and particularly provided H7 HA polypeptides, have an amino acid residue at a position corresponding to 226 (a "Residue 226") that is not glutamine. In some embodiments, provided HA polypeptides, and particularly provided H7 HA polypeptides, have an amino acid residue at a position corresponding to 228 (a "Residue 228") that is not glycine.

In some embodiments, provided HA polypeptides, and particularly provided H7 HA polypeptides, have an amino acid residue at a position corresponding to 122 (a "Residue 122") that is alanine. In some embodiments, provided HA polypeptides, and particularly provided H7 HA polypeptides, have an amino acid residue at a position corresponding to 174 (a "Residue 174") that is serine. In some embodiments, provided HA polypeptides, and particularly provided H7 HA polypeptides, have an amino acid residue at a position corresponding to 186 (a "Residue 186") that is valine. In some embodiments, provided HA polypeptides, and particularly provided H7 HA polypeptides, have a an amino acid residue at a position corresponding to 202 ("Residue 202") that is valine.

In some embodiments, provided HA polypeptides, and particularly provided H7 HA polypeptides, have an amino acid at Residue 226 that is a nonpolar amino acid. In some embodiments, provided HA polypeptides, and particularly provided H7 HA polypeptides, have a Residue 226 that is selected from the group consisting of alanine, cysteine, glycine, isoleucine, leucine, methionine, phenylalanine, proline, tryptophan and valine. In some embodiments, provided HA polypeptides, and particularly provided H7 HA polypeptides, have a Residue 226 that is selected from the group consisting of leucine and isoleucine. In some embodiments, provided HA polypeptides, and particularly provided H7 HA polypeptides, have a Residue 226 that is leucine.

In some embodiments, provided HA polypeptides, and particularly provided H7 HA polypeptides, have an amino acid residue at Residue 228 that is a polar amino acid. In some embodiments, provided HA polypeptides, and particularly provided H7 HA polypeptides, have a Residue 228 that is selected from the group consisting of arginine, asparagine, aspartic acid, glutamic acid, glutamine, histidine, lysine, serine, glycine, threonine, and tyrosine. In some embodiments, provided HA polypeptides, and particularly provided H7 HA polypeptides, have Residue 228 that is selected from the group consisting of arginine, asparagine, serine, glycine, and threonine. In some embodiments, provided HA polypeptides, and particularly provided H7 HA polypeptides, have a Residue 228 that is threonine. In some embodiments, provided HA polypeptides, and particularly provided H7 HA polypeptides, have a Residue 228 that is serine.

In some embodiments, provided HA polypeptides, and particularly provided H7 HA polypeptides, have one or more of the following amino acid substitutions: alanine at Residue 122 (A122), serine at Residue 174 (S174), valine at Residue 186 (V186), valine at Residue 202 (V202), leucine or isoleucine at Residue 226 (L/I226), serine at Residue 228 (S228).

In some embodiments, provided HA polypeptides, and particularly provided H7 HA polypeptides, have one or more of the following set of amino acid substitutions:
A122, S174, V186, V202, L/I226, and S228;
S174, V186, V202, L/I226, and S228;
A122, V186, V202, L/I226, and S228;
A122, S174, V202, L/I226, and S228;
A122, S174, V186, L/I226, and S228;
A122, S174, V186, V202, and S228;
V186, V202, L/I226, and S228;
S174, V202, L/I226, and S228;
A122, V202, L/I226, and S228;
A122, V186, L/I226, and S228;
S174, V186, L/I226, and S228;
A122, S174, L/I226, and S228;
S174, L/I226, and S228;
V202, L/I226, and S228;
A122, L/I226, and S228;
V186, L/I226, and S228;
L/I226 and S228.

In some embodiments, provided HA polypeptides, and particularly provided H7 HA polypeptides, has an amino acid sequence that includes A122, S174, V186, V202, I/L226, S/T228, or combinations thereof. In some embodiments, provided HA polypeptides, and particularly provided H7 HA polypeptides, has an amino acid sequence that includes I/L226, and S/T228. In some embodiments, provided HA polypeptides, and particularly provided H7 HA polypeptides, has an amino acid sequence that includes A122, S174, V186, and V202. In some embodiments, provided HA polypeptides, and particularly provided H7 HA polypeptides, has an amino acid sequence that includes S174, I/L226, and S/T228.

In some embodiments, provided HA polypeptides, and particularly provided H7 HA polypeptides, have at least one substitution in a position other than 122, 174, 186, 202, 226, and/or 228, as compared with a particular wild-type reference or parent HA polypeptide (e.g., a wild-type reference or parent H7 HA polypeptide). In some such embodiments, affinity and/or specificity of the variant for umbrella-topology glycans is increased.

In some embodiments, provided HA polypeptides, and particularly provided H7 HA polypeptides, have one or more amino acid substitutions at positions corresponding to residues 122, 174, 186, 202, 226 and 228, and additionally a genetic change characteristic of human-adapted viruses (e.g., K627 in PB2). In some embodiments, provided HA polypeptides, and particularly provided H7 HA polypeptides, have an amino acid substitution at position 228, and additionally a genetic change characteristic of human-adapted viruses (e.g., K627 in PB2). In some embodiments, provided HA polypeptides, and particularly provided H7 HA polypeptides, have at least one amino acid substitution that is found in the corresponding human-adapted HA (e.g., human-adapted H3 HA).

In some embodiments, provided HA polypeptides have an open binding site as compared with a reference or parent HA, and particularly with parent wild-type HAs.

In some embodiments, the provided H7 HA polypeptides are H7N9 HA polypeptides. In particular, the present invention describes amino acid substitutions that, when present in a provided H7 HA polypeptide as described herein, results in a significant level of one or more activities selected from the group consisting of human receptor binding, human infection and/or human transmission. In some embodiments, an activity is considered significant if it is observed at a level above a designated threshold. In some embodiments, an activity is considered significant if it is observed at a level relatively higher than a reference activity—such as the same activity in a comparable reference HA polypeptide, for example that lacks one or more particular sequence elements or features, or as a different activity by the same HA polypeptide (e.g., binding to a different target).

In particular, the present invention describes amino acid substitutions that, when present in a provided H7 HA polypeptide as described herein, results in a significant increase in the extent and intensity of staining to apical surface of the tracheal section including extensive staining of non-ciliated goblet cells in a fashion similar to that of other human-adapted HAs and *Sambus nigra* agglutinin I (SNA I).

As described herein, the present invention defines amino acid substitutions that contribute to relevant activities of H7 HA polypeptides. In particular, in accordance with the present invention provided H7 HA polypeptides typically show at least 80%, 81%, 82%, 83%, 84%, 85%, 86%, 87%, 88%, 89%, 90%, 91%, 92%, 93%, 94%, 95%, 96%, 97%, 98%, 99% or greater overall sequence identity with a reference HA (e.g., with a reference H7 HA), but have a sequence that is not 100% identical to the reference HA in that the provided HA has an amino acid sequence that includes one or more substitutions at residues, compared to the referenced H7 HA, corresponding to positions 122, 131, 135, 137, 145, 156, 158, 159, 174, 186, 189, 190, 192, 193, 196, 202, 222, 224, 225, 226, 227, and 228.

In some embodiments, the present invention provides methods of raising antibodies by administering to an organism a provided HA polypeptide.

In some embodiments, the reference H7 HA polypeptide is an HA polypeptide selected from any of the following:

```
A/Shanghai/1/2013|A/H7N9
                                                  (SEQ ID NO.: 17)
MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSSCRRSGSSFYAEMKWLLSNTDNAAFPQMTKSYKNT

RKNPALIVWGIHHSGSTAEQTKLYGSGNKLVTVGSSNYQQSFVPSPGARTQVNGQSGRI

DFHWLMLNPNDTVTFSFNGAFIAPDRASFLRGKSMGIQSGVQVDADCEGDCYYSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFTEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIAMGLVFICVKNGNMRCTICI

A/Shanghai/2/2013|A/H7N9
                                                  (SEQ ID NO.: 18)
MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI
```

-continued

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/Anhui/1/2013|A/H7N9

(SEQ ID NO.: 19)
MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/Hangzhou/1/2013|A/H7N9

(SEQ ID NO.: 20)
MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGISGRID

FHWLMLNPNDTVTFSFNGAFIAPDRASFLRGKSMGIQSGVQVDANCEGDCYHSGGTIIS

NLPFQNIDSRAVGKCPRYVKQRSLLLATGMKNVPEIPKGRGLFGAIAGFIENGWEGLIDG

WYGFRHQNAQGEGTAADYKSTQSAIDQITGKLNRLIEKTNQQFELIDNEFNEVEKQIGN

VINWTRDSITEVWSYNAELLVAMENQHTIDLADSEMDKLYERVKRQLRENAEEDGTGC

FEIFHKCDDDCMASIRNNTYDHSKYREEAMQNRIQIDPVKLSSGYKDVILWFSFGASCFI

LLAIVMGLVFICVKNGNMRCTICI

A/Chicken/Shanghai/S1053/2013|A/H7N9

(SEQ ID NO.: 21)
MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

-continued

A/Environment/Shanghai/S1088/2013|A/H7N9
(SEQ ID NO.: 22)
MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/Pigeon/Shanghai/S1069/2013|A/H7N9
(SEQ ID NO.: 23)
MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTITFSFNGAFIAPDRASFLRGKSMGIQSGVQVDANCEGDCYHSGGTIIS

NLPFQNIDSRAVGKCPRYVKQRSLLLATGMKNVPEIPKGRGLFGAIAGFIENGWEGLIDG

WYGFRHQNAQGEGTAADYKSTQSAIDQITGKLNRLIEKTNQQFELIDNEFNEVEKQIGN

VINWTRDSITEVWSYNAELLVAMENQHTIDLADSEMDKLYERVKRQLRENAEEDGTGF

EIFHKCDDDCMASIRNNTYDHSKYREEAMQNRIQIDPVKLSSGYKDVILWFSFGASCFIL

LAIVMGLVFICVKNGNMRCTICI

A/Zhejiang/DTID-ZJU01/2013|A/H7N9
(SEQ ID NO.: 24)
MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/chicken/Jiangsu/K27/2013|A/H7N9
(SEQ ID NO.: 25)
MNTQILVFALIAIIPTNADKICLGHHAVSNGTKVNTLTERGVEVVNATETVERTNIPRICS

KGKMTVDLGQCGLLGTITGPPQCDQFLEFSADLIIERREGSDVCYPGKFVNEEALRQILR

ESGGIDKEAMGFTYSGIRTNGATSACRRSGSSFYAEMKWLLSNTDNAAFPQMTKSYKN

TRKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

-continued

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/chicken/Jiangsu/K89/2013|A/H7N9

(SEQ ID NO.: 26)

MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/chicken/Jiangsu/K27/2013|A/H7N9

(SEQ ID NO.: 27)

MNTQILVFALIAIIPTNADKICLGHHAVSNGTKVNTLTERGVEVVNATETVERTNIPRICS

KGKMTVDLGQCGLLGTITGPPQCDQFLEFSADLIIERREGSDVCYPGKFVNEEALRQILR

ESGGIDKEAMGFTYSGIRTNGATSACRRSGSSFYAEMKWLLSNTDNAAFPQMTKSYKN

TRKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/Hangzhou/2/2013|A/H7N9

(SEQ ID NO.: 28)

MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQITKSYKNTR

KSPALIVWGIHHSVSTAEQTKLYGSGNKLVTVGSSNYQQSFVPSPGARPQVNGLSGRID

FHWLMLNPNDTVTFSFNGAFIAPDRASFLRGKSMGIQSGVQVDANCEGDCYHSGGTIIS

NLPFQNIDSRAVGKCPRYVKQRSLLLATGMKNVPEIPKGRGLFGAIAGFIENGWEGLIDG

WYGFRHQNAQGEGTAADYKSTQSAIDQITGKLNRLIEKTNQQFELIDNEFNEVEKQIGN

VINWTRDSITEVWSYNAELLVAMENQHTIDLADSEMDKLYERVKRQLRENAEEDGTGC

FEIFHKCDDDCMASIRNNTYDHSKYREEAMQNRIQIDPVKLSSGYKDVILWFSFGASCFI

LLAIVMGLVFICVKNGNMRCTICI

A/Hangzhou/3/2013|A/H7N9

(SEQ ID NO.: 29)

MNTQILVFALIAIIPTNADKICLGHHAVSNGTKVNTLTERGVEVVNATETVERTNIPRICS

KGKMTVDLGQCGLLGTITGPPQCDQFLEFSADLIIERREGSDVCYPGKFVNEEALRQILR

ESGGIDKEAMGFTYSGIRTNGATSACRRSGSSFYAEMKWLLSNTDNAAFPQMTKSYKN

TRKSPALIVWGIHHSVSTAEQTKLYGSGNKLVTVGSSNYQQSFVPSPGARPQVNGLSGRI

-continued

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/Environment/Hangzhou/34/2013|A/H7N9
(SEQ ID NO.: 30)
MNTQILVFALIAIIPTNADKICLGHHAVSNGTKVNTLTERGVEVVNATETVERTNIPRICS

KGKKTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/chicken/Zhejiang/DTID-ZJU01/2013|A/H7N9
(SEQ ID NO.: 31)
MNTQILVFALIAIIPTNADKICLGHHAVSNGTKVNTLTERGGEVVNATETVERTNIPRICS

KGKKTVDLGQGGPRGTITGPPQCDQFLEFSADLIMERREGSDVCYPGKFVNEEALRQIL

RESGGIDKEAMGFTYSGIRTNGATSACRRSGSSFYAEMKWLLSNTDNAAFPQMTKSYK

NTRKSPALIVWGIHHSVSTAEQTKLYGSGNKLVTVGSSNYQQSFVPSPGARPQVNGQSG

RIDFHWLMLNPNDTVTFSFNGAFIAPDRASFLRGKSMGIQSGVQVDANCEGDCYHSGGT

IISNLPFQNIDSRAVGKCPRYVKQRSLLLATGMKNVPEIPKGRGLFGAIAGFIENGWEGLI

DGWYGFRHQNAQGEGTAADYKSTQSAIDQITGKLNRLIEKTNQQFELIDNEFNEVEKQI

GNVINWTRDSITEVWSYNAELLVAMENQHTIDLADSEMDKLYERVKRQLRENAEEDGT

GCFEIFHKCDDDCMASIRNNTYDHSKYREEAMQNRIQIDPVKLSSGYKDVILWFSFGAS

CFILLAIVMGLVFICVKNGNMRCTICI

A/Shanghai/3/2013|A/H7N9
(SEQ ID NO.: 32)
MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCHHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

-continued

A/Shanghai/4/2013|A/H7N9

(SEQ ID NO.: 33)

MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/Zhejiang/01/2013|A/H7N9

(SEQ ID NO.: 34)

MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGISGRID

FHWLMLNPNDTVTFSFNGAFIAPDRASFLRGKSMGIQSGVQVDANCEGDCYHSGGTIIS

NLPFQNIDSRAVGKCPRYVKQRSLLLATGMKNVPEIPKGRGLFGAIAGFIENGWEGLIDG

WYGFRHQNAQGEGTAADYKSTQSAIDQITGKLNRLIEKTNQQFELIDNEFNEVEKQIGN

VINWTRDSITEVWSYNAELLVAMENQHTIDLADSEMDKLYERVKRQLRENAEEDGTGC

FEIFHKCDDDCMASIRNNTYDHSKYREEAMQNRIQIDPVKLSSGYKDVILWFSFGASCFI

LLAIVMGLVFICVKNGNMRCTICI

A/Zhejiang/1/2013|A/H7N9

(SEQ ID NO.: 35)

MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGISGRID

FHWLMLNPNDTVTFSFNGAFIAPDRASFLRGKSMGIQSGVQVDANCEGDCYHSGGTIIS

NLPFQNIDSRAVGKCPRYVKQRSLLLATGMKNVPEIPKGRGLFGAIAGFIENGWEGLIDG

WYGFRHQNAQGEGTAADYKSTQSAIDQITGKLNRLIEKTNQQFELIDNEFNEVEKQIGN

VINWTRDSITEVWSYNAELLVAMENQHTIDLADSEMDKLYERVKRQLRENAEEDGTGC

FEIFHKCDDDCMASIRNNTYDHSKYREEAMQNRIQIDPVKLSSGYKDVILWFSFGASCFI

LLAIVMGLVFICVKNGNMRCTICI

A/Zhejiang/2/2013|A/H7N9

(SEQ ID NO.: 36)

MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

-continued

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/Fujian/1/2013|A/H7N9
(SEQ ID NO.: 37)
MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/Shanghai/4664T/2013|A/H7N9
(SEQ ID NO.: 38)
MNTQILVFALIAIIPANADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCHHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/Shanghai/4655T/2013|A/H7N9
(SEQ ID NO.: 39)
GMIDGWYGFRHQNAQGEGTAADYKSTQSAIDQITGKLNRLIEKTNQQFELIDNEFTEVE

KQIGNVINWTRDSITEVWSYNAELLVAMENQHTIDLADSEMDKLYERVKRQLRENAEE

DGTGCFEIFHKCDDDCMASIRNNTYDHSKYREEAMQNRIQIDPVKLSSGYKDVILWFSF

GASCFILLAIAMGLVFICVKNGNMRCTICI

A/Shanghai/4659T/2013|A/H7N9
(SEQ ID NO.: 40)
GMIDGWYGFRHQNAQGEGTAADYKSTQSAIDQITGKLNRLIEKTNQQFELIDNEFNEVE

KQIGNVINWTRDSITEVWSYNAELLVAMENQHTIDLADSEMDKLYERVKRQLRENAEE

DGTGCFEIFHKCDDDCMASIRNNTYDHSKYREEAMQNRIQIDPVKLSSGYKDVILWFSF

GASCFILLAIVMGLVFICVKNGNMRCTICI

A/Shanghai/4665T/2013|A/H7N9
(SEQ ID NO.: 41)
GMIDGWYGFRHQNAQGEGTAADYKSTQSAIDQITGKLNRLIEKTNQQFELIDNEFTEVE

KQIGNVINWTRDSITEVWSYNAELLVAMENQHTIDLADSEMDKLYERVKRQLRENAEE

DGTGCFEIFHKCDDDCMASIRNNTYDHSKYREEAMQNRIQIDPVKLSSGYKDVILWFSF

GASCFILLAIAMGLVFICVKNGNMRCTICI

A/Shanghai/Patient6/2013|A/H7N9
(SEQ ID NO.: 42)
MNAQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNAAFPQMTKSYKNT

RKSPALIVWGIHHSVSTAEQTKLXXXXXXXXXXXXXXXXXXXXXXXXXXXXXXXXX

XXXXXXXXXXXXXXXXXXXXXXXXXXXXXXXXXMGIQSGVQVDANCEGDC

YHSGGTIISNLPFQNIDSRAVGKCPRYVKQRSLLLATGMKNVPEIPKGRGLFGAIAGFIEN

GWEGLTDGWYGFRHQNAQGEGTAADYKSTQSAIDQITGKFNRLIGKTHQQFELIDNEF

NEVEKQIGNVINWTRDSITEVWSYNAELLVAMENQHTIDLADSEMDKLYERVKRQLRE

NAEEDGTGCFEIFHKCDDDCMASIRNNTYDRSKSREEAMQNRIQIDPVKLSSGYKDVIL

WFSFGASCFILLAIVMGLVFICVKNGNMRCTICI

A/Shanghai/Patient3/2013|A/H7N9
(SEQ ID NO.: 43)
MNTQILVFALIAIIPTNADKICLGHHAVSNGTKVNTLTERGVEVVNATETVERTNIPRICS

KGKRTVDLGQCGLLGTITGPPQCDQFLEFSADLIIERREGSDVCYPGKFVNEEALRQILRE

SGGIDKEAMGFTYSGIRTNGATSACRRSGSSFYAEMKWLLSNTDNASFPQMTKSYKNT

RKSPALIVWGIHHSVSTAEQTKLYGSGNKLVTVGSSNYQQSFVPSPGARPQVNGLSGRI

DFHWLMLNPNDTVTFSFNGTFIAPDRASFLRGKSMGIQSGVQVDANCEGDCYHSGGTI

MSNLPFQNIDSRAVGKCPRYVKQGSLLLATGMKNVPEIPKGRGLFGAIAGFIENGWEGLI

DGWYGFRHQNAQGEGTAADYKSTQSAIDQITGKFNRLIEKTHQQFELIDNEFNEVEKQI

GNVINWTRDSITEVWSYNAELLVAMENQHTIDLADSEMDKLYERVKRQLRENAEEDGT

GCFEIFHKCDDDCMASIRNNTYDHSKSREEAMQNRIQIDPVKLSSGYKDVILWFSFGASC

FILLAIVMGLVFICVKNGNMRCTICI

A/Shanghai/Patient5/2013|A/H7N9
(SEQ ID NO.: 44)
MNTQILVFALIAIIPTNADKICLGHHAVSNGTKVNTLTERGVEVVNATETVERTNIPRICS

KGKRTVXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXXXX

XXXXXXXXXXXXXXXXXXXXXXXXXXXXXXXXXXXXXXXXXXXXXXXX

XXXXXXXQVNGLSGRIDFHWLMLNPNDTVXXXXXXXXXXXXXXXXXXXXXXXXX

XXXXXXXXXXXXXXXXXXXXXXXXXXXXXXXXXXXXXXXXXXXXXXXX

XXXXXXXXXXXXXXXXXXXXXXXXXXXXXXXXXXXADYKSTQSAIDQI

TGXXXXXXXXXXXXXXXXXXXXXXXXXXXXXXXXXXXXXXXXXXELLVAM

ENQHTIDLADSEMDKLYERVKRQLRENAEEDGTGCFEIFHKCDDDCMASIRNNTYDHS

KSREEAMQNRIQIDPVKLSSGYKDVILWFSFGASCFILLAIVMGLVFICVKNGNMRCTICI

A/Zhejiang/HZ1/2013|A/H7N9
(SEQ ID NO.: 45)
MNTQILVFALIAIIPTNADKICLGHHAVSNGTKVNTLTERGVEVVNATETVERTNIPRICS

KGKMTVDLGQCGLLGTITGPPQCDQFLEFSADLIIERREGSDVCYPGKFVNEEALRQILR

ESGGIDKEAMGFTYSGIRTNGATSACRRSGSSFYAEMKWLLSNTDNAAFPQMTKSYKN

TRKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

-continued

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/Nanjing/1/2013|A/H7N9

(SEQ ID NO.: 46)

MNTQILVFALIAIIPTNADKICLGHHAVSNGTKVNTLTERGVEVVNATETVERTNIPRICS

KGKMTVDLGQCGLLGTITGPPQCDQFLEFSADLIIERREGSDVCYPGKFVNEEALRQILR

ESGGIDKEAMGFTYSGIRTNGATSACRRSGSSFYAEMKWLLSNTDNAAFPQMTKSYKN

TRKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/environment/Nanjing/2913/2013|A/H7N9

(SEQ ID NO.: 47)

MNTQILVFALIAIIPTNADKICLGHHAVSNGTKVNTLTERGVEVVNATETVERTNIPRICS

KGKMTVDLGQCGLLGTITGPPQCDQFLEFSADLIIERREGSDVCYPGKFVNEEALRQILR

ESGGIDKEAMGFTYSGIRTNGATSACRRSGSSFYAEMKWLLSNTDNAAFPQMTKSYKN

TRKSPALIVWGIHHSVSTAEQTKLYGSGNKLVTVGSSNYQQSFVPSPGARPQVNGLSGRI

DFHWLMLNPNDTVTFSFNGAFIAPDRASFLRGKSMGIQSGVQVDANCEGDCYHSGGTII

SNLPFQNIDSRAVGKCPRYVKQRSLLLATGMKNVPEIPKGRGLFGAIAGFIENGWEGLID

GWYGFRHQNAQGEGTAADYKSTQSAIDQITGKLNRLIEKTNQQFELIDNEFNEVEKQIG

NVINWTRDSITEVWSYNAELLVAMENQHTIDLADSEMDKLYERVKRQLRENAEEDGTG

CFEIFHKCDDDCMASIRNNTYDHSKYREEAMQNRIQIDPVKLSSGYKDVILWFSFGASCF

ILLAIVMGLVFICVKNGNMRCTICI

A/American black duck/Wisconsin/10OS3949/2010 (H7N8)

(SEQ ID NO.: 56)

MNTQILALIACMLIGAKGDKICLGHHAVANGTKVNTLTERGIEVVNATETVETANIKKIC

TQGKRPTDLGQCGLLGTLIGPPQCDQFLEFDADLIIERREGTDVCYPGKFTNEESLRQILR

GSGGIDKESMGFTYSGIRTNGATSACRRSGSSFYAEMKWLLSNSDNAAFPQMTKSYRNP

RNKPALIIWGVHHSGSATEQTKLYGSGNKLITVGSSKYQQSFTPSPGARPQVNGQSGRID

FHWLLLDPNDTVTFTFNGAFIAPDRASFFRGESLGVQSDVPLDSGCEGDCFHNGGTIVSS

LPFQNINPRTVGKCPRYVKQTSLLLATGMRNVPENPKTRGLFGAIAGFIENGWEGLIDG

WYGFRHQNAQGEGTAADYKTTQSAIDQITGKLNRLIDKTNQQFELIDNEFSEIEQQIGNV

INWTRDSMTEVWSYNAELLVAMENQHTIDLADSEMNKLYERVRKQLRENAEEDGTGC

FEIFHKCDDQCMESIRNNTYDHTQYRAESLQNRIQIDPVKLSSGYKDIILWFSFGASCFLL

LAIAMGLVFICIKNGNMRCTICI

A/American green-winged teal/Illinois/10OS3329/2010 (H7N7)

(SEQ ID NO.: 57)

MNTQILALIACMLIGAKGDKICLGHHAVANGTKVNTLTERGIEVVNATETVETANIKKIC

TQGKRPTDLGQCGLLGTLIGPPQCDQFLEFDADLIIERREGTDVCYPGKFTNEESLRQILR

GSGGIDKESMGFTYSGIRTNGVTSACRRSGSSFYAEMKWLLSNSDNAAFPQMTKSYRNP

RNKPALIIWGVHHSGSATEQTKLYGSGNKLITVGSSKYQQSFTPSPGARPQVNGQSGRID

```
FHWLLLDPNDTVTFTFNGAFIAPDRASFFRGESLGVQSDVPLDSGCEGDCFHNGGTIVSS

LPFQNINPRTVGKCPRYVKQTSLLLATGMRNVPENPKTRGLFGAIAGFIENGWEGLIDG

WYGFRHQNAQGEGTAADYKSTQSAIDQITGKLNRLIDKTNQQFELIDNEFSEIEQQIGNV

INWTRDSMTEVWSYNAELLVAMENQHTIDLADSEMNKLYERVRKQLRENAEEDGTGC

FEIFHKCDDQCMESIRNNTYDHTQYRTESLQNRIQIDPVKLSSGYKDIILWFSFGASCFLL

LAIAMGLVFICIKNGNMRCTICI

>A/Guinea fowl/New York/19501-4/2006 (H7N2)
                                                    (SEQ ID NO.: 58)
MNIQILAFIACVLTGAKGDKICLGHHAVANGTKVNTLTEKGIEVVNATETVETADVKKI

CTQGKRATDLGRCGLLGTLIGPPQCDQFLEFSSDLIIERREGTDVCYPGRFTNEESLRQIL

RRSGGISKESMGFTYSGIRTNGTASACTRSGSSFYAEMKWLLSNSDNSAFPQMTKAYRN

PRNKPALIIWGVHHSESASEQTKLYGSGNKLITVRSSKYQQSFTPSPGTRRIDFHWLLLDP

NDTVTFTFNGAFIAPDRASFFRGESLGVQSDAPLDSSCRGDCFHSGGTIVSSLPFQNINSR

TVGRCPRYVKQKSLLLATGMRNVPEKPKPRGLFGAIAGFIENGWEGLINGWYGFRHQN

AQGEGTAADYKSTQSAIDQITGKLNRLIGKTNQQFELIDNEFNEIEQQIGNVINWTRDAM

TEIWSYNAELLVAMENQHTIDLADSEMSKLYERVKKQLRENAEEDGTGCFEIFHKCDD

QCMESIRNNTYDHTQYRTESLQNRIQIDPVKLSSGYKDIILWFSFGASCFILLAIAMGLVFI

CIKNGNMQCTICI

A/Netherlands/219/2003 (H7N7)
                                                    (SEQ ID NO.: 59)
SKSRGYKMNTQILVFALVASIPTNADKICLGHHAVSNGTKVNTLTERGVEVVNATETVE

RTNVPRICSKGKRTVDLGQCGLLGTITGPPQCDQFLEFSADLIIERREGSDVCYPGKFVNE

EALRQILRESGGIDKETMGFTYSGIRTNGTTSACRRSGSSFYAEMKWLLSNTDNAAFPQ

MTKSYKNTRKDPALIIWGIHHSGSTTEQTKLYGSGNKLITVGSSNYQQSFVPSPGARPQV

NGQSGRIDFHWLILNPNDTVTFSFNGAFIAPDRASFLRGKSMGIQSEVQVDANCEGDCY

HSGGTIISNLPFQNINSRAVGKCPRYVKQESLLLATGMKNVPEIPKRRRRGLFGAIAGFIE

NGWEGLIDGWYGFRHQNAQGEGTAADYKSTQSAIDQITGKLNRLIEKTNQQFELIDNEF

TEVERQIGNVINWTRDSMTEVWSYNAELLVAMENQHTIDLADSEMNKLYERVKRQLRE

NAEEDGTGCFEIFHKCDDDCMASIRNNTYDHSKYREEAIQNRIQIDPVKLSSGYKDVILW

FSFGASCFILLAIAMGLVFICVKNGNMRCTICI

A/duck/Thailand/CU-LM7302T/2010 (H7N6)
                                                    (SEQ ID NO.: 60)
MNTQILVFALVAIIPTNADKICLGHHAVSNGTKVNTLTERGVEVVNATETVERTNIPRICS

KGKKTVDLGQCGLLGTITGPPQCDQFLEFSADLIIERREGSDVCYPGKFVNEESLRQILRE

SGGIDKETMGFTYSGIRTNGATSACRRSGSSFYTEMKWLLSNTDNAAFPQTTKSYKNTR

KDPALIIWGIHHSGSTAEQTKLYGSGNKLITVGSSNYQQSFVPSPGARPQVNGQSGRIDF

HWLILNPNDTVTFSFNGAFIAPDRASFLRGKSIGIQSGVQVDAGCEGNCYHNGGTIISNLP

FQNINSRAVGKCPRYVKQESLLLATGMKNVPEIPKGRGLFGAIAGFIENGWEGLIDGWY

GFRHQNAQGEGTAADYKSTQSAIDQITGKLNRLIEKTNQQFELIDNEFTEVEKQIGNVI

NWTRDSMTEVWSYNAELLVAMENQHTIDLADSEMNKLYERVRRQLRENAEEDGTGCF

EIFHKCDDDCMASIRNNTYDHSKYREEAMQNRIQIDPVKLSSGYKDVILWFSFGASCFIL

LAIAMGLVFICVKNGNMRCTICI
```

-continued

A/mallard/California/1390/2010 (H7N5)
(SEQ ID NO.: 61)
MNTQILALIACMLIGAEGDKICLGHHAVANGTKVNTLTERGIEVVNATETVETADIKKIC

TQGKRPTDLGQCGLLGTLIGPPQCDQFLEFDADLIIERREGTDVCYPGKFTNEESLRQILR

GSGGIDKESMGFTYSGIRTNGATSACRRSGSSFYAEMKWLLSNSDNAAFPQMTKSYRNP

RNKPALIIWGVHHSGSATEQTKLYGSGNKLITVGSSKYQQSFTPSPGARPQVNGQSGRID

FHWLLLDPNDTVTFTFNGAFIAPDRASFFRGESLGVQSDVPLDSGCEGNCFHSGGTIVSS

LPFQNINPRTVGKCPRYVKQTSLLLATGMRNVPENPKTRGLFGAIAGFIENGWEGLIDG

WYGFRHQNAQGEGTAADYKSTQSAIDQITGKLNRLIDKTNQQFELIDNEFSEIEQQIGNV

INWTRDSMTEMWSYNAELLVAMENQHTIDLADSEMNKLYERVRKQLRENAEEDGTGC

FEIFHKCDDQCMESIRNNTYDHTQYRTESLQNRIQIDPVKLSSGYKDIILWFSFGASCFLL

LAIAMGLVFICIKNGNMRCTICI

A/mallard/Interior Alaska/10BM05347R0/2010 (H7N3)

(SEQ ID NO.: 62)

MNTQILALIACMLIGAKGDKICLGHHAVANGTKVNTLTERGIEVVNATETVETANIKKIC

TQGKRPTDLGQCGLLGTLIGPPQCDQFLEFDADLIIERREGTDVCYPGKFTNEESLRQILR

GSGGIDKESMGFTYSGIRTNGATSACRRSGSSFYAEMKWLLSNSDNAAFPQMTKSYRNP

RNKPALIIWGVHHSGSATEQTKLYGSGNKLITVGSSKYQQSFTPSPGARPQVNGQSGRID

FHWLLLDPNDTVTFTFNGAFIAPDRASFFRGESLGVQSDVPLDSGCEGNCFHSGGTIVSS

LPFQNINPRTVGKCPRYVKQTSLLLATGMRNVPENPKTRGLFGAIAGFIENGWEGLIDG

WYGFRHQNAQGEGTAADYKSTQSAIDQITGKLNRLIDKTNQQFELIDNEFSEIEQQIGNV

INWTRDSMTEVWSYNAELLIAMENQHTIDLADSEMNKLYERVRKQLRENAEEDGTGCF

EIFHKCDDQCMESIRNNTYDHTQYRTESLQNRIQIDPVKLSSGYKDIILWFSFGASCFLLL

AIAMGLVFICIKNGNMRCTICI

A/mallard/Missouri/10MO053/2010 (H7N4)

(SEQ ID NO.: 63)

MNTQILALIACMLIGAKGDKICLGHHAVANGTKVNTLTERGIEVVNATETVETANIKKIC

TQGKRPTDLGQCGLLGTLIGPPQCDQFLEFDADLIIERREGTDVCYPGKFTNEESLRQILR

GSGGIDKESMGFTYSGIRTNGATSACRRSGSSFYAEMKWLLSNSDNAAFPQMTKSYRNP

RNKPALIIWGVHHSGSATEQTKLYGSGNKLITVGSSKYQQSFTPSPGARPQVNGQSGRID

FHWLLLDPNDTVTFTFNGAFIAPDRASFFRGESLGVQSDVPLDSGCEGDCFHSGGTIVSS

LPFQNINPRTVGKCPRYVKQTSLLLATGMRNVPENPKTRGLFGAIAGFIENGWEGLIDG

WYGFRHQNAQGEGTAADYKSTQSAIDQITGKLNRLIDKTNQQFELIDNEFSEIEQQIGNV

INWTRDSMTEVWSYNAELLVAMENQHTIDLADSEMNKLYERVRKQLRENAEEDGTGC

FEIFHKCDDQCMESIRNNTYNHTQYRTESLQNRIQIDPVKLSSGYKDIILWFSFGASCFLL

LAIAMGLVFICIKNGNMRCTICI

A/mallard/Netherlands/22/2007 (H7N1)

(SEQ ID NO.: 64)

MNTQILVFALVAIIPTNADKICLGHHAVSNGTKVNTLTERGVEVVNATETVERTNVPRIC

SKGKRTVDLGQCGLLGTITGPPQCDQFLEFSADLIIERREGSDVCYPGKFVNEEALRQILR

ESGGIDKETMGFTYSGIRTNGATSACRRSGSSFYAEMKWLLSNTDNAAFPQMTKSYKN

TRKDPALIIWGIHHSGSTTEQTKLYGSGNKLITVGSSNYQQSFVPSPGARPQVNGQSGRI

DFHWLMLNPNDTITFSFNGAFIAPDRASFLRGKSMGIQSGVQVDANCEGNCYHSGGTIIS

NLPFQNINSRAVGKCPRYVKQESLMLATGMKNVPEIPKGRGLFGAIAGFIENGWEGLID

GWYGFRHQNAQGEGTAADYKSTQSAIDQITGKLNRLIEKTNQQFELIDNEFTEVEKQIG

```
-continued
NVINWTRDSITEVWSYNAELLVAMENQHTIDLADSEMNKLYERVRRQLRENAEEDGTG

CFEIFHKCDDDCMASIRNNTYDHSKYREEAMQNRIQIDPVKLSSGYKDVILWFSFGASCF

ILLAIAMGLVFICVKNGNMRCTICI

A/turkey/Italy/214845/2002 (H7N3)
                                                (SEQ ID NO.: 65)
MNTQILVFALVAIIPTNADKICLGHHAVSNGTKVNTLTERGVEVVNATETVERTNVPRIC

SKGKRTVDLGQCGLLGTITGPPQCDQFLEFSADLIIERREGSDVCYPGKFVNEEALRQILR

ESGGIDKETMGFTYSGIRTNGATSACRRSGSSFYAEMKWLLSNTDNAAFPQMTKSYKN

TRKDPALIIWGIHHSGSTTEQTKLYGSGNKLITVGSSNYQQSFVPSPGARPQVNGQSGRI

DFHWLMLNPNDTVTFSFNGAFIAPDRASFLRGKSMGIQSSVQVDANCEGDCYHSGGTII

SNLPFQNINSRAVGKCPRYVKQESLMLATGMKNVPEIPKGRGLFGAIAGFIE

NGWEGLIDGWYGFRHQNAQGEGTAADYKSTQSAIDQITGKLNRLIEKTNQQFELIDNEF

TEVEKQIGNVINWTRDSMTEVWSYNAELLVAMENQHTIDLADSEMNKLYERVKRQLR

ENAEEDGTGCFEIFHKCDDDCMASIRNNTYDHSRYREEAMQNRIQIDPVKLSSGYKDVI

LWFSFGASCFILLAIAMGLVFICVKNGNMRCTICI
```

In some embodiments, the reference pandemic (human-adapted) HA polypeptide is an HA polypeptide selected from any of the following:

```
A/Aichi/1/68 (H3N2 pandemic)
                                                (SEQ ID NO.: 48)
MKTIIALSYIFCLALGQDLPGNDNSTATLCLGHHAVPNGTLVKTITDDQI

EVTNATELVQSSSTGKICNNPHRILDGIDCTLIDALLGDPHCDVFQNETW

DLFVERSKAFSNCYPYDVPDYASLRSLVASSGTLEFITEGFTWTGVTQNG

GSNACKRGPGSGFFSRLNWLTKSGSTYPVLNVTMPNNDNFDKLYIWGIHH

PSTNQEQTSLYVQASGRVTVSTRRSQQTIIPNIGSRPWVRGLSSRISIYW

TIVKPGDVLVINSNGNLIAPRGYFKMRTGKSSIMRSDAPIDTCISECITP

NGSIPNDKPFQNVNKITYGACPKYVKQNTLKLATGMRNVPEKQTRGLFGA

IAGFIENGWEGMIDGWYGFRHQNSEGTGQAADLKSTQAAIDQINGKLNRV

IEKTNEKFHQIEKEFSEVEGRIQDLEKYVEDTKIDLWSYNAELLVALENQ

HTIDLTDSEMNKLFEKTRRQLRENAEEMGNGCFKIYHKCDNACIESIRNG

TYDHDVYRDEALNNRFQIKGVELKSGYKDWILWISFAISCFLLCVVLLGF

IMWACQRGNIRCNICI

A/South Carolina/1/1918 (H1N1 pandemic)
                                                (SEQ ID NO.: 49)
MEARLLVLLCAFAATNADTICIGYHANNSTDTVDTVLEKNVTVTHSVNLL

EDSHNGKLCKLKGIAPLQLGKCNIAGWLLGNPECDLLLTASSWSYIVETS

NSENGTCYPGDFIDYEELREQLSSVSSFEKFEIFPKTSSWPNHETTKGVT

AACSYAGASSFYRNLLWLTKKGSSYPKLSKSYVNNKGKEVLVLWGVHHPP

TGTDQQSLYQNADAYVSVGSSKYNRRFTPEIAARPKVRDQAGRMNYYWTL

LEPGDTITFEATGNLIAPWYAFALNRGSGSGIITSDAPVHDCNTKCQTPH

GAINSSLPFQNIHPVTIGECPKYVRSTKLRMATGLRNIPSIQSRGLFGAI

AGFIEGGWTGMIDGWYGYHHQNEQGSGYAADQKSTQNAIDGITNKVNSVI

EKMNTQFTAVGKEFNNLERRIENLNKKVDDGFLDIWTYNAELLVLLENER
```

```
-continued
TLDFHDSNVRNLYEKVKSQLKNNAKEIGNGCFEFYHKCDDACMESVRNGT

YDYPKYSEESKLNREEIDGVKLESMGVYQILAIYSTVASSLVLLVSLGAI

SFWMCSNGSLQCRICI

A/Albany/6/58 (H2N2 pandemic)
                                                (SEQ ID NO.: 50)
MAIIYLILLFTAVRGDQICIGYHANNSTEKVDTILERNVTVTHAKDILEK

THNGKLCKLNGIPPLELGDCSIAGWLLGNPECDRLLSVPEWSYIMEKENP

RDGLCYPGSFNDYEELKHLLSSVKHFEKVKILPKDRWTQHTTTGGSRACA

VSGNPSFFRNMVWLTKKGSNYPVAKGSYNNTSGEQMLIIWGVHHPNDETE

QRTLYQNVGTYVSVGTSTLNKRSTPDIATRPKVNGLGSRMEFSWTLLDMW

DTINFESTGNLIAPEYGFKISKRGSSGIMKTEGTLGNCETKCQTPLGAIN

TTLPFHNVHPLTIGECPKYVKSEKLVLATGLRNVPQIESRGLFGAIAGFI

EGGWQGMVDGWYGYHHSNDQGSGYAADKESTQKAFDGITNRVNSVIEKMN

TQFEAVGKEFSNLERRLENLNKKMEDGFLDVWTYNAELLVLMENERTLDF

HDSNVKNLYDKVKMQLRDNVKELGNGCFEFYPKCDDECMNSVKNGTYDYP

KYEEESKLNRNEIKGVKLSSMGVYQILAIYATVAGSLSLAIMMAGISFWM

CSNGSLQCRICI
```

Portions or Fragments of HA Polypeptides

Among other things, the present invention further provides characteristic portions (which may or may not show glycan binding activity) of HA polypeptides in accordance with the invention and nucleic acids that encode them. In general, a characteristic portion is one that contains a continuous stretch of amino acids, or a collection of continuous stretches of amino acids, that together are characteristic of the HA polypeptide. Each such continuous stretch generally will contain at least two amino acids. Furthermore, those of ordinary skill in the art will appreciate that typically at least 5, at least 10, at least 15, at least 20 or more amino acids are required to be characteristic of a H5 HA polypeptide. In general, a characteristic portion is one that, in addition to the sequence identity specified above, shares at least one functional characteristic with the relevant intact HA polypeptide. In some embodiments, characteristic portions of HA polypeptides in accordance with the invention share glycan binding characteristics with the relevant full-length HA polypeptides.

Binding Agents

As described herein, binding to HA receptor glycans correlates with provided HA polypeptide's ability to mediate influenza infection of particular hosts, including for example, humans. In some embodiments, the present invention provides that binding to umbrella-topology glycans on HA receptors correlates with provided HA polypeptide's ability to mediate influenza infection in hosts. In some embodiments, the present invention provides binding agents (e.g., antibodies) that bind to provided HA polypeptides.

In some embodiments, the present invention provides binding agents that specifically bind to HA polypeptides (e.g., engineered and/or variant HA polypeptides as described herein). In some embodiments, provided binding agents discriminate between a test HA polypeptide (which test polypeptide may, for example, be a provided engineered or variant HA polypeptide) and a reference HA polypeptide with which the test HA polypeptide shows a specified degree of overall sequence identity as described herein and/or that that has an amino acid sequence that differs from that of the test HA polypeptide with respect to one or more of the features described herein.

In some embodiments, provided binding agents distinguish between a reference HA polypeptide that includes sequence of any reference HA polypeptide (e.g., H7 HA polypeptide), and a polypeptide of otherwise identical sequence with one or more substitutions at amino acid positions 122, 131, 135, 137, 145, 156, 158, 159, 174, 186, 189, 190, 192, 193, 196, 202, 222, 224, 225, 226, 227, and 228.

In some embodiments, provided binding agents distinguish between a reference HA polypeptide that includes sequence of any reference HA polypeptide (e.g., H7 HA polypeptide), and a polypeptide of otherwise identical sequence with serine at amino acid position 228. In some embodiments, provided binding agents distinguish between a reference HA polypeptide that includes sequence of any reference HA polypeptide (e.g., H7 HA polypeptide), and a polypeptide of otherwise identical sequence with leucine or isoleucine at amino acid position 226. In some embodiments, provided binding agents distinguish between a reference HA polypeptide that includes sequence of any reference HA polypeptide (e.g., H7 HA polypeptide), and a polypeptide of otherwise identical sequence with valine at amino acid position 202. In some embodiments, provided binding agents distinguish between a reference HA polypeptide that includes sequence of any reference HA polypeptide (e.g., H7 HA polypeptide), and a polypeptide of otherwise identical sequence with valine at amino acid position 186. In some embodiments, provided binding agents distinguish between a reference HA polypeptide that includes sequence of any reference HA polypeptide (e.g., H7 HA polypeptide), and a polypeptide of otherwise identical sequence with serine at amino acid position 174. In some embodiments, provided binding agents distinguish between a reference HA polypeptide that includes sequence of any reference HA polypeptide (e.g., H7 HA polypeptide), and a polypeptide of otherwise identical sequence with alanine at amino acid position 122. In some embodiments, provided binding agents distinguish between a reference HA polypeptide that includes sequence of any reference HA polypeptide (e.g., H7 HA polypeptide), and a polypeptide of otherwise identical sequence with amino acids selected from the group consisting of S228, L/I226, V202, V186, S174, A122, and combinations thereof.

In some embodiments, provided binding agents are detecting agents for HA polypeptides. In some embodiments, provided detecting binding agents bind, directly or indirectly, to one or more HA polypeptides. In some embodiments, provided binding agents detect pandemic strains of HA polypeptides. In some embodiments, provided binding agents detect pandemic strains of H7 HA polypeptides. In some embodiments, provided binding agents detect pandemic strains of H7N9 HA polypeptides.

In some embodiments, provided binding agents are competing agents in that they compete with one or more HA polypeptides (e.g., with a reference HA polypeptide and/or with one or more engineered and/or variant HA polypeptides as described herein) for binding to HA receptors, and particularly to human HA receptors. In some embodiments, provided binding agents compete with an interaction between a glycan on HA receptor and HA polypeptide interaction. In some embodiments, glycans on HA receptors are umbrella-topology glycans.

In some embodiments, provided binding agents do not bind directly or indirectly to HA polypeptides.

In some embodiments, a binding agent as described herein is an agent that specifically binds to one or more target entities. In some embodiments, the target entity is an HA polypeptide (e.g., a reference HA polypeptide, and/or an engineered and/or variant HA polypeptide as described herein). In some embodiments, the target entity is an HA receptor. In some embodiments, the target entity is a glycan on an HA receptor (e.g., an umbrella-topology glycan). HA polypeptide (e.g., a reference HA polypeptide, and/or an engineered and/or variant HA polypeptide as described herein). In some embodiments, the target entity is an HA polypeptide fragment. In some embodiments, the target entity is a nucleic acid that encodes an HA polypeptide. In some embodiments, the target entity is an antibody that binds to an HA polypeptide.

In some embodiments, binding agents are polypeptides, glycans, small molecules, and/or glycomimetics. In some embodiments, binding agents are non-HA polypeptides. In some embodiments, binding agents are aptamers and/or lectins. In some embodiments, binding agents are peptidomimetics, scaffold proteins, stapled peptides, and/or mimotopes. In some embodiments, binding agents are nucleic acids.

In some embodiments, binding agents are antibody agents. In some embodiments, binding agents are antibodies or antibody-like entities that bind to HA polypeptides. In some embodiments, such antibodies or antibody-like entities bind specifically to HA polypeptides. In some embodiments, provided antibodies or antibody-like entities discriminate between HA polypeptides and their cognate reference HAs. In some embodiments, provided antibodies or antibody-like entities discriminate between HA polypeptides and otherwise identical HAs that differ only in presence or absence of one or more of the features specifically set forth herein.

The present invention provides binding agents with designated binding specificity, and also provides binding agents with designated binding characteristics with respect to HA polypeptides and/or glycans on HA receptors.

Certain particular binding agents provided by the present invention are described in more detail below.

Non-HA Polypeptides

In some embodiments, binding agents provided in accordance with the present invention are polypeptides whose amino acid sequence does not include a characteristic HA sequence. Such polypeptides are referred to herein as "non-HA polypeptides". In some embodiments, a non-HA polypeptide has an amino acid sequence selected in advance (e.g., via rational design, including for example, introduction of strategic amino acid alterations [e.g., additions, deletions, and/or substitutions] as compared with a reference sequence). In some embodiments, a non-HA polypeptide has an amino acid sequence that is determined stochastically and, for example, identified on the basis of the desirable binding characteristics defined herein.

Antibodies

In some embodiments, binding agents provided in accordance with the present invention are antibodies or antibody-like entities (e.g., that bind to HA polypeptides or umbrella topology glycans and/or to umbrella topology glycan mimics). Antibodies suitable for the invention include antibodies or fragments of antibodies that bind immunospecifically to any HA polypeptide (or umbrella topology glycan) epitope. As used herein, the term "antibodies" is intended to include immunoglobulins and fragments thereof which are specifically reactive to the designated protein or peptide, or fragments thereof.

As described herein, the present invention provides antibodies that bind to HA polypeptides, and in some embodiments bind to multiple influenza strains. In some embodiments, such antibodies are useful in the prophylaxis, treatment, diagnosis, and/or study of influenza.

In some embodiments, antibodies or antibody-like entities that bind to HA polypeptides do so in a manner that interferes with binding between such HA polypeptides and an HA receptor, such that levels of observed binding are reduced when the antibody or antibody-like entities are present as compared with when they are absent. In some embodiments, antibodies or antibody-like entities that bind to HA polypeptides do so in a manner that does not significantly interfere with binding between such HA polypeptides and an HA receptor.

Suitable antibodies include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular ImmunoPharmaceuticals ("SMIPs™"), single chain antibodies, cameloid antibodies, and antibody fragments. As used herein, the term "antibodies" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. Antibody polypeptides for use herein may be of any type (e.g., IgA, IgD, IgE, IgG, IgM).

As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules; and multi specific antibodies formed from antibody fragments. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region.

Antibodies can be generated using methods well known in the art. For example, protocols for antibody production are described by Harlow and Lane, 1988, Antibodies: A Laboratory Manual. Typically, antibodies can be generated in mouse, rat, guinea pig, hamster, camel, llama, shark, or other appropriate host. Alternatively, antibodies may be made in chickens, producing IgY molecules (Schade et al., 1996, ALTEX 13(5):80-85). In some embodiments, antibodies suitable for the present invention are subhuman primate antibodies. For example, general techniques for raising therapeutically useful antibodies in baboons may be found, for example, in Goldenberg et al., international patent publication number WO 91/11465, 1991; and in Losman et al., 1990, Int. J. Cancer 46:310). In some embodiments, monoclonal antibodies may be prepared using hybridoma methods (Milstein and Cuello, 1983, Nature 305(5934):537-40). In some embodiments, monoclonal antibodies may also be made by recombinant methods (U.S. Pat. No. 4,166,452, 1979).

In some embodiments, antibodies suitable for the invention may include humanized or human antibodies. Humanized forms of non-human antibodies are chimeric Igs, Ig chains or fragments (such as Fv, Fab, Fab', F(ab')2 or other antigen-binding subsequences of Abs) that contain minimal sequence derived from non-human Ig. Generally, a humanized antibody has one or more amino acid residues introduced from a non-human source. These non-human amino acid residues are often referred to as "import" residues, which are typically taken from an "import" variable domain. Humanization is accomplished by substituting rodent complementarity determining regions (CDRs) or CDR sequences for the corresponding sequences of a human antibody (Riechmann et al., 1988, Nature 332(6162):323-7; Verhoeyen et al., 1988, Science. 239(4847):1534-6). Such "humanized" antibodies are chimeric Abs (U.S. Pat. No. 4,816,567, 1989), wherein substantially less than an intact human variable domain has been substituted by the corresponding sequence from a non-human species. In some embodiments, humanized antibodies are typically human antibodies in which some CDR residues and possibly some FR residues are substituted by residues from analogous sites in rodent Abs. Humanized antibodies include human Igs (recipient antibody) in which residues from a CDR of the recipient are replaced by residues from a CDR of a non-human species (donor antibody) such as mouse, rat or rabbit, having the desired specificity, affinity and capacity. In some instances, corresponding non-human residues replace Fv framework residues of the human Ig. Humanized antibodies may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region (Fc), typically that of a human Ig (Riechmann et al., 1988, Nature 332(6162):323-7; Verhoeyen et al., 1988, Science. 239(4847):1534-6).

Human antibodies can also be produced using various techniques, including phage display libraries (Hoogenboom et al., 1991, Mol Immunol. 28(9):1027-37; Marks et al., 1991, J Mol Biol. 222(3):581-97) and the preparation of human monoclonal antibodies (Reisfeld and Sell, 1985, Cancer Surv. 4(1):271-90). Similarly, introducing human Ig genes into transgenic animals in which the endogenous Ig genes have been partially or completely inactivated can be exploited to synthesize human antibodies. Upon challenge, human antibody production is observed, which closely resembles that seen in humans in all respects, including gene rearrangement, assembly, and antibody repertoire (Fishwild et al., 1996, Nat Biotechnol. 14(7):845-51; Lonberg et al., 1994, Nature 368(6474):856-9; Lonberg and Huszar, 1995, Int. Rev. Immunol. 13(1):65-93; Marks et al., 1992, Biotechnology (N Y). 10(7):779-83).

In some embodiments, antibodies comprise a conjugate, in which an antibody moiety comprises or consists of the antibody or a functional portion thereof with a conjugated moiety. In some particular embodiments, antibodies as described herein are provided and/or utilized in association with one or more active agents or "payloads", such as a therapeutic or detection agent. In some such embodiments, association between the antibody and the active agent and/or payload comprises at least one covalent interaction so that an antibody conjugate is provided.

In some embodiments, an antibody is a therapeutic payload agent is an effector entity having a desired activity, e.g., anti-viral activity, anti-inflammatory activity, cytotoxic activity, etc. Therapeutic agents can be or comprise any class of chemical entity including, for example, proteins, carbohydrates, lipids, nucleic acids, small organic molecules, non-biological polymers, metals, ions, radioisotopes, etc. In some embodiments, therapeutic agents for use in accordance with the present invention may have a biological activity relevant to the treatment of one or more symptoms or causes of influenza infection (e.g., for example, anti-viral, pain-relief, anti-inflammatory, immunomodulatory, sleep-inducing activities, etc). In some embodiments, therapeutic agents for use in accordance with the present invention have one or more other activities.

In some embodiments, an antibody is a payload detection agent that is or comprises any moiety which may be detected using an assay, for example due to its specific functional properties and/or chemical characteristics. Non-limiting examples of such agents include enzymes, radiolabels, haptens, fluorescent labels, phosphorescent molecules, chemiluminescent molecules, chromophores, luminescent molecules, photoaffinity molecules, colored particles or ligands, such as biotin.

Many appropriate payload detection agents are known in the art, as are systems for their attachment to antibodies (see, for e.g., U.S. Pat. Nos. 5,021,236; 4,938,948; and 4,472,509). Examples of such payload detection agents include paramagnetic ions, radioactive isotopes, fluorochromes, NMR-detectable substances, X-ray imaging agents, among others. For example, in some embodiments, a paramagnetic ion is one or more of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III).

In some embodiments, a radioactive isotope is one or more of astatine211, 14carbon, 51chromium, 36chlorine, 57cobalt, 58cobalt, copper67, 152Eu, gallium67, 3hydrogen, iodine123, iodine125, iodine131, indium111, 59iron, 32phosphorus, radium223, rhenium186, rhenium188, 75selenium, 35sulphur, technicium99m, thorium227 and/or yttrium90. Radioactively labeled antibody agents may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Provided antibodies may be labeled with technetium99m by ligand exchange process, for example, by reducing pertechnate with stannous solution, chelating the reduced technetium onto a Sephadex column and applying the antibody to this column. In some embodiments, provided antibodies are labeled using direct labeling techniques, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

In some embodiments, a fluorescent label is or comprises one or more of Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, among others.

Several methods are known in the art for the attachment or conjugation of an antibody agent to a payload. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Provided antibodies may also be reacted with an enzyme in the presence of a coupling agent such as glutaraldehyde or periodate. Conjugates with fluorescein markers are prepared in the presence of these coupling agents or by reaction with an isothiocyanate.

Lectins

In some embodiments, binding agents provided in accordance with the present invention are lectins. Lectins are sugar-binding proteins which may bind to a soluble carbohydrate or to a carbohydrate moiety which is a part of a glycoconjugate (e.g., a glycopeptide or glycolipid). Lectins typically agglutinate certain animal cells and/or precipitate glycoconjugates by recognizing a particular sugar moiety. For example, SNA-1 is a lectin that has a high affinity for α2-6 sialic acids. As yet another example, polyporus squamosus lectins (PSL1a and PSL1b) have high affinity for binding sialylated glycoconjugates containing Neu5Acα2, 6Galβ1,4Glc/GlcNAc trisaccharide sequences of asparagine-linked glycoproteins. Non-limiting exemplary lectins that may act as binding agents include SNA-1, SNA-1', PSL1a, PSL1b, and polypeptides derived therefrom.

Amino acid sequences of exemplary lectins are provided below:

```
Sambucus Nigra Lectin 1
(Genbank Accession No. U27122):
                                    (SEQ ID NO.: 51)
MRLVAKLLYLAVLAICGLGIHGALTHPRVTPPVYPSVSFNLTGADTYEPF

LRALQEKVILGNHTAFDLPVLNPESQVSDSNRFVLVPLTNPSGDTVTLAI

DVVNLYVVAFSSNGKSYFFSGSTAVQRDNLFVDTTQEELNFTGNYTSLER

QVGFGRVYIPLGPKSLDQAISSLRTYTLTAGDTKPLARGLLVVIQMVSEA
```

```
ARFRYIELRIRTSITDASEFTPDLLMLSMENNWSSMSSEIQQAQPGGIFA

GVVQLRDERNNSIEVTNFRRLFELTYIAVLLYGCAPVTSSSYSNNAIDAQ

IIKMPVFRGGEYEKVCSVVEVTRRISGWDGLCVDVRYGHYIDGNPVQLRP

CGNECNQLWTFRTDGTIRWLGKCLTASSSVMIYDCNTVPPEATKWVVSID

GTITNPHSGLVLTAPQAAEGTALSLENNIHAARQGWTVGDVEPLVTFIVG

YKQMCLRENGENNFVWLEDCVLNRVQQEWALYGDGTIRVNSNRSLCVTSE

DHEPSDLIVILKCEGSGNQRWVFNTNGTISNPNAKLLMDVAQRDVSLRKI

ILYRPTGNPNQQWITTTHPA

Sambucus Nigra Lectin 1'
(Genbank Accession No. U66191):
                                          (SEQ ID NO.: 52)
MKVVATILYLVVLAICGLGIHGAHPTHSAPPTVYPSVSFNLTEANSNEYR

HFLQELRGKVILGSHRAFDLPVLNPESKVSDSDRFVLVRLTNPSRKKVTL

AIDVVTFYVVAFAQNDRSYFFSGSSEVQRENLFVDTTQEDLNFKGDYTSL

EHQVGFGRVYIPLGPKSLAQSISSLSTYKSSAGDNKRLARSLLVVIQMVS

EAARFRYIQLRIQASITDAKEFTPDLLMLSMENKWSSMSSEIQQAQPGGA

FAQVVKLLDQRNHPIDVTNFRRLFQLTSVAVLLHGCPTVTKMPAYIIKMP

VFNGGEDEERCSVVEEVTRRIGGRDGFCAEVKNGDEKDGTPVQLSSCGEQ

SNQQWTFSTDGTIQSLGKCLTTSSSVMIYNCKVVPPESTKWVVSIDGTIT

NPRSGLVLTAPKAAEGTLVSLEKNVHAARQGWIVGNVEPLVTFIVGYEQM

CLETNPGNNDVSLGDCSVKSASKVDQKWALYGDGTIRVNNDRSLCVTSEG

KSSNEPIIILKCLGWANQRWVFNTDGTISNPDSKLVMHVDQNDVPLRKII

LSHPSGTSNQQWIASTHPA

Polyporous squamosus lectin 1a (UniProt Q75WT9)
                                          (SEQ ID NO.: 53)
MSFQGHGIYYIASAYVANTRLALSEDSSANKSPDVIISSDAVDPLNNLWL

IEPVGEADTYTVRNAFAGSYMDLAGHAATDGTAIIGYRPTGGDNQKWIIS

QINDVWKIKSKETGTFVTLLNGDGGGTGTVVGWQNITNNTSQNWTFQKLS

QTGANVHATLLACPALRQDFKSYLSDGLYLVLTRDQISSIWQASGLGSTP

WRSEIFDCDDFATVFKGAVAKWGNENFKANGFALLCGLMFGSKSSGAHAY

NWFVERGNFSTVTFFEPQNGTYSANAWDYKAYFGLF

Polyporous squamosus lectin 1b (UniProt Q75WT8)
                                          (SEQ ID NO.: 54)
MSFEGHGIYHIPHAHVANIRMALANRGSGQNGTPVIAWDSNNDAFDHMWL

VEPTGEADTYTIHNVSTGTYMDVTASAVADNTPIIGYQRTGNDNQKWIIR

QVQTDGGDRPWKIQCKATGTFATLYSGGGSGTAIVGWRLVNSNGNQDWVF

QKLSQTSVNVHATLLACGATVGQDFKNYLYDGLYLVLPRDRISAIWKASG

LGETARRDGIYDSDEFAMTFKSAAATWGKENFKADGFAILCGMMFGTKAS

TNRHAYNWVVERGSFSTVTFFEPQNGTYSDDAWGYKAYFGLF
```

Glycan Decoys

In some embodiments, provided binding agent is an umbrella-topology glycan decoy. In some embodiments, an "umbrella-topology glycan decoy" refers to any substance that shares sufficient structural similarity with umbrella-topology glycans to bind to HA polypeptides. In some embodiments, an "umbrella-topology glycan decoy" refers to any substance that is able to compete away the interaction between HA and umbrella-topology glycans. In some embodiments, an "umbrella-like topology glycan decoy" can be any substance that is able to contact any or all of the residues (including any combination of individual residues) in the glycan binding site of HA that are capable of interacting with umbrella-topology glycans.

In some embodiments, an umbrella-topology glycan decoy is or comprises an umbrella-topology glycan mimic. In some embodiments, an umbrella-topology glycan mimic is or comprises a glycan. In some embodiments, an umbrella-topology glycan decoy is or comprises an umbrella-topology glycan moiety. In some embodiments, an umbrella-topology glycan decoy is or comprises an isolated umbrella-topology glycan moiety (i.e. an umbrella-topology glycan moiety that is not associated with any other moiety). In some embodiments, an umbrella-topology glycan moiety has a structure that is or is substantially similar to any of the structures shown in FIGS. 8 and 10.

In some embodiments, glycan decoys may include entire complex physiological N-linked and/or O-linked glycans, glycoproteins, and/or glycolipids that are defined by any or all of the structural features of umbrella-topology glycans."

In some embodiments, three-dimensional structural topology of a decoy is classified using a parameter θ. In some embodiments, residue positions of the glycan binding site of HA that interacts with an umbrella-like topology glycan decoy are shown in FIG. 8.

In some embodiments, an umbrella-topology glycan decoy is or comprises a small molecule. In some embodiments, an umbrella-topology glycan decoy is or comprises a peptide (e.g., peptide, polypeptide, protein, etc.). In some embodiments, an umbrella-topology glycan decoy is or comprises a lipid. In some embodiments, an umbrella-topology glycan decoy is or comprises a nucleic acid.

An umbrella-topology glycan decoy can be any substance that is capable of interacting with HA amino acid residues that are involved in or are capable of binding to umbrella-topology glycans.

Aptamers

In some embodiments, binding agents provided in accordance with the present invention are aptamers. Aptamers are macromolecules composed of nucleic acid (e.g., RNA, DNA) that bind tightly to a specific molecular target (e.g., an umbrella topology glycan). A particular aptamer may be described by a linear nucleotide sequence and is typically about 15 to about 60 nucleotides in length. Without wishing to be bound by any theory, it is contemplated that the chain of nucleotides in an aptamer form intramolecular interactions that fold the molecule into a complex three-dimensional shape, and this three-dimensional shape allows the aptamer to bind tightly to the surface of its target molecule. Given the extraordinary diversity of molecular shapes that exist within the universe of all possible nucleotide sequences, aptamers may be obtained for a wide array of molecular targets, including proteins and small molecules. In addition to high specificity, aptamers have very high affinities for their targets (e.g., affinities in the picomolar to low nanomolar range for proteins). Aptamers are chemically stable and can be boiled or frozen without loss of activity. Because they are synthetic molecules, they are amenable to a variety of modifications, which can optimize their function for particular applications. For example, aptamers can be modified to dramatically reduce their sensitivity to degradation by enzymes in the blood for use in in vivo applications. In addition, aptamers can be modified to alter their biodistribution or plasma residence time.

Identification and/or characterization of aptamers that bind (directly or indirectly and/or specifically) to HA polypeptides can be achieved through any of a variety of approaches, as will be appreciated by those of ordinary skill in the art.

For example, aptamers can be selected using the SELEX (Systematic Evolution of Ligands by Exponential Enrichment) method (Tuerk and Gold, 1990, Science 249:505-510). In the SELEX method, a large library of nucleic acid molecules (e.g., $10^{15}$ different molecules) is produced and/or screened with the target molecule (e.g., a HA polypeptide or fragment thereof). The target molecule is allowed to incubate with the library of nucleotide sequences for a period of time. Several methods, known in the art, can then be used to physically isolate the aptamer target molecules from the unbound molecules in the mixture, which can be discarded. The aptamers with the highest affinity for the target molecule can then be purified away from the target molecule and amplified enzymatically to produce a new library of molecules that is substantially enriched for aptamers that can bind the target molecule. The enriched library can then be used to initiate a new cycle of selection, partitioning, and amplification. After 5-15 cycles of this iterative selection, partitioning and amplification process, the library is reduced to a small number of aptamers that bind tightly to the target molecule. Individual molecules in the mixture can then be isolated, their nucleotide sequences determined, and their properties with respect to binding affinity and specificity measured and compared. Isolated aptamers can then be further refined to eliminate any nucleotides that do not contribute to target binding and/or aptamer structure, thereby producing aptamers truncated to their core binding domain (see, Jayasena, 1999, Clin. Chem. 45:1628-50 for review of aptamer technology).

Peptidomimetic

In some embodiments, binding agents provided in accordance with the present invention include one or more antibody-like binding peptidomimetics. Liu et al. Cell Mol Biol (Noisy-le-grand). 2003 March; 49(2):209-16 describe "antibody like binding peptidomimetics" (ABiPs), which are peptides that act as pared-down antibodies and have certain advantages of longer serum half-life as well as less cumbersome synthesis methods. Likewise, in some aspects, antibody-like molecules are cyclic or bicyclic peptides. For example, methods for isolating antigen-binding bicyclic peptides (e.g., by phage display) and for using the such peptides are provided in U.S. Patent Publn. No. 20100317547.

Scaffold Protein

In some embodiments, binding agents provided in accordance with the present invention include one or more antibody-like binding scaffold proteins. For example, in some embodiments, one or more CDRs arising from an antibody may be grafted onto a protein scaffold. In general, protein scaffolds may meet the greatest number of the following criteria: (Skerra A., J. Mol. Recogn., 2000, 13:167-187): good phylogenetic conservation; known three-dimensional structure (as, for example, by crystallography, NMR spectroscopy or any other technique known to a person skilled in the art); small size; few or no post-transcriptional modifications; and/or easy to produce, express and purify. The origin of such protein scaffolds can be, but is not limited to, fibronectin (e.g., fibronectin type III domain 10), lipocalin, anticalin (Skerra A., J. Biotechnol., 2001, 74(4):257-75), protein Z arising from domain B of protein A of *Staphylococcus aureus*, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat". For example, anticalins or lipocalin derivatives are described in US Patent Publication Nos. 20100285564, 20060058510, 20060088908, 20050106660, and PCT Publication No. WO2006/056464. Scaffolds derived from toxins such as, for example, toxins from scorpions, insects, plants, mollusks, etc., and the protein inhibitors of neuronal NO synthase (PIN) may also be used in accordance with the present invention.

Mimotope

In some embodiments, binding agents provided in accordance with the present invention include a mimotope, which can be used to disrupt the interaction between an influenza virus and the HA polypeptide receptor. In some embodiment, the mimotope is used to elicit an antibody response identical or similar to the that elicited by its corresponding target epitope. In some embodiments, the target epitope is a sequence that is conserved across more than one influenza subtype. In some embodiment, the conserved epitope is a sequence that is conserved across influenza types 1 and 2. For example, an HA sequences from all influenza subtypes located within the HA-1 (head) and HA-2 (stalk) domains. In some embodiments, the epitope is a conserved sequence located within the HA-1/HA-2 interface membrane proximal epitope region (MPER). In some embodiments, the epitope is a conserved sequence located within the canonical α-helix and/or residues in its vicinity. In some embodiments, a mimotope is a peptide. In some embodiments, a mimotope is a small molecule, carbohydrate, lipid, or nucleic acid. In some embodiments, mimotopes are peptide or non-peptide mimotopes of conserved influenza epitopes. In some embodiments, by mimicking the structure of a defined viral epitope, a mimotope interferes with the ability of influenza virus particles to bind to its natural binding partners, e.g., by binding to the natural binding partner itself.

Stapled Peptide

In some embodiments, binding agents provided in accordance with the present invention include a stapled peptide. In some embodiments, the stapled peptide comprises an amino acid sequences encoding one or more CDRs and/or FRs comprising at least greater than 65, 70, 75, 80, 85, 86, 87, 88, 89, 90, 91, 92, 93, 94, 95, 96, 97, 98 or 99% homology and/or identity with the corresponding CDRs and/or FRs of anti-HA antibodies from Tables 2 and 3 as discussed below. In some embodiments, the stapled peptide comprises an amino acid sequence encoding one or more VH and/or VL chain sequence comprising at least greater than 65, 70, 75, 80, 85, 86, 87, 88, 89, 90, 91, 92, 93, 94, 95, 96, 97, 98 or 99% homology and/or identity with the corresponding VH and VL chains of anti-HA antibodies.

Nucleic Acid

In certain embodiments, binding agents provided in accordance with the present invention are or comprise a nucleic acid, such as DNA or RNA. In certain embodiments, nucleic acids can be DNA or RNA, and can be single stranded or double-stranded. In some embodiments, nucleic acids may include one or more non-natural nucleotides. In some embodiments, nucleic acids include only natural nucleotides. In some embodiments the nucleic acid is designed to mimic an epitope within a HA polypeptide. In some embodiments the nucleic acid is designed to mimic a conserved epitope within one or more influenza HA polypeptide subtypes. In some embodiments, a provided binding agent is or comprises one or more oligonucleotides. In some embodiments, a provided binding agent is or comprises one or more oligonuclotides comprising a secondary structure such as loop, hairpin, fold or combinations thereof. In some embodiments, a provided binding agent is or comprises one or more oligonuclotides comprising a higher ordered (tertiary or quaternary) structure. In some embodiments, a provided binding agent is or comprises an aptamer.

Characterization and/or Identification of Binding Agents

The present invention provides a variety of systems for testing, characterizing, and/or identifying binding agents as discussed above, including detecting and competing agents. In some embodiments, provided binding agents are used to identify and/or to characterize other influenza agents (e.g., antibodies, polypeptides, small molecules, etc.).

The present invention provides a variety of technologies for identification and/or characterization of useful agents (e.g., agents useful in the treatment, prevention, and/or analysis of influenza infection) and/or interactions.

In some embodiments, the present invention provides systems for identifying and/or characterizing agents that compete with HA polypeptides (e.g., H7 HA) for binding to HA receptors, and particularly to human HA receptors. In some embodiments, provided binding agents compete with a HA receptor glycan and HA polypeptide interaction.

In some embodiments, a method of identifying and/or characterizing a binding agent that competes with a HA receptor glycan and HA polypeptide interaction includes the steps of providing a collection of test binding agents; contacting the test agents with at least one HA receptor glycan and at least one HA polypeptide that binds to the receptor glycan; and determining that observed binding between the at least one HA receptor glycan and at least one HA polypeptide is reduced when the binding agent is present as compared with when it is absent. In some embodiments, such a method is used for identifying and/or characterizing a binding agent that competes with a HA receptor glycan and H7 HA polypeptide interaction. In some embodiments, the H7 HA is H7N9.

In some embodiments of the present invention, a variety of binding studies and/or formats are useful for the identification and/or characterization of useful agents as described herein. In some embodiments, the present invention utilizes systems for analyzing binding interactions between HA polypeptides and HA receptors. In some such embodiments, analysis methods comprise steps of 1) providing a source of HA polypeptides or binding components thereof; 2) providing a source of HA receptors or binding components thereof; and 3) contacting the provided sources with one another under conditions and for a time sufficient that binding between the HA polypeptides (or binding components thereof) and HA receptors (or binding components thereof) can be assessed. Such approaches can be utilized, for example, to identify or characterize HA polypeptides, in particular provided (i.e., engineered and/or variant) HA polypeptides, of interest, and/or to identify and/or characterize agents that bind thereto and/or inhibit interaction thereof with HA receptors.

In some embodiments, suitable sources of HA polypeptides or binding components thereof include, but are not limited to, pathological samples, such as blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. Alternatively or additionally, other suitable sources for samples containing HA polypeptides include, but are not limited to, environmental samples such as soil, water, and flora. Yet other samples include laboratory samples, for example of engineered HA polypeptides designed and/or prepared by researchers. Other samples that have not been listed may also be applicable. In some embodiments, sources (and/or samples contacted with HA receptors or binding components thereof) comprise intact virus or virus-like particles; in some embodiments, such sources and/or samples comprises HA polypeptides. In some embodiments, HA polypeptides are utilized in trimer form.

In some embodiments, suitable sources of HA receptors or binding components thereof include tissue samples; in some embodiments, suitable sources include isolated HA receptors or binding components thereof. In some embodiments, suitable sources include collections of glycans, for example in glycan arrays, comprising HA receptor glycans. In some embodiments, suitable sources include glycan collections comprising α2-3-linked and/or α2-6-linked glycans. In some embodiments, suitable sources include glycan collections comprising cone-topology and/or umbrella-topology glycans. In some embodiments, suitable sources include glycans found on human upper respiratory tract HA receptors.

It will be appreciated that a variety of binding interactions can usefully be studied in accordance with the present invention. In addition to HA polypeptide-HA receptor interactions, various antibody-antigen interaction or other ligand-target interactions may be studied, as described herein. For example, interactions between HA polypeptides and detecting or competing agents may be analyzed, in the presence or absence of HA receptors (or binding components thereof)

In some embodiments, one or both interacting components utilized in a binding study is detectably labeled (directly or indirectly) prior to, during, or after the contacting step. In some such embodiments, at least one interacting component is spatially localized, for example on an array. To give but one example, in some embodiments, a detectably labeled HA polypeptide or binding component thereof is contacted with a collection of glycans, for example on an array in which different glycans are distinctly localized. In some such embodiments, binding can be assessed by detecting and/or quantifying localized label (e.g., using a scanning device).

Alternatively or additionally, binding between or among interacting components or entities can be measured using, for example, calorimetric, fluorescence, or radioactive detection systems, or other labeling methods, or other methods that do not require labeling. In general, fluorescent detection typically involves utilizing a first interacting partner (e.g., an HA polypeptide or binding component thereof, or an HA receptor or binding portion thereof) that is or becomes labeled with a fluorescent molecule and monitoring fluorescent signals. Alternatively or additionally, one or both of the interacting components or entities can be tagged with a tag (e.g., biotin or streptavidin, antigen epitope, nucleic acid, etc) that itself interacts detectably with a partner (e.g., streptavidin or biotin, antibody, complementary nucleic acid).

In some embodiments, fluorescence quenching methods can be utilized in which one interacting component or entity is fluorescently labeled and the other is provided in a context that squelches the fluorescence if/when binding occurs.

Alternatively or additionally, binding studies can utilize live cells or tissue samples that have been grown in the presence of a radioactive substance, yielding a radioactively labeled probe. Binding in such embodiments can be detected by measuring radioactive emission.

In some embodiments, such methods are useful to determine the fact of binding and/or the extent of binding between interacting components or entities. In some embodiments, such methods can further be used to identify and/or characterize agents that interfere with or otherwise alter interactions of interest.

In some embodiments, methods described herein may be of particular use in, for example, identifying whether a molecule thought to be capable of interacting with a carbohydrate can actually do so, or to identify whether a molecule unexpectedly has the capability of interacting with a carbohydrate.

The present invention also provides methods of using glycan collections, for example, to detect a particular agent in a test sample. For instance, such methods may comprise steps of (1) contacting a collection of glycans (e.g., a glycan array) with a test sample (e.g., with a sample known or thought to contain an HA polypeptide); and, (2) detecting the binding of any agent in the test sample to the glycan collection.

Binding studies may be utilized in accordance with the present invention, for example, to determine kinetics of interaction between binding agent and glycan. For example, provided methods for determining interaction kinetics may include steps of (1) contacting a glycan collection with a sample comprising the agent being tested; and, (2) measuring kinetics of interaction between the binding agent and the glycan(s).

The kinetics of interaction of between binding entities or components (e.g., a binding agent and glycans in a collection, for example on an array) can be measured by real time changes in, for example, colorimetric or fluorescent signals, as detailed above. Such methods may be of particular use in, for example, determining whether a particular binding agent is able to interact with a specific carbohydrate with a higher degree of binding than does a different binding agent interacting with the same carbohydrate.

In some embodiments, provided binding agents are characterized by systems and methods that involve contacting the binding agent with one or more candidate substrates, such as regions of HA polypeptides, N-glycans on HA polypeptides, HA receptors, sialylated HA receptors, glycans on sialylated HA receptors and/or umbrella topology glycans on sialylated HA receptors.

In some embodiments, an agent and/or candidate substrate may be free in solution, fixed to a support, and/or expressed in and/or on the surface of a cell. The candidate substrate and/or agents may be labeled, thereby permitting detection of binding. Either the agent or the candidate substrate is the labeled species. Competitive binding formats may be performed in which one of the substances is labeled, and one may measure the amount of free label versus bound label to determine the effect on binding.

In some embodiments, binding assays involve, for example, exposing a candidate substrate to an agent and detecting binding between the candidate substrate and the agent. A binding assay may be conducted in vitro (e.g., in a candidate tube, comprising substantially only the components mentioned; in cell-free extracts; and/or in substantially purified components). Alternatively or additionally, binding assays may be conducted in cyto and/or in vivo (e.g., within a cell, tissue, organ, and/or organism; described in further detail below).

In certain embodiments, at least one agent is contacted with at least one candidate substrate and an effect detected. In some embodiments, for example, an agent is contacted with a candidate substrate, and binding between the two entities is monitored. In some embodiments, an assay may involve contacting a candidate substrate with a characteristic portion of an agent. Binding of the agent to the candidate substrate is detected. It will be appreciated that fragments, portions, homologs, variants, and/or derivatives of agents may be employed, provided that they comprise the ability to bind one or more candidate substrates.

Binding of an agent to the candidate substrate may be determined by a variety of methods well-known in the art. The present invention provides assays involving solid phase-bound agents and detecting their interactions with one or more candidate substrates. Thus, an agent may comprise a detectable marker, such as a radioactive, fluorescent, and/or luminescent label. Furthermore, candidate substrate can be coupled to substances which permit indirect detection (e.g. by means of employing an enzyme which uses a chromogenic substrate and/or by means of binding a detectable antibody). Changes in the conformation of agents as the result of an interaction with a candidate substrate may be detected, for example, by the change in the emission of the detectable marker. Alternatively or additionally, solid phase-bound protein complexes may be analyzed by means of mass spectrometry.

In some embodiments, the agent can be non-immobilized. In some embodiments, the non-immobilized component may be labeled (with for example, a radioactive label, an epitope tag, an enzyme-antibody conjugate, etc.). Alternatively or additionally, binding may be determined by immunological detection techniques. For example, the reaction mixture may be subjected to Western blotting and the blot probed with an antibody that detects the non-immobilized component. Alternatively or additionally, enzyme linked immunosorbent assay (ELISA) may be utilized to assay for binding.

In certain embodiments, cells may be directly assayed for binding between agents and candidate substrates. Immunohistochemical techniques, confocal techniques, and/or other techniques to assess binding are well known to those of skill in the art. Various cell lines may be utilized for such screening assays, including cells specifically engineered for this purpose. Examples of cells used in the screening assays include mammalian cells, fungal cells, bacterial cells, or viral cells. A cell may be a stimulated cell, such as a cell stimulated with a growth factor. One of skill in the art would understand that the invention disclosed herein contemplates a wide variety of in cyto assays for measuring the ability of agents to bind to candidate substrates.

Depending on the assay, cell and/or tissue culture may be required. A cell may be examined using any of a number of different physiologic assays. Alternatively or additionally, molecular analysis may be performed, including, but not limited to, western blotting to monitor protein expression and/or test for protein-protein interactions; mass spectrometry to monitor other chemical modifications; etc.

In some embodiments, a binding assays described herein may be performed using a range of concentrations of agents and/or candidate substrates. In some embodiments, the binding assays described herein are used to assess the ability of a candidate substrate to bind to an agent over range of antibody concentrations (e.g. greater than about 100 µg/ml, about 100 µg/ml, about 50 µg/ml, about 40 µg/ml, about 30 µg/ml, about 20 µg/ml, about 10 µg/ml, about 5 µg/ml, about 4 µg/ml, about 3 µg/ml, about 2 µg/ml, about 1.75 µg/ml, about 1.5 µg/ml, about 1.25 µg/ml, about 1.0 µg/ml, about 0.9 µg/ml, about 0.8 µg/ml, about 0.7 µg/ml, about 0.6 µg/ml, about 0.5 µg/ml, about 0.4 µg/ml, about 0.3 µg/ml, about 0.2 µg/ml, about 0.1 µg/ml, about 0.05 µg/ml, about 0.01 µg/ml, and/or less than about 0.01 µg/ml).

In some embodiments, any of the binding studies described herein can be executed in a high throughput fashion. Using high throughput assays, it is possible to screen up to several thousand agents in a single day. In some embodiments, each well of a microtiter plate can be used to run a separate assay against a selected candidate substrate, or, if concentration and/or incubation time effects are to be observed, every 5-10 wells can test a single candidate substrate. Thus, a single standard microtiter plate can assay up to 96 binding interactions between agents and candidate substrates; if 1536 well plates are used, then a single plate can assay up to 1536 binding interactions between agents and candidate substrates; and so forth. It is possible to assay many plates per day. For example, up to about 6,000, about 20,000, about 50,000, or more than about 100,000 assay screens can be performed on binding interactions between antibodies and candidate substrates using high throughput systems in accordance with the present invention.

In some embodiments, such methods utilize an animal host. As used herein, an "animal host" includes any animal model suitable for influenza research. For example, animal hosts suitable for the invention can be any mammalian hosts, including primates, ferrets, cats, dogs, cows, horses, rodents such as, mice, hamsters, rabbits, and rats. In certain embodiments, an animal host used for the invention is a ferret. In particular, in some embodiments, an animal host is naïve to viral exposure or infection prior to administration of an agent (optionally in a provided composition). In some embodiments, the animal host is inoculated with, infected with, or otherwise exposed to virus prior to or concurrent with administration of an agent. An animal host used in the practice of the present invention can be inoculated with, infected with, or otherwise exposed to virus by any method known in the art. In some embodiments, an animal host may be inoculated with, infected with, or exposed to virus intranasally.

In some embodiments, a suitable animal host may have a similar distribution of umbrella vs. cone topology glycans and/or $\alpha$2,6 glycans vs. $\alpha$ 2,3 glycans to the distribution found in the human respiratory tract. For example, it is contemplated that a ferret as an animal host may be more representative than a mouse when used as model of disease caused by influenza viruses in humans (Tumpey, et al. Science (2007) 315; 655-659). Without wishing to be bound any theories, the present invention encompasses the idea that ferrets may have a more similar distribution of glycans in the respiratory tract to those in the human respiratory tract than mouse does to human.

Naïve and/or inoculated animals may be used for any of a variety of studies. For example, such animal models may be used for virus transmission studies as in known in the art. It is contemplated that the use of ferrets in virus transmission studies may serve as a reliable predictor for virus transmission in humans. For example, air transmission of viral influenza from inoculated animals (e.g., ferrets) to naïve animals is known in the art (Tumpey, et al. Science (2007) 315; 655-659). Virus transmission studies may be used to test agents. For example, agents may be administered to a suitable animal host before, during or after virus transmission studies in order to determine the efficacy of said agent in blocking virus binding and/or infectivity in the animal host. Using information gathered from virus transmission studies in an animal host, one may predict the efficacy of an agent in blocking virus binding and/or infectivity in a human host.

Nucleic Acids

The present invention also provides nucleic acids that encode polypeptides described herein, including for example HA polypeptides, antibodies, etc, and/or fragments thereof.

In some embodiments, the present invention provides nucleic acids which encode an HA polypeptide or a characteristic or biologically active portion of an HA polypeptide. In some embodiments, the invention provides nucleic acids which are complementary to nucleic acids which encode an HA polypeptide or a characteristic or biologically active portion of an HA polypeptide.

In some embodiments, the invention provides nucleic acid molecules which hybridize to nucleic acids encoding an HA polypeptide or a characteristic or biologically active portion of an HA polypeptide. Such nucleic acids can be used, for example, as primers or as probes. To give but a few examples, such nucleic acids can be used as primers in polymerase chain reaction (PCR), as probes for hybridization (including in situ hybridization), and/or as primers for reverse transcription-PCR (RT-PCR).

In some embodiments, nucleic acids can be DNA and/or RNA, and can be single stranded or double-stranded. In some embodiments, nucleic acids in accordance with the invention may include one or more non-natural nucleotides; in some embodiments, nucleic acids in accordance with the invention include only natural nucleotides.

Production of Polypeptides

The present invention provides that polypeptides (e.g., HA polypeptides, non-HA polypeptides, antibodies, etc.) and/or fragments, such as characteristic fragments thereof may be produced by any available means.

Methods for generating antibodies (e.g., monoclonal antibodies and/or polyclonal antibodies) are well known in the art. It will be appreciated that a wide range of animal species can be used for the production of antisera, including rabbit, mouse, rat, hamster, guinea pig or goat. The choice of animal may be decided upon the ease of manipulation, costs or the desired amount of sera, as would be known to one of skill in the art. It will be appreciated that antibodies can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

In some embodiments, polypeptides may be produced, for example, by utilizing a host cell system engineered to express nucleic acids encoding a polypeptide of interest. In some embodiments, such encoding nucleic acids are heterologous to the host cell system and are introduced into the system through action of the hand of man. Alternatively or additionally, the host cell system may be manipulated to express the encoding polypeptide at a particular (e.g., elevated) level and/or at a particular time. Alternatively or additionally, provided polypeptides may be synthesized in vitro, for example utilizing in vitro transcription and/or translation systems and/or through chemical synthesis (e.g., using an automated peptide synthesizer).

Those skilled in the art will be aware of a wide variety of host cell systems that can appropriately be used to produce polypeptides as described herein. Exemplary sources for polypeptide preparations suitable for the invention include, but are not limited to, conditioned culture medium derived from culturing a recombinant cell line that expresses a protein of interest, or from a cell extract of, e.g., antibody-producing cells, mammalian cells, bacteria, fungal cells, insect cells, transgenic plants or plant cells, transgenic animals or animal cells, or serum of animals, ascites fluid, hybridoma or myeloma supernatants. Suitable bacterial cells include, but are not limited to, *Escherichia coli* cells. Examples of suitable *E. coli* strains include: HB101, DH5α, GM2929, JM109, KW251, NM538, NM539, and any *E. coli* strain that fails to cleave foreign DNA. Suitable fungal host cells that can be used include, but are not limited to, *Saccharomyces cerevisiae, Pichia pastoris* and *Aspergillus* cells. Suitable insect cells include, but are not limited to, S2 Schneider cells, D. Mel-2 cells, SF9, SF21, High-5™, Mimic™-SF9, MG1 and KC1 cells. Suitable exemplary recombinant cell lines include, but are not limited to, BALB/c mouse myeloma line, human retinoblasts (PER.C6), monkey kidney cells, human embryonic kidney line (293), baby hamster kidney cells (BHK), Chinese hamster ovary cells (CHO), mouse sertoli cells, African green monkey kidney cells (VERO-76), human cervical carcinoma cells (HeLa), canine kidney cells, buffalo rat liver cells, human lung cells, human liver cells, mouse mammary tumor cells, TRI cells, MRC 5 cells, FS4 cells, and human hepatoma line (Hep G2).

Polypeptides of interest can be expressed using various vectors (e.g., viral vectors) known in the art and cells can be cultured under various conditions known in the art (e.g., fed-batch). Various methods of genetically engineering cells to produce antibodies are well known in the art. See e.g. Ausabel et al., eds. (1990), Current Protocols in Molecular Biology (Wiley, New York).

In some embodiments, provided HA polypeptides (or certain fragments thereof) may be produced in the context of intact virus or virus-like particles.

In some embodiments, provided HA polypeptides (or certain fragments thereof) can be isolated and/or purified from influenza virus. For example, virus may be grown in eggs, such as embryonated hen eggs, in which case the harvested material is typically allantoic fluid. Alternatively or additionally, virus may be grown in a tissue culture system. Suitable cell substrates for growing the virus include, for example, dog kidney cells such as Madin-Darby Canine Kidney cells (MDCK) or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

Provided polypeptides may be purified, if desired, using filtration, centrifugation and/or various chromatographic methods such as HPLC or affinity chromatography. In some embodiments, fragments of provided polypeptides are obtained by methods which include digestion with enzymes, such as pepsin or papain, and/or by cleavage of disulfide bonds by chemical reduction.

Also, it will be appreciated by those of ordinary skill in the art that polypeptides, and particularly antibodies as described herein, may be generated, identified, isolated, and/or produced by culturing cells or organisms that produce antibodies (whether alone or as part of a complex, including as part of a virus particle or virus), under conditions that allow ready screening and/or selection of polypeptides capable of binding to influenza antigens (e.g., influenza HA). To give but one example, in some embodiments, it may be useful to produce and/or study a collection of antibodies under conditions that reveal and/or favor those variants that bind to HA polypeptides (e.g., with particular specificity and/or affinity). In some embodiments, such a collection of antibodies results from evolution in nature. In some embodiments, such a collection of antibodies results from engineering. In some embodiments, such a collection of antibodies results from a combination of engineering and natural evolution.

It will be appreciated that provided polypeptides may be engineered, produced, and/or purified in such a way as to improve characteristics and/or activity of the polypeptide. For example, improved characteristics of provided antibodies include, but are not limited to, increased stability, improved binding affinity and/or avidity, increased binding specificity, increased production, decreased aggregation, decreased nonspecific binding, among others.

Also, it will be appreciated by those of ordinary skill in the art that polypeptides, and particularly HA polypeptides as described herein, may be generated, identified, isolated, and/or produced by culturing cells or organisms that produce the polypeptide (whether alone or as part of a complex, including as part of a virus particle or virus), under conditions that allow ready screening and/or selection of polypeptides that show desired binding and/or activity characteristics as described herein.

Glycan Arrays

To rapidly expand the current knowledge of known specific glycan-glycan binding protein (GBP) interactions, the Consortium for Functional Glycomics (CFG; functionalglycomics.org), an international collaborative research initiative, has developed glycan arrays comprising several glycan structures that have enabled high throughput screening of GBPs for novel glycan ligand specificities. The glycan arrays comprise both monovalent and polyvalent glycan motifs (i.e. attached to polyacrylamide backbone), and each array comprises 264 glycans with low (10 μM) and high (100 μM) concentrations, and six spots for each concentration (see, functionalglycomics.org/static/consortium/resources/resourcecoreh5).

The arrays predominantly comprise synthetic glycans that capture the physiological diversity of N- and O-linked glycans. In addition to the synthetic glycans, N-linked glycan mixtures derived from different mammalian glycoproteins are also represented on the array.

As used herein, a glycan "array" refers to a set of one or more glycans, optionally immobilized on a solid support. In some embodiments, an "array" is a collection of glycans present as an organized arrangement or pattern at two or more locations that are physically separated in space. Typically, a glycan array will have at least 4, at least 8, at least 16, at least 24, at least 48, at least 96, or several hundred or thousand discrete locations. In general, glycan arrays in accordance with the invention may have any of a variety of formats. Various different array formats applicable to biomolecules are known in the art. For example, a huge number of protein and/or nucleic acid arrays are well known. Those of ordinary skill in the art will immediately appreciate standard array formats appropriate for glycan arrays of the present invention.

In some embodiments, glycan arrays in accordance with the invention are present in "microarray" formats. A microarray may typically have sample locations separated by a distance of about 50μ to about 200μ or less and immobilized sample in the nano to micromolar range or nano to picogram range. Array formats known in the art include, for example, those in which each discrete sample location has a scale of, for example, ten µ.

In some embodiments, glycan arrays in accordance with the invention comprise a plurality of glycans spatially immobilized on a support. The present invention provides glycan molecules arrayed on a support. As used herein, "support" refers to any material which is suitable to be used to array glycan molecules. As will be appreciated by those of ordinary skill in the art, any of a wide variety of materials may be employed. To give but a few examples, support materials which may be of use in the invention include hydrophobic membranes, for example, nitrocellulose, PVDF or nylon membranes. Such membranes are well known in the art and can be obtained from, for example, Bio-Rad, Hemel Hempstead, UK.

In some embodiments, the support on which glycans are arrayed may comprise a metal oxide. Suitable metal oxides include, but are not limited to, titanium oxide, tantalum oxide, and aluminum oxide. Examples of such materials may be obtained from Sigma-Aldrich Company Ltd, Fancy Road, Poole, Dorset. BH12 4QH UK.

In some embodiments, such a support is or comprises a metal oxide gel. A metal oxide gel is considered to provide a large surface area within a given macroscopic area to aid immobilization of the carbohydrate-containing molecules.

Additional or alternative support materials which may be used in accordance with the present invention include gels, for example silica gels or aluminum oxide gels. Examples of such materials may be obtained from, for example, Merck KGaA, Darmstadt, Germany.

In some embodiments, glycan arrays are immobilized on a support that can resist change in size or shape during normal use. For example a support may be a glass slide coated with a component material suitable to be used to array glycans. Also, some composite materials can desirable provide solidity to a support.

As demonstrated herein, arrays in accordance with the invention are useful for the identification and/or characterization of different HA polypeptides and their binding characteristics. Indeed, the present invention provides arrays of α2-6 sialylated glycans, and optionally α2-3 sialylated glycans, that can be used to characterize HA polypeptide binding capabilities and/or as a diagnostic to detect, for example, human-binding HA polypeptides. In some embodiments, arrays in accordance with the invention contain glycans (e.g., α2-6 sialylated glycans, and particularly long α2-6 sialylated glycans) in an umbrella topology. As will be clear to those of ordinary skill in the art, such arrays are useful for characterizing or detecting any HA polypeptides, including for example, those found in natural influenza isolates in addition to those designed and/or prepared by researchers.

In some embodiments, such arrays include glycans representative of about 10%, about 15%, about 20%, about 25%, about 30% about 35%, about 40%, about 45%, about 50%, about 55%, about 60%, about 65%, about 70%, about 75%, about 80%, about 85%, about 90% about 95%, or more of the glycans (e.g., the umbrella glycans, which will often be α2-6 sialylated glycans, particularly long α2-6 sialylated glycans) found on human HA receptors, and particularly on human upper respiratory tract HA receptors. In some embodiments, arrays in accordance with the invention include some or all of the glycan structures depicted in FIG. 9. In some embodiments, arrays include at least about 10%, about 15%, about 20%, about 25%, about 30% about 35%, about 40%, about 45%, about 50%, about 55%, about 60%, about 65%, about 70%, about 75%, about 80%, about 85%, about 90%, about 95%, or more of these depicted glycans.

The present invention provides methods for identifying or characterizing HA proteins using glycan arrays. In some embodiments, for example, such methods comprise steps of (1) providing a sample containing HA polypeptide, (2) contacting the sample with a glycan array comprising, and (3) detecting binding of HA polypeptide to one or more glycans on the array.

Suitable sources for samples containing HA polypeptides to be contacted with glycan arrays according to the present invention include, but are not limited to, pathological samples, such as blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. Alternatively or additionally, other suitable sources for samples containing HA polypeptides include, but are not limited to, environmental samples such as soil, water, and flora. Yet other samples include laboratory samples, for example of engineered HA polypeptides designed and/or prepared by researchers. Other samples that have not been listed may also be applicable.

A wide variety of detection systems suitable for assaying HA polypeptide binding to glycan arrays in accordance with the invention are known in the art. For example, HA polypeptides can be detectably labeled (directly or indirectly) prior to or after being contacted with the array; binding can then be detected by detection of localized label. In some embodiments, scanning devices can be utilized to examine particular locations on an array.

Alternatively or additionally, binding to arrayed glycans can be measured using, for example, calorimetric, fluorescence, or radioactive detection systems, or other labeling methods, or other methods that do not require labeling. In general, fluorescent detection typically involves directly probing the array with a fluorescent molecule and monitoring fluorescent signals. Alternatively or additionally, arrays can be probed with a molecule that is tagged (for example, with biotin) for indirect fluorescence detection (in this case, by testing for binding of fluorescently-labeled streptavidin). Alternatively or additionally, fluorescence quenching methods can be utilized in which the arrayed glycans are fluorescently labeled and probed with a test molecule (which may or may not be labeled with a different fluorophore). In such embodiments, binding to the array acts to squelch the fluorescence emitted from the arrayed glycan, therefore binding is detected by loss of fluorescent emission. Alternatively or additionally, arrayed glycans can be probed with a live tissue sample that has been grown in the presence of a radioactive substance, yielding a radioactively labeled probe. Binding in such embodiments can be detected by measuring radioactive emission.

Such methods are useful to determine the fact of binding and/or the extent of binding by HA polypeptides to glycan arrays in accordance with the invention. In some embodiments, such methods can further be used to identify and/or characterize agents that interfere with or otherwise alter interactions between glycans on HA receptors and HA polypeptides.

Methods described below may be of particular use in, for example, identifying whether a molecule thought to be capable of interacting with a carbohydrate can actually do so, or to identify whether a molecule unexpectedly has the capability of interacting with a carbohydrate.

The present invention also provides methods of using arrays in accordance with the invention, for example, to detect a particular agent in a test sample. For instance, such methods may comprise steps of (1) contacting a glycan array with a test sample (e.g., with a sample thought to contain an HA polypeptide); and, (2) detecting the binding of any agent in the test sample to the array.

Yet further, binding to arrays in accordance with the invention may be utilized, for example, to determine kinetics of interaction between binding agent and glycan. For example, methods in accordance with the invention for determining interaction kinetics may include steps of (1) contacting a glycan array with the molecule being tested; and, (2) measuring kinetics of interaction between the binding agent and arrayed glycan(s).

The kinetics of interaction of a binding agent with any of the glycans in an array in accordance with the invention can be measured by real time changes in, for example, colorimetric or fluorescent signals, as detailed above. Such methods may be of particular use in, for example, determining whether a particular binding agent is able to interact with a specific carbohydrate with a higher degree of binding than does a different binding agent interacting with the same carbohydrate.

It will be appreciated, of course, that glycan binding by HA polypeptides in accordance with the invention can be evaluated on glycan samples or sources not present in an array format per se. For example, HA polypeptides in accordance with the invention can be bound to tissue samples and/or cell lines to assess their glycan binding characteristics. Appropriate cell lines include, for example, any of a variety of mammalian cell lines, particularly those expressing HA receptors containing umbrella topology glycans (e.g., at least some of which may be α2-6 sialylated glycans, and particularly long α2-6 sialylated glycans). In some embodiments, utilized cell lines express individual glycans with umbrella topology. In some embodiments, utilized cell lines express a diversity of glycans. In some embodiments, cell lines are obtained from clinical isolates; in some they are maintained or manipulated to have a desired glycan distribution and/or prevalence. In some embodiments, tissue samples and/or cell lines express glycans characteristic of mammalian upper respiratory epithelial cells.

Treatment

The present invention provides systems, compositions, and methods to treat (e.g., alleviate, ameliorate, relieve, delay onset of, inhibit progression of, reduce severity of, and/or reduce incidence of one or more symptoms or features of and/or prevent influenza infection. In some embodiments, provided HA polypeptides or fragments thereof, nucleic acids that encode them, expression systems that produce them, and/or binding agents such as those described herein may be used for a variety of therapeutic purposes, e.g., treating influenza infection and/or developing vaccines to immunize subjects against influenza infection.

Therapy

The present invention provides systems and methods for treating patients suffering from, susceptible to, and/or displaying symptoms of influenza infection. In some embodiments, the invention provides systems and methods useful for stratifying patients suffering from, susceptible to, and/or displaying symptoms of influenza infection.

In some embodiments, the present invention provides systems and methods used in the treatment of one or more of the following symptoms: fever, sore throat, muscle pains, severe headache, coughing, weakness, general discomfort, pneumonia, nausea, and/or vomiting. In certain embodiments, these symptoms are caused by influenza infection.

In some embodiments, provided binding agents (e.g., those that bind to provided HA polypeptides and inhibit the ability of the said HA polypeptides expressed on the surface of influenza virus to interact with one or more glycans on HA receptors, e.g., umbrella-topology glycans associated with human upper respiratory epithelial tissues, such as trachea and bronchus) in accordance with the invention may be utilized for therapeutic applications.

In some embodiments, therapeutic applications comprise administering a therapeutically effective amount of at least one binding agent in accordance with the invention to a subject in need thereof. In some embodiments, administration of binding agents to a subject may alleviate, ameliorate, relieve, delay onset of, inhibit progression of, reduce severity of, and/or reduce incidence of one or more signs, symptoms, and/or features of influenza infection.

In some embodiments, administration of binding agents reduces the level of influenza virions circulating in a subject (e.g., influenza virions that are capable of infecting new cells). In some embodiments, administration of binding agents reduces the level of influenza virions circulating in a subject by about 10%, about 20%, about 30%, about 40%, about 50%, about 60%, about 70%, about 80%, about 90%, about 95%, about 99%, or about 100% relative to non-treated controls.

In some embodiments, binding agents may be used in vitro to reduce viral load in a subject. For reducing viral load of a body component, particularly a body component of a patient infected with influenza, a patient's blood is passed through a device comprising binding agents bound to a surface or solid support for capturing influenza virions (see, for example, U.S. Pat. Nos. 5,698,390 and 4,692,411). Various other devices found in the literature can be used with the subject antibodies to achieve a similar result. A body component can be a biological fluid (e.g., blood, serum, etc.), a tissue, an organ, such as the liver, and the like.

In some embodiments, the "level of influenza virions circulating in a subject" refers to an absolute number of virions circulating in a subject. In some embodiments, the "level of influenza virions circulating in a subject" refers to the number of virions per unit volume (e.g., milliliter, liter, etc.) of the subject's blood. In some embodiments, the "level of influenza virions circulating in a subject" refers to viral load.

In some embodiments, administration of binding agents inhibits binding of virus to HA receptors. In some embodiments, administration of binding agents inhibits binding of virus to at least one HA receptor by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of binding agents kills and/or inactivates influenza virions in a subject. In some embodiments, administration of influenza antibodies kills and/or inactivates about 10%, about 20%, about 30%, about 40%, about 50%, about 60%, about 70%, about 80%, about 90%, about 95%, about 99%, or about 100% of influenza virions in a subject relative to non-treated controls.

In some embodiments, administration of binding agents inhibits virus-mediated fusion with a target cell. In some embodiments, administration of binding agents inhibits virus-mediated fusion with a target cell by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of binding agents inhibits conformational changes of one or more proteins associated with virus entry. In some embodiments, administration of binding agents inhibits conformational changes of one or more proteins associated with virus entry by about 2-fold, about 3-fold, about 4-fold, about 5-fold, about 10-fold, about 50-fold, about 100-fold, about 500-fold, about 1000-fold, about 10,000-fold, or greater than about 10,000-fold relative to non-treated controls.

In some embodiments, administration of binding agents results in conformational changes in HA polypeptides and/or HA receptors. For example, administered interfering agents and/or binding agents may bind to HA polypeptides and/or HA receptors, thereby sterically blocking the HA polypeptide's and/or HA receptors' ability to recognize and/or interact with one another. In some embodiments, administered binding agents may bind to HA polypeptides and/or HA receptors, thereby changing the three-dimensional conformation of the HA polypeptides and/or HA receptors in such a way that renders HA polypeptides and/or HA receptors incapable of recognizing one another.

In some embodiments, the present invention provides a method of treating influenza infection comprising steps of (1) providing a patient exhibiting symptoms of influenza infection, and (2) administering a therapeutic amount of one or more binding agents to the patient. In some embodiments, the present invention provides a method of treating influenza infection comprising steps of (1) providing a patient suffering from influenza infection, and (2) administering a therapeutic amount of one or more binding agents to the patient. In some embodiments, the present invention provides a method of treating influenza infection comprising steps of (1) providing a patient susceptible to influenza infection, and (2) administering a therapeutic amount of one or more binding agents to the patient.

In some embodiments, the present invention provides methods of treating influenza infection comprising steps of (1) providing a patient exhibiting symptoms of, suffering from, and/or susceptible to influenza infection, and (2) administering an agent that competes away the binding of HA polypeptides (e.g. HA polypeptides associated with influenza virus particles) with umbrella-topology glycans in human upper respiratory tissues.

In some embodiments, the present invention provides a method of preventing and/or delaying the onset of influenza infection comprising steps of (1) providing a patient susceptible to influenza infection, and (2) administering a therapeutic amount of one or more binding agents to the patient.

In some embodiments, treatment and/or vaccination regimens are particularly tailored for the individual being treated and/or vaccinated. The present invention provides systems, compositions, and methods useful for determining whether a patient is infected with H7 HA influenza or non-H7 HA influenza. Such methods can be utilized to stratify patients into treatment and/or vaccination categories. In some embodiments, such methods may be advantageous because the treatment and/or vaccination is tailored to the particular individual being treated and/or vaccinated. To give but one particular example, if a patient is classified as being infected with H7 HA influenza, therapies that are useful for treatment of H7 HA influenza can be administered to the patient, and therapies that are not useful for treatment of H7 HA influenza will not be administered. This avoids or reduces the risk of adverse reactions from administering therapeutics that are not needed. Such methods eliminate the expense of treating and/or vaccinating patients who would not benefit from such treatment and/or vaccination.

Vaccines

In some embodiments, one or more provided HA polypeptides or fragments thereof, nucleic acids that encode them, expression systems that produce them, and/or binding agents (e.g., entities that bind to HA polypeptides and/or fragments, variants, and/or characteristic portions thereof entities that bind to umbrella-topology glycans) in accordance with the invention may be utilized for prophylactic applications. In some embodiments, prophylactic applications involve systems and methods for preventing, inhibiting progression of, and/or delaying the onset of influenza infection.

In some embodiments, influenza vaccines are used to prevent and/or delay onset of infection by influenza. In some embodiments, vaccination is tailored to a particular HA polypeptide. For example, vaccines may comprise at least one antigen comprising an HA polypeptide (e.g., H7 HA polypeptide) and/or variant, fragment, and/or characteristic portion thereof. In some embodiments, vaccines may comprise provided HA polypeptides and a pharmaceutically acceptable carrier. In some embodiments, a vaccine may be formulated into a vaccine composition. In some embodiments, the at least one antigen comprising an HA polypeptide (e.g., H7 HA polypeptide) and/or variant, fragment, and/or characteristic portion thereof in a vaccine may be formulated into a vaccine composition. In some embodiments, it is desirable for vaccine compositions to comprise antigens that have a native conformation, mediate a protective response (e.g., complement activation, virus neutralization, etc.), and/or can induce a strong antibody response.

In some embodiments, the present invention provides a quantitative metric to compare antigenicity of two HAs. In some embodiments, the metric is called antigenic intactness (AI), and is directly proportional to the fraction of residues conserved in the immunodominant antigenic sites between two HAs. In some embodiments, AI values can be applied to predict vaccine-induced cross-reactive antibody responses. In some embodiments, strains that are antigenically related to each other have AI>80%. In some embodiments strains that are not related to each other have AI<80%. In some embodiments, the cut off for AI is 80% for evaluating the effectiveness of an influenza strain as a vaccine.

In some embodiments, the present invention provides a method of evaluating vaccine composition which includes the steps: of providing a test vaccine composition that includes a provided HA polypeptide, particularly a provided H7 HA polypeptide; and determining that the test vaccine composition has at least one activity selected from the group consisting of: mediates a protective response, induces a strong antibody response, prevents transmissibility of the virus in ferrets, and combinations thereof.

For example, the present invention describes that AI values between the recent WHO-recommended HA vaccines strains, particularly H7 HA vaccines strains [(A/Canada/rv444/2004 (H7N3), A/mallard/Netherlands/12/2000 (H7N3) and A/New York/107/2003 (H7N2)), and the novel A/Anhui/1/2013 H7N9 HA] can be computed. The novel H7N9 HA has AI values of 67%, 89% and 70% with A/Canada/rv444/2004 (H7N3), A/mallard/Netherlands/12/2000 (H7N3) and A/New York/107/2003 (H7N2), respectively, suggesting that only /mallard/Netherlands/12/2000 (H7N3) may be effective as a vaccine component. However, amino acid differences between A/Anhui/1/2013 (H7N9)

and A/mallard/Netherlands/12/2000 (H7N3) at certain antigenic sites (i.e., 122 in site A, 188 and 189 in site B) might limit this mallard strain to be effective.

In some embodiments, the present invention provides a method of evaluating effectiveness of a vaccine. In some embodiments, a method of evaluating vaccine induced cross-reactive antibody responses includes steps of providing a test HA strain for which vaccine has to be developed; determine the antigenic intactness (AI) of the test strain and a reference HA strain, which reference strain has been approved and/or recommended for vaccine development; and if the AI value of the test strain is at least 80% with the reference strain, suggesting that the two strains are antigenically related to each other.

In some embodiments, interfering agents may be utilized for passive immunization (i.e., immunization wherein antibodies are administered to a subject). In some embodiments, influenza vaccines for passive immunization may comprise antibody interfering agents, such as those described herein. In some embodiments, passive immunization occurs when antibodies are transferred from mother to fetus during pregnancy. In some embodiments, antibodies are administered directly to an individual (e.g., by injection, orally, etc.).

The present invention provides influenza vaccines for active immunization (i.e., immunization wherein microbes, proteins, peptides, epitopes, mimotopes, etc. are administered to a subject). In some embodiments, influenza vaccines may comprise one or more interfering agents and/or binding agents, as described herein.

In some embodiments, vaccines comprise at least one HA polypeptide (and/or to variants, fragments, and/or characteristic portions thereof), e.g., any of the HA polypeptides, variants, fragments, characteristic portions, and/or combinations thereof described herein. In some embodiments, vaccines comprise H7 HA polypeptides (and/or to variants, fragments, and/or characteristic portions thereof). In some embodiments, vaccines comprise HA polypeptides having one or more of the following: arginine at Residue 137, threonine at Residue 193, leucine at Residue 226, and/or serine at Residue 228. In some embodiments, vaccines comprise HA polypeptides having each of the following: arginine at Residue 137, threonine at Residue 193, leucine at Residue 226, and/or serine at Residue 228. In some embodiments, vaccines comprise HA polypeptides having one or more of the following: alanine at Residue 122, serine at Residue 174, valine at Residue 186, valine at residue 202, leucine at Residue 226, and/or serine at Residue 228. In some embodiments, vaccines comprise HA polypeptides having each of the following: alanine at Residue 122, serine at Residue 174, valine at Residue 186, valine at residue 202, leucine at Residue 226, and/or serine at Residue 228.

In some embodiments, vaccines comprise live active virus particles comprising one or more of any HA polypeptide described herein, live attenuated virus particles comprising one or more of any HA polypeptide described herein, virus-like particles (VLPs) comprising one or more of any HA polypeptide described herein, subunit vaccines comprising one or more of any HA polypeptide described herein, and/or combinations thereof.

In some embodiments, a vaccine composition comprises at least one adjuvant. Any adjuvant may be used in accordance with the present invention. A large number of adjuvants are known; a useful compendium of many such compounds is prepared by the National Institutes of Health and can be found on the internet (niaid.nih.gov/daids/vaccine/pdf/compendium.pdf). See also Allison (1998, Dev. Biol. Stand., 92:3-11), Unkeless et al. (1998, Annu Rev. Immunol., 6:251-281), and Phillips et al. (1992, Vaccine, 10:151-158). Hundreds of different adjuvants are known in the art and could be employed in the practice of the present invention. Exemplary adjuvants that can be utilized in accordance with the invention include, but are not limited to, cytokines, aluminum salts (e.g., aluminum hydroxide, aluminum phosphate, etc.; Baylor et al., Vaccine, 20:S18, 2002), gel-type adjuvants (e.g., calcium phosphate, etc.); microbial adjuvants (e.g., immunomodulatory DNA sequences that include CpG motifs; endotoxins such as monophosphoryl lipid A (Ribi et al., 1986, Immunology and Immunopharmacology of bacterial endotoxins, Plenum Publ. Corp., NY, p 407, 1986); exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500, 161), Q57, saponins (e.g., QS21, Ghochikyan et al., Vaccine, 24:2275, 2006), squalene, tetrachlorodecaoxide, CPG 7909 (Cooper et al., Vaccine, 22:3136, 2004), poly[di(carboxylatophenoxy)phosphazene] (PCCP; Payne et al., Vaccine, 16:92, 1998), interferon-γ (Cao et al., Vaccine, 10:238, 1992), block copolymer P1205 (CRL1005; Katz et al., Vaccine, 18:2177, 2000), interleukin-2 (IL-2; Mbwuike et al., Vaccine, 8:347, 1990), polymethyl methacrylate (PMMA; Kreuter et al., J. Pharm. Sci., 70:367, 1981), etc.

In some embodiments, the present invention provides for vaccines and the administration of these vaccines to a human subject. In certain embodiments, vaccines are compositions comprising one or more of the following: (1) inactivated virus, (2) live attenuated influenza virus, for example, replication-defective virus, (3) provided HA polypeptides or fragments thereof, binding (including detecting and competing) agents, nucleic acids, expression systems, cells or organisms as described herein.

In some embodiments, the present invention provides inactivated flu vaccines. In certain embodiments, inactivated flu vaccines comprise one of three types of antigen preparation: inactivated whole virus, sub-virions where purified virus particles are disrupted with detergents or other reagents to solubilize the lipid envelope ("split" vaccine) or purified HA polypeptide ("subunit" vaccine). In certain embodiments, virus can be inactivated by treatment with formaldehyde, beta-propiolactone, ether, ether with detergent (such as Tween-80), cetyl trimethyl ammonium bromide (CTAB) and Triton N101, sodium deoxycholate and tri(n-butyl) phosphate. Inactivation can occur after or prior to clarification of allantoic fluid (from virus produced in eggs); the virions are isolated and purified by centrifugation (Nicholson et al., eds., *Textbook of Influenza*, Blackwell Science, Malden, M A, 1998). To assess the potency of the vaccine, the single radial immunodiffusion (SRD) test can be used (Schild et al., *Bull. World Health Organ.*, 52:43-50 & 223-31, 1975; Mostow et al., *J. Clin. Microbiol.*, 2:531, 1975).

The present invention also provides live, attenuated flu vaccines, and methods for attenuation are well known in the art. In certain embodiments, attenuation is achieved through the use of reverse genetics, such as site-directed mutagenesis.

In some embodiments, influenza virus for use in vaccines is grown in eggs, for example, in embryonated hen eggs, in which case the harvested material is allantoic fluid. Alternatively or additionally, influenza virus may be derived from any method using tissue culture to grow the virus. Suitable cell substrates for growing the virus include, for example, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus (including upper airway epithelial cells) for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

In some embodiments, provided vaccine compositions do not include adjuvants (e.g., provided compositions are essentially free of adjuvants). In some embodiments, provided vaccine compositions do not include an alum adjuvant (e.g., provided compositions are essentially free of alum). In some embodiments, provided vaccine compositions include a pharmaceutically acceptable carrier.

In some embodiments, vaccine compositions are formulated or otherwise designed or prepared for administration prior to symptoms, and/or to exposure. It will be appreciated by those skilled in the art, however, that in many embodiments vaccine compositions may alternatively or additionally be administered after exposure, infection, and/or development of symptoms.

In some embodiments, prophylactic applications may include administering vaccines. In some embodiments, vaccination is tailored to the individual patient. For example, as described below, serum may be collected from a patient and tested for presence of influenza, and in some embodiments for one or more particular influenza subtypes. In some embodiments, appropriate recipients of provided vaccines are individuals suffering from or susceptible to infection with one or more influenza subtypes bound and/or neutralized by a provided antibody.

Pharmaceutical Compositions

The present invention provides a variety of compositions that comprise or otherwise deliver HA polypeptides or fragments thereof, binding agents, including detecting and competing agents and/or related entities in accordance with the invention. For example, in some embodiments, binding agent polypeptide(s), nucleic acids encoding such polypeptides, characteristic or biologically active fragments of such polypeptides or nucleic acids, antibodies that bind to and/or compete with such polypeptides or fragments, small molecules that interact with or compete with such polypeptides or with glycans that bind to them, etc. are included in pharmaceutical compositions in accordance with the invention.

In some embodiments the present invention provides at least one binding agent and at least one pharmaceutically acceptable excipient. Such pharmaceutical compositions may optionally comprise and/or be administered in combination with one or more additional therapeutically active substances. In some embodiments, provided pharmaceutical compositions are useful in medicine. In some embodiments, provided pharmaceutical compositions are useful as prophylactic agents (i.e., vaccines) in the treatment or prevention of influenza infection or of negative ramifications and/or symptoms associated or correlated with influenza infection. In some embodiments, provided pharmaceutical compositions are useful in therapeutic applications, for example in individuals suffering from or susceptible to influenza infection. In some embodiments, a subject is considered to be suffering from an influenza infection if the subject is displaying one or more symptoms commonly associated with influenza infection. In some embodiments, the subject is known or believed to have been exposed to the influenza virus. In some embodiments, a subject is considered to be susceptible to an influenza infection if the subject is known or believed to have been exposed to the influenza virus. In some embodiments, a subject is known or believed to have been exposed to the influenza virus if the subject has been in contact with other individuals known or suspected to have been infected with the influenza virus and/or if the subject is or has been present in a location in which influenza infection is known or thought to be prevalent. In some embodiments, a therapeutically effective amount of pharmaceutical composition is administered to a subject suffering from or susceptible to influenza infection. In some embodiments, pharmaceutical compositions are formulated for administration to humans.

In some embodiments, subjects suffering from or susceptible to influenza infection are tested for antibodies to provided binding agents prior to, during, or after administration of provided therapeutic compositions. In some embodiments, subjects having such antibodies are not administered therapeutic compositions comprising provided binding agents. In some embodiments, an appropriate dose of pharmaceutical composition and/or binding agent is selected based on detection (or lack thereof) of such antibodies.

In some embodiments, selection of a particular subject for treatment, particular binding agent or composition for administration, and/or particular dose or regimen for administration, is memorialized, for example in a written, printed, or electronic storage form.

Provided therapeutic compositions may be administered prior to or after development of one or more symptoms of influenza infection.

In some embodiments, pharmaceutical compositions provided here may be provided in a sterile injectable form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g. lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservative.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer).

Liquid dosage forms and/or reconstituted solutions may comprise particulate matter and/or discoloration prior to administration. In some embodiments, a solution should not be used if discolored or cloudy and/or if particulate matter remains after filtration.

Formulations of the pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutical composition will include a therapeutic agent that is encapsulated, trapped, or bound within a lipid vesicle, a bioavailable and/or biocompatible and/or biodegradable matrix, or other microparticle.

In some embodiments, provided compositions further comprise one or more adjuvants. Any adjuvant may be used in accordance with the present invention. A large number of adjuvants are known; a useful compendium of many such compounds is prepared by the National Institutes of Health and can be found on the internet (niaid.nih.gov/daids/vaccine/pdf/compendium.pdf). See also Allison (1998, Dev. Biol. Stand., 92:3-11), Unkeless et al. (1998, Annu Rev. Immunol., 6:251-281), and Phillips et al. (1992, Vaccine, 10:151-158). Hundreds of different adjuvants are known in the art and could be employed in the practice of the present invention.

Pharmaceutical compositions may be administered using any amount and any route of administration effective for treatment and/or vaccination. The exact amount required will vary from subject to subject, depending on the species, age, and general condition of the subject, the severity of the infection, the particular composition, its mode of administration, its mode of activity, and the like. Pharmaceutical compositions are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and/or vaccinated and the severity of the disorder; the activity of the specific vaccine composition employed; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed; and like factors, well known in the medical arts.

Pharmaceutical compositions of the present invention may be administered by any route. In some embodiments, therapeutic compositions of the present invention are administered by a variety of routes, including oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol, and/or through a portal vein catheter.

At present the oral or nasal spray or aerosol route (e.g., by inhalation) is most commonly used to deliver therapeutic agents directly to the lungs and respiratory system. However, the invention encompasses the delivery of the provided pharmaceutical composition by any appropriate route taking into consideration likely advances in the sciences of drug delivery.

In some embodiments, preparations for inhaled or aerosol delivery comprise a plurality of particles. In some embodiments, such preparations have a mean particle size of 4, 5, 6, 7, 8, 9, 10, 11, 12, or 13 microns. In some embodiments, preparations for inhaled or aerosol delivery are formulated as a dry powder. In some embodiments, preparations for inhaled or aerosol delivery are formulated as a wet powder, for example through inclusion of a wetting agent. in some embodiments, the wetting agent is selected from the group consisting of water, saline, or other liquid of physiological pH.

In some embodiments, provided compositions are administered as drops to the nasal or buccal cavity. In some embodiments, a dose may comprise a plurality of drops (e.g., 1-100, 1-50, 1-20, 1-10, 1-5, etc.)

In some embodiments, provided compositions are administered using a device that delivers a metered dosage of composition (e.g., of binding agent).

Suitable devices for use in delivering intradermal therapeutic compositions described herein include short needle devices such as those described in U.S. Pat. Nos. 4,886,499, 5,190,521, 5,328,483, 5,527,288, 4,270,537, 5,015,235, 5,141,496, 5,417,662. Intradermal compositions may also be administered by devices which limit the effective penetration length of a needle into the skin, such as those described in WO99/34850, and functional equivalents thereof. Also suitable are jet injection devices which deliver liquid vaccines to the dermis via a liquid jet injector or via a needle which pierces the stratum corneum and produces a jet which reaches the dermis. Jet injection devices are described for example in U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Also suitable are ballistic powder/particle delivery devices which use compressed gas to accelerate vaccine in powder form through the outer layers of the skin to the dermis. Additionally, conventional syringes may be used in the classical mantoux method of intradermal administration.

General considerations in the formulation and manufacture of pharmaceutical agents may be found, for example, in *Remington's Pharmaceutical Sciences,* 19*th* ed., Mack Publishing Co., Easton, Pa., 1995.

Provided pharmaceutical compositions may be administered in any dose appropriate to achieve a desired outcome. In some embodiments, the desired outcome is reduction in intensity, severity, and/or frequency, and/or delay of onset of one or more symptoms of infection (e.g., influenza infection).

Pharmaceutical compositions in accordance with the present invention may be administered either alone or in combination with one or more other therapeutic agents. By "in combination with," it is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In will be appreciated that therapeutically active agents utilized in combination may be administered together in a single composition or administered separately in different compositions. In general, each agent will be administered at a dose and/or on a time schedule determined for that agent.

In some embodiments, provided pharmaceutical compositions are formulated to reduce immunogenicity of included agents. For example, in some embodiments, an included active agent is associated with (e.g., bound to) an agent, such as polyethylene glycol and/or carboxymethyl cellulose, that masks its immunogenicity. In some embodiments, an included active agent has additional glycosylation that reduces immunogenicity.

In some embodiments, the present invention provides kits for administration of provided pharmaceutical compositions. For example, in some embodiments, the invention provides a kit comprising at least one dose of a binding agent. In some embodiments, the invention provides a kit comprising an initial unit dose and a subsequent unit dose of a binding agent. In some such embodiments, the initial unit dose is greater than the subsequent unit dose or wherein the two doses are equal.

In some embodiments, provided kits (particularly those for administration of provided compositions) comprise at least one component of a delivery device, e.g., an inhaler. In some such embodiments, the invention provides a kit comprising at least one component of a delivery device, e.g., an inhaler and a dose of an of a binding agent.

Combination Therapy

Pharmaceutical compositions of the present invention may be administered in combination with one or more other therapeutic agents including, but not limited to, vaccines and/or antibodies. By "in combination with," it is not intended to imply that the agents must be administered at the same time or formulated for delivery together, although these methods of delivery are within the scope of the invention. In general, each agent will be administered at a dose and on a time schedule determined for that agent. Additionally, the invention encompasses the delivery of the pharmaceutical compositions in combination with agents that may improve their bioavailability, reduce or modify their metabolism, inhibit their excretion, or modify their distribution within the body. Although the pharmaceutical compositions of the present invention can be used for treatment of any subject (e.g., any animal) in need thereof, they are most preferably used in the treatment of humans.

In some embodiments pharmaceutical compositions of the present invention may be administered in combination with one or more other pharmaceutical agents (e.g., anti-influenza vaccine, anti-viral agent, pain relievers, anti-inflammatories, antibiotics, steroidal agents, antibodies, sialydase, etc). In some embodiments, pharmaceutical compositions of the present invention and/or agents (e.g., antibodies) may be administered in combination with an adjuvant.

In some embodiments, pharmaceutical compositions of the present invention are administered in combination with one or more anti-viral agents. In some embodiments, such anti-viral agents include, but are not limited to, acyclovir, ribavirin, amantadine, remantidine, zanamivir (RELENZA®), oseltamivir (TAMIFLU®), amantadine, rimantadine and/or combinations thereof.

In some embodiments, pharmaceutical compositions of the present invention are administered in combination one or more vaccines. In some embodiments, the vaccine is an anti-viral vaccine. In some embodiments, the vaccine is an anti-influenza vaccine. In some embodiments, the anti-influenza vaccine is to treat seasonal influenza (e.g., commonly referred to as the "flu"). In some embodiments, the anti-influenza vaccine is the flu shot and/or FluMist. In some embodiments, the anti-influenza vaccine is targeted to a specific combination of one or more HA polypeptides (e.g., H1, H2, H3, H4, H5, H6, H7, H8, H9, H10, H11, H12, H13, H14, H15, or H16 polypeptides). In some embodiments, the anti-influenza vaccine is specific for one or more combinations of H1N1, H2N2, H3N2, H5N1, H7N7, H1N2, H9N2, H7N2, H7N3, or H10N7 viruses. In some embodiments, the anti-influenza vaccine is specific to H1N1 viruses. In some embodiments, the anti-influenza vaccine is specific to H3N2 viruses. In some embodiments, the anti-influenza vaccine is specific to H1N1 and H3N2 viruses.

In some embodiments pharmaceutical compositions may be administered in combination with one or more other pharmaceutical agents used to treat the symptoms associated with influenza virus infection. In some embodiments, pharmaceutical agents used to treat the symptoms associated with influenza infection are pain relievers, anti-inflammatories, antibiotics and/or combinations thereof. In some embodiments, pharmaceutical agents used to treat the inflammation symptoms associated with influenza infection is selected from the group consisting of NSAID, Steroid, Glucocorticoid, and/or combinations thereof. In some embodiments, NSAID pharmaceutical agents used to treat the influenza symptoms associated with influenza infection is selected from the group consisting of acetaminophen, ibuprofen, aspirin, naproxen and/or combinations thereof.

Diagnostics/Detection Applications

The present invention provides a variety of compositions useful in the detection, identification, and/or characterization of influenza viruses and/or infections. In some embodiments, the invention provides compositions comprising binding agents, which compositions can be contacted with clinical, pathological, or environmental samples in order to assess, for example, presence or level of a particular influenza strain, extent or progress of an influenza infection, etc.

In some embodiments, binding agents in accordance with the invention are used for diagnostic applications. For example, by virtue of the variety of binding profiles of binding agents, diagnostic assays may be employed which will detect a strain of pandemic HA polypeptide. In some embodiments, diagnostic assays using binding profiles of provided binding agents will detect provided HA polypeptide with particular glycan binding and/or infectivity characteristics.

Presented herein, among other things, are methods for defining and understanding the requirements for an HA polypeptide (e.g., H7 HA) to switch its binding preference to human receptors in a manner characteristic of human adapted HAs in the context of the changes in the molecular environment of the receptor binding site. In some embodiments, a combination of structural and inter-residue interaction network analyses are combined to define mutations in the receptor binding site of H7 HA (e.g., H7N9) that can switch its glycan receptor binding preference to human receptors in a manner similar to pandemic H3 HA strains.

In some embodiments, the present invention provides methods of monitoring influenza in a sample. In some embodiments, the present invention provides methods of monitoring a population for human infective and/or human transmissible influenza. In some embodiments, methods of determining pandemic risk from a strain of influenza are provided. In some embodiments, a method of monitoring influenza includes the steps of obtaining a sample from a source suspected to contain influenza, contacting the sample with one or more agents that specifically binds to an HA (e.g., H7 HA) polypeptide, detecting the binding of the agent with the sample, so that the presence and/or level of HA polypeptide in the sample is determined. In some embodiments, binding of the one or more agents to the sample indicates the presence of a human infective HA (e.g., H7 HA) polypeptide. In some embodiments, binding of the one or more agents to the sample indicates the absence of a human infective HA (e.g., H7 HA) polypeptide. In some embodiments, obtaining, contacting and detecting steps are repeated at least once after a period of time has elapsed since the first obtaining, contacting and detecting steps were completed. In some embodiments, methods of monitoring influenza further comprise contacting the sample from the source with one or more agents that specifically bind to an HA that does not infect humans.

In some embodiment, methods according to the present invention may be used to analyze any of a variety of sample sources including environmental sources, laboratory sources, human patient sources, or animal sources, for example. In some embodiments, analysis of one or more samples occurs at least twice. In some embodiments, each analysis is separated by a period of time to allow for longitudinal monitoring of a subject or population, for example. In some embodiments, the period of time may be: 1 hour, 12 hours, 1 day, 2 days, 3 days, 4 days, 5 days, 6 days, 1 week, 2 weeks, 3 weeks, 1 month, 2 months, 3 months, 4 months, 5 months, 6 months, or 1 year.

In some embodiments, the present invention provides methods for identifying human-adapted HA polypeptide variants. In some embodiments, a method for identifying human-adapted H7 HA polypeptide variants includes steps of providing at least one test H7 HA polypeptide and determining in a binding assay one or more of whether the test polypeptide shows: at least comparable human binding under comparable conditions with that observed for a provided human-adapted H7 HA polypeptide, or increased human binding under comparable conditions as compared with that of a reference non-human-adapted HA polypeptide; or at least comparable human binding under comparable conditions with that observed for a known human-adapted reference HA polypeptide. In some embodiments, a method for identifying human-adapted H7 HA polypeptide variants includes steps of providing at least one test H7 HA polypeptide whose amino acid sequence includes a sequence element that: is at least ten amino acids in length; is substantially identical to corresponding portion of a reference H7 HA polypeptide, which portion includes one or more of amino acid positions 122, 131, 135, 137, 145, 156, 158, 159, 174, 186, 189, 190, 192, 193, 196, 202, 222, 224, 225, 227, 228; and differs from that of the portion in at least one residue so that the sequence element is not more than 90% identical to the portion; and determining in a binding assay one or more of whether the test polypeptide shows: increased human binding under comparable conditions as compared with that of a reference non-human-adapted HA polypeptide; or at least comparable human binding under comparable conditions with that observed for a known human-adapted reference HA polypeptide. In some embodiments, the binding assay comprises contacting the HA polypeptide with an HA receptor or HA-binding component thereof under conditions that permit assessment of a binding parameter selected from the group consisting of: association constant, dissociation constant, stability, affinity, and combinations thereof.

For diagnostic purposes, binding agents may be used in a wide variety of formats for detecting HA protein. For diagnostic purposes, a wide variety of labels may be employed, which for the most part have been mentioned previously. These include, but are not limited to, fluorophores, chemiluminescent moieties, radioisotopes, enzymes, particles (e.g., colloidal carbon particles, gold particles, latex particles, etc.) ligands for which there are high affinity receptors, and prolabels, which can be activated to provide a detectable signal.

In some embodiments, a surface is coated with a protein, which can bind to influenza antigens as free protein (e.g., circulating proteins) or as part of an intact or partially intact virion. One may use binding agents of the invention to detect presence of provided HA polypeptide.

Where the sample is assayed for influenza HA protein, detection employs labeled subject antibodies, the selection depending upon whether one is interested in genotyping or detection of HA protein. After washing away non-specifically bound antibody, the presence of labeled antibodies is determined by detecting the presence of the label in accordance with known techniques. Alternatively or additionally, where the subject antibodies are bound to a surface, a labeled lectin for HA may be employed to detect the presence of HA protein.

Binding agents in accordance with the invention can be used to measure the reactivity of other binding agents, including antibodies in sera, monoclonal antibodies, antibodies expressed as a result of genetic engineering, etc. In some embodiments, intact virions are used. In some embodiments, conformationally conserved envelope proteins are used.

Labeled subject antibodies may be used in assaying for the presence of influenza from biopsy material. Labeled antibody may be incubated with immobilized biopsy material, such as a lung slice, with a solution of one or more of the subject labeled antibodies. After washing away non-specifically bound antibodies, the presence of the antibodies bound to the cells of the biopsied tissue may be detected in accordance with the nature of the label.

In some embodiments, influenza binding agents in accordance with the invention can be used to identify influenza receptors. Those skilled in the art will appreciate the multitude of ways this can be accomplished (Sambrook J., Fritsch E. and Maniatis T. Molecular Cloning: A Laboratory Manual. Cold Spring Harbor Press, Cold Spring Harbor, N.Y., 1989; and Ausubel et al., eds., Current Protocols in Molecular Biology, 1987). Typically, protein and peptide receptors can be identified by determining whether a binding agent able to bind HA can inhibit attachment of influenza virions to a cell susceptible to influenza infection. Thus, receptors for influenza HA proteins and peptides can be identified in this manner. A susceptible cell can be incubated in the presence of influenza and anti-influenza HA binding agent, and a cell-binding assay can be utilized to determine whether attachment is decreased in the presence of the binding agent.

Cells expressing putative receptors for influenza and/or libraries of putative receptors for influenza may be screened for their abilities to bind influenza. For example, cells expressing a putative influenza receptor (e.g., a receptor for influenza HA) can be contacted with an influenza protein or peptide in the presence of an antibody for a time and under conditions sufficient to allow binding of the influenza protein or peptide to putative receptor on the surface of the cell. Alternatively or additionally, influenza proteins, peptides, or virions can be pre-incubated with antibody prior to contacting the putative receptor on the cell surface. Binding can be detected by any means known in the art, e.g., flow cytometry etc. (see Ausubel et al. or Sambrook et al., supra). A decrease in binding to the surface of the cell in the presence of antibody compared to binding in the absence of the cell in the absence of the antibody indicates the identification of an influenza receptor.

In some embodiments, methods of identifying influenza receptors (e.g., such as HA receptors) include the use of solid supports, such as beads, columns, and the like. For example, receptors for influenza proteins and peptides (e.g., HA proteins and/or fragments thereof) and/or influenza virions can be identified by attaching an influenza antibody to a solid support and then contacting the antibody with an influenza protein or peptide for a time sufficient for the influenza protein or peptide to bind to the antibody. This provides an influenza protein ligand for putative influenza receptors that can be contacted with the antibody:ligand complex on the solid support for a time and under conditions sufficient to allow binding of a receptor to the influenza protein or peptide. Proteins can be expressed from a library or provided as a cell extract or purified protein preparation from natural or recombinant cells. Once specific binding complexes between the influenza protein peptide are formed, unbound influenza proteins or peptides, e.g., library proteins or peptide that did not bind specifically to the influenza proteins or peptides, are removed, e.g., by standard washing steps. Bound proteins are then eluted and identified, e.g., by gel electrophoresis.

Kits

The invention provides a variety of kits for conveniently and/or effectively carrying out methods in accordance with the present invention. Kits typically comprise one or more influenza binding agents in accordance with the invention. In some embodiments, kits comprise a collection of different influenza binding agents to be used for different purposes (e.g., diagnostics, treatment, and/or prophylaxis). Typically kits will comprise sufficient amounts of influenza binding agents to allow a user to perform multiple administrations to a subject(s) and/or to perform multiple experiments. In some embodiments, kits are supplied with or include one or more influenza antibodies that have been specified by the purchaser.

In some embodiments, the present invention provides a diagnostic kit for determining pandemic risk in a strain of influenza, wherein the kit comprises at least one antibody agent that binds to a human-adapted HA polypeptide. In some embodiments, the present invention provides a diagnostic kit for determining pandemic risk in a H7 strain of influenza, wherein the kit comprises at least one antibody agent that binds to a human-adapted H7 HA polypeptide provided herein.

In certain embodiments, kits for use in accordance with the present invention may include one or more reference samples; instructions (e.g., for processing samples, for performing tests, for interpreting results, for solubilizing influenza binding agents); buffers; and/or other reagents necessary for performing tests. In certain embodiments kits can comprise panels of antibodies. Other components of kits may include cells, cell culture media, tissue, and/or tissue culture media.

Kits may comprise instructions for use. For example, instructions may inform the user of the proper procedure by which to prepare a pharmaceutical composition comprising influenza binding agents and/or the proper procedure for administering pharmaceutical compositions to a subject.

In some embodiments, kits include a number of unit dosages of a pharmaceutical composition comprising influenza binding agents. A memory aid may be provided, for example in the form of numbers, letters, and/or other markings and/or with a calendar insert, designating the days/times in the treatment schedule in which dosages can be administered. Placebo dosages, and/or calcium dietary supplements, either in a form similar to or distinct from the dosages of the pharmaceutical compositions, may be included to provide a kit in which a dosage is taken every day.

Kits may comprise one or more vessels or containers so that certain of the individual components or reagents may be separately housed. Kits may comprise a means for enclosing the individual containers in relatively close confinement for commercial sale, e.g., a plastic box, in which instructions, packaging materials such as Styrofoam, etc., may be enclosed.

In some embodiments, kits are used in the treatment, diagnosis, and/or prophylaxis of a subject suffering from and/or susceptible to influenza. In some embodiments, provided kits comprise at least one component of a delivery device, e.g., a syringe, needle, applicator, inhaler, etc. In some such embodiments, the invention provides a kit comprising at least one component of a delivery device, e.g., an inhaler and/or syringe and a dose of an of an agent. In some embodiments, kits comprise (i) at least one influenza binding agent; (ii) a syringe, needle, applicator, inhaler, etc. for administration of the at least one influenza binding agent to a subject; and (iii) instructions for use.

In some embodiments, kits are used in the treatment, diagnosis, and/or prophylaxis of a subject suffering from and/or susceptible to influenza. In some embodiments, such kits comprise (i) at least one influenza binding agent (i.e., a pan-influenza antibody) provided as a lyophilized powder; and (ii) a diluent for reconstituting the lyophilized powder. Such kits may optionally comprise a syringe, needle, applicator, etc. for administration of the at least one influenza binding agent to a subject; and/or instructions for use.

The present invention provides kits containing reagents for the generation of vaccines comprising at least one influenza binding agent. In some embodiments, such kits may include (i) cells expressing influenza binding agents, characteristic portions thereof, and/or biologically active portions thereof; (ii) media for growing the cells; and (iii) columns, resin, buffers, tubes, and other tools useful for antibody purification. In some embodiments, such kits may include (i) plasmids containing nucleotides encoding influenza binding agents, characteristic portions thereof, and/or biologically active portions thereof; (ii) cells capable of being transformed with the plasmids, such as mammalian cell lines, including but not limited to, Vero and MDCK cell lines; (iii) media for growing the cells; (iv) expression plasmids containing no nucleotides encoding influenza binding agents as negative controls; (v) columns, resin, buffers, tubes, and other tools useful for antibody purification; and (vi) instructions for use.

In some embodiments, kits are used to detect the presence of influenza in one or more samples. Such samples may be pathological samples, including, but not limited to, blood, serum/plasma, peripheral blood mononuclear cells/peripheral blood lymphocytes (PBMC/PBL), sputum, urine, feces, throat swabs, dermal lesion swabs, cerebrospinal fluids, cervical smears, pus samples, food matrices, and tissues from various parts of the body such as brain, spleen, and liver. Such samples may be environmental samples, including, but not limited to, soil, water, and flora. Other samples that have not been listed may also be applicable. In some embodiments, such kits comprise (i) at least one influenza binding agent; (ii) a sample known to contain influenza, as a positive control; and (iii) a sample known not to contain influenza, as a negative control; and (iv) instructions for use.

In some embodiments, kits are used to neutralize influenza in one or more samples. Such kits may provide materials needed to treat an influenza-containing sample with at least one influenza binding agent and to test the ability of the treated sample to infect cultured cells relative to untreated sample. Such kits may include (i) at least one influenza binding agent; (ii) cells capable of being cultured and infected with influenza; (iii) binding agent that is incapable of binding to and neutralizing influenza, as a negative control; (iv) a binding agent that is capable of binding to and neutralizing influenza, as a positive control; (v) a sample known not to contain influenza, as a negative control; (vi) a sample known to contain influenza, as a positive control; and (vii) instructions for use.

EXAMPLES

The present invention will be better understood in connection with the following Examples. However, it should be understood that these examples are for illustrative purposes only and are not meant to limit the scope of the invention. Various changes and modifications to the disclosed embodiments will be apparent to those skilled in the art and such changes and modifications including, without limitation, those relating to the formulations and/or methods of the invention may be made without departing from the spirit of the invention and the scope of the appended claims.

Example 1: Molecular and Structural Characterization of H7N9 Binding to Glycans on HA Receptors Studies in this Example illustrate the development of a homology-based structural model to understand glycan receptor binding properties of H7N9 HA. Analysis of the receptor-binding site (RBS) of an H7N9 HA by comparison with the RBS of a human-adapted H3 HA virus in this Example, assists in outlining the structural similarities and differences between the H7N9 HA and HAs of human-adapted viruses.

Given that H7N9 is a newly emerged subtype, there are a limited set of HA sequences available, and this restricts a comprehensive analysis of sequence evolution of the RBS of H7N9. Therefore, in this Example, a representative human isolate of H7N9 was chosen (i.e., A/Anhui/1/2013; Anh13) in order to understand receptor binding properties of H7N9. Anh13 was also chosen as it shares substantial sequence identity with many other reported strains of H7N9, including A/Shanghai/2/2013 and A/Hangzhou/1/2013. Additionally, while there are changes in the HA sequence of Anh13 compared to the HA sequence of other reported H7N9 strains, including A/Shanghai/2/2013, the HA of Anh13 contains an important Q226L mutation, which has been reported to be important for altered receptor specificity for group 2 viruses, including H3 and H7. Anh13 (and related viruses) are also therefore more likely than viruses such as A/Shanghai/2/2013 to be of concern from the standpoint of altered receptor specificity and hence human transmissibility.

Figure 1:
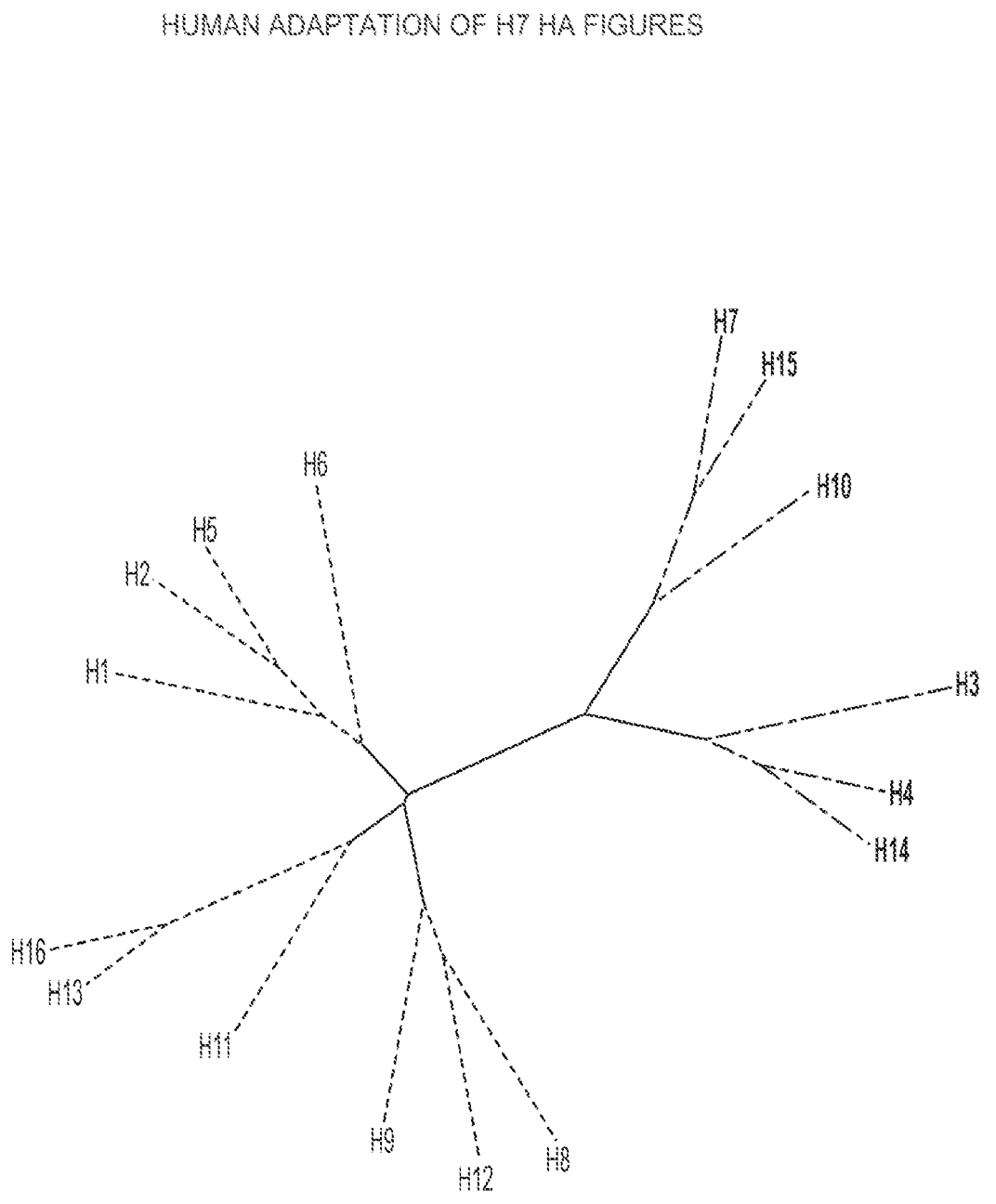

Since there is no crystallography-based structural data for Anh13 HA, the work in this Example discusses the use of homology-based structural model of Anh13 HA centered on comparison of its RBS with H3 HA (which is phylogenetically closest to H7 HA; as shown in FIG. 1).

A framework that incorporates descriptors of the structural topology of the human glycan receptor as well as inter-amino acid interaction networks within the RBS to define the molecular features of the RBS of H5 HA for high avidity/specificity binding to human glycan receptors has been defined (Chandrasekaran et al. Nat. Biotechnol. 26, 107-113 (2008); Soundararajan et al. Sci Rep 1 (2011)). Thus, in this Example, the molecular features of the RBS of Anh13 were compared with those of H3 HA. The H3 HA used in this study was the A/Aichi/1/68 or Aich 68, a strain from the 1967-68 pandemic, which has been co-crystallized with both avian and human receptors (Lin et al. PNAS 109, 21474-21479 (2012)). More importantly, since Aich68 represented a human-adapted virus, comparison of its HA to that of Anh13 provided an important benchmark to address the question of whether the HA from Anh13 shared structural characteristics with HAs of human-adapted viruses and if not, which structural characteristics were missing.

Structural analysis of both H7 and H3 HAs indicated that the structural topology of the human glycan receptor bound in the RBS of HA was such that it had a clearly defined base region consisting of the terminal Neu5Acα2→6Galβ1→ motif and an extension region consisting of at least a disaccharide→4GlcNAcβ1→3Galβ1→. On the other hand, the topology of the avian receptor bound within the HA RBS was such that majority of the contacts with residues within the RBS involved the terminal Neu5Acα2→3Galβ1→motif in the base region (FIG. 2). The 130- (residues 131-138), 140- (residues 140-145) and 220- (residues 219-228) loops in the RBS made contacts with the disaccharide motif in the base region and thus played an important role in dictating the avian or human receptor binding preference (residue position numbering is based on Aichi68 HA-glycan co-crystal structure PDB ID:2YPG). Additionally, residues within the 190-helix (residues 190-196) and a part of the 150-loop (residues 156-160), if properly positioned, made contacts with the extension region of the human receptor. Taken together, these 4 loops and 1 helix in the RBS that made contact with the base and potentially with the extension region of the human receptor and their network of interactions with spatially proximal residues in the RBS constituted a complete set of molecular features that should be analyzed to understand the receptor binding preference of an HA.

Comparison of these features between Anh13 and Aichi68 HA showed many similarities as well as some important differences (Table 2). First, many of the residues in the 130-loop, 140-loop and 220-loop were similar between the HA of Anh13 and Aichi68. Based on this level of similarity, it was deduced that the network of inter-residue contacts involving these residues were also similar (FIGS. 2A and 2C).

Certain structural differences noted in this analysis included part of the 190-helix and the 150-loop required for contact with the extension region of the human receptor. In the Aich68 HA, the residues interacting with the extension region included Q189, S193, K156 and S159 (FIG. 2C), whereas in H7 HA, these residues included K193, T158, D159 and N160 (FIG. 2B). Furthermore, in the case of the H7 HA, R131 was positioned to make an additional contact with the extension region (FIG. 2B). In addition to the differences in the amino acids at these positions, and also of note, were differences between Aich68 and Anh13 in the inter-residue interaction network governed by the residue at position 228. This position was a Ser in Aichi68 but a Gly in Anh13.

The S228 position in H3 is important for the inter-amino acid network involving S186, T187 and E190, which positions E190 to make contacts with the sialic acid of both avian and human receptors (FIG. 2C). On the other hand G228 in H7 HA does not possess this inter-amino acid network and therefore the network of inter-residue contacts involving E190 in H7 was different from that of H3 HA and instead includes 193 (and its network) and 189 (FIG. 2A).

Extending this analysis, the E190 in H7 HA was positioned to make additional contacts with the extension region instead of the contact with the sialic acid in the base region (FIG. 2B). Therefore, Anh13 H7 HA lacked at least two contacts involving the 190 and 226 HA positions with the Neu5Acα2→3Galβ1→terminal motif as observed in avian-adapted HAs. In the case of human receptor contacts, Anh13 had lower contacts with the base region owing to the absence of the S228 residue. Structural analysis in this Example pointed to the H7N9 HA having a substantially lower binding to avian receptors than typical avian-adapted HAs as well as lower binding to human receptors than the human-adapted H3 HAs. Further, the RBS of H7N9 HA was such that a single G228→S amino acid change would modify the inter-amino acid network in the RBS to position the E190 and S228 residues for optimal contacts with both avian and human receptors.

Example 2: Characterization of Binding of H7N9 HA to Glycan Receptors in the Human Respiratory Tract Studies in this Example characterize binding of the H7N9 HA to physiological glycan receptors in the human respiratory tract.

Figure 3:
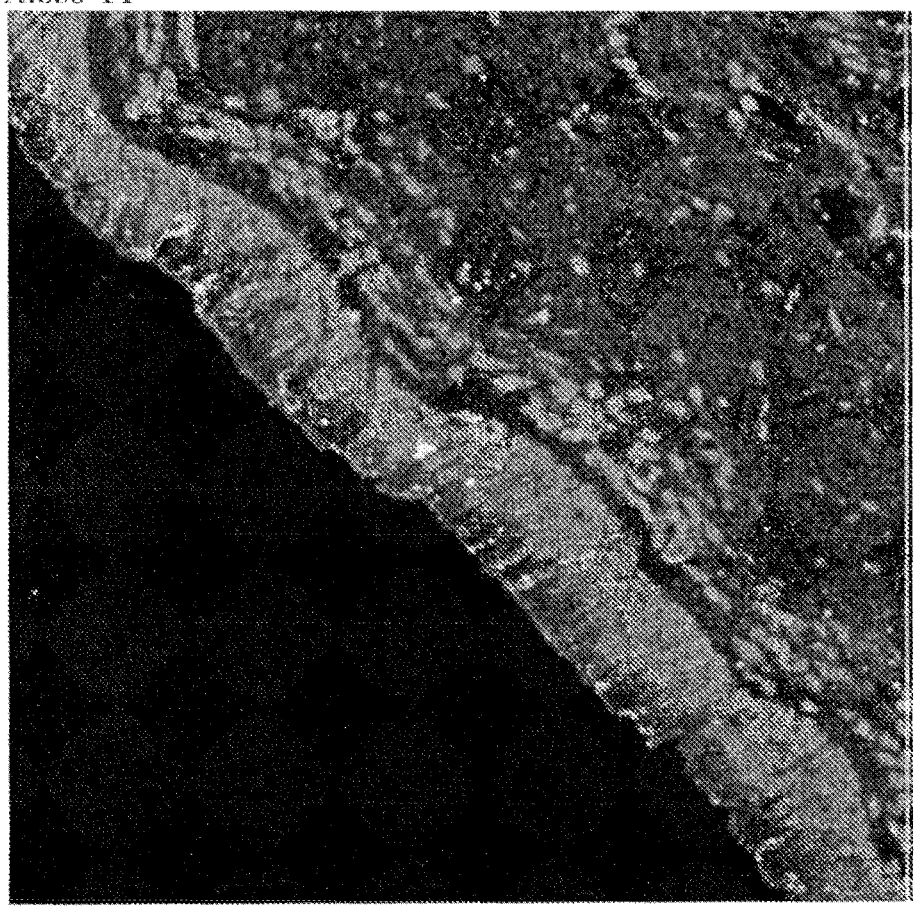
FIG. 3.
Figure 4:
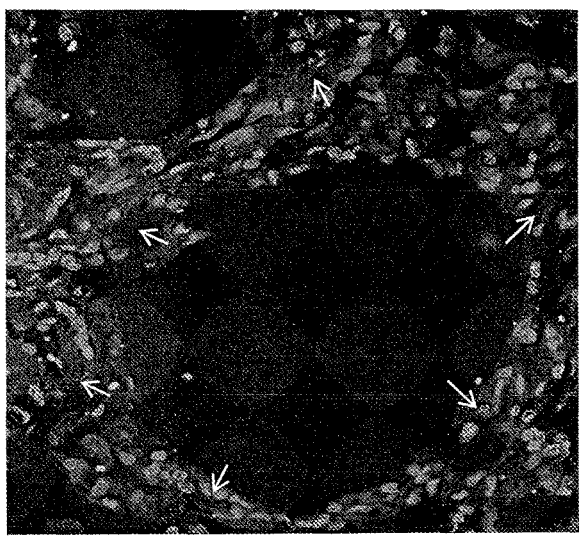
FIG. 4.
Figure 4:
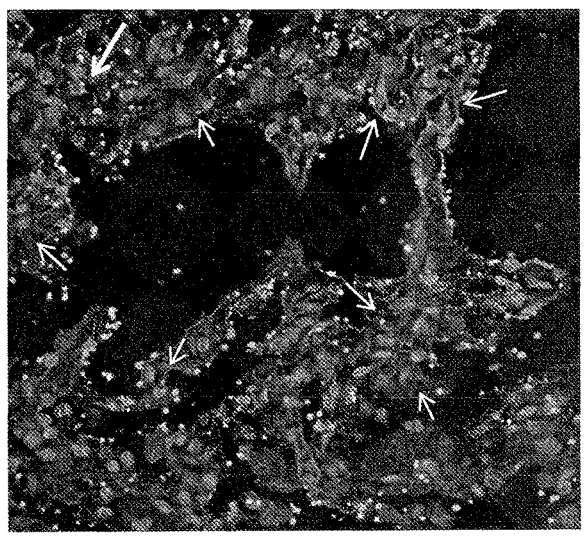

To validate the structural analyses, binding of Anh13 to tissue sections, representative of human respiratory tract, which display the physiologically relevant receptors for influenza A viruses was analyzed (FIG. 3) Anh13 stained the apical surface and submucosal region of the human trachea, which express glycans known to be receptors of human adapted viruses (Jayaraman et al. PLoS ONE in press (2012); Shinya et al. Nature 440, 435-436 (2006)). However, the intensity and the extent of tracheal apical surface staining by Anh13 was substantially lower than what is typically observed for human-adapted HAs (FIG. 3). Furthermore, Anh13 HA also showed minimal binding to deep lung alveolar section—a region that is extensively stained by avian-adapted HAs (FIG. 4A).

Figure 5:
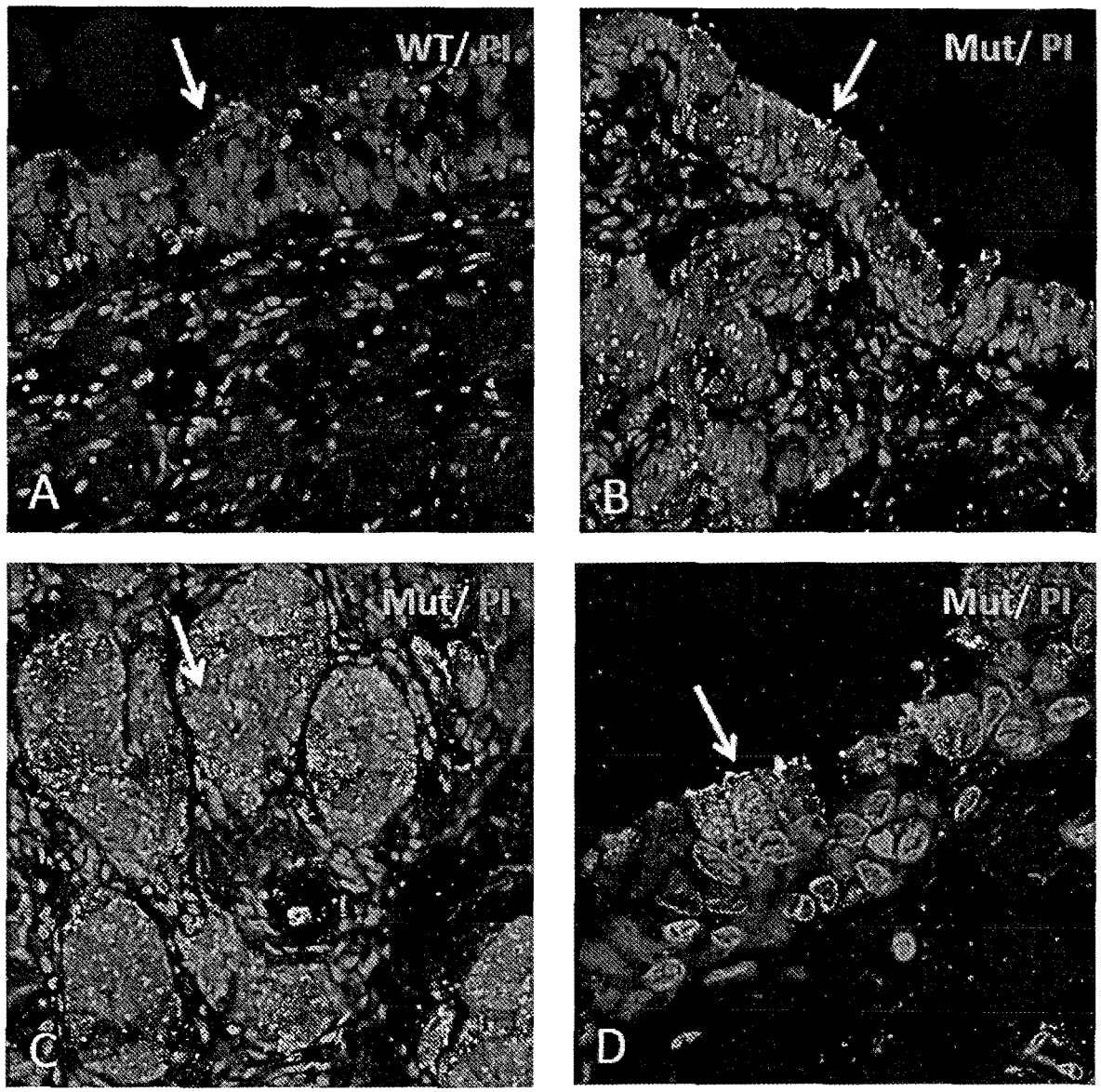
FIG. 5.
Figure 6:
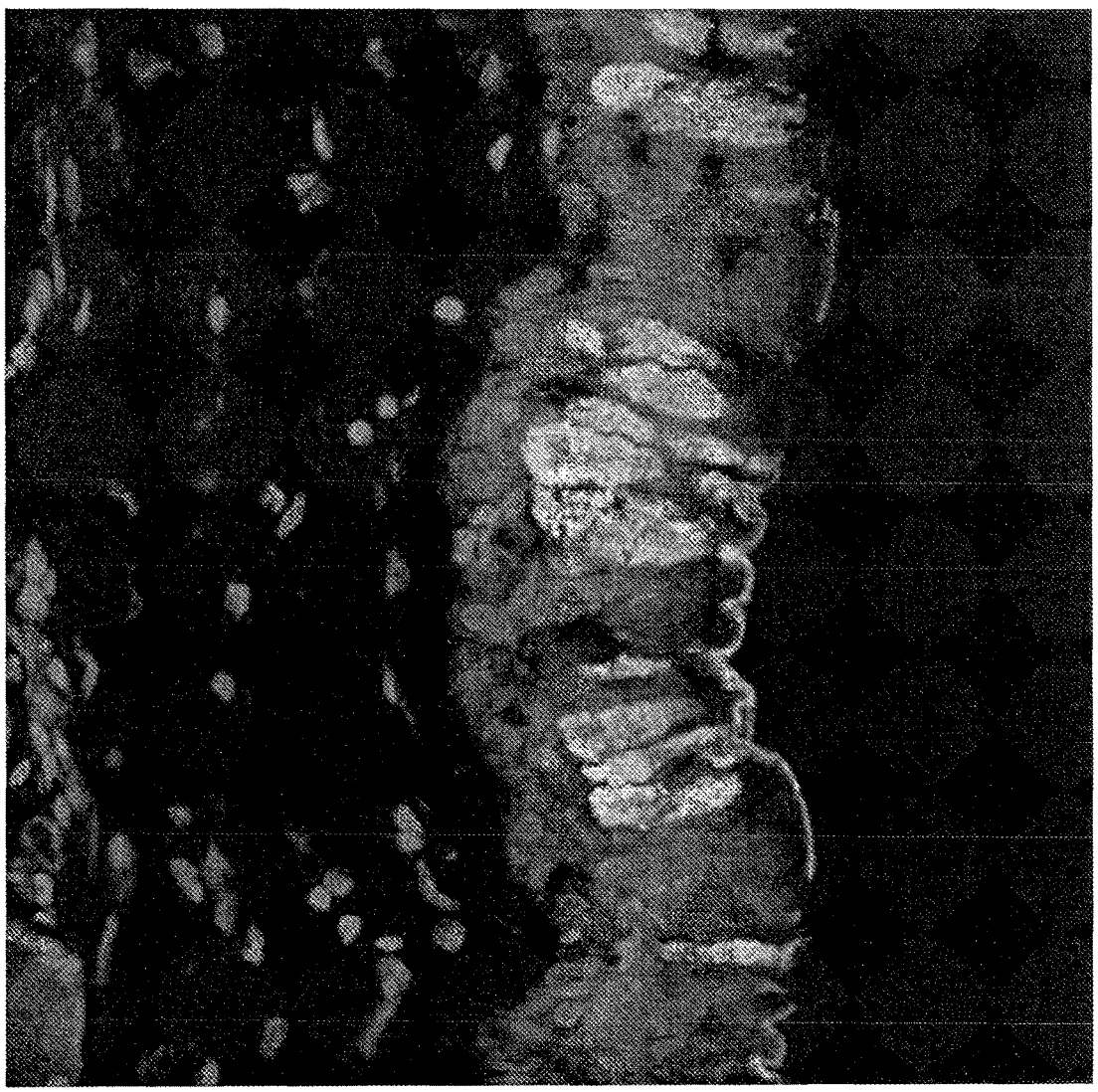
FIG. 6.

In contrast, the G228→S mutant Anh13 HA showed a dramatic and significant increase in the extent and intensity of staining to apical surface of the tracheal section including extensive staining of non-ciliated goblet cells in a fashion similar to that of other human-adapted HAs and Sambucus nigra agglutinin I (SNA I) (FIG. 5 and FIG. 6). Interestingly the G228→S mutation also substantially increased its binding to the alveolar sections (FIG. 4B). These results were consistent with the structural analyses of the RBS features of H7N9 HA discussed above.

Example 3: Characterization of Antigenic Properties of H7N9 HA

Analysis in this Example illustrates that a subset of H7N9 HA sequences demarcating coevolving amino acids are in the antigenic regions of H7 HA. Specifically, studies in this Example show that novel mutations on H7 HA can impact the effectiveness of the current WHO recommended prepandemic H7 vaccines.

In the context of H7N9 evolution, two mutations 174S and 226L can be unique to the novel H7N9 HA sequences. The residue at 226, as noted above, is a determinant of the receptor-binding specificity of H7 HA, with human viruses favoring L/I at this position, and avian viruses favoring Q at this position. These two positions are also part of a larger cluster of coevolving positions (122A, 174S, 186V, 202V, 226L), all within the 50-230 HA region, which demarcates the novel virus from its previous H7 ancestors (see, Methods section below). The above observations indicated that the novel H7N9 HA has evolved to be distinct from its predecessors.

Figure 7:
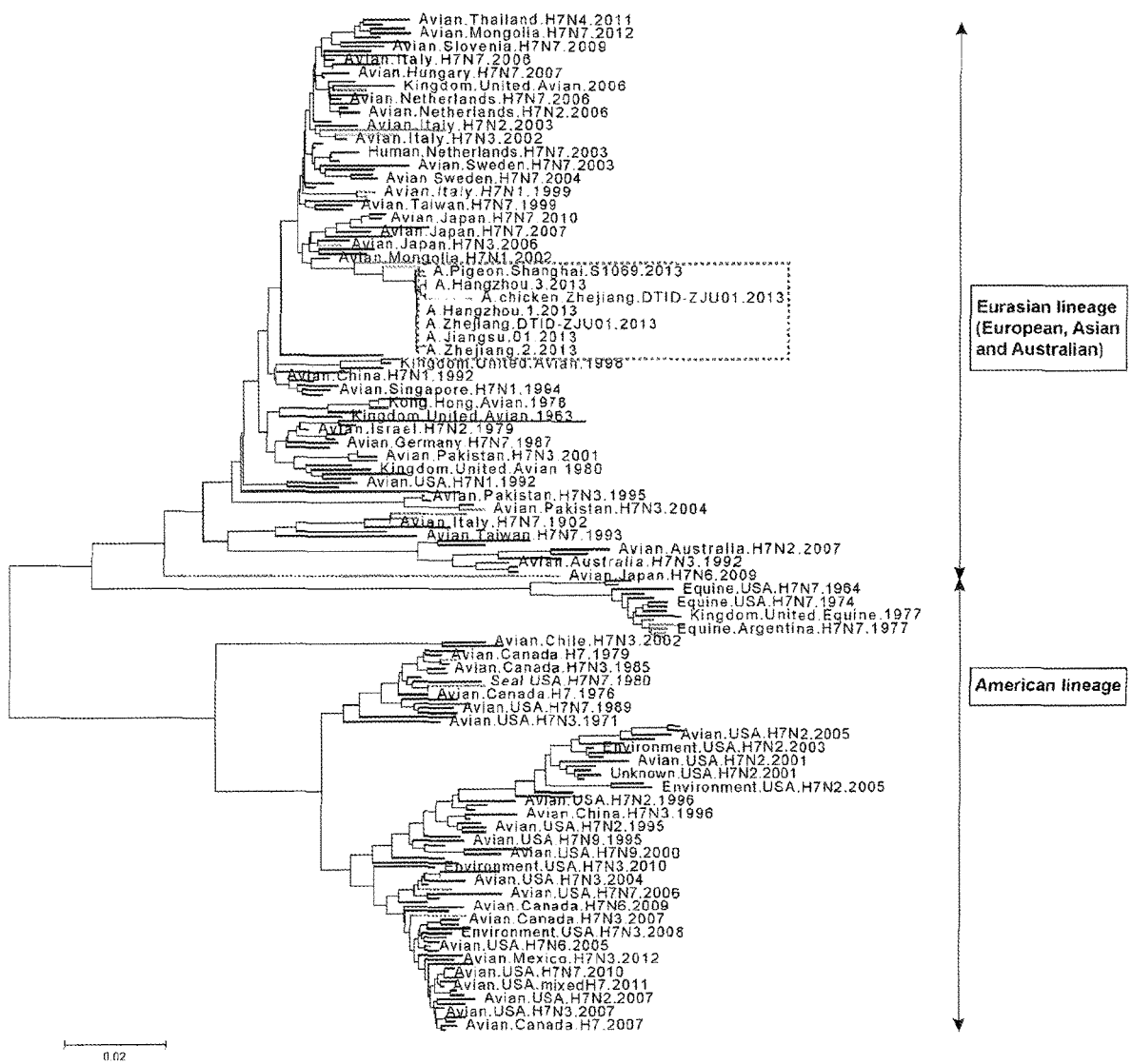
FIG. 7.

Previous H7 strains carrying single mutations (from the coevolving cluster) were predominantly from the Eurasian lineage suggesting that viruses from this lineage had higher potential to generate novel variants when compared to the American lineage (FIG. 7). Nucleotide analyses of the RBS-proximal region of HA (residues 50-230 of HA1) of Eurasian sequences from 1902 to 2013 showed strong diversifying (positive) selection at 156 (see, Methods section below). The same position had been shown to be under selection pressure in H1 subtype as well (Li et al. Virology Journal 8, 183 (2011)).

A quantitative metric to compare the antigenicity of two HAs has been defined in previous studies. Briefly, the metric, called antigenic intactness (AI), is directly proportional to the fraction of residues conserved in the immunodominant antigenic sites between two HAs. Studies have shown good agreement between AI values and antigenic relatedness metric computed from ferret antisera hemagglutinin inhibition (HI) cross-reactivity data (Tharakaraman et al. In press (2013)), indicating that AI values can be applied to predict vaccine-induced cross-reactive antibody responses. Strains that are antigenically related had AI>80% whereas strains that are not related to each other had AI<80% (Tharakaraman et al. In press (2013)). Keeping 80% as the cutoff, the AI values between the recent WHO-recommended H7 vaccines strains (A/Canada/rv444/2004 (H7N3), A/mallard/Netherlands/12/2000 (H7N3) and A/New York/107/2003 (H7N2)), and the novel A/Anhui/1/2013 H7N9 HA were computed. The novel H7N9 HA had AI values of 67%, 89% and 70% with A/Canada/rv444/2004 (H7N3), A/mallard/Netherlands/12/2000 (H7N3) and A/New York/107/2003 (H7N2), respectively, suggesting that only /mallard/Netherlands/12/2000 (H7N3) could be effective as a vaccine component. However, amino acid differences between A/Anhui/1/2013 (H7N9) and A/mallard/Netherlands/12/2000 (H7N3) at certain antigenic sites (122 in site A, 188 and 189 in site B) can limit this mallard strain to be effective.

Also, given that it is generally known that the 220 loop, which includes the 228 position, is an antigenic site for some HA subtypes (224 and 225 are part of antigenic site Ca in H1 subtype; 222 is part of antigenic site I-C in H2 subtype; 220 is part of antigenic site D in H3, a subtype that is phylogenetically closest to H7). Thus, antibody response targeting this region in H7N9 cannot be excluded.

Discussion

The emergence of a novel H7N9 influenza A virus subtype poses significant global health concern given that it has led to severe infection and mortality in humans. Although preliminary genetic analysis of this subtype has led to predictions about its human host adaptation based on hallmark genetic signatures including strong binding to human receptors; this virus has not yet resulted in a widespread infection in humans resulting from aerosol human-to-human transmission. Earlier studies had highlighted the importance of binding property of H7N9 HA to glycans on HA receptors, since this property is one of the many important factors that govern human adaptation of the virus (Gao et al. New England Journal of Medicine 368, 1888-1897 (2013); Liu et al. Lancet doi: 10.1016/S0140-6736(13)60938-1 (2013)). The glycan receptor-binding properties of H7N9 HA were therefore experimentally characterized in this study to assess the human adaptation of this HA. This study provides the first report on the glycan binding data of the novel H7N9 HA.

Structural analyses and binding of H7N9 HA to human respiratory tissues demonstrated that it possesses a distinct binding tropism when compared to either an avian-adapted or a human-adapted HA. Results in this study shed new light on the distinct tropism of this novel H7N9 HA that is contrary to the expected strong human receptor-binding preference predicted from earlier sequence analyses. This distinct tropism would likely impinge on the aerosol transmissibility of the H7N9 viruses in ferrets when compared to the efficient transmission observed in the past pandemic viruses. In certain embodiments, the limited human- and avian-receptor binding of the H7N9 HA suggests that this currently circulating subtype could be an intermediate in the adaptation to the human host.

Structural and experimental analyses in this study pointed to an important role for G228→S amino acid change in the RBS, should it emerge in the current H7N9 HA, in substantially increasing its binding to human receptors in the human respiratory tract.

Further, of note, within the context of this study, was the increased binding of the mutant HA to the non-cilicated goblet cells in the human trachea. This is significant as binding to goblet cells is one of the hallmarks of human adapted HAs (Jayaraman et al. PLoS ONE 6, e17616 (2011); Matrosovich et al. PNAS 101, 4620-4624 (2004); Srinivasan et al. PNAS 105, 2800-2805 (2008)). Even in cultures of differentiated human airway epithelial cells, the human influenza A viruses are found to predominantly infect non-cilicated cells as compared to avian influenza A viruses which target the cilicated cells Matrosovich et al. PNAS 101, 4620-4624 (2004).

Studies have been conducted to analyze the receptor specificity of influenza HA using 'prototypic' glycan arrays containing limited sets of glycans capped with α2-3 or α2-6 linked sialic acid. With H1, H2 and H3 HA, in most cases, the observed binding on glycan array correlated to observed binding of these HAs on physiological glycans from respiratory tract tissue sections. However, as noted in a previous study of HA from H7N2 A/Netherlands/219/2003, it was observed that introduction of 226L and 228S resulted in significant staining of the apical region of tracheal tissues despite having modest binding to α2-6 sialylated glycans on the glycan array (Srinivasan et al. PLoS One 8, 49597 (2013)). In the present study, with Anh13 it was again observed that the presence of 226L and 228S on the HA resulted in significant binding to the apical and submucosal regions of the trachea that was not captured by the affinity of the HA to limited set of glycans in the array (data not shown).

The significance of the change in residue 156 in receptor binding or other HA function is unclear although the neighboring 158 glycosylation is known to have an influence on human receptor binding (Stevens et al. J Mol Biol. 381, 1382-1394 (2008)). Significantly, a subset of the H7N9 demarcating coevolving positions (122, 186 and 202) appeared to be in the antigenic regions of H7, which could have implications on the effectiveness of the current WHO recommended pre-pandemic H7 vaccines. Furthermore, the reported poor immunogenicity of vaccine candidates based on H7N9 is a challenge for potential vaccine strategy. The fact that the wild-type virus bound poorly to human receptor supported the notion of poor uptake by human cells to engender an appropriate human immune response. Thus, mutant forms of H7N9 HA, such as G228S with higher specificity to human receptors, can potentially have important applications for the generation of appropriate vaccine countermeasures. A component of vaccine assessment is the use of serological assays to investigate cross-reactivity of heterologous strains. In this context, the correlation between AI score with cross-neutralization responses based on WHO data has been demonstrated (Tharakaraman et al. In press (2013)). Therefore. taken together, the novel mutations on the antigenic regions of H7N9 HA and the results of the AI analysis could impinge on H7 vaccine development.

In summary, this study reported the glycan-binding properties of the novel H7N9 HA and also reported on the effects of a single amino acid G228→S amino acid change in dramatically increasing glycan receptor binding of this HA. In light of the continued circulation of H7N9 in human subtypes this study facilitates monitoring the evolution of H7N9 including the acquisition of amino acid changes such as G228→S that would make it closer to human adaptation. This analysis therefore sets the stage for in vitro studies in human respiratory tract cell cultures and in vivo studies in ferret and mice to investigate the replication potential, virulence, pathogenicity and respiratory droplet transmission using these recombinant wild-type and mutant HA H7N9 viruses. Taken together, these findings have important implications for surveillance of H7N9 mutations in clinical settings, as well as for vaccine development efforts.

gation, filtered through a 0.45 μm filter system (Nalgene, Rochester, N.Y.) and supplemented with 1:1000 diluted protease inhibitor cocktail (Calbiochem filtration and supplemented with 1:1000 diluted protease inhibitor cocktail (EMD Millipore, MA). HA was purified from the supernatant using His-trap columns (GE Healthcare) on an AKTA Purifier FPLC system. Eluting fractions containing

TABLE 2

Amino acid differences in the RBS of HAs. Certain amino acids in the 130-, 140-, 150-, 220-loop, and 190-helix that bind to the base and extension region of the glycan receptors in Aichi68 and Anh13 are shown. The 150-loop has amino acids (positions 153 and 155) that are involved in contacts with the sialic acid in the base region and those that are involved in binding to extension region.

| | Base (Neu5Acα2->3/6Galβ1-) | | | | | | | | | | | | | |
|---|---|---|---|---|---|---|---|---|---|---|---|---|---|---|
| | 130-loop | | | | 140-loop | 220-loop | | | | | | | 150-loop | |
| Virus Strain/HA | 131 | 133 | 136 | 138 | 145 | 219 | 221 | 222 | 225 | 226 | 227 | 228 | 153 | 155 |
| Aichi68 | T | N | S | A | S | S | P | W | G | L | S | S | W | T |
| Anh13 | R | N | T | A | S | A | P | Q | G | L | S | G | W | L |

| | Extension (-4GlcNAcβ1-3Galβ1-4-) | | | | | | | | | | |
|---|---|---|---|---|---|---|---|---|---|---|---|
| | 150-loop | | | | | 190-Helix | | | | | |
| Virus Strain/HA | 156 | 157 | 158 | 159 | 160 | 186 | 187 | 188 | 189 | 190 | 192 | 193 |
| Aichi68 | K | S | G | S | T | S | T | N | Q | E | T | S |
| Anh13 | S | N | T | D | N | V | S | T | A | E | T | K |

| | Base (Neu5Acα2->3/6Galβ1-) | | | | | | | | | | | | | | | |
|---|---|---|---|---|---|---|---|---|---|---|---|---|---|---|---|---|
| | 130-loop | | | | | 140-loop | 220-loop | | | | | | | 150-loop | |
| HA | 131 | 133 | 135 | 136 | 137 | 138 | 145 | 219 | 221 | 222 | 224 | 225 | 226 | 227 | 228 | 153 | 155 |
| Aichi68 H3N2 | T | N | G | S | N | A | S | S | P | W | R | G | L | S | S | W | T |
| Nor04 H3N2 | T | N | G | S | S | A | N | S | P | R | R | D | I | P | S | W | T |
| Mal05 H3N2 | T | N | G | S | S | A | N | S | P | R | R | N | I | P | S | W | T |
| Tklt02 H7N3 | R | N | A | T | S | A | S | A | P | Q | N | G | Q | S | G | W | L |
| Neth03 H7N7 | R | N | T | T | S | A | S | A | P | Q | N | G | L | S | G | W | L |
| Anh13 H7N9 | R | N | A | T | S | A | S | A | P | Q | N | G | L | S | G | W | L |

| | Extension (-4GlcNAcβ1-3Galβ1-4-) | | | | | | | | | | |
|---|---|---|---|---|---|---|---|---|---|---|---|
| | 150-loop | | | | | 190-Helix | | | | | |
| HA | 156 | 157 | 158 | 159 | 160 | 186 | 187 | 188 | 189 | 190 | 192 | 193 |
| Aichi68 H3N2 | K | S | G | S | T | S | T | N | Q | E | T | S |
| Nor04 H3N2 | H | L | K | F | K | G | T | D | N | D | I | S |
| Mal05 H3N2 | H | L | K | F | K | G | T | D | N | D | I | F |
| Tklt02 H7N3 | S | N | T | D | N | G | S | T | T | E | T | K |
| Neth03 H7N7 | S | N | T | D | N | G | S | T | T | E | T | K |
| Anh13 H7N9 | S | N | T | D | N | V | S | T | A | E | T | K |

Methods

Cloning, Baculovirus Synthesis, and Mammalian Expression and Purification of HA

Anh13 wild-type and G228→S mutant HA sequences were codon-optimized for mammalian expression, synthesized (DNA2.0, Menlo Park, Calif.) and sub-cloned into modified pcDNA3.3 vector for expression under CMV promoter. Recombinant expression of HA was carried out in HEK 293-F FreeStyle suspension cells (Invitrogen, Carlsbad, Calif.) cultured in 293-F FreeStyle Expression Medium (Invitrogen, Carlsbad, Calif.) maintained at 37° C., 80% humidity and 8% $CO_2$. Cells were transfected with Polyethylene-imine Max (PEI-MAX, PolySciences, Warrington, Pa.) with the HA plasmid and were harvested seven days post-infection. The supernatant was collected by centrifu- HA were pooled, concentrated and buffer exchanged into 1×PBS pH 7.4 using 100K MWCO spin columns (Millipore, Billerica, Mass.). The purified protein was quantified using BCA method (Pierce, Rockford, Ill.).

Homology Modeling of HA

A structural model of Anh13 HA was built using the MODELLER homology modeling software. The crystal structure of A/Netherlands/219/2003 (Neth03) HA (PDB: 4DJ6) was used as a template to build the model. The structural model of Anh13 bound to avian receptor was constructed by superimposing the HA1 from co-crystal structure of Neth03-avian receptor complex (PDB ID: 4DJ7) on Anh13 HA1. The structural model of Anh13 in complex with human receptor was constructed by superimposing the HA1 from co-crystal structure of Aichi68-human receptor complex (PDB ID: 2YPG) with HA1 of Anh13. The final models were subject to energy minimization (500 steps conjugate gradient+500 steps steepest descent) with potentials assigned using AMBER force field.

Coevolution, Phylogeny and Selection Analyses of H7 HA Sequences

A total of 625 non-redundant full-length H7 HA sequences were downloaded from GISAID. To further eliminate redundancy, the sequences were grouped according to subtype, host, year and country and a representative sequence was chosen from each group. This led to a total of 231 HA sequences. Coevolving groups of amino acids were predicted using CAPS online server for protein coevolution (bioinf.gen.tcd.ie/caps/). The results indicated functionally or structurally linked regions that are subjected to strong selective constraints. A phylogeny tree was constructed from the 231 HA sequences using the Neighbor Joining method found in MEGA 5.1 software (megasoftware.net/). Protein coding nucleotide sequences were extracted for the 114 Eurasian HA sequences and the region encoding residues 50-230 of HA1 was employed for finding individual codons under diversifying/positive selection. Positively selected sites were predicted using DataMonkey (datamonkey.org/), which uses a normalized dN-dS>0 at p-value <0.1 threshold to detect positive selection.

Binding of HA to Human Tissue Sections

The human tracheal epithelia has been extensively benchmarked as a tissue section representative of human upper respiratory tract that is a predominant physiological target site for human adapted influenza A viruses (Jayaraman et al. PLoS ONE in press (2012); Shinya et al. Nature 440, 435-436 (2006)). The apical surface and submucosal regions of the human trachea have been shown to predominantly display human receptors (Chandrasekaran et al. Nat. Biotechnol 26, 107-113 (2008)). On the other hand, human alveolar tissue sections representative of deep lung region have been shown to predominantly express avian receptors and are typically stained by HA from avian-adapted influenza A viruses Chandrasekaran et al. Nat. Biotechnol 26, 107-113 (2008)). Paraffinized human tracheal and alveolar (US BioChain) tissue sections were deparaffinized, rehydrated and incubated with 1% BSA in PBS for 30 minutes to prevent non-specific binding. HA was pre-complexed with primary antibody (mouse anti 6×His tag, Abcam) and secondary antibody (Alexa fluor 488 goat anti mouse, Invitrogen) in a molar ratio of 4:2:1, respectively, for 20 minutes on ice. The tissue binding was performed over two different HA concentrations (40 µg/ml and 20 µg/ml) by diluting the pre-complexed stock HA in 1% BSA-PBS. Tissue sections were then incubated with the HA-antibody complexes for 3 hours at room temperature. The tissue sections were counterstained by propidium iodide (Invitrogen; 1100 in TBST). The tissue sections were mounted and then viewed under a confocal microscope (Zeiss LSM 700 laser scanning confocal microscopy). Sialic-acid specific binding of HAs to tissue sections was confirmed by loss of staining after pre-treatment with Sialidase A (from *Arthrobacter ureafaciens*, Prozyme). This enzyme has been demonstrated to cleave the terminal Neu5Ac from both Neu5Acα2→3Gal and Neu5Acα2→6Gal motifs. In the case of sialidase pre-treatment, tissue sections were incubated with 0.2 units of Sialidase A for 3 hours at 37° C. prior to incubation with the proteins. Pre-treatment of human tissue sections with Sialidase A resulted in complete loss of HA staining.

Capturing Network Inter-Amino Acid Contacts for RBS Residues (RBSN)

The coordinates of Neth03 H7 HA—avian receptor (PDB ID: 4DJ7) and Aichi68 H3 HA—human receptor complexes (PDB ID: 2YPG) were uploaded into the PDBePISA server (ebi.ac.uk/msd-srv/prot_int/pistart) to determine important residues in the HA RBS that make contact with the corresponding glycan receptor (interface cut-off of 30% was used). For these residues, their environment was defined using a distance threshold of 7 Å and the contacts including putative hydrogen bonds (including water-bridged ones), disulfide bonds, pi-bonds, polar interactions, salt bridges, and Van der Waals interactions (non-hydrogen) occurring between pairs of residues within this threshold distance was computed as described previously (Soundararajan et al. Sci Rep 1 (2011)). These data were assembled into an array of eight atomic interaction matrices. A weighted sum of the eight atomic interaction matrices were then computed to produce a single matrix that accounts for the strength of atomic interaction between residue pairs within the RBS, using weights derived from relative atomic interaction energies. The inter-residue interaction network calculated in this fashion generated a matrix that described all the contacts made by RBS residues with spatial proximal neighboring residues in their environment. Each element i, j was the sum of the path scores of all paths between residues i and j. The degree of networking score for each residue was computed by summing across the rows of the matrix, which was meant to correspond to the extent of "networking" for each residue. The degree of networking score was normalized (RBSN score) with the maximum score for each protein so that the scores varied from 0 (absence of any network) to 1 (most networked).

EQUIVALENTS AND SCOPE

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein.

The publications discussed above and throughout the text are provided solely for their disclosure prior to the filing date of the present application. Nothing herein is to be construed as an admission that the inventors are not entitled to antedate such disclosure by virtue of prior disclosure.

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. A polypeptide whose amino acid sequence includes a sequence element that:
   i) at least 95% identical to at least ten continuous amino acids of a reference H7 HA polypeptide selected from the group consisting of SEQ ID NO: 17-38, 43, 45-47, 56-58 and 60-65, wherein the at least ten continuous amino acids includes amino acid position 228; and
   ii) has a serine residue at its position corresponding to the reference H7 polypeptide amino acid position 228.

2. The polypeptide of claim 1, wherein the polypeptide further comprises approximately residues 50-220 of the reference H7 HA polypeptide.

3. The polypeptide of claim 1, wherein the portion further includes amino acid position 226, and wherein the sequence element has a leucine or isoleucine residue at its position corresponding to the reference H7 HA polypeptide position 226.

4. The polypeptide of claim 1, wherein the polypeptide further includes amino acid position 122, and wherein the sequence element has an alanine residue at its position corresponding to the reference H7 HA polypeptide position 122.

5. The polypeptide of claim 1, wherein the polypeptide further includes amino acid position 174, and wherein the sequence element has a serine residue at its position corresponding to the reference H7 HA polypeptide position 174.

6. The polypeptide of claim 1, wherein the polypeptide further includes amino acid position 186, and wherein the sequence element has a valine residue at its position corresponding to the reference H7 HA polypeptide position 186.

7. The polypeptide of claim 1, wherein the polypeptide further includes amino acid position 202, and wherein the sequence element has a valine residue at its position corresponding to the reference H7 HA polypeptide position 202.

8. The polypeptide of claim 1, wherein the polypeptide further includes at least one amino acid position selected from the group consisting of 122, 174, 186, 202, 226, and combinations thereof, and wherein the sequence element has:
   alanine residue at its position 122;
   serine residue at its position 174;
   valine residue at its position 202;
   leucine or isoleucine residue at its position 226;
   corresponding to the reference H7 HA polypeptide.

9. The polypeptide of claim 1, wherein the polypeptide is between 100 amino acids and 600 amino acids in length.

10. The polypeptide of claim 1, wherein the polypeptide is between 200 amino acids and 600 amino acids in length.

11. A nucleic acid that encodes the polypeptide of claim 1.

12. A cell line that expresses the polypeptide of claim 1.

13. The polypeptide of claim 1, wherein the polypeptide further has an amino acid sequence that includes L226, I226, S174, A122, V186, V202, or combinations thereof.

14. A vaccine composition comprising at least one polypeptide whose amino acid sequence includes a sequence element that:
   i) at least 95% identical to at least ten continuous amino acids of a reference H7 HA polypeptide selected from the group consisting of SEQ ID NO: 17-38, 43, 45-47, 56-58 and 60-65, wherein the at least ten continuous amino acids includes amino acid position 228; and
   ii) has a serine residue at its position corresponding to the reference H7 polypeptide amino acid position 228;
   and a pharmaceutically acceptable carrier.

15. A polypeptide whose amino acid sequence includes a sequence element that:
   i) at least 80% identical to at least ten continuous amino acids of a reference H7 HA polypeptide selected from the group consisting of SEQ ID NO: 17-38, 43, 45-47, 56-58 and 60-65, wherein the at least ten continuous amino acids includes amino acid position 228; and
   ii) has a serine residue at its position corresponding to the reference H7 polypeptide amino acid position 228.

16. A nucleic acid that encodes the polypeptide of claim 15.

17. A cell line that expresses the polypeptide of claim 15.

18. The polypeptide of claim 15, wherein the polypeptide further has an amino acid sequence that includes L226, I226, S174, A121, V186, V202, or combinations thereof.

19. A vaccine composition comprising, the polypeptide of claim 15.

* * * * *